US009512425B2

(12) United States Patent
Mittal et al.

(10) Patent No.: US 9,512,425 B2
(45) Date of Patent: Dec. 6, 2016

(54) INHIBITING MIGRATION OF CANCER CELLS

(71) Applicant: Cornell University, Ithaca, NY (US)

(72) Inventors: Vivek Mittal, Greenlawn, NY (US); Seongho Ryu, New York, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 14/437,432

(22) PCT Filed: Oct. 23, 2013

(86) PCT No.: PCT/US2013/066376
§ 371 (c)(1),
(2) Date: Apr. 21, 2015

(87) PCT Pub. No.: WO2014/066498
PCT Pub. Date: May 1, 2014

(65) Prior Publication Data
US 2015/0275210 A1      Oct. 1, 2015

Related U.S. Application Data

(60) Provisional application No. 61/717,397, filed on Oct. 23, 2012.

(51) Int. Cl.
| | |
|---|---|
| *A61K 48/00* | (2006.01) |
| *C12N 15/11* | (2006.01) |
| *C12N 15/113* | (2010.01) |
| *A61K 9/127* | (2006.01) |
| *C07H 21/04* | (2006.01) |

(52) U.S. Cl.
CPC ............. *C12N 15/113* (2013.01); *A61K 9/127* (2013.01); *C12N 15/111* (2013.01); *C12N 2310/141* (2013.01); *C12N 2320/30* (2013.01)

(58) Field of Classification Search
CPC ........................ C12N 15/113; C12N 2310/141
See application file for complete search history.

(56) References Cited

U.S. PATENT DOCUMENTS

2007/0298118 A1* 12/2007 Lotvall .................. C12N 15/87
                                                                 424/577
2010/0310583 A1* 12/2010 Lieberman ......... A61K 31/7105
                                                                 424/174.1

FOREIGN PATENT DOCUMENTS

| EP | 2486929 A1 | 8/2012 |
|---|---|---|
| WO | WO-2009082744 A2 | 7/2009 |
| WO | WO-2014066498 A1 | 5/2014 |

OTHER PUBLICATIONS

Song et al., miR-708 promotes the development of bladder carcinoma via direct repression of Caspase-2, 2013, Journal of Cancer Research and Clinical Oncology, vol. 139, pp. 1189-1198.*
Lei et al., Regulatory roles of microRNA-708 and microRNA-31 in proliferation, apoptosis and invasion of colorectal cancer cells, 2014, Oncology Letters, vol. 8, pp. 1768-1774.*
Morgenbesser et al., Identification of genes potentially involved in the acquisition of androgen-independent and metastatic tumor growth in an autochthonous genetically engineered mouse prostate cancer model, 2007, The Prostate, vol. 67, pp. 83-106.*
Hu et al., Molecular characterization of a metastatic neuroendocrine cell cancer arising in the prostates of transgenic mice, 2002, The Journal of Biological Chemistry, vol. 277, pp. 44462-44474.*
TargetScan Human Release 6.2, Jun. 2012., Select human miR-28-5p/708/1407/1653/3139 microRNA family; predicted miRNA targets of miR-28-5p/708/1407/1653/3139. Total 6 pages. accessed and retrieved from www.targetscan.org on Nov. 19, 2015.*
"International Application Serial No. PCT/US2013/066376, International Search Report mailed Jan. 21, 2014", 7 pgs.
"International Application Serial No. PCT/US2013/066376, Written Opinion mailed Jan. 21, 2014", 6 pgs.
Becker, M, et al., "Distinct gene expression patterns in a tamoxifen-sensitive human mammary carcinoma xenograft and its tamoxifen-resistant subline MaCa 3366/TAM", Molecular Cancer Therapeutics, American Association of Cancer Research, US, vol. 4, No. 1, (2005), 19 pgs.
Jang, J S, et al., "Increased miR-708 Expression in NSCLC and Its Association with Poor Survival in Lung Adenocarcinom from Never Smokers", Clinical Cancer Research, vol. 18, No. 13, (May 9, 2012), 11 pgs.
Ming, Shi, et al., "Metastasis-related miRNAs, active players in breast cancer invasion, and metastasis", Cancer and Metastasis Reviews, Kluwer Academic Publishers, DO, vol. 29, No. 4, (Oct. 12, 2010), 785-799.
Robin, T P, "EWS/FLII Regulates EYA3 in Ewing Sarcoma via Modulation of miRNA-708, Resulting in Increased Cell Survival and Chemoresistance", Molecular Cancer Research, vol. 10, No. 8, (Jun. 20, 2012), 12 pgs.
Saini, S, et al., "MicroRNA-708 Induces Apoptosis and Suppresses Tumorigenicity in Renal Cancer Cells", Cancer Research, vol. 71, No. 19, (Aug. 18, 2011), 13 pgs.
Saini, S, et al., "miRNA-708 Control of CD44+ Prostate Cancer-Initiating Cells", Cancer Research, vol. 72, No. 14, (May 2, 2012), 14 pgs.
Scott, Valastyan, et al., "A Pleiotropically Acting MicroRNA, miR-31, Inhibits Breast Cancer Metastasis", Cell, Cell Press, US, vol. 137, No. 6, (Jun. 12, 2009), 15 pgs.
Seongho, Ryu, et al., "Suppression of miRNA-708 by Polycomb Group Promotes Metastases by Calcium-Induced Cell Migration", Cancer Cell, vol. 23, No. 1, (Jan. 14, 2013), 63-76.
Volinia, S, et al., "Breast cancer signatures for invasiveness and prognosis defined by deep sequencing of microRNA", Proceedings of the National Academy of Sciences, vol. 109, No. 8, (Feb. 6, 2012), 6 pgs.
Wang, L, et al., "MicroRNA-mediated breast cancer metastasis: from primary site to distant organs", Oncogene, vol. 31, No. 20, (Oct. 3, 2011), 2499-2511.
Yu, J, "MicroRNA Alterations of Pancreatic Intraepithelial Neoplasias", Clinical Cancer Research, vol. 18, No. 4, (Nov. 23, 2011), 981-992.

(Continued)

*Primary Examiner* — Dana Shin
(74) *Attorney, Agent, or Firm* — Schwegman Lundberg & Woessner, P.A.

(57) ABSTRACT

As described herein, increased expression of microRNA-708 reduces migration and metastasis of cancer cells.

13 Claims, 53 Drawing Sheets
(29 of 53 Drawing Sheet(s) Filed in Color)

(56) References Cited

OTHER PUBLICATIONS

Yu, Z, et al., "microRNA 17/20 inhibits cellular invasion and tumor metastasis in breast cancer by heterotypic signaling", Proceedings of the National Academy of Sciences, vol. 107, No. 18, (Apr. 20, 2010), 8231-8236.
Zhang, H, et al., "The microRNA network and tumor metastasis", Oncogene, vol. 29, No. 7, (Nov. 23, 2009), 937-948.
"European Application Serial No. 13786118.3, Office Action mailed Jun. 5, 2015", 2 pgs.
"European Application Serial No. 13786118.3, Response filed Dec. 7, 2015 to Office Action mailed Jun. 5, 2015", 7 pgs.
"International Application Serial No. PCT/US2013/066376, International Preliminary Report on Patentability mailed May 7, 2015", 8 pgs.
"European Application Serial No. 13786118.3, Communication Pursuant to Article 94(3) EPC mailed Mar. 30, 2016", 4 pgs.
Ohno, Shin-Ichiro, et al., "Focus on Extracellular Vesicles: Development of Extracellular Vesicle-Based Therapeutic Systems.", International Journal of Molecular Sciences 2016, 17, 172; doi:10.3390/ijms17020172, www.mdpi.com/journal/ijms, (2016), 19.

\* cited by examiner

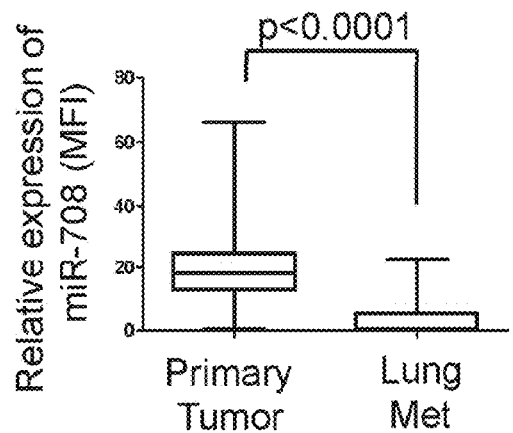
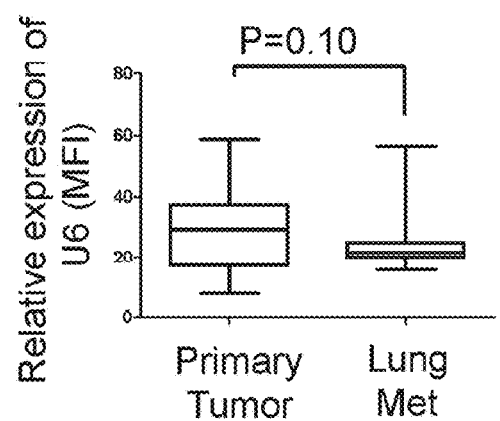
Fig.1M          Fig.1N
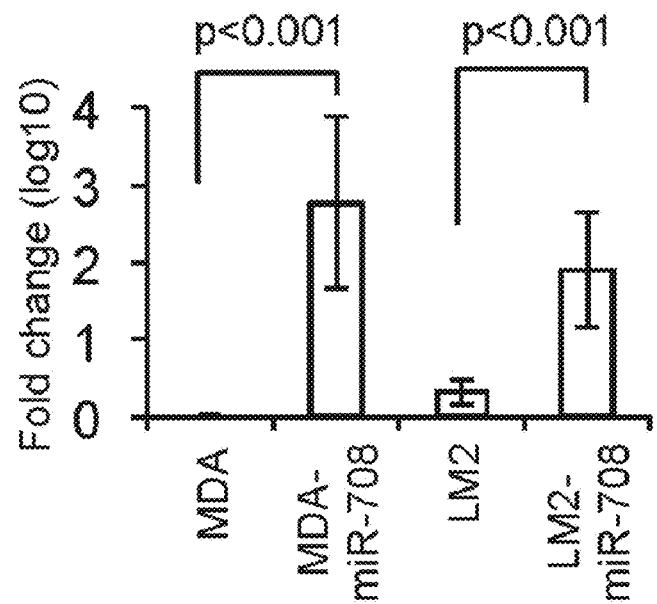
Fig.1O

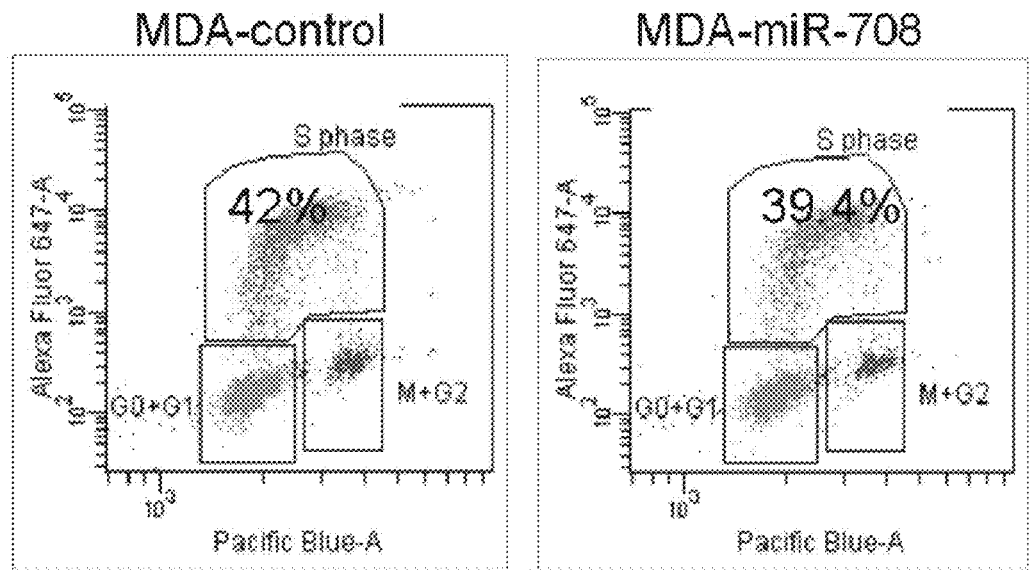
Fig. 1P
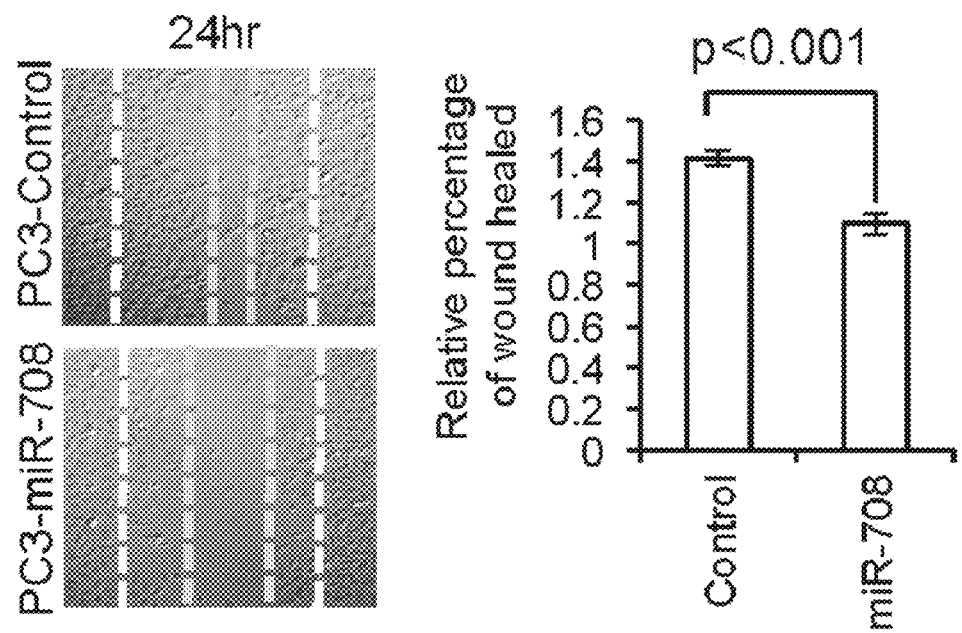
Fig. 1Q
Fig. 1R

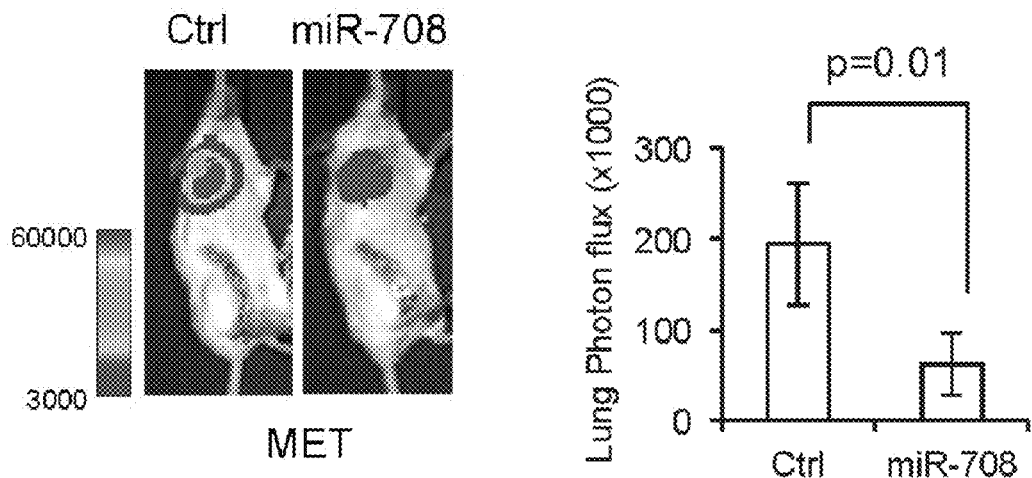
Fig.2E
Fig.2F
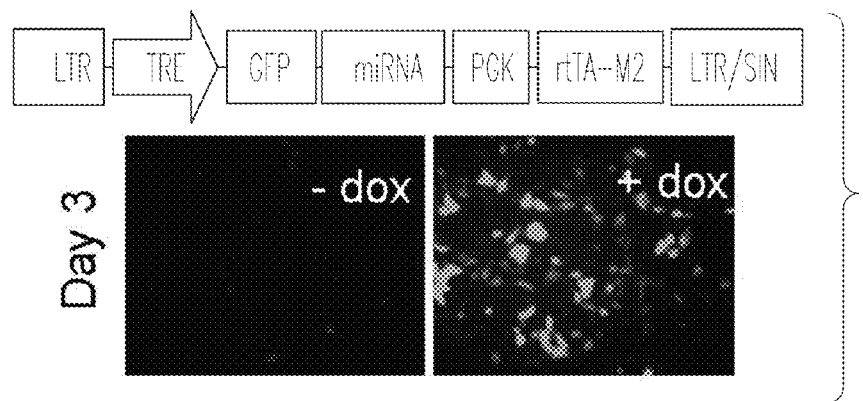
Fig.2G
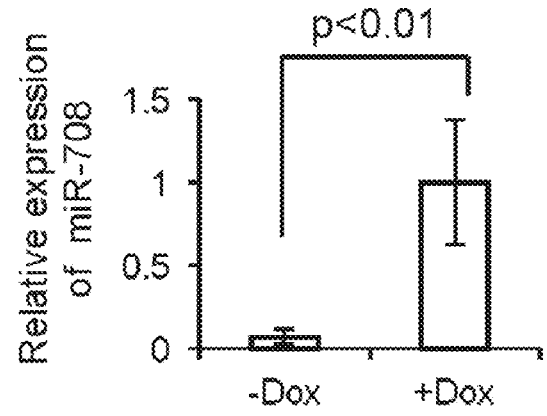
Fig.2H

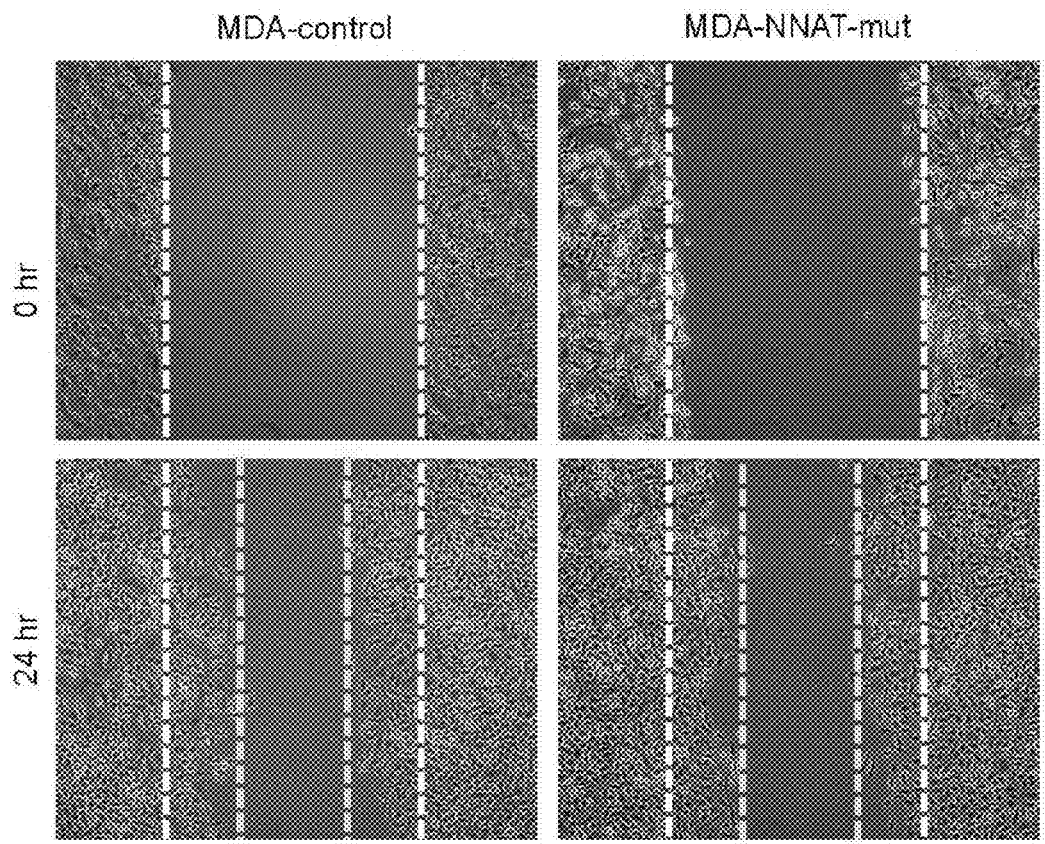
*Fig. 4G*
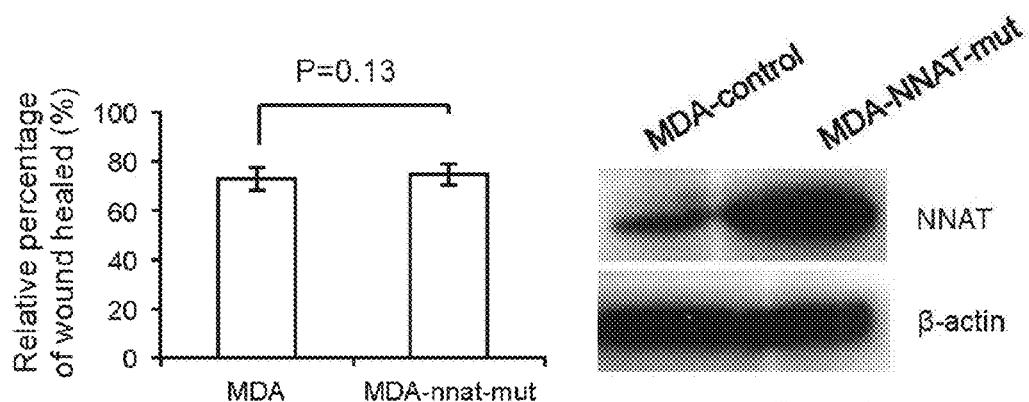
*Fig. 4H*          *Fig. 4I*

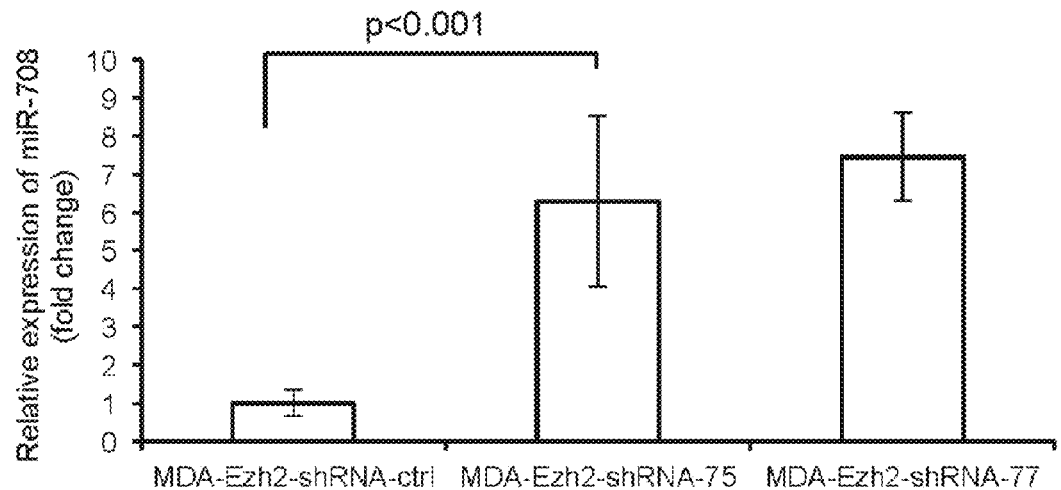
Fig. 5N
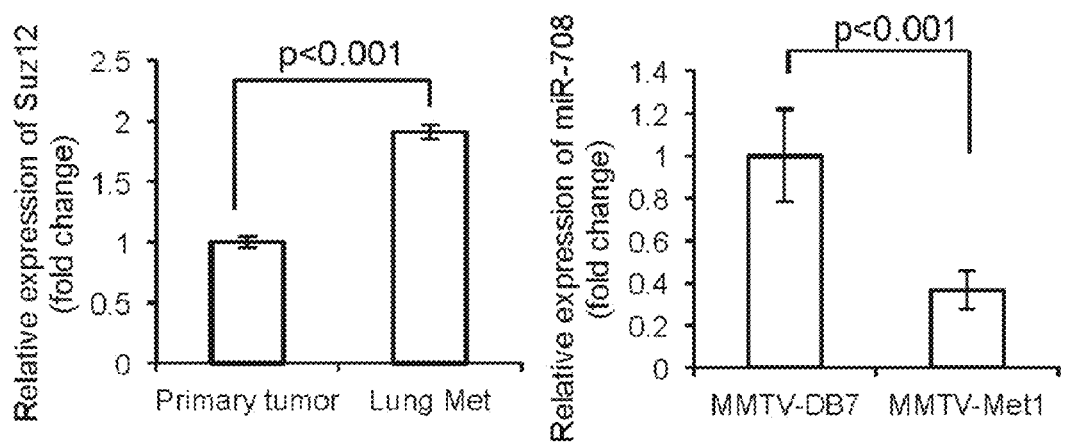
Fig. 5O
Fig. 5P

INHIBITING MIGRATION OF CANCER CELLS

CROSS-REFERENCE TO RELATED APPLICATION

This patent application is a U.S. National Stage Filing under 35 U.S.C. 371 from International Application No. PCT/US2013/066376, filed on 23 Oct. 2013 and published as WO 2014/066498 on 1 May 2014, which claims the benefit of priority, under 35 U.S.C. Section §119(e), to U.S. Provisional Patent Application Ser. No. 61/717,397 filed on Oct. 23, 2012, the contents of which applications and publications are incorporated by reference herein in their entirety.

BACKGROUND

Breast cancer is one of the most common cancers and is often identified as being the second cause of cancer death in women. In 2001, the incidence rates of breast cancer were 90-100/100,000 in the United States and 50-70/100,000 in Europe. The incidence of the disease is growing worldwide. Risk factors for breast cancer include race, age, and mutations in the tumor suppressor genes BRCA-1 and -2 and p53. Alcohol consumption, fat-rich diet, lack of exercise, exogenous post-menopausal hormones and ionizing radiation also increase the risk of developing breast cancer. Estrogen receptor and progesterone receptor negative breast cancer ("ER-" and "PR-" breast cancer, respectively), large tumor size, high grade cytology and age below 35 years are associated with a bad prognosis (Goldhirsch et al. (2001). J. Clin. Oncol. 19: 3817-27). In 2005 an estimated 212,000 new cases of invasive and 58,000 new cases of non-invasive breast cancer will be diagnosed, with 40,000 women expected to die from breast cancer.

New strategies are needed for treatment of cancers.

SUMMARY

As described herein, increased expression of microRNA-708 reduces migration and metastasis of cancer cells.

One aspect of the invention is a method of inhibiting migration of cancer cells that includes contacting the cancer cells with microRNA-708 to thereby inhibit migration of cancer cells.

Another aspect of the invention is a composition that includes microRNA-708 nucleic acids and a carrier or vehicle selected from the group consisting of one or more liposomes, exosomes, microvesicles, or any combination thereof. For example, the microRNA-708 nucleic acids can be encapsulated in liposomes, exosomes, microvesicles, or a combination thereof.

As demonstrated by the data described herein, use of the methods and compositions described herein can significantly reduce the metastatic burden in animals with cancer.

DESCRIPTION OF THE FIGURES

The patent or application file contains at least one drawing executed in color. Copies of this patent or patent application publication with color drawing(s) will be provided by the Office upon request and payment of the necessary fee.

FIG. 1A-1R illustrate that miR-708 is down-regulated in metastatic cancer cells and affects cell migration. FIG. 1A is a heat map obtained from high throughput miR-SEQ profiling of non-metastatic (MCF-10A, lane 1; MCF7, lane 2) and metastatic breast cancer cells (MDA, lanes 3 and 4; LM2, lanes 5 and 6). Each row represents a miRNA that was differentially regulated (2 fold or more in sequence read frequencies), and each column represents the average of two biological replicates). The relatively high expression is indicated by red boxes, while the relatively low expression is shown by green boxes. FIG. 1G (lower graph), graphically illustrates the fold change in miR-708 expression levels in MCF7 cells stably expressing the miR-708-sponge compared with MCF7 and MDA controls as detected by quantitative RT-PCR. FIG. 1M graphically illustrates miR-708 expression in primary tumor cells versus lung metastatic cells. FIG. 1N graphically illustrates U6 (control) expression in primary tumor cells versus lung metastatic cells. FIG. 1O shows expression of miR-708 from a lentiviral delivery system used to stably transform the human metastatic breast tumor cell line MDA-MB-231 (MDA) and MDA-MB-LM2 (LM2) cell lines. FIG. 1P shows that no significant change in cell proliferation was observed in MDA cells transformed with the miR-708 lentiviral expression system. FIG. 1Q shows that MDA cells stably expressing miR-708 exhibited suppressed migration rates compared with controls. FIG. 1R graphically illustrates MDA cell (control) migration compared to miR-708-expressing MDA cells.

FIG. 2A shows representative bioluminescence (BLI) images of animals showing primary tumors (PT) at day 60 after orthotopic injections into the mammary fat pad of MDA-miR-708 cells and vector control MDA cells (n=10 per group, p=0.76.). The scale bar depicts the photon flux (photons per second) emitted from these mice, where darker (blue) colors indicate low photon flux while lighter colors (yellow, green and red) indicate increased photon flux (red color indicates the highest photon flux). FIG. 2E shows representative bioluminescence images of animals exhibiting lung metastases derived from orthotopic injections into the mammary fat pad of LM2-miR-708 cells and control LM2 cells (n=10, per group, p<0.01) at day 67. Primary tumors were resected at day 60. The scale bar depicts the photon flux (photons per second) emitted from these mice. As shown, the animal receiving miR-708 had significantly lower photon flux. FIG. 2F graphically illustrates photon flux from pulmonary metastases as assessed by bioluminescence measurements (day 67). FIG. 2G shows a schematic of a lentiviral vector used to inducibly express miR-708 following doxycycline (Dox) administration by food (200 mg/kg). Dox administration resulted in the inducible expression of GFP in MDA cells stably infected with lentivirus, as shown in the images below the schematic diagram. FIG. 2H graphically illustrates miR-708 expression levels in the presence of Dox (+Dox) or absence of Dox (−Dox) as assessed by quantitative RT-PCR. FIG. 2N graphically illustrates the photon flux of the primary tumors as assessed by bioluminescence measurements at day 60 after tumor cell injection.

FIG. 3A shows a Venn diagram illustrating the number of genes identified as potential targets of miR-708 as predicted by three algorithms; TargetScan, miRanda and TargetRank. FIG. 3B shows a schematic diagram of a dual luciferase vector used for cloning 3'-UTR of candidate genes and dual luciferase assay results exhibiting repression of candidate genes by miR-708 plotted as ratios of Renilla and Firefly luciferase activity in 293T cells. The symbol * indicates p<0.01. FIG. 3C shows Western blots of endogenous candidate proteins in MDA-708 and MDA control cells. β-actin served as an internal control. FIG. 3D shows complementarity between the 3'-UTR sequences of Nnat and miR-708 (SEQ ID NOs: 117-119). Also shown are nucleotides mutated in the seed sequences to generate a Nnat-3'-UTR-mutant. FIG. 3E graphically illustrates repression of expression from wild type UTR (Nnat-UTR) or mutant UTR (Nnat-UTR-mut) as assessed by dual luciferase assays following transfection of synthetic miR-708 or scrambled (SCR) miRNA. FIG. 3F shows Western blot immunostained for NNAT expression from Nnat cDNA with a wild type UTR (Nnat) or mutant UTR (Nnat-mut) in the presence of synthetic miR-708 or scrambled (SCR) miRNA. β-actin served as an internal control. As shown, miR-708 suppressed expression from NNAT. FIG. 3G graphically illustrates Nnat expression in a panel of non-metastatic and metastatic breast cancer cells as assessed by quantitative-RT-PCR. FIG. 3H shows genes associated with metastasis-related functions such as cell proliferation, apoptosis, cell cycle, migration, adhesion, invasion, and cell differentiation as detected by algorithms. FIG. 3I graphically illustrates Nnat expression in different cell types (MCF7, MDA, and MDA-miR-708, where MDA-miR-708 cells express a miR-708 transgene). FIG. 3J shows a Western blot immunostained for NNAT expression in the presence or absence of doxycycline-induced miR-708 expression.

FIG. 4A shows representative calcium traces of MDA-control and MDA-miR-708 cells stimulated with ATP. The dotted lines represent the initial rate of calcium regulation back to baseline. FIG. 4A (left panel), slope=0.72 (ratio/min) and FIG. 4A (right panel), slope=0.3 (ratio/min). FIG. 4D (lower panel), graphically illustrates cell migration as percentage of wound healed that was performed with $1 \times 10^6$ MDA control, MDA-miR-708 and MDA-miR-708-Nnat-mut cells either in the presence of $Ca^{2+}$ inhibitor, BAPTA-AM at 24 hrs. For each cell line, cell migration was normalized to the migration of the no BAPTA control. Data represent mean±s.d. of nine randomly selected areas from three independent experiments. p<0.001 between BAPTA treated MDA-control vs. MDA-miR-708 and MDA-miR-708-nnat-mut versus MDA-miR-708. FIG. 4G shows representative images of a cell migration assay performed with 1×10⁶ MDA control (MDA) and MDA expressing NNAT-mut cells. Cells were plated into 6 well dishes and allowed to grow for 12 hours, after which a scratch was created and cells imaged immediately (0 hr) or after 24 hr. FIG. 4H graphically illustrates of migration data from assays described in FIG. 4G. Data represent mean±s.d. of nine randomly selected areas from three independent experiments. FIG. 4I shows a Western blot illustrating Nnat protein levels following overexpression of Nnat-mut in MDA cells. FIG. 4U graphically illustrates the mean±SD of six randomly selected areas of images like those shown in FIG. 4T from two independent experiments.

FIG. 5A graphically illustrates SUZ12 levels in nonmetastatic (MCF7) and metastatic (MDA) breast cancer cells as detected by Western blot analysis. β-actin served as an internal control. As shown, 7.5-fold change was observed in MDA compared to MCF7. FIG. 5H shows graphically illustrates % input of β-actin as detected by ChIP-PCR following pull down with indicated antibodies in breast cancer cell lines MCF10A, MCF7, MDA and MDA-LM2ChIP-PCR. As shown, GAPDH is relatively enriched relative to the β-actin gene shown in FIG. 5I. IgG, control antibody; PolII, RNA polymerase II; an anti-histone H3K27M3 antibody.

FIG. 5S graphically illustrates Nnat expression in control and Suz12 knockdown MMTV-Met1 cells, showing that Suz12 knockdown reduces of Nnat expression.

FIG. 6A shows representative images of human primary breast tumors (upper panels) and matched lymph node metastases (lower panels). with detection of miR-708 and control U6 by in situ hybridization (red areas in the left-most panels). FIG. 6B graphically illustrates miR-708 expression (top) and control U6 expression (bottom) in human primary breast tumors (n=6) and matched lymph node metastasis (n=6). FIG. 6C shows representative images showing miR-708 in situ hybridization (red areas in the left-most panels) in lung metastases (Met) and human normal lungs (top to rows) and control U6 in situ hybridization (bottom two rows). FIG. 6D graphically illustrates miR-708 expression in normal lungs and lungs from breast cancer patients with metastases (n=10 sections each, 2 independent cases). FIG. 6E graphically illustrates U6 expression in normal lungs and lungs from breast cancer patients with metastases (n=10 sections each, 2 independent cases). FIG. 6F shows confocal microscopy images illustrating U6 and miR-708 in situ hybridization signals in primary breast tumors and matched metastases. U6 signals are confined to the nucleus and the miR-708 signals are both nuclear and cytoplasmic. DAPI marks nucleus of all cells. Scale bar, 20 µm. FIG. 6G shows images illustrating in situ hybridization for miR-708 (left panel) and U6 (right panel) in human normal lungs from samples like those shown in FIG. 6C. The hybridization signals are localized with DAPI+ cells. Scale bar, 50 µm. FIG. 6H graphically illustrates miR-708 expression in luminal type A primary breast tumor (n=10) compared to matched metastasis (n=10). FIG. 6I graphically illustrates miR-708 expression in luminal type B primary breast tumor (n=6) compared to matched metastasis (n=6). FIG. 6J graphically illustrates miR-708 expression in triple negative primary breast tumor (n=5) compared to matched metastatic tumor (Met) (n=5). FIG. 6K graphically compares the relationship between Nnat and miR-708 expression in primary human breast tumors (n=19) and matched metastases (n=19). The ratios of NNAT (y-axis) and miR-708 expression (x-axis) in Met versus primary tumors are plotted. $R2=0.50$ and $p<0.05$.

FIG. 7A shows representative bioluminescence (BLI) images of animals showing primary tumors derived from orthotopic injections of control MDA cells (Ctrl), MDA-miR-708 cells and MDA-miR-708-Nnat mut cells (n=10 per group) into the mammary fat pad. The color scale bar depicts the photon flux (photons per second) emitted from these mice at day 30. FIG. 7B graphically illustrates photon flux from primary tumors as assessed by bioluminescence measurements as a function of time (in weeks). FIG. 7C shows representative bioluminescence images of animals from FIG. 7A after day 30 showing lung metastases (n=9, per group, $p<0.05$) at day 37. Primary tumors were resected at day 30. The color scale bar depicts the photon flux (photons per second) emitted from these mice. FIG. 7D graphically illustrates pulmonary metastases as assessed by bioluminescence measurements (day 37). FIG. 7E graphically illustrates the number of metastatic nodules in the lungs of mice derived from primary tumors shown in FIG. 7A (8 lungs from each group, 5-6 sections evaluated per lung). FIG. 7F shows H&E stained lungs showing metastatic nodules (within the dotted lines). FIG. 7G graphically illustrates the number of circulating tumor cells (CTCs) in the peripheral blood of mice bearing control MDA-LM2 tumors and MDA-LM2 tumors that express miR-708. The tumors express GFP, which was used to quantify CTC abundance in the peripheral blood by PCR analysis. CTC numbers were determined by generating a standard curve with predetermined number of MDA-LM2 cells spiked into the mouse blood. FIG. 7H graphically illustrates the size of primary tumors (weight in gram) as a function of time where the primary tumors were generated from orthotopic injections into the mammary fat pad of control MDA-LM2 cells, MDA-LM2-miR-708 cells and MDAmiR-708-Nnat mut cells (n=10 per group).

FIG. 8A shows representative bioluminescence of animals (at day 35 after tumor cells introduction) showing lung metastases. FIG. 8B graphically illustrates the quantity of bioluminescence from pulmonary metastases as a function of time (in weeks) in animals receiving the miR-708 liposome formulation compared to control animals, which did not receive the miR-708 liposomes (controls, n=5; liposome miR-708, n=7).

DETAILED DESCRIPTION

Figure 1A:
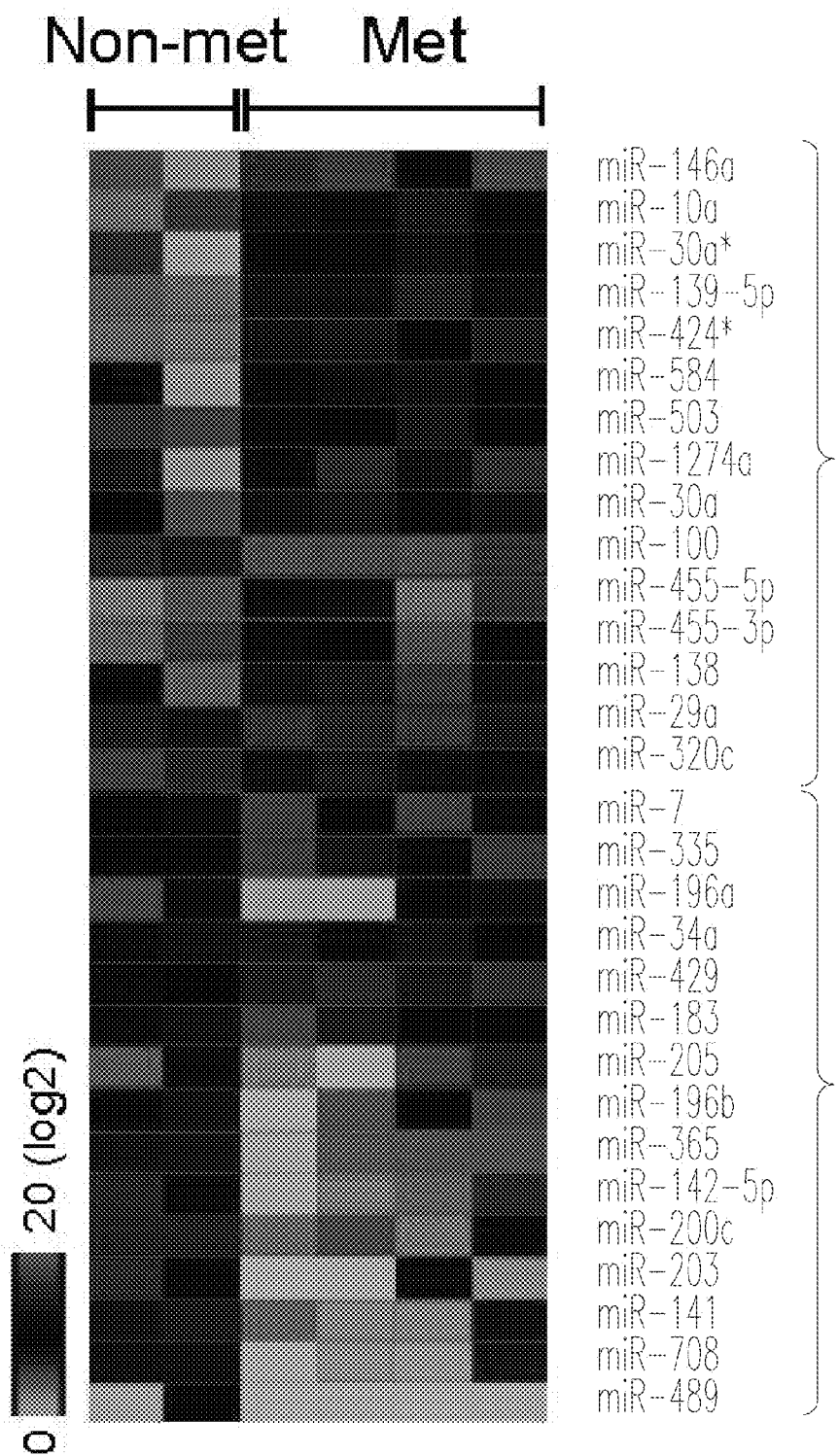

Triple-negative breast cancer patients (TNBC: ER-, PR-, Her2-patients), comprising 10-20% of all breast cancers have the worst outcome due to high rates of recurrence and metastatic spread. Currently, no FDA approved targeted therapies exist for the treatment of triple-negative breast cancer patients. As such, such breast cancer patients exhibit the highest mortality and relapse rates within 5 years of a diagnosis. Moreover, there is no permanent cure even for non-triple-negative breast cancer patients that have developed metastasis. Surgical resection and standard chemotherapy comprise main therapeutic options for women with triple-negative breast cancer. However, these treatments fail after initial tumor shrinkage, and patients eventually succumb to metastatic relapse. Therefore, novel targeted therapies are necessary for the treatment of such cancer patients.

As described herein, microRNA-708 (miR-708) is highly suppressed in metastatic lesions compared to matched primary tumors both in human and murine breast cancer. As shown herein, metastatic lesions have reduced levels of miR-708 compared to matched primary tumors. Reduced miR-708 levels were also observed in triple-negative breast cancer cells compared to luminal subtypes. Importantly, ectopic expression of miR-708 impaired lung metastasis derived from orthotopic breast tumors. Conditional expression of miR-708 in metastatic breast cancer cells following colonization in the lungs did not affect seeding but impaired metastases. These data indicate that miR-708 can be a therapeutic agent against metastatic breast cancer. Proof of the therapeutic value of miR-708 administration is shown, for example, in Example 10 and FIG. 8.

A therapeutic composition can include a miR-708 nucleic acid (e.g., in a carrier or expressed from an expression vector). Sequences for miR-708 are available, for example, from the database maintained by the National Center for Biotechnology Information (NCBI) data at ncbi.nlm.nih.gov. For example, miR-708 nucleic acids can include the following human sequence (SEQ ID NO:1; NCBI accession number NR_030598.1, GI:262206056).

```
  1  AACTGCCCTC AAGGAGCTTA CAATCTAGCT GGGGGTAAAT
 41  GACTTGCACA TGAACACAAC TAGACTGTGA GCTTCTAGAG
 81  GGCAGGGA
```

Other examples of miR-708 sequences include SEQ ID NO:65, 100-109, and 116.

A miR-708 nucleic acid may be prepared using methods available in the art, for example, by expression from an expression vector encoding the sequence of the miR-708 nucleic acid or a complement thereof. Alternatively, it may be prepared by chemical synthesis using naturally-occurring nucleotides, modified nucleotides or any combinations thereof. In some embodiments, the miR-708 nucleic acids are made from modified nucleotides or non-phosphodiester bonds, for example, that are designed to increase biological stability of the miR-708 nucleic acids or to increase intracellular stability of the duplex formed between the miR-708 nucleic acids and other nucleic acids.

For example, the miR-708 nucleic acids can be peptide nucleic acids that have peptide bonds rather than phosphodiester bonds.

Naturally-occurring nucleotides that can be employed in miR-708 nucleic acids include the ribose or deoxyribose nucleotides adenosine, guanine, cytosine, thymine and uracil. Examples of modified nucleotides that can be employed in miR-708 nucleic acids include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-N6-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine. Thus, miR-708 nucleic acids may include modified nucleotides, as well as natural nucleotides such as combinations of ribose and deoxyribose nucleotides, and may be of same length as SEQ ID NO:1, 65, 100, 101, 102, 103, 104, 105, 106, 107, 108, 109, or 116. The miR-708 nucleic acids can also be longer and include other useful sequences. In some embodiments, the miR-708 nucleic acids are somewhat shorter. For example, the miR-708 nucleic acids can include a segment that has nucleic acid sequence SEQ ID NO:1, 65, 100, 101, 102, 103, 104, 105, 106, 107, 108, 109, or 116, or one that is missing up to 5 nucleotides from the 5' or 3' end.

The nucleic acids encoding any miR-708 nucleic acids can be inserted into or employed with any suitable expression system. A quantity of miR-70-8 nucleic acids can also be generated from such expression systems. Recombinant expression is usefully accomplished using a vector, such as a plasmid. The vector can include a promoter operably linked to nucleic acid encoding a miR-708 nucleic acid. The vector can also include other elements required for transcription and translation. As used herein, vector refers to any carrier containing exogenous DNA. Thus, vectors are agents that transport the exogenous nucleic acid into a cell without degradation and include a promoter yielding expression of the nucleic acid in the cells into which it is delivered. Vectors include but are not limited to plasmids, viral nucleic acids, viruses, phage nucleic acids, phages, cosmids, and artificial chromosomes. A variety of prokaryotic and eukaryotic expression vectors suitable for carrying, encoding and/or expressing miR-708 nucleic acids can be produced. Such expression vectors include, for example, pET, pET3d, pCR2.1, pBAD, pUC, and yeast vectors. The vectors can be used, for example, in a variety of in vivo and in vitro situations.

The expression cassette, expression vector, and sequences in the cassette or vector can be heterologous. As used herein, the term "heterologous" when used in reference to a expression cassette, expression vector, regulatory sequence, promoter, or nucleic acid refers to a expression cassette, expression vector, regulatory sequence, or nucleic acid that has been manipulated in some way. For example, a heterologous promoter can be a promoter that is not naturally linked to a nucleic acid of interest, or that has been introduced into cells by cell transformation procedures. A heterologous nucleic acid or promoter also includes a nucleic acid or promoter that is native to an organism but that has been altered in some way (e.g., placed in a different chromosomal location, mutated, added in multiple copies, linked to a non-native promoter or enhancer sequence, etc.). Heterologous nucleic acids may comprise sequences that comprise cDNA forms; the cDNA sequences may be expressed in either a sense (to produce mRNA) or anti-sense orientation (to produce an anti-sense RNA transcript that is complementary to the mRNA transcript). Heterologous coding regions can be distinguished from endogenous coding regions, for example, when the heterologous coding regions are joined to nucleotide sequences comprising regulatory elements such as promoters that are not found naturally associated with the coding region, or when the heterologous coding regions are associated with portions of a chromosome not found in nature (e.g., genes expressed in loci where the protein encoded by the coding region is not normally expressed). Similarly, heterologous promoters can be promoters that at linked to a coding region to which they are not linked in nature.

Viral vectors that can be employed include those relating to lentivirus, adenovirus, adeno-associated virus, herpes virus, vaccinia virus, polio virus, AIDS virus, neuronal trophic virus, Sindbis and other viruses. Also useful are any viral families which share the properties of these viruses which make them suitable for use as vectors. Retroviral vectors that can be employed include those described in by Verma, I. M., Retroviral vectors for gene transfer. In Microbiology-1985, American Society for Microbiology, pp. 229-232, Washington, (1985). For example, such retroviral vectors can include Murine Maloney Leukemia virus, MMLV, and other retroviruses that express desirable properties. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral nucleic acid.

A variety of regulatory elements can be included in the expression cassettes and/or expression vectors, including promoters, enhancers, translational initiation sequences, transcription termination sequences and other elements. A "promoter" is generally a sequence or sequences of DNA that function when in a relatively fixed location in regard to the transcription start site. For example, the promoter can be upstream of the miR-708 nucleic acid segment. A "promoter" contains core elements required for basic interaction of RNA polymerase and transcription factors and can contain upstream elements and response elements. "Enhancer" generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 by in length, and they function in cis. Enhancers function to increase transcription from nearby promoters. Enhancers, like promoters, also often contain response elements that mediate the regulation of transcription. Enhancers often determine the regulation of expression.

Expression vectors used in eukaryotic host cells (yeast, fungi, insect, plant, animal, human or nucleated cells) can also contain sequences necessary for the termination of transcription which can affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs.

The expression of miR-708 from an expression cassette or expression vector can be controlled by any promoter capable of expression in prokaryotic cells or eukaryotic cells. Examples of prokaryotic promoters that can be used include, but are not limited to, SP6, T7, T5, tac, bla, trp, gal, lac, or maltose promoters. Examples of eukaryotic promoters that can be used include, but are not limited to, constitutive promoters, e.g., viral promoters such as CMV, SV40 and RSV promoters, as well as regulatable promoters, e.g., an inducible or repressible promoter such as the tet promoter, the hsp70 promoter and a synthetic promoter regulated by CRE. Vectors for bacterial expression include pGEX-5X-3, and for eukaryotic expression include pCIneo-CMV.

The expression cassette or vector can include nucleic acid sequence encoding a marker product. This marker product is used to determine if the gene has been delivered to the cell and once delivered is being expressed. Preferred marker genes are the *E. coli* lacZ gene which encodes β-galactosidase and green fluorescent protein. In some embodiments the marker can be a selectable marker. When such selectable markers are successfully transferred into a host cell, the transformed host cell can survive if placed under selective pressure. There are two widely used distinct categories of selective regimes. The first category is based on a cell's metabolism and the use of a mutant cell line which lacks the ability to grow independent of a supplemented media. The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)).

Gene transfer can be obtained using direct transfer of genetic material, in but not limited to, plasmids, viral vectors, viral nucleic acids, phage nucleic acids, phages, cosmids, and artificial chromosomes, or via transfer of genetic material in cells or carriers such as cationic liposomes. Such methods are well known in the art and readily adaptable for use in the method described herein. Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)). Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991).

For example, the miR-708 nucleic acid molecule, expression cassette and/or vector of the can be introduced to a cell by any method including, but not limited to, calcium-mediated transformation, electroporation, microinjection, lipofection, particle bombardment and the like. The cells can be expanded in culture and then administered to a subject, e.g. a mammal such as a human. The amount or number of cells administered can vary but amounts in the range of about $10^6$ to about $10^9$ cells can be used The cells are generally delivered in a physiological solution such as saline or buffered saline. The cells can also be delivered in a vehicle such as a population of liposomes, exosomes or microvesicles.

The miR-708 can be produced by a transgenic cell that produces exosomes or microvesicles that contain miR-708. Exosomes and microvesicles mediate the secretion of a wide variety of proteins, lipids, mRNAs, and micro RNAs, interact with neighboring cells, and can thereby transmit signals, proteins, lipids, and nucleic acids from cell to cell (see, e.g., Shen et al., J Biol Chem. 286(16): 14383-14395 (2011); Hu et al., Frontiers in Genetics 3 (April 2012); Pegtel et al., Proc. Nat'l Acad Sci 107(14): 6328-6333 (2010); WO/2013/084000; each of which is incorporated herein by reference in its entirety.

Thus transgenic cells with a heterologous expression cassette or expression vector that expresses miR-708 can be administered to a subject and the exosomes produced by the transgenic cells deliver miR-708 to tumor and cancer cells in the subject.

Exosomes are produced by many different types of cells including immune cells such as B lymphocytes, T lymphocytes, dendritic cells (DCs) and mast cells. Exosomes are also produced, for example, by glioma cells, platelets, reticulocytes, neurons, intestinal epithelial cells, tumor cells, HELA cells, human embryonic kidney cells (HEK cells), B2M17 cells, Bend3 cells, primary bone marrow-derived dendritic cells, BV-2 microglia cells and EUR02A cells. Any of these cells can be host cells or transgenic cells that express miR-708 (e.g., from a heterologous expression cassette or a heterologous expression vector).

The microRNA can also be formulated in a delivery vehicle such as a liposome, microvesicle, or exosome. Exosomes and microvesicles containing miR-708 can be isolated from the host or transgenic cells described above and can be formulated into a suspension for administration to a subject such as a cancer patient. Exosomes have also been isolated from physiological fluids, such as plasma, urine, amniotic fluid and malignant effusions.

Exosomes and/or microvesicles can be obtained from any suitable cell type as discussed above, or by isolation from physiological fluids, cell culture media, or tissue supernatants. Exosomes and microvesicles produced from cells can be collected by any suitable method. Typically a preparation of exosomes and/or microvesicles can be prepared from cell culture or tissue supernatant by centrifugation, filtration or combinations of these methods. For example, exosomes and/or microvesicles can be prepared by differential centrifugation, where a low speed (<20000 g) centrifugation is used to pellet larger particles followed by high speed (>100000 g) centrifugation to pellet exosomes and/or microvesicles, size filtration with appropriate filters (for example, 0.22 µm filter), gradient ultracentrifugation (for example, with sucrose gradient) or a combination of these methods.

Exosomes and/or microvesicles can also be loaded with exogenous miR-708, followed by formulation into a suspension for delivery to a subject.

The exosomes and/or microvesicles can be delivered by or derived from dendritic cells, or immature dendritic cells. Exosomes and/or microvesicles produced from immature dendritic cells do not express MHC-II, MHC-I or CD86. Such exosomes and/or microvesicles do not stimulate naive T cells to a significant extent and are unable to induce a response in a mixed lymphocyte reaction. Such properties can be useful for treatment of certain diseases. For example, exosomes and/or microvesicles produced by, or derived from, immature dendritic cells can be used in delivery of microRNA biotherapeutics, for in vivo use, for example, in the treatment of cancer conditions.

Metastatic Cancer Treatment

According to the invention, miR-708 is useful for preventing, treating and/or diagnosing metastatic cancer. Thus, one aspect of the invention is a method of treating or inhibiting the establishment and/or growth metastatic tumors in an animal, where the metastatic tumors are at distal sites from a primary tumor site within the animal. Such a method involves administering miR-708 to the animal to thereby treat or inhibit the establishment and/or growth of metastatic tumors in an animal. Both human and veterinary uses are contemplated.

As illustrated herein miR-708 prevents or substantially inhibits the migration of metastatic cancer cells. The methods of treating or inhibiting the migration of cancer cells and/or the establishment of metastatic tumors in an animal can include administering to a subject animal (e.g., a human), a therapeutically effective amount of miR-708. The methods of treating or inhibiting the establishment and/or growth metastatic tumors in an animal can also include administering miR-708 with one or more other anti-cancer or chemotherapeutic agents. For example, as illustrated herein neuronatin and Suz-12 are expressed in metastatic cancer cells and are correlated with metastasis. Hence, the methods can include administering inhibitors of neuronatin and Suz-12 such as inhibitory nucleic acids and antibodies that bind to neuronatin and Suz-12 nucleic acids and proteins.

In some embodiments, the methods can also include a detection step to ascertain whether the animal has cancer or is in need of treatment to inhibit the development of metastatic tumors. Such a detection step can include any available assay for cancer. For example, samples from a subject suspected of having cancer can be tested to determine the relative expression levels of miR-708, neuronatin and/or Suz-12. Methods for detection of miR-708, neuronatin and/or Suz-12 expression levels are available to those of skill in the art, and procedures are described herein for such detection. For example, a test sample from the animal can be tested to determine whether the test sample expressed at least about two-fold more neuronatin and/or Suz-12 than a control non-metastatic cancer sample.

The term "animal" as used herein, refers to an animal, such as a warm-blooded animal, which is susceptible to or has a disease associated with protease expression, for example, cancer. Mammals include cattle, buffalo, sheep, goats, pigs, horses, dogs, cats, rats, rabbits, mice, and humans. Also included are other livestock, domesticated animals and captive animals. The term "farm animals" includes chickens, turkeys, fish, and other farmed animals. Mammals and other animals including birds may be treated by the methods and compositions described and claimed herein. In some embodiments, the animal is a human.

As used herein, the term "cancer" includes solid animal tumors as well as hematological malignancies. The terms "tumor cell(s)" and "cancer cell(s)" are used interchangeably herein.

"Solid animal tumors" include cancers of the head and neck, lung, mesothelioma, mediastinum, esophagus, stomach, pancreas, hepatobiliary system, small intestine, colon, colorectal, rectum, anus, kidney, urethra, bladder, prostate, urethra, penis, testis, gynecological organs, ovaries, breast, endocrine system, skin central nervous system; sarcomas of the soft tissue and bone; and melanoma of cutaneous and intraocular origin. In addition, a metastatic cancer at any stage of progression can be treated, such as micrometastatic tumors, megametastatic tumors, and recurrent cancers.

The term "hematological malignancies" includes childhood leukemia and lymphomas, Hodgkin's disease, lymphomas of lymphocytic and cutaneous origin, acute and chronic leukemia, plasma cell neoplasm and cancers associated with AIDS.

The inventive methods and compositions can also be used to treat cancer of the adrenal cortex, cancer of the cervix, cancer of the endometrium, cancer of the esophagus, cancer of the head and neck, cancer of the liver, cancer of the pancreas, cancer of the prostate, cancer of the thymus, carcinoid tumors, chronic lymphocytic leukemia, Ewing's sarcoma, gestational trophoblastic tumors, hepatoblastoma, multiple myeloma, non-small cell lung cancer, retinoblastoma, or tumors in the ovaries. A cancer at any stage of progression can be treated or detected, such as primary, metastatic, and recurrent cancers. Information regarding numerous types of cancer can be found, e.g., from the American Cancer Society (www.cancer.org), or from, e.g., Wilson et al. (1991) Harrison's Principles of Internal Medicine, 12th Edition, McGraw-Hill, Inc.

In some embodiments, the cancer and/or tumors to be treated are those that originate as breast or prostate cancers.

Treatment of, or treating, metastatic cancer can include the reduction in cancer cell migration or the reduction in establishment of at least one metastatic tumor. The treatment also includes alleviation or diminishment of more than one symptom of metastatic cancer such as coughing, shortness of breath, hemoptysis, lymphadenopathy, enlarged liver, nausea, jaundice, bone pain, bone fractures, headaches, seizures, systemic pain and combinations thereof. The treatment may cure the cancer, e.g., it may prevent metastatic cancer, it may substantially eliminate metastatic tumor formation and growth, and/or it may arrest or inhibit the migration of metastatic cancer cells.

Anti-cancer activity can be evaluated against varieties of cancers (e.g., breast or prostate cancer) using methods available to one of skill in the art. Anti-cancer activity, for example, can determined by identifying the lethal dose ($LD_{100}$) or the 50% effective dose (ED50) or the dose that inhibits growth at 50% ($GI_{50}$) of an agent of the present invention that prevents the migration of cancer cells. In one aspect, anti-cancer activity is the amount of the agent that reduces 50%, 60%, 70%, 80%, 90%, 95%, 97%, 98%, 99% or 100% of cancer cell migration, for example, when measured by detecting expression of a cancer cell marker at sites distal from a primary tumor site, or when assessed using available methods for detecting metastases.

Inhibitory Nucleic Acids

As illustrated herein neuronatin and Suz-12 are expressed in metastatic cancer cells and are correlated with metastasis. Inhibitory nucleic acids can reduce the expression of neuronatin and Suz-12 proteins, and can help reduce metastasis. Such an inhibitory nucleic acid can have at least one segment that will hybridize to a neuronatin or Suz-12 nucleic acid under intracellular or stringent conditions. The inhibitory nucleic acid can reduce expression of a nucleic acid encoding neuronatin or Suz-12. A nucleic acid encoding neuronatin or Suz-12 may be genomic DNA as well as messenger RNA. An inhibitory nucleic acid may be incorporated into a plasmid vector or viral DNA. It may be single strand or double strand, circular or linear. An example of a nucleic acid encoding neuronatin is set forth in SEQ ID NO:112. An example of a Suz-12 nucleic acid is set forth in SEQ ID NO:114, which can be inhibited by inhibitory nucleic acids as described in the Examples. See FIGS. 5A, 5E, 5J-5L. Neuronatin and Suz-12 encoding nucleic acids to which inhibitory nucleic acids bind can also be a fragment of the sequences set forth in SEQ ID NO:112 or 114 (respectively). In some embodiments such a fragment of a neuronatin or Suz-12 nucleic acid encodes a biologically active neuronatin or Suz-12 polypeptide.

An inhibitory nucleic acid is a polymer of ribose nucleotides or deoxyribose nucleotides having more than 13 nucleotides in length. An inhibitory nucleic acid may include naturally-occurring nucleotides; synthetic, modified, or pseudo-nucleotides such as phosphorothiolates; as well as nucleotides having a detectable label such as $^{32}P$, biotin or digoxigenin. An inhibitory nucleic acid can reduce the expression and/or activity of a neuronatin or Suz-12 nucleic acid. Such an inhibitory nucleic acid may be completely complementary to a segment of the neuronatin or Suz-12 nucleic acid. Alternatively, some variability is permitted in the inhibitory nucleic acid sequences relative to neuronatin or Suz-12 sequences.

An inhibitory nucleic acid can hybridize to a neuronatin or Suz-12 nucleic acid under intracellular conditions or under stringent hybridization conditions, and is sufficiently complementary to inhibit expression of a neuronatin or Suz-12 nucleic acid.

As used herein, the terms "hybridize" and "hybridization" refer to the annealing of a complementary sequence to the target nucleic acid, i.e., the ability of two polymers of nucleic acid (polynucleotides) containing complementary sequences to anneal through base pairing. The terms "annealed" and "hybridized" are used interchangeably throughout, and are intended to encompass any specific and reproducible interaction between a complementary sequence and a target nucleic acid, including binding of regions having only partial complementarity. Certain bases not commonly found in natural nucleic acids may be included in the inhibitory nucleic acids and include, for example, inosine and 7-deazaguanine. Those skilled in the art of nucleic acid technology can determine duplex stability empirically considering a number of variables including, for example, the length of the complementary sequence, base composition and sequence of the oligonucleotide, ionic strength and incidence of mismatched base pairs. The stability of a nucleic acid duplex is measured by the melting temperature, or "$T_m$". The $T_m$ of a particular nucleic acid duplex under specified conditions is the temperature at which on average half of the base pairs have disassociated.

Intracellular conditions refer to conditions such as temperature, pH and salt concentrations typically found inside a cell, e.g. an animal or mammalian cell. One example of such an animal or mammalian cell is a breast or prostate cancer cell. Generally, stringent hybridization conditions are selected to be about 5° C. lower than the thermal melting point (Tm) for the specific sequence at a defined ionic strength and pH. However, stringent conditions encompass temperatures in the range of about 1° C. to about 20° C. lower than the thermal melting point of the selected sequence, depending upon the desired degree of stringency as otherwise qualified herein.

The term "stringency" is used in reference to the conditions of temperature, ionic strength, and the presence of other compounds, under which nucleic acid hybridizations are conducted. "High stringency conditions" when used in reference to nucleic acid hybridization include conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1×SSPE, 1.0% SDS at 42° C. when a probe of about 500 nucleotides in length is employed. In general, the stringency of hybridization is determined by the wash step. Hence, a wash step involving 0.1×SSPE, 1.0% SDS at a temperature of at least 42° C. can yield a high stringency hybridization product. In some instances the high stringency hybridization conditions include a wash in 1×SSPE, 1.0% SDS at a temperature of at least 50° C., or at about 65° C.

Inhibitory oligonucleotides that comprise, for example, 2, 3, 4, or 5 or more stretches of contiguous nucleotides that are precisely complementary to a neuronatin or Suz-12 coding sequence, each separated by a stretch of contiguous nucleotides that are not complementary to adjacent coding sequences, can inhibit the function of a neuronatin or Suz-12 nucleic acid. In general, each stretch of contiguous nucleotides is at least 4, 5, 6, 7, or 8 or more nucleotides in length. Non-complementary intervening sequences may be 1, 2, 3, or 4 nucleotides in length. One skilled in the art can easily use the calculated melting point of an inhibitory nucleic acid hybridized to a sense nucleic acid to estimate the degree of mismatching that will be tolerated for inhibiting expression of a particular target nucleic acid. Inhibitory nucleic acids of the invention include, for example, a short hairpin RNA, a small interfering RNA, a ribozyme or an antisense nucleic acid molecule.

The inhibitory nucleic acid molecule may be single or double stranded (e.g. a small interfering RNA (siRNA)), and may function in an enzyme-dependent manner or by steric blocking. Inhibitory nucleic acid molecules that function in an enzyme-dependent manner include forms dependent on RNase H activity to degrade target mRNA. These include single-stranded DNA, RNA, and phosphorothioate molecules, as well as the double-stranded RNAi/si RNA system that involves target mRNA recognition through sense-antisense strand pairing followed by degradation of the target mRNA by the RNA-induced silencing complex. Steric blocking inhibitory nucleic acids, which are RNase-H independent, interfere with gene expression or other mRNA-dependent cellular processes by binding to a target mRNA and getting in the way of other processes. Steric blocking inhibitory nucleic acids include 2'-O alkyl (usually in chimeras with RNase-H dependent antisense), peptide nucleic acid (PNA), locked nucleic acid (LNA) and morpholino antisense.

Small interfering RNAs, for example, may be used to specifically reduce neuronatin or Suz-12 translation such that the level of neuronatin or Suz-12 polypeptide is reduced. SiRNAs mediate post-transcriptional gene silencing in a sequence-specific manner. See, for example, website at invitrogen.com/site/us/en/home/Products-and-Services/Applications/rnai.html. Once incorporated into an RNA-induced silencing complex, siRNA mediate cleavage of the homologous endogenous mRNA transcript by guiding the complex to the homologous mRNA transcript, which is then cleaved by the complex. The siRNA may be homologous to any region of the neuronatin or Suz-12 mRNA transcript. The region of homology may be 30 nucleotides or less in length, preferable less than 25 nucleotides, and more preferably about 21 to 23 nucleotides in length. SiRNA is typically double stranded and may have two-nucleotide 3' overhangs, for example, 3' overhanging UU dinucleotides. Methods for designing siRNAs are known to those skilled in the art. See, for example, Elbashir et al. Nature 411: 494-498 (2001); Harborth et al. Antisense Nucleic Acid Drug Dev. 13: 83-106 (2003).

The pSuppressorNeo vector for expressing hairpin siRNA, commercially available from IMGENEX (San Diego, Calif.), can be used to generate siRNA for inhibiting neuronatin or Suz-12 expression. The construction of the siRNA expression plasmid involves the selection of the target region of the mRNA, which can be a trial-and-error process. However, Elbashir et al. have provided guidelines that appear to work ~80% of the time. Elbashir, S. M., et al., Analysis of gene function in somatic mammalian cells using small interfering RNAs. Methods, 2002. 26(2): p. 199-213. Accordingly for synthesis of synthetic siRNA, a target region may be selected preferably 50 to 100 nucleotides downstream of the start codon. The 5' and 3' untranslated regions and regions close to the start codon should be avoided as these may be richer in regulatory protein binding sites. As siRNA can begin with AA, have 3' UU overhangs for both the sense and antisense siRNA strands, and have an approximate 50% G/C content. An example of a sequence for a synthetic siRNA is 5'-AA(N19)UU, where N is any nucleotide in the mRNA sequence and should be approximately 50% G-C content. The selected sequence(s) can be compared to others in the human genome database to minimize homology to other known coding sequences (e.g., by Blast search, for example, through the NCBI website).

SiRNAs may be chemically synthesized, created by in vitro transcription, or expressed from an siRNA expression vector or a PCR expression cassette. See, e.g., website at invitrogen.com/site/us/en/home/Products-and-Services/Applications/rnai.html. When an siRNA is expressed from an expression vector or a PCR expression cassette, the insert encoding the siRNA may be expressed as an RNA transcript that folds into an siRNA hairpin. Thus, the RNA transcript may include a sense siRNA sequence that is linked to its reverse complementary antisense siRNA sequence by a spacer sequence that forms the loop of the hairpin as well as a string of U's at the 3' end. The loop of the hairpin may be of any appropriate lengths, for example, 3 to 30 nucleotides in length, preferably, 3 to 23 nucleotides in length, and may be of various nucleotide sequences including, AUG, CCC, UUCG, CCACC, CTCGAG, AAGCUU, CCACACC and UUCAAGAGA (SEQ ID NO:115). SiRNAs also may be produced in vivo by cleavage of double-stranded RNA introduced directly or via a transgene or virus. Amplification by an RNA-dependent RNA polymerase may occur in some organisms. Examples of siRNA sequences that can hybridize to a neuronatin or Suz-12 nucleic acid include those available from Labome (see, e.g., website at labome.com/gene/human/Suz12-siRNA.html; labome.com/gene/human/neuronatin-siRNA.html).

Compositions

The invention also relates to compositions containing miR-708, a miR-708 expression cassette, a miR-708 expression vector, a Suz-12 inhibitor, a Nnat inhibitor, a miR-708 diagnostic imaging agent (e.g., a labeled SUZ12, Nnat, or miR-708 nucleic acid probe), or any combination thereof. The compositions can include cells expressing miR-708 (e.g., transgenic cells with a heterologous expression cassette or expression vector from which miR-708 is expressed). The compositions can include delivery vehicles containing miR-708, such as exosomes, microvesicles, liposomes or combinations thereof that contain miR-708.

The compositions of the invention can be pharmaceutical compositions. In other embodiments, the compositions are used as diagnostic imaging compositions. In some embodiments, the compositions can include a pharmaceutically acceptable carrier. In some embodiments, the miR-708 sequence includes SEQ ID NO:1, 65, 100, 101, 102, 103, 104, 105, 106, 107, 108, 109, or 116. The miR-708 can be any nucleic acid, any modified nucleic acid (e.g., with non-natural nucleotides) or any peptide nucleic acid that is has at least 95% sequence identity to any of SEQ ID NO:1, 65, 100, 101, 102, 103, 104, 105, 106, 107, 108, 109, or 116. Diagnostic probes or primers for detection of miR-708 can specifically binds to a nucleic acid with a sequence such as SEQ ID NO:1, 65, 100, 101, 102, 103, 104, 105, 106, 107, 108, 109, or 116.

By "pharmaceutically acceptable" it is meant a carrier, diluent, excipient, and/or salt that is compatible with the other ingredients of the formulation, and not deleterious to the recipient thereof. Exosomes, microvesicles and liposomes are useful vehicles for delivery of miR-708 nucleic acids.

In some embodiments, the therapeutic agents of the invention (e.g., miR-708, miR-708 expression cassettes, a miR-708 expression vectors, Suz-12 inhibitors, Nnat inhibitors, miR-708 expressing cells, and/or combinations thereof), can be administered in a "therapeutically effective amount." Such a therapeutically effective amount is an amount sufficient to obtain the desired physiological effect, e.g., treatment of cancer or reduction in symptoms of cancer.

To achieve the desired effect(s), the miR-708, miR-708 expression cassettes, miR-708 expression vectors, Suz-12 inhibitors, Nnat inhibitors, miR-708 expressing cells, and/or combinations thereof, may be administered as single or divided dosages.

For example, miR-708 can be administered in dosages of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. The amount administered will vary depending on various factors including, but not limited to, the severity of disease, the weight, the physical condition, the health, the age of the mammal, and if the nucleic acid is chemically modified. Such factors can be readily determined by the clinician employing animal models or other test systems that are available in the art.

Cells that express miR-708 can be used to deliver miR-708 to disease sites, for example, to treat a human patient or other subjects in need of such treatment. The cells are administered in a manner that permits them become localized or to migrate to a diseased site. Devices are available that can be adapted for administering cells, for example, to tumor sites.

For therapy, transgenic cells, exosomes, microvesicles, liposomes and/or pharmaceutical compositions containing miR-708 can be administered locally or systemically. Cells, exosomes, microvesicles, liposomes and/or pharmaceutical compositions can be introduced by injection, catheter, implantable device, or the like. For example, cells, exosomes, microvesicles, liposomes and/or pharmaceutical compositions containing miR-708 can be administered in any physiologically acceptable excipient or carrier that does not adversely affect the cells, exosomes, microvesicles, liposomes and/or pharmaceutical compositions. For example, cells, exosomes, microvesicles, liposomes and/or pharmaceutical compositions can be administered intravenously, into the site of tumor, into lymph nodes, into metastatic tumor sites, and the like. Methods of administering the cells, exosomes, microvesicles, liposomes and/or pharmaceutical compositions to subjects, particularly human subjects, include injection into any such target sites in the subjects.

Cells, liposomes exosomes and/or microvesicles can be included in the compositions in varying amounts depending upon the disease or injury to be treated. For example, the compositions can be prepared in liquid form for local or systemic administration containing about $10^3$ to about $10^{12}$, or about $10^4$ to about $10^{10}$, or about $10^5$ to about $10^8$ cells, liposomes exosomes and/or microvesicles.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the therapeutic agents and compositions of the invention may be essentially continuous over a preselected period of time or may be in a series of spaced doses. Both local and systemic administration is contemplated.

To prepare the composition nucleic acids, expression cassettes, expression vectors, Suz-12 inhibitors, Nnat inhibitors, cells, exosomes, microvesicles, liposomes, and other agents are synthesized or otherwise obtained, and purified as necessary or desired. Non-labile components can be lyophilized. However, the cells, liposomes, exosomes and/or microvesicles should be maintained in a solution, medium, liquid carrier, solid matrix, or semi-solid carrier that does not adversely affect their viability. The components can be stabilized, for example, by addition of nuclease inhibitors, chelating agents, physiological salts, and the like. These agents can be adjusted to the appropriate concentration, and optionally combined with other agents.

The absolute weight of a mir-708 nucleic acid, a miR-708 expression cassette, a miR-708 expression vector, a Suz-12 inhibitor, and/or a Nnat inhibitor to be administered in a unit dose can vary widely. For example, about 0.01 to about 2 g, or about 0.1 to about 500 mg, of at least one nucleic acid, expression vector, or expression cassette, or a plurality of nucleic acids, expression vectors, or expression cassettes can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily, bi-weekly, and weekly doses of the therapeutic agents such as mir-708 nucleic acid, expression vector, expression cassette, Suz-12 inhibitor, and/or Nnat inhibitor can vary as well. Such daily doses can range, for example, from about 0.1 g/day to about 50 g/day, from about 0.1 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

Thus, one or more suitable unit dosage forms comprising the miR-708 nucleic acids, expression vectors, expression cassettes, cells, Suz-12 inhibitors, Nnat inhibitors, exosomes, liposomes and/or microvesicles can be administered by a variety of routes including parenteral (including subcutaneous, intravenous, intramuscular and intraperitoneal), oral, rectal, dermal, transdermal, intrathoracic, intrapulmonary and intranasal (respiratory) routes. The miR-708 nucleic acids, expression vectors, or expression cassettes may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

The compositions can be prepared in many forms that include aqueous solutions, suspensions, tablets, hard or soft gelatin capsules, and liposomes and other slow-release formulations, such as shaped polymeric gels. However, administration of nucleic acids, cells, exosomes, liposomes, and/or microvesicles often involves parenteral or local administration in an aqueous solution or protective vehicle.

Thus while the nucleic acids, inhibitors, expression cassettes, and/or expression vectors may sometimes be administered in an oral dosage form, that oral dosage form is typically formulated such that the nucleic acids, inhibitors, expression cassettes, and/or expression vectors is released into the intestine after passing through the stomach. Such formulations are described in U.S. Pat. No. 6,306,434 and in the references contained therein.

Liquid pharmaceutical compositions may be in the form of, for example, aqueous or oily suspensions, solutions, emulsions, syrups or elixirs, dry powders for constitution with water or other suitable vehicle before use. Such liquid pharmaceutical compositions may contain conventional additives such as suspending agents, emulsifying agents, non-aqueous vehicles (which may include edible oils), or preservatives.

A nucleic acids, expression cassettes, expression vectors, cells, inhibitors, liposomes, exosomes, and/or microvesicles can be formulated for parenteral administration (e.g., by injection, for example, bolus injection or continuous infusion) and may be presented in unit dosage form in ampoules, prefilled syringes, small volume infusion containers or multi-dose containers with an added preservative. The pharmaceutical compositions may take such forms as suspensions, solutions, or emulsions in oily or aqueous vehicles, and may contain formulatory agents such as suspending, stabilizing and/or dispersing agents. Suitable carriers include saline solution and other materials commonly used in the art.

The compositions can also contain other ingredients such as other anti-cancer or chemotherapeutic agents, vitamins, anti-microbial agents, or preservatives.

The anti-cancer agents useful in the compositions and methods described herein include cytotoxins, photosensitizing agents and chemotherapeutic agents. These agents include, but are not limited to, folate antagonists, pyrimidine antimetabolites, purine antimetabolites, 5-aminolevulinic acid, alkylating agents, platinum anti-tumor agents, anthracyclines, DNA intercalators, epipodophyllotoxins, DNA topoisomerases, microtubule-targeting agents, vinca alkaloids, taxanes, epothilones and asparaginases. Further information can be found in Bast et al., Cancer Medicine, edition 5, which is available free as a digital book (see website at ncbi.nlm.nih.gov/books/NBK20812/).

Folic acid antagonists are cytotoxic drugs used as antineoplastic, antimicrobial, anti-inflammatory, and immune-suppressive agents. While several folate antagonists have been developed, and several are now in clinical trial, methotrexate (MTX) is the antifolate with the most extensive history and widest spectrum of use. MTX is an essential drug in the chemotherapy regimens used to treat patients with acute lymphoblastic leukemia, lymphoma, osteosarcoma, breast cancer, choriocarcinoma, and head and neck cancer, as well as being an important agent in the therapy of patients with nonmalignant diseases, such as rheumatoid arthritis, psoriasis, and graft-versus-host disease.

Pyrimidine antimetabolites include fluorouracil, cytosine arabinoside, 5-azacytidine, and 2',2'-difluoro-2'-deoxycytidine. Purine antimetabolites include 6-mercatopurine, thioguanine, allopurinol (4-hydroxypyrazolo-3,4-d-pyrimidine), deoxycoformycin (pentostatin), 2-fluoroadenosine arabinoside (fludarabine; 9-β-d-arabinofuranosyl-2-fluoradenine), and 2-chlorodeoxyadenosine (Cl-dAdo, cladribine). In addition to purine and pyrimidine analogues, other agents have been developed that inhibit biosynthetic reactions leading to the ultimate nucleic acid precursors. These include phosphonacetyl-L-aspartic acid (PALA), brequinar, acivicin, and hydroxyurea.

Alkylating agents and the platinum anti-tumor compounds form strong chemical bonds with electron-rich atoms (nucleophiles), such as sulfur in proteins and nitrogen in DNA. Although these compounds react with many biologic molecules, the primary cytotoxic actions of both classes of agents appear to be the inhibition of DNA replication and cell division produced by their reactions with DNA. However, the chemical differences between these two classes of agents produce significant differences in their anti-tumor and toxic effects. The most frequently used alkylating agents are the nitrogen mustards. Although thousands of nitrogen mustards have been synthesized and tested, only five are commonly used in cancer therapy today. These are mechlorethamine (the original "nitrogen mustard"), cyclophosphamide, ifosfamide, melphalan, and chlorambucil. Closely related to the nitrogen mustards are the aziridines, which are represented in current therapy by thiotepa, mitomycin C, and diaziquone (AZQ). Thiotepa (triethylene thiophosphoramide) has been used in the treatment of carcinomas of the ovary and breast and for the intrathecal therapy of meningeal carcinomatosis. The alkyl alkane sulfonate, busulfan, was one of the earliest alkylating agents. This compound is one of the few currently used agents that clearly alkylate through an SN2 reaction. Hepsulfam, an alkyl sulfamate analogue of busulfan with a wider range of anti-tumor activity in preclinical studies, has been evaluated in clinical trials but thus far has demonstrated no superiority to busulfan.

Photosensitizing agents induce cytotoxic effects on cells and tissues. Upon exposure to light the photosensitizing compound may become toxic or may release toxic substances such as singlet oxygen or other oxidizing radicals that are damaging to cellular material or biomolecules, including the membranes of cells and cell structures, and such cellular or membrane damage can eventually kill the cells. A range of photosensitizing agents can be used, including psoralens, porphyrins, chlorines, aluminum phthalocyanine with 2 to 4 sulfonate groups on phenyl rings (e.g., AlPcS2a or AlPcS4), and phthalocyanins. Such drugs become toxic when exposed to light. For example, the photosensitizing agent can be an amino acid called 5-aminolevulinic acid, which is converted to protoporphyrin IX, a fluorescent photosensitizer. The structure of 5-aminolevulinic acid is shown below.

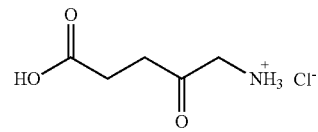

Topoisomerase poisons are believed to bind to DNA, the topoisomerase, or either molecule. Many topoisomerase poisons, such as the anthracyclines and actinomycin D, are relatively planar hydrophobic compounds that bind to DNA with high affinity by intercalation, which involves stacking of the compound between adjacent base pairs. Anthracyclines intercalate into double-stranded DNA and produce structural changes that interfere with DNA and RNA syntheses. Several of the clinically relevant anthracyclines are shown below.

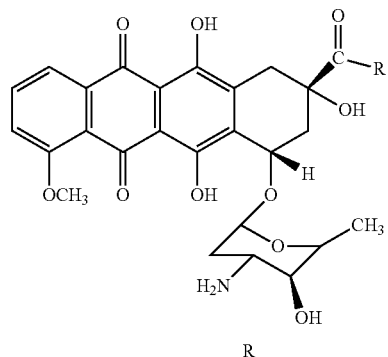

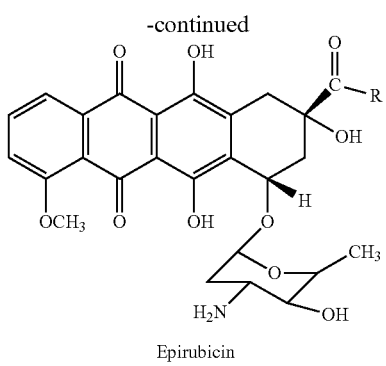

Epirubicin

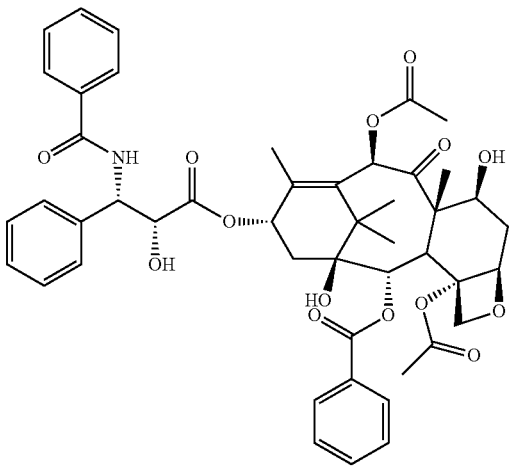 [SMILES: CC(=O)O[C@H]1C(=O)[C@@]2(C)C([C@H](OC(=O)c3ccccc3)[C@]3(O)C[C@H](OC(=O)[C@H](O)[C@@H](NC(=O)c4ccccc4)c4ccccc4)C(C)=C1C3(C)C)[C@]1(OC(C)=O)CO[C@@H]1C[C@@H]2O]

Idarabicin

Non-intercalating topoisomerase-targeting drugs include epipodophyllotoxins such as etoposide and teniposide. Etoposide is approved in the United States for the treatment of testicular and small cell lung carcinomas. Etoposide phosphate is more water soluble than etoposide and is rapidly converted to etoposide in vivo. Other non-intercalating topoisomerase-targeting drugs include topotecan and irinotecan.

Unique classes of natural product anticancer drugs have been derived from plants. As distinct from those agents derived from bacterial and fungal sources, the plant products, represented by the Vinca and Colchicum alkaloids, as well as other plant-derived products such as paclitaxel (Taxol) and podophyllotoxin, do not target DNA. Rather, they either interact with intact microtubules, integral components of the cytoskeleton of the cell, or with their subunit molecules, the tubulins. Clinically useful plant products that target microtubules include the Vinca alkaloids, primarily vinblastine (VLB), vincristine (VCR), vinorelbine (Navelbine, VRLB), and a newer Vinca alkaloid, vinflunine (VFL; 20',20'-difluoro-3',4'-dihydrovinorelbine), as well as the two taxanes, paclitaxel and docetaxel (Taxotere). The structure of paclitaxel is provided below.

Preferably a paclitaxel moiety is linked to the peptide by C10 and/or C2 hydroxyl moiety.

Examples of drugs that can be used in the methods and compositions described herein include but are not limited to, aldesleukin, 5-aminolevulinic acid, asparaginase, bleomycin sulfate, camptothecin, carboplatin, carmustine, cisplatin, cladribine, cyclophosphamide (lyophilized), cyclophosphamide (non-lyophilized), cytarabine (lyophilized powder), dacarbazine, dactinomycin, daunorubicin, diethyistilbestrol, doxorubicin (doxorubicin, 4'-epidoxorubicin, 4- or 4'-deoxydoxorubicin), epoetin alf a, esperamycin, etidronate, etoposide, N,N-bis(2-chloroethyl)-hydroxyaniline, 4-hydroxycyclophosphamide, fenoterol, filgrastim, floxuridine, fludarabine phosphate, fluorocytidine, fluorouracil, fluorouridine, goserelin, granisetron hydrochloride, idarubicin, ifosfamide, interferon alpha-2a, interferon alpha-2b, leucovorin calcium, leuprolide, levamisole, mechiorethamine, medroxyprogesterone, melphalan, methotrexate, mitomycin, mitoxantrone, muscarine, octreotide, ondansetron hydrochloride, oxyphenbutazone, paclitaxel, pamidronate, pegaspargase, plicamycin, salicylic acid, salbutamol, sargramostim, streptozocin, taxol, terbutaline, terfenadine, thiotepa, teniposide, vinblastine, vindesine and vincristine. Other drugs that can be used in the methods and compositions described herein include those, for example, disclosed in WO 98/13059; Payne, 2003; US 2002/0147138 and other references available to one of skill in the art.

It will be appreciated that the amount of miR-708 for use in treatment will vary not only with the particular carrier selected but also with the route of administration, the nature of the condition being treated and the age and condition of the patient. Ultimately the attendant health care provider may determine proper dosage. In addition, a pharmaceutical composition may be formulated as a single unit dosage form.

The following non-limiting examples illustrate some aspects of the invention.

Example 1

Materials and Methods

This Example illustrates some of the procedures used in the development of the invention.

miRNA Library Construction, Deep Sequencing and Data Analysis

Total RNA extraction, library construction, and high-throughput sequencing was performed as described (Ryu et al., 2011). Sequencing images from a Solexa 1× genome sequencer were analyzed using the Illumina Pipeline v1.3.2 software to remove background noise and extract the first 36 bases of the runs. Sequence reads were aligned to the hg18 genome (UCSC genome browser) using Eland software (Illumina, San Diego, Calif.). Next the linker sequences were identified and trimmed from individual reads using a customized Perl script. Reads in which the linker sequences were either mutated or absent were discarded. Next, the high confidence trimmed reads were aligned to known miRNAs available in the miRBase (v16, see website at mirbase.org), to obtain sequences that match to known miRNAs, and to calculate their frequencies. Sequences were collapsed to obtain a set of unique reads.

Mice and Cell Lines

All animal work was conducted in accordance with a protocol approved by the Institutional Animal Care and Use Committee at Weill Cornell Medical College. CB-17 SCID mice were obtained from Charles River (Wilmington, Mass.). MMTV-PyMT/WAP-Cre/CAG-CAT-EGFP transgenic mice were a gift from Jeffery Segall (Albert Einstein College of Medicine, NY). The MMTV-PyMT mice express the polyoma middle T antigen (PyMT) oncogene, driven by the Mouse Mammary Tumor Virus promoter. The tumor cells express green fluorescent protein (GFP) from a Cre-activatable CAG-CAT-EGFP construct.

Human breast and prostate cell lines were obtained from various sources including ATCC and Dr. Randy Watnick (Kang et al., 2009). MCF10A, MCF7, MDA-MB-361, MDA-MB-435, MDAMB-436, and MDA-MB-231 breast cell lines were maintained as described (Ryu et al., 2011).

HMEC cells were grown in Gibco HuMEC Ready Medium and SUM149 cells were grown in Ham's F-12 (Cellgro) with 5% fetal bovine serum (FBS), insulin (Sigma) and hydrocortisone (Sigma). T47D cells were grown in DMEM (Cellgro) with 15% FBS, non-essential amino acid (GIBCO), 5% antibiotics-antimycotic solution (Dediatech), and 5% glutamine (Mediatech). BT549 cells were grown in RPMI (Cellgro) with 10% FBS, non-essential amino acid (GIBCO), 5% antibiotics-antimycotic solution (Mediatech), and 5% glutamine (Mediatech). MMTV derived cell lines, MMTV-DB7 and MMTV-Met1 were grown in DMEM with 10% FBS (Borowsky et al., 2005). Human prostate cell lines RWPE1 and RWPE2 were grown in Keratinocyte Serum free medium (K-SFM, GIBCO) with bovine pituitary extract (BPE, GIBCO) and human recombinant epidermal growth factor (EGF, GIBCO), and PC3 and LN4 cells were grown in RPMI (Mediatech) with 10% FBS (Hyclone), 5% glutamine (Mediatech) and 5% antibiotics-antimycotic solution (Mediatech).

Human Samples

Human primary breast tumor and matched metastatic tissue were obtained from Department of Medicine, Weill Cornell Medical College (New York), consented according to approved Institutional Review Board (IRB) protocols from the institution (Table 1).

TABLE 1

Summary of the patient samples.

| ID | Molecular subtype | Stage at Diagnosis | relapse | synchronous | Metastases | ER+ | PR+ | Her2+ | Survival |
|---|---|---|---|---|---|---|---|---|---|
| 97-8329 | HER2 | 3 | no relapse | yes | LN | neg | neg | pos | alive |
| 93 17497 | HER2 | 3 | relapse | no | | n/a | n/a | n/a | dead |
| 87 2228c | HER2 | 3 | relapse | no | | n/a | n/a | pos | dead |
| sp 96-9706 | HER2 | 3 | no relapse | no | | n/a | n/a | n/a | alive |
| H-02-41827 | Luminal | 4 | relapse | no | LN | pos | neg | neg | dead |
| sp 96-11984 | Luminal | 3 | no relapse | no | | n/a | n/a | n/a | alive |
| sp 97-8288 | Luminal | 3 | no relapse | no | | n/a | n/a | n/a | alive |
| SP 95-15605 | Luminal | 3 | no relapse | no | | n/a | n/a | n/a | alive |
| sp95-1462 | Luminal | 3 | no relapse | no | | n/a | n/a | n/a | alive |
| S-0915991-b1 | Luminal | 2 | relapse | no | | n/a | n/a | n/a | dead |
| sp 95 709 | Luminal | 3 | relapse | no | | n/a | n/a | n/a | dead |
| SP96-9706 | Luminal | 3C | no relapse | no | | neg | neg | pos | alive |
| SP09-4902 | Luminal | 1 | no relapse | no | | pos | neg | pos | alive |
| SP95-11062 | Luminal | 3C | no relapse | no | | pos | pos | pos | alive |
| SP09-4902 | Luminal | 1 | no relapse | no | | n/a | n/a | n/a | alive |
| 95-12528 | Luminal | 3B | unknown | yes | LN | pos | pos | pos | unknown |
| s 97 8138 | Luminal | 3 | no relapse | no | | n/a | n/a | n/a | alive |
| 95-11062 | Luminal | 3 | no relapse | no | | n/a | n/a | n/a | alive |
| 95-2159 | Luminal | 3 | no relapse | no | | n/a | n/a | n/a | alive |
| S93-2913 | Luminal | 3B | relapse | no | Hip Bone | pos | pos | pos | dead |
| S08-24498 | Luminal A | 1 | no relapse | no | | pos | pos | neg | alive |
| S08-29285 | Luminal A | 1 | no relapse | no | | pos | pos | neg | alive |
| SP95-2488 | luminal A | 3C | no relapse | no | | pos | pos | neg | alive |
| S06-122 | Luminal A | 3A | no relapse | Yes | LN | pos | pos | neg | alive |
| S08-24498 | Luminal A | 1 | No Relapse | no | | n/a | n/a | n/a | alive |
| S08-29285 | Luminal A | 1 | No Relapse | no | | n/a | n/a | n/a | alive |
| 95-7355/65 | Luminal A | 3B | relapse | yes | LN | pos | pos | neg | dead |
| sp02 23510 | Luminal A | 2 | relapse | no | bladder | pos | neg | neg | dead |
| S94-5187 | Luminal A | 2 | relapse | no | Ovary/Stomach | pos | pos | neg | dead |
| S05-29559A | Luminal A | 3C | relapse | yes | LN | pos | neg | neg | dead |
| SP95-7163 | Luminal A | 3B | relapse | no | Ileocecal valve | pos | neg | neg | dead |
| SP95-2159 | luminal B | 3A | no relapse | no | | pos | neg | neg | alive |
| SP97-4458 | luminal B | 3C | no relapse | no | | pos | neg | neg | alive |
| 98-2759 | luminal B | 3 | no relapse | yes | LN | pos | pos | neg | alive |
| SP96-9326 | luminal B | 3C | relapse | no | | pos | pos | neg | dead |
| SP97-5947 | luminal B | 3C | relapse | no | | pos | pos | neg | dead |
| SP96-6054 | luminal B | 3C | relapse | no | | pos | pos | neg | dead |
| AP97-19817 | luminal B | 3C | relapse | no | | pos | pos | neg | dead |
| S95-5107 | Luminal B | 2 | relapse | no | LN | pos | pos | neg | dead |

TABLE 1-continued

Summary of the patient samples.

| ID | Molecular subtype | Stage at Diagnosis | relapse | synchronous | Metastases | ER+ | PR+ | Her2+ | Survival |
|---|---|---|---|---|---|---|---|---|---|
| S07-23447 | Luminal B | 3 | relapse | no | CW | pos | pos | neg | dead |
| 98-9971 | luminal B | 3B | unknown | yes | LN | n/a | n/a | n/a | alive |
| 97-8237 | luminal B | 3A | unknown | yes | LN | pos | pos | neg | unknown |
| 98-11386 | luminal B | 3B | unknown | yes | LN | pos | pos | neg | alive |
| sp-973718 | luminal B | 3 | no relapse | no | | n/a | n/a | n/a | alive |
| SP95-3486 | luminal B | 3 | relapse | no | | n/a | n/a | n/a | dead |
| SP08-16009 | TNBC | 2A | no relapse | no | | neg | neg | neg | alive |
| 09:S30016 | TNBC | 2A | no relapse | no | | neg | neg | neg | alive |
| 76 | TNBC | 1 | no relapse | no | | neg | neg | neg | alive |
| 98-12583 | TNBC | 3B | no relapse | yes | LN | neg | neg | neg | alive |
| SP08-16009 | TNBC | 2A | No Relapse | no | | neg | neg | neg | alive |
| 1568535 | TNBC | 3 | relapse | no | CW | neg | neg | neg | alive |
| 503-41092 | TNBC | 3 | relapse | no | CW | neg | neg | neg | dead |
| S05-3289 | TNBC | 2 | relapse | no | liver | neg | neg | neg | dead |
| 96-6337 | TNBC | 3 | relapse | no | | neg | neg | neg | dead |
| 93-13826 | TNBC | 3 | relapse | no | | neg | neg | neg | dead |

TNBC, triple negative breast cancer;
pos, positive;
neg, negative

Generation of miRNA and miRNA 'Sponge' in Lentiviral Constructs, Virus Generation and Transduction To express miRNA-708 in cells, about 500 bp of pri-miRNA containing the mature miR-708 sequence 5'-AAGGAGCUUACAAUCUAGCUGGG-3' (SEQ ID NO: 2) was amplified and cloned into the pZEO lentiviral construct in fusion with a GFP reporter as described (Ryu et al., 2011). miRNA sponge was generated according to (Ebert et al., 2007). Briefly, the sponge contains twelve miR-708 binding sites, 5'-CCCAGCTAGATCATAGCTCCTT-3' (SEQ ID NO: 3) which is fused with GFP and driven by an EF1α promoter. In particular, miRNA-708 was designed and cloned into the Xho I/EcoR I site of the lentiviral vector. To express miRNA-708 inducibly in cells, a doxycycline inducible construct was generated. The approximate 500 bp of pri-miRNA was fused with GFP and driven by TRE promoter. The transactivator rtTA-M2 was expressed under the PGK promoter. A miRNA-scramble served as a nonspecific control. For cloning miRNA sponge we followed a previously described method (Ebert et al., 2007). Briefly, the sponge contains twelve miR-708 binding sites, 5'-CCCAGCTAGATCATAGCTCCTT-3' (SEQ ID NO: 3) was fused with GFP and driven by an EF1α promoter. Lentivirus was generated and titer estimated as described (Ryu et al., 2011). A vector containing Nnat coding sequence and 3'-UTR was purchased from Origene (Cat#SC126815, Origene, Md.). To generate Nnat-mut, the miR-708 binding site was mutated in the Nnat 3'-UTR and cloned it into the pMSCV retroviral vector (Addgene, MA). To generate breast cancer cells stably expressing miRNAs, cells were transduced with lentivirus and sorted by flow cytometry (Aria II, BD Bioscience) to obtain stable cell lines.

Mouse Pulmonary Metastasis Models

For orthotopic injection, 1×10⁶ viable MDA-MB-231, MDA-Cont, or MDA-miR-708 cells were injected into CB-17 SCID mice fat pads in a volume of 0.1 ml. Tumor growth and pulmonary metastases (following resection of primary tumor) were monitored by live animal bioluminescent imaging (Xenogen IVIS system) once per week.

Bioluminescent Imaging and Analysis

Mice inoculated with firefly luciferase were anaesthetized and injected retro-orbitally with 75 mg/kg of D-luciferin (30 mg/mL in PBS). Images were taken with mice in a supine position using the Xenogen IVIS system coupled to Living Image acquisition and analysis software (Xenogen). For bioluminescence (BLI) plots, photon flux was calculated for each mouse by using a rectangular region of interest encompassing the thorax of the mouse.

Quantitative miRNA PCR miR-708 expression was measured by using Custom TaqMan microRNA Assays (Applied Biosystems, CA). RNU48 (Applied Biosystems) was used for normalization. 10 ng of RNA were used to make cDNA using TaqMan microRNA assays kit, and QPCR was performed as per the manufacturer's protocol (Applied Biosystems, CA).

Quantitative RT-PCR Analysis

Total RNA was extracted using the RNeasy kit (Qiagen) and converted to cDNA using Superscript II reverse transcriptase (Invitrogen). QPCR primers for Nnat were purchased from SABiosciences (Cat #PPT11378, SABiosciences), and quantitative PCR performed using iQ™ SYBER Green master mix (Biorad, Hercule, Calif.). Each sample was run in triplicate to minimize pipetting error. A standard protocol of initial denaturation at 95° C. for 3 min, 40 cycles of 95° C. for 20 sec, 60° C. for 30 sec, and 72° C. for 30 sec, followed by final extension at 72° C. for 5 min and melt curve analysis was applied on a Biorad CFX96 Real Time System (BioRad) coupled with Bio-Rad-CFX Manager software. The relative abundance of each transcript was compared with the control.

3'-UTR Luciferase Assay

The 3'-UTR of a gene of interest was amplified by PCR and cloned into a pmirGLO Dual-Luciferase miRNA Target Expression Vector (Promega). To express miRNA, synthetic premiRNA precursor for miR-708 and control scrambled miRNA were purchased from Applied Biosystems (Ambion). The miRNA precursor and pmirGLO Dual-Luciferase 3'-UTR vector were co-transfected into 297T cells using the siPORT NeoFX Transfection Agent following manufacturer's instructions (Ambion). Cells were harvested and lysed at 48 hr post-transfection. The interaction between miR-708 and target 3'-UTR was measured by Dual-luciferase assay system (Promega).

Western Blot Analysis

Cells were homogenized in 1×RIPA lysis buffer (Millipore) containing protease inhibitors (Roche Applied Science) and 1× phosphatase inhibitor (Thermo Scientific). Samples were boiled in 1× NuPAGE LDS sampling buffer (Invitrogen), and loaded onto 4-20% gradient Tris-HCl gels (BioRad). Western blotting was performed using antibodies specific for NNAT (Cat#AB27266, Abcam), EPDR1 (Cat# SC81820, Santa Cruz), SSRP1 (Cat#SC56782, Santa Cruz), HOXB3 (Cat# SC17161, Santa Cruz), HNRNPK (Cat# SC28380, Santa Cruz), CNTFR, Phospho-p44/42 MAPK (Erk1/2, Cat #4370, Cell Signaling), p44/42 MAPK (Erk1/2, Cat #4695, Cell Signaling), VINCULIN (Cat#V9131, Sigma-Aldrich), and β-ACTIN (Sigma-Aldrich).

Cell Proliferation Assays

For cell proliferation assays, $1 \times 10^6$ MDA cells were cultured separately in suspension in non-adhesive 6-well dishes (Corning Inc) for 2 days. EdU (10 nM) was administrated to culture medium for 30 min to label proliferating cells. Cells were harvested, washed once with PBS, and fixed with 4% paraformaldehyde for 15 min at room temperature. Fixed cells were permeabilized and stained for EdU incorporation and DNA contains with the Click-iT® EdU Cell Proliferation Assay kit (Invitrogen Inc) according to the standard protocol. Flow analyses of cell phases were performed using an LSRII coupled with Diva software (BD Bioscience).

Wound Healing and Transwell Migration Assay

Cells were plated in triplicate into 6-well plates ($5 \times 10^5$ cell/well) and cultured in DMEM containing 10% FBS. A scratch wounded was generated using sterile plastic 200 µl pipette tip, and floating debris removed by washing with PBS. Cell migration was photographed and measured under phase-contrast microscopy. To measure cell migration after depletion of intracellular calcium, a scratch was made and the wound healing was monitored for 48 hr in the presence of 20 µM of BAPTA-AM (Invitrogen). The percentage of wound healed area was measured as a ratio of occupied area to the total area using Image J program (NIH).

For transwell assays, 10,000 cells were plated in triplicate on 8 micron inserts in 24 well plates containing DMEM. At 12 hr post-seeding, inserts were transferred into fresh 24-well plates with 500 µl of 1% DMEM inside the insert, and 1 ml of 20% DMEM outside the insert, and cell migration was allowed for 24 hr (MDA) and 60 hr (MCF7). After migration, the insert was washed twice with fresh PBS and fixed with methanol for 10 min. After fixation, non-migrating cells were carefully removed using a cotton swap. Fixed cells were stained with 5% crystal violet in methanol for 1 min. After staining, images were obtained using a computerized Zeiss microscope (Axiovert 200M) and analyzed using Axiovision 4.6 software (Carl Zeiss Inc.).

Immunostaining and Microscopy

For immunofluorescence staining, cells were fixed overnight in paraformaldehyde before incubation with primary antibodies; mouse-monoclonal VINCULIN (Cat#V9131, Sigma-Aldrich, 1:400) and rabbit-polyclonal phosphorylated FAK (pS910, Cat #44596G, Invitrogen, 1:1000). Alexa Flour 568 or Alexa Fluor 647 anti-mouse IgG, and Alexa Fluor 647 anti-rabbit IgG (Invitrogen), were used for visualization. Following incubation with secondary antibodies the tissue sections were treated with Rhodamine Phalloidin (Cat# R415, Invitrogen). Fluorescent images were obtained using a computerized Zeiss fluorescent microscope (Axiovert 200M), fitted with an apotome and an HRM camera. Images were analyzed using Axiovision 4.6 software (Carl Zeiss Inc.).

Immunohistochemical Staining of Mouse and Human Breast Tumors

Paraffin embedded sections (5 µm) were deparaffinized following standard protocols. A rabbit polyclonal anti-Nnat antibody (Cat# ab27266, Abcam, 1:1000) was used for staining, and signals detected with Polymer/HRP and DAB solution from Envision™ G/2 Doublestain system, Rabbit/Mouse (DAKO) according to manufacturer's suggestions. Images were obtained with an Axiovert 40 CFL microscope coupled with Axioversion 4.8.2 software (Carl Zeiss). For nodule counting, lungs were perfused, isolated and OCT embedded and sectioned for immunohistochemical analysis. Cryosections (8 µm) were mounted on glass slides and stained with hematoxylin and eosin (H&E).

In Situ Hybridization with miR-708 LNA Probes

Tissue sections were obtained from primary human breast tumors and matched lymph node metastases, as well as from spontaneous primary breast tumors and matched lung metastases harvested from mice (MMTV-PyMT/WAP-Cre/CAG-CAT-EGFP, 15 week). Slides were thawed for 60 min (primary tumor) or 1 min (lung tissue) at room temperature. Sections were treated in proteinase K at either 40 µg/ml (primary tumor) for 30 min, or at 4 µg/ml (lung tissue) for 10 min, at room temperature. Sections were quenched with 0.2% glycine/PBS for 1 min twice and washed two times in PBS for 1 min. Sections were then fixed with 10% formaldehyde and treated with 0.03% EDC solution (Sigma) (Pena et al., 2009) before being acetylated with acetic anhydride with triethanolamine for 30 min at RT and washed with 5×SSC for 5 min. Following this, sections were hybridized with DIG labeled miR-708 or U6 LNA probes (Exiqon, MA) overnight at Tm −30° C., then rinsed twice with 5×SSC at room temperature and washed three times at hybridization temp in 2×SSC/50% formamide for 20 min and washed four times with PBS with 0.1% Tween 20 (PBST). Sections were blocked for endogenous peroxidase activity (30 min in 3% $H_2O_2$ in PBST) and incubated with blocking buffer (0.5% blocking reagent with 10% serum) for 1 hour then with anti-DIG Ab-POD, Fab fragments (Roche, Ind.) overnight at 4° C. Sections were washed twice with PBST for 5 min and incubated with 200$1 of TSA/Cy4 (Perkin Elmer, MA) solution for 10 min at RT in the dark, washed three times with PBST for 3 minutes, and mounted using vectashield containing DAPI (Vector, CA).

To quantify miRNA from FFPE (formalin fixed paraffin embedded) specimens, we isolated total RNA including small RNA using miRNeasy FFPE kit (Qiagen) and quantified miRNA using TaqMan microRNA Assays (Applied Biosystems, CA). RNU48 (Applied Biosystems) was used for normalization. 10 ng of RNA were used to make cDNA using TaqMan microRNA assays kit, and quantitative PCR was performed as per the manufacturer's protocol (Applied Biosystems, CA).

Chromatin Immunoprecipitations

Chromatin immunoprecipitation (ChIP) assays were performed using the EZ CHIP chromatin immunoprecipitation Kit (Millipore, CA) following the manufacturer's protocol. Briefly, 1×106 cells were cultured and fixed for 10 min at 37° C. in 1% paraformaldehyde. Lysates were sheared by ultrasonication (Covaris, MA) and cleared by centrifugation and diluted in ChIP dilution buffer containing protease inhibitor cocktail. Lysates were precleared using Protein G Agarose and 'input DNA' was collected from supernatant after centrifugation. Immunoprecipitated complexes were immuno-precipitated with a SUZ12 antibody (Abcam, cat #12073) and/or an anti-histone H3K27M3 antibody (Millipore, Cat #07-449) overnight at 4° C. Mouse IgG (negative control, Millipore, Cat #12-371B) and RNA PolII (positive control, Millipore, Cat #05-623B) were used as controls.

DNA was then extracted using spin columns. The contents of each specific DNA locus were amplified by real-time PCR (iQ SYBR Green Supermix; Bio-Rad) using four different locations upstream of miR-708. Amplification efficiency was calculated and the data expressed as enrichment related to input.

All ChIP-QPCR control primers were used following manufacturer's instructions (Abcam # ab8898).

The contents of each specific DNA locus were amplified by real-time PCR (iQ SYBR Green Supermix; Bio-Rad) using four different locations upstream of miR-708:

708 Upstream Primers:

```
U250-Fwd
                                    (SEQ ID NO: 4)
5'-CAGGAAACCAGGAATAGGTG-3'
and
U250-Rev
                                    (SEQ ID NO: 5)
5'-GAATTGATCGCAGAGGAGGA-3', U500-Fwd
                                    (SEQ ID NO: 6)
5'-CCCAGGACACCAAGTCAGTT-3'
and
U500-Rev
                                    (SEQ ID NO: 7)
5'-ATCGCGGGCAATTACATAAG-3', U1000-Fwd
                                    (SEQ ID NO: 8)
5'-GGTACTGTTGAGGGCTCTGC-3'
and
U1000-Rev
                                    (SEQ ID NO: 9)
5'-CCATTTTTAAATGCGGTCGT-3', U1500-Fwd
                                    (SEQ ID NO: 10)
5'-CCTCAGTTGGCTCCTAGACG-3'
and
U1500-Rev
                                    (SEQ ID NO: 11)
5'-GAAGAGGCAAGCTGTTCTGG-3'.
```

Amplification efficiency was calculated and the data expressed as enrichment related to input.

Knock Down PRC2 Complex

To knockdown polycomb complex, several different shRNAs were used, mouse Suz12 shRNA: TRCN0000123889, TRCN0000123890, TRCN0000123891, TRCN0000123892, TRCN0000123893 human Ezh2 shRNA: TRCN0000010475, TRCN0000040074, TRCN0000040075, TRCN0000040077, (Mission shRNA, Sigma), human Suz12 shRNA: #191944, #191945, #191946, #191947, #191948 (MSKCC shRNA library), ON-TARGET mouse siRNA (Dharmacon). To quantify expression of polycomb complex, human and mouse Suz12, Ezh2 and Nnat QPCR primers were purchased (RT2 qPCR primers, SAbioscience).

Circulating Tumor Cell Measurements

To measure number of CTC in blood, 100 µl of peripheral blood was collected from mice bearing orthotopic OFF expressing MDA and MDA-mir-708 breast tumors. Total RNA was isolated and subjected to Taqman Q-PCR for GFP transgene. To convert quantitative-PCR data into number of CTCs, a standard curve was generated by serially diluting GFP+MDA tumor spiked into 100$1 of normal wild type mouse blood.

Intracellular Calcium Measurements

MDA-control, MDA-miR-708, and MDA-miR-708-Nnat-mut cells were grown on coverslips and used 2-3 days after plating. Cells were loaded with 10% M Fura-2 (Molecular Probes), a membrane-permeable $Ca^{2+}$-indicator dye, at 37° C. for 30 min. Cells were then washed and incubated in HEPES-buffered $Na^+$-Ringer's solution (140 mM NaCl, 5 mM KCl, 10 mM HEPES, 2 mM $CaCl_2$, and 1 mM $MgCl_2$, pH 7.4). Individual vials (50 mg) of the acetoxymethyl derivative of Fura-2 (Invitrogen/Molecular Probes) were stored dry at 0° C. and reconstituted in dimethyl sulfoxide at a concentration of 10 mM for each experiment. At the concentrations used, dimethyl sulfoxide had no effect on any preparation in these studies. The coverslip with the dye-loaded cells was attached to the bottom of a flow-through superfusion chamber and mounted on the stage of an inverted epifluorescence microscope (Nikon Eclipse TE-2000). The cells in the chamber were superfused and maintained at 37° C. as previously described (O'Connor and Silver, 2007). Cells were first visualized under transmitted light with a Nikon CF Fluor oil immersion objective (X40/1.3 numerical aperture) before the start of the fluorescence measurements. Images were obtained at 340 nm and 380 nm excitation and at 510 nm emission wavelengths. The ratio was determined from the images at 340 nm and 380 nm. The imaging workstation was controlled with the MetaFluor software package (Universal Imaging). Cells in the experimental field of view were analyzed singularly and independently from their neighbors. Results are expressed as means±SEM, where n refers to the total number of individually analyzed cells.

In Situ Hybridization with miR-708 LNA Probes

Tissue sections were obtained from primary human breast tumor and matched lymph node metastases, as well as from spontaneous primary breast tumors and matched lung metastases harvested from mice (MMTV-PyMT/WAP-Cre/CAG-CAT-EGFP, 15 week). Slides were thawed for 60 min (primary tumor) or 1 min (lung tissue) at room temperature. Sections were treated in proteinase K at either 40 µg/ml (primary tumor) for 30 minutes, or 4 µg/ml (lung tissue) for 10 minutes, at room temperature. Sections were quenched with 0.2% glycine/PBS for 1 min twice and washed two times in PBS for 1 min. Sections were then fixed with 10% formaldehyde and treated with 0.03% EDC solution (Sigma) (Pena et al., 2009) before being acetylated with acetic anhydride with triethanolamine for 30 min at RT and washed with 5×SSC for 5 min. Following this, sections were hybridized with DIG labeled miR-708 or U6 LNA probes (Exiqon, MA) overnight at Tm-30° C., then rinsed twice with 5×SSC at room temperature and washed three times at hybridization temp in 2×SSC/50% formamide for 20 min and washed four times with PBS with 0.1% Tween 20 (PBST). Sections were blocked for endogenous peroxidase activity (30 min in 3% $H_2O_2$ in PBST) and incubated with blocking buffer (0.5% blocking reagent with 10% serum) for 1 hour then with anti-DIG Ab-POD, Fab fragments (Roche, Ind.) overnight at 4° C. Sections were washed twice with PBST for 5 min and incubated with 200 µl of TSA/Cy4 (Perkin Elmer, MA) solution for 10 min at room temperature in the dark, washed three times with PBST for 3 minutes, and mounted using vectashield containing DAPI (Vector, CA).

To quantify miRNA from FFPE (formalin fixed paraffin embedded) specimens, total RNA was isolated including small RNA using miRNeasy FFPE kit (Qiagen) and quantified miRNA using TaqMan microRNA Assays (Applied Biosystems, CA). RNU48 (Applied Biosystems) was used for normalization. 10 ng of RNA were used to make cDNA using TaqMan microRNA assays kit, and QPCR was performed as per the manufacturer's protocol (Applied Biosystems, CA).

Statistical Analysis

Results are expressed as mean±s.d. Analyses of different treatment groups were performed using the non-parametric Mann-Whitney T-test using the GraphPad Prism statistical program. P values less than 0.05 were considered significant. Error bars depict standard deviations, except where indicated otherwise.

Example 2

Identification of Differentially Regulated miRNAs in Metastasis

To identify miRNAs that regulate the metastatic cascade without affecting primary tumor growth, a human triple negative breast cancer (TNBC) model with varying grades of metastatic potential (Kang et al., 2009; Minn et al., 2005) was used. These included normal primary breast epithelial cells, and tumor cells with low and high metastatic potential (Table 2).

TABLE 2

| Cell | Tumorigenic | Metastatic |
|---|---|---|
| Breast | | |
| MCF10A | − | − |
| MCF7 | + | − |
| MDA-MB-231 | + | + |
| MDA231-LM2 | + | +++ |
| Prostate | | |
| RWPE1 | − | − |
| RWPE2 | + | − |

TABLE 2-continued

Human cancer cell lines with diverse tumorigenic and metastatic potential.

| Cell | Tumorigenic | Metastatic |
|---|---|---|
| PC3 | + | ++ |
| LN4 | + | +++ |

Normal primary epithelial cells (MCF10A, RWPE1), cells with tumorigenic potential including nonmetastatic (MCF7, RWPE2) and metastatic (MDA-MB-231, MDA-LM2, PC3 and LN4) cells.

Total RNA was size fractionated and used to generate libraries for Mir-Seq. Sequence reads obtained from each breast cancer cell line in duplicate were used for identifying miRNAs as described (Ryu et al., 2011). Alignment of sequence reads to known miRNA sequences in the miRNA database (miRBase v16) revealed that about 80% of reads that matched known human miRNAs (Table 3).

TABLE 3

Numbers of sequencing reads at each step of miRNA data analysis from breast cancer cells.

| | MCF10A | MCF7 | MDA | LM2 |
|---|---|---|---|---|
| Flow cell Reads | 6,509,611 | 6,680,794 | 7,739,594 | 7,533,299 |
| Reliable Reads | 4,363,442 | 4,616,346 | 4,656,589 | 5,205,726 |
| | (67.0%) | (69.1%) | (60.2%) | (69.1%) |
| With linker SEQ | 3,056,709 | 3,565,093 | 3,197,724 | 2,451,120 |
| | (70.4%) | (77.4%) | (68.8%) | (47.1%) |
| Match with known human miRNA Sanger DB (V.16) | 2,536,616 | 2,973,587 | 2,465,790 | 2,090,402 |
| | (82.9%) | (83.4%) | (77.1%) | (85.3%) |

Hierarchical clustering analysis revealed groups of differentially regulated miRNAs in metastatic tumor cells (FIG. 1A), and microRNAs, which were up- and down-regulated, were identified (Tables 4 and 5).

TABLE 4

Upregulated miRNAs in metastatic cells

| miRNA | mature sequence | MCF10A | MCF7 | MDA | LM2 | fold change (met/nonmet) |
|---|---|---|---|---|---|---|
| miR-146a | TGAGAACTGAAT TCCATGGGTT (SEQ ID NO: 12) | 106.1323 | 22.36254 | 98600.9 | 213301.8 | 6973.776528 |
| miR-22 | AAGCTGCCAGTT GAAGAACTGT (SEQ ID NO: 13) | 113192 | 49497.88 | 146605.5 | 199470.7 | 3.495868305 |
| miR-17 | CAAAGTGCTTAC AGTGCAGGTAG (SEQ ID NO: 14) | 87047.24 | 10951.26 | 25364.8 | 140957.3 | 7.593747267 |
| miR-24 | TGGCTCAGTTCA GCAGGAACAG (SEQ ID NO: 15) | 169111.2 | 60817.59 | 191998.6 | 138203.7 | 2.714694058 |
| miR-27a | TTCACAGTGGCT AAGTTCCGC (SEQ ID NO: 16) | 58332.82 | 12054.47 | 45602.97 | 97856.57 | 5.950468729 |
| miR-100 | AACCCGTAGATC CGAACTTGTG (SEQ ID NO: 17) | 54088.78 | 391.8769 | 259514.3 | 82319.82 | 436.1498637 |
| miR-151-5p | TCGAGGAGCTCA CAGTCTAGT (SEQ ID NO: 18) | 17601.73 | 16072.28 | 27034.68 | 61790.14 | 2.7632932 |

TABLE 4-continued

Upregulated miRNAs in metastatic cells

| miRNA | mature sequence | MCF10A | MCF7 | MDA | LM2 | fold change (met/nonmet) |
|---|---|---|---|---|---|---|
| miR-222 | AGCTACATCTGGCTACTGGGT (SEQ ID NO: 19) | 23678.75 | 1337.493 | 23081.74 | 56071.41 | 29.59011926 |
| miR-23a | ATCACATTGCCAGGGATTTCC (SEQ ID NO: 20) | 53866.53 | 16192.61 | 72244.18 | 54504.88 | 3.913793797 |
| miR-18a | TAAGGTGCATCTAGTGCAGATAG (SEQ ID NO: 21) | 40974.57 | 5874.959 | 20194.09 | 52136.95 | 6.155876528 |
| miR-29b | TAGCACCATTTGAAATCAGTGTT (SEQ ID NO: 22) | 72274.87 | 4235.039 | 93208.68 | 36083.06 | 15.26452716 |
| miR-20a | TAAAGTGCTTATAGTGCAGGTAG (SEQ ID NO: 23) | 84224.12 | 11670.05 | 45521.98 | 32644.56 | 3.349023204 |
| miR-221 | AGCTACATTGTCTGCTGGGTTTC (SEQ ID NO: 24) | 33914.9 | 480.262 | 243294.8 | 31749.4 | 78.12837131 |
| miR-27b | TTCACAGTGGCTAAGTTCTGC (SEQ ID NO: 25) | 18087.45 | 22347.63 | 72286.65 | 29519.07 | 2.27777432 |
| miR-130a | CAGTGCAATGTTAAAAGGGCAT (SEQ ID NO: 26) | 10534.57 | 80.931 | 111942.06 | 25927.85 | 233.9638831 |
| miR-19b | TGTGCAAATCCATGCAAAACTGA (SEQ ID NO: 27) | 28391.02 | 2209.632 | 5753.356 | 22079.57 | 6.298091871 |
| miR-92a | TATTGCACTTGTCCCGGCCTGT (SEQ ID NO: 28) | 32949.72 | 2288.433 | 20362.32 | 21455.08 | 9.136687345 |
| miR-28-5p | AAGGAGCTCACAGTCTATTGAG (SEQ ID NO: 29) | 4882.087 | 3525.827 | 3972.103 | 21276.65 | 3.580543544 |
| miR-125b | TCCCTGAGACCCTAACTTGTGA (SEQ ID NO: 30) | 34406.85 | 524.987 | 259014.64 | 21157.2 | 76.35598672 |
| miR-29a | TAGCACCATCTGAAATCGGTTA (SEQ ID NO: 31) | 25445.54 | 583.555 | 869324.65 | 16388.06 | 73.44002657 |
| miR-30c | TGTAAACATCCTACACTCTCAGC (SEQ ID NO: 32) | 7931.206 | 1744.278 | 5210.949 | 15474.75 | 5.929588465 |
| miR-130b | CAGTGCAATGATGAAAGGGCAT (SEQ ID NO: 33) | 4749.734 | 2128.701 | 3962.874 | 11712.67 | 3.68195044 |
| miR-181b | AACATTCATTGCTGTCGGTGGGT (SEQ ID NO: 34) | 6636.392 | 2425.803 | 7186.845 | 11175.87 | 3.784874324 |

TABLE 4-continued

Upregulated miRNAs in metastatic cells

| miRNA | mature sequence | MCF10A | MCF7 | MDA | LM2 | fold change (met/nonmet) |
|---|---|---|---|---|---|---|
| miR-320a | AAAAGCTGGGTT GAGAGGGCGA (SEQ ID NO: 35) | 11428.58 | 3086.03 | 8593.126 | 10754 | 3.134629968 |
| miR-30a | TGTAAACATCCTC GACTGGAAG (SEQ ID NO: 36) | 1545.786 | 113.9425 | 12564.44 | 9919.326 | 98.66281141 |
| miR-181a | AACATTCAACGC TGTCGGTGAGT (SEQ ID NO: 37) | 8378.211 | 2677.115 | 14681.49 | 9500.476 | 4.516422626 |
| miR-423-5p | TGAGGGGCAGA GAGCGAGACTTT (SEQ ID NO: 38) | 5441.467 | 1108.543 | 2953.105 | 8916.809 | 5.353835588 |
| miR-424 | CAGCAGCAATTC ATGTTTTGAA (SEQ ID NO: 39) | 4466.298 | 5439.422 | 15389.19 | 8107.839 | 2.159883057 |
| miR-138 | AGCTGGTGTTGT GAATCAGGCCG (SEQ ID NO: 40) | 2123.895 | 68.1525 | 13611.66 | 5680.931 | 141.5398251 |
| miR-139-5p | TCTACAGTGCAC GTGTCTCCAG (SEQ ID NO: 41) | 73.66832 | 51.11438 | 804.2721 | 5425.387 | 60.93842884 |
| let-7c | TGAGGTAGTAGG TTGTATGGTT (SEQ ID NO: 42) | 2327.419 | 1860.35 | 13147.22 | 4940.006 | 4.86124243 |
| miR-27b* | AGAGCTTAGCTG ATTGGTGAAC (SEQ ID NO: 43) | 554.3853 | 394.0067 | 1416.605 | 4737.385 | 7.809501147 |
| miR-27a* | AGGGCTTAGCTG CTTGTGAGCA (SEQ ID NO: 44) | 1048.837 | 326.919 | 937.4658 | 3190.515 | 6.313460411 |
| miR-941 | CACCCGGCTGTG TGCACATGTGC (SEQ ID NO: 45) | 287.1816 | 203.3926 | 644.3407 | 3030.233 | 9.0332033 |
| miR-10a | TACCCTGTAGAT CCGAATTTGTG (SEQ ID NO: 46) | 46.19878 | 197.0033 | 4774.384 | 2910.778 | 19.50515785 |
| miR-30a* | CTTTCAGTCGGA TGTTTGCAGC (SEQ ID NO: 47) | 238.4856 | 12.77859 | 2106.353 | 2590.214 | 183.7669723 |
| miR-320b | AAAAGCTGGGTT GAGAGGGCAA (SEQ ID NO: 48) | 327.1373 | 543.0902 | 965.4743 | 2504.025 | 3.194219865 |
| miR-584 | TTATGGTTTGCCT GGGACTGAG (SEQ ID NO: 49) | 1247.367 | 19.16789 | 1522.723 | 2032.252 | 92.73256784 |
| miR-100* | CAAGCTTGTATCT ATAGGTATG (SEQ ID NO: 50) | 275.944 | 1.064883 | 592.2572 | 1956.648 | 1196.800581 |
| miR-503 | TAGCAGCGGGAA CAGTTCTGCAG (SEQ ID NO: 51) | 234.7397 | 154.408 | 2007.046 | 1812.999 | 12.36996964 |

TABLE 4-continued

Upregulated miRNAs in metastatic cells

| miRNA | mature sequence | MCF10A | MCF7 | MDA | LM2 | fold change (met/nonmet) |
|---|---|---|---|---|---|---|
| miR-29a* | ACTGATTTCTTTT GGTGTTCAG (SEQ ID NO: 52) | 1171.201 | 26.62207 | 964.672 | 1684.471 | 49.75464966 |
| miR-574-5p | TGAGTGTGTGTG TGTGAGTGTGT (SEQ ID NO: 53) | 1701.863 | 305.6214 | 966.694 | 1616.427 | 4.226016089 |
| miR-1274b | TCCCTGTTCGGG CGCCA (SEQ ID NO: 54) | 1865.432 | 154.408 | 5891.709 | 1610.378 | 24.29306373 |
| miR-107 | AGCAGCATTGTA CAGGGCTATCA (SEQ ID NO: 55) | 2725.728 | 1515.328 | 5051.357 | 1561.991 | 2.182150327 |
| miR-19a | TGTGCAAATCTAT GCAAAACTGA (SEQ ID NO: 56) | 4561.193 | 493.0408 | 1512.166 | 1540.822 | 3.096080618 |
| miR-92b | TATTGCACTCGTC CCGGCCTCC (SEQ ID NO: 57) | 2941.738 | 704.9524 | 2147.286 | 1524.189 | 2.604058853 |
| miR-218 | TTGTGCTTGATCT AACCATGT (SEQ ID NO: 58) | 967.6771 | 444.0561 | 2207.993 | 1280.742 | 3.928259275 |
| miR-455-3p | GCAGTCCATGGG CATATACAC (SEQ ID NO: 59) | 59.93355 | 177.8354 | 1242.507 | 1120.46 | 6.643691565 |
| miR-17* | ACTGCAGTGAAG GCACTTGTAG (SEQ ID NO: 60) | 1267.345 | 254.507 | 1722.046 | 1061.489 | 5.468483239 |
| miR-320c | AAAAGCTGGGTT GAGAGGGT (SEQ ID NO: 61) | 158.5742 | 292.8428 | 602.739 | 1037.295 | 2.800197209 |
| miR-720 | TCTCGCTGGGGC CTCCA (SEQ ID NO: 62) | 579.3576 | 107.5532 | 559.6664 | 560.9863 | 5.209761537 |

TABLE 5

Down-regulated miRNAs in metastatic cells

| miRNA | mature sequence | MCF10A | MCF7 | MDA | LM2 | fold change (met/nonmet) |
|---|---|---|---|---|---|---|
| miR-489 | GTGACATCACATAT ACGGCAGC (SEQ ID NO: 63) | 7.491694 | 1212.902 | 1.141465 | 1.512092 | −932.3587095 |
| miR-203 | GTGAAATGTTTAGG ACCACTAG (SEQ ID NO: 64) | 277.1927 | 2340.612 | 1.782931 | 22.68139 | −707.9923184 |
| miR-708 | AAGGAGCTTACAAT CTAGCTGGG (SEQ ID NO: 65) | 6841.165 | 7363.665 | 9.980515 | 514.1114 | −376.0635822 |
| miR-141 | TAACACTGTCTGGT AAAGATGG (SEQ ID NO: 66) | 10415.95 | 19511.85 | 42.32931 | 710.6834 | −244.2043428 |

TABLE 5-continued

Down-regulated miRNAs in metastatic cells

| miRNA | mature sequence | MCF10A | MCF7 | MDA | LM2 | fold change (met/nonmet) |
|---|---|---|---|---|---|---|
| miR-200c | TAATACTGCCGGGT AATGATGGA (SEQ ID NO: 67) | 47112.76 | 33688.63 | 85.29775 | 3914.807 | −201.7794128 |
| miR-196a | TAGGTAGTTTCATG TTGTTGGG (SEQ ID NO: 68) | 136.0991 | 1006.314 | 10.99026 | 810.4815 | −46.40291868 |
| miR-200b | TAATACTGCCTGGT AATGATGA (SEQ ID NO: 69) | 278.4413 | 20671.51 | 439.2035 | 2174.389 | −28.28635528 |
| miR-342-5p | AGGGGTGCTATCTG TGATTGA (SEQ ID NO: 70) | 298.4191 | 1000.99 | 19.81957 | 263.1041 | −27.15483861 |
| miR-342-3p | TCTCACACAGAAAT CGCACCCGT (SEQ ID NO: 71) | 4048.012 | 9710.667 | 283.8909 | 1170.36 | −21.25139683 |
| miR-429 | TAATACTGTCTGGT AAAACCGT (SEQ ID NO: 72) | 117.3699 | 9599.919 | 417.7225 | 586.6918 | −19.67218149 |
| miR-200a | TAACACTGTCTGGT AACGATGT (SEQ ID NO: 73) | 133.6019 | 5858.985 | 363.3056 | 644.1514 | −12.61127321 |
| miR-365 | TAATGCCCCTAAAA ATCCTTAT (SEQ ID NO: 74) | 663.0149 | 601.6588 | 42.62939 | 93.74973 | −10.26571106 |
| miR-183 | TATGGCACTGGTAG AATTCACT (SEQ ID NO: 75) | 2231.276 | 7656.508 | 736.7744 | 949.594 | −9.227428448 |
| miR-205 | TCCTTCATTCCACC GGAGTCTG (SEQ ID NO: 76) | 515408.5 | 969.0434 | 20.56586 | 29119.88 | −8.534450739 |
| miR-196b | TAGGTAGTTTCCTG TTGTTGGG (SEQ ID NO: 77) | 1197.422 | 630.4106 | 51.0343 | 140.6246 | −8.4178092 |
| miR-182 | TTTGGCAATGGTAG AACTCACACT (SEQ ID NO: 78) | 3162.743 | 10554.05 | 847.458 | 2650.698 | −8.217695794 |
| miR-96 | TTTGGCACTAGCAC ATTTTTGCT (SEQ ID NO: 79) | 3288.853 | 9755.392 | 1012.733 | 1633.06 | −7.803211298 |
| miR-193b | AACTGGCCCTCAAA GTCCCGCT (SEQ ID NO: 80) | 4699.789 | 5108.243 | 1237.031 | 450.6035 | −7.732942067 |
| miR-195 | TAGCAGCACAGAAA TATTGGC (SEQ ID NO: 81) | 84.90586 | 1191.604 | 420.4127 | 105.8465 | −7.046109595 |
| miR-497 | CAGCAGCACACTGT GGTTTGT (SEQ ID NO: 82) | 139.8449 | 1633.53 | 288.5737 | 210.1808 | −6.716363582 |
| miR-301a | CAGTGCAATAGTAT TGTCAAAGC (SEQ ID NO: 83) | 3988.078 | 8073.942 | 1409.194 | 1400.198 | −5.747881629 |

TABLE 5-continued

Down-regulated miRNAs in metastatic cells

| miRNA | mature sequence | MCF10A | MCF7 | MDA | LM2 | fold change (met/nonmet) |
|---|---|---|---|---|---|---|
| miR-34a | TGGCAGTGTCTTAG CTGGTTGT (SEQ ID NO: 84) | 3250.146 | 1377.958 | 328.8687 | 231.3501 | −5.073077843 |
| miR-335 | TCAAGAGCAATAAC GAAAAATGT (SEQ ID NO: 85) | 1876.669 | 1110.673 | 337.3032 | 173.8906 | −4.839997099 |
| miR-454 | TAGTGCAATATTGC TTATAGGGT (SEQ ID NO: 86) | 2388.602 | 7939.766 | 1765.402 | 2313.501 | −3.964677263 |
| miR-7 | TGGAAGACTAGTGA TTTTGTTGT (SEQ ID NO: 87) | 1129.997 | 4231.844 | 686.9677 | 2771.665 | −3.843501595 |
| miR-149 | TCTGGCTCCGTGTC TTCACTCCC (SEQ ID NO: 88) | 443.2585 | 1004.185 | 279.7225 | 296.3701 | −3.489104627 |
| miR-185 | TGGAGAGAAAGGC AGTTCCTGA (SEQ ID NO: 89) | 2122.647 | 3447.026 | 989.1824 | 1023.687 | −3.425994366 |
| miR-345 | GCTGACTCCTAGTC CAGGGCTC (SEQ ID NO: 90) | 414.5404 | 3833.578 | 1873.117 | 822.5783 | −3.353536179 |
| let-7e | TGAGGTAGGAGGTT GTATAGTT (SEQ ID NO: 91) | 6586.447 | 10853.29 | 5760.691 | 2339.207 | −3.261876948 |
| miR-421 | ATCAACAGACATTA ATTGGGCGC (SEQ ID NO: 92) | 593.0924 | 1162.852 | 341.7397 | 393.144 | −3.180284647 |
| miR-652 | AATGGCGCCACTAG GGTTGTG (SEQ ID NO: 93) | 4612.386 | 5776.989 | 1480.239 | 3290.313 | −2.829248384 |
| miR-101 | TACAGTACTGTGAT AACTGAA (SEQ ID NO: 94) | 2052.724 | 876.3986 | 351.1372 | 396.1682 | −2.354037258 |
| miR-21 | TAGCTTATCAGACT GATGTTGA (SEQ ID NO: 95) | 627840.1 | 2139794 | 1027088 | 857270.2 | −2.289707451 |
| miR-98 | TGAGGTAGTAAGTT GTATTGTT (SEQ ID NO: 96) | 4674.817 | 6916.414 | 3522.742 | 2705.133 | −2.260067339 |
| miR-125a-5p | TCCCTGAGACCCTT TAACCTGTGA (SEQ ID NO: 97) | 12848.25 | 7950.415 | 4867.602 | 2827.613 | −2.222519436 |
| miR-152 | TCAGTGCATGACAG AACTTGG (SEQ ID NO: 98) | 66.17663 | 1479.122 | 265.2031 | 1678.423 | −2.221288744 |
| miR-339-3p | TGAGCGCCTCGAC GACAGAGCCG (SEQ ID NO: 99) | 641.7884 | 1503.615 | 599.2304 | 910.2796 | −2.080529568 |

Previously discovered metastatic miRNAs were also identified including miR-200 family, miR-10, and miR-196 (Valastyan and Weinberg, 2009), further validating the inventors' miRNA profiling approach.

Figure 1B:
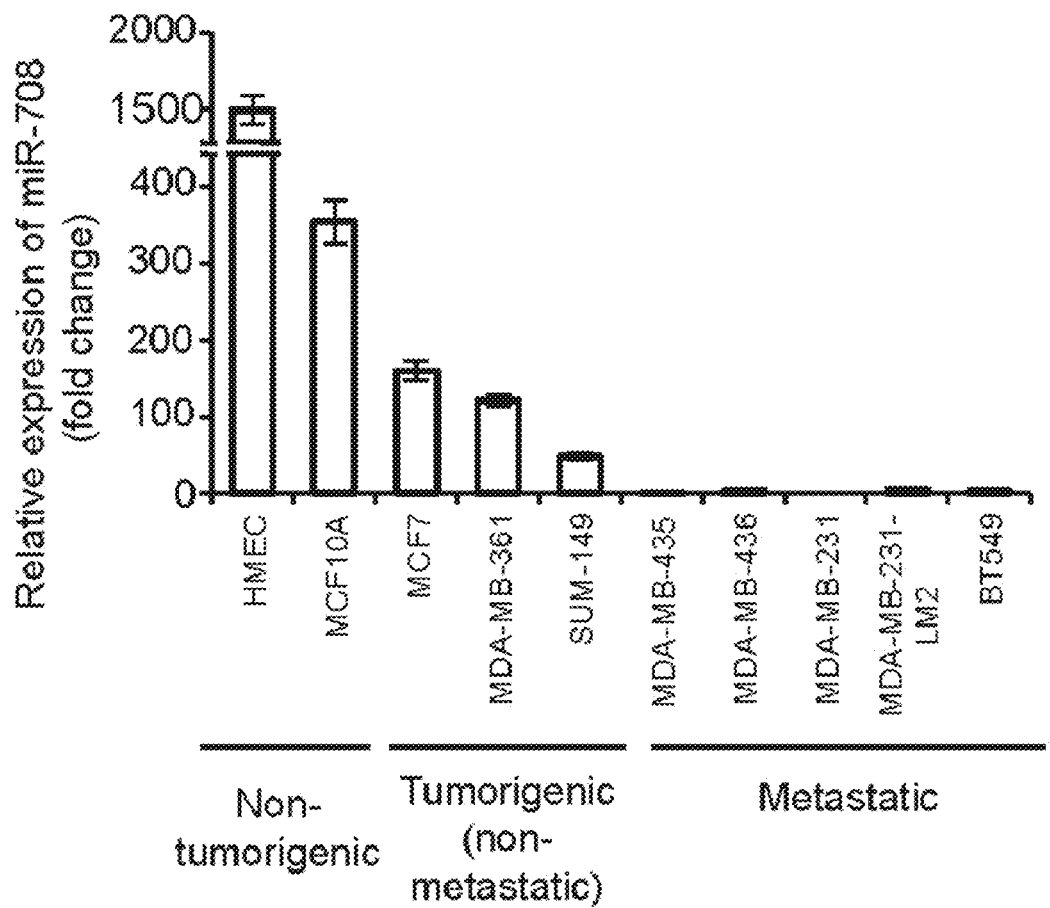
FIG. 1B graphically illustrates the relative expression of miR-708 as detected by quantitative RT-PCR analysis of miR-708 in a panel of non-tumorigenic and tumorigenic (non-metastatic and metastatic) breast cancer cells. miR-708 expression analysis was performed in triplicate and normalized to the internal control, RNU48. Y-axis depicts fold change in miR-708.
Figure 1C:
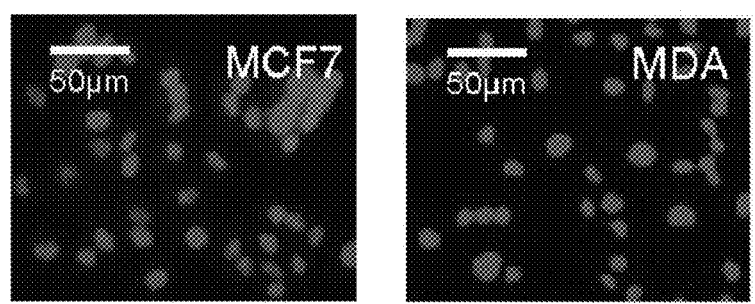
FIG. 1C shows microscopy images illustrating miR-708 expression as detected by in situ hybridization (red) in non-metastatic MCF7 and metastatic MDA breast cancer cells; the lighter color (red) surrounding the bright nuclei is more visible in the MCF7 cells).
Figure 1D:
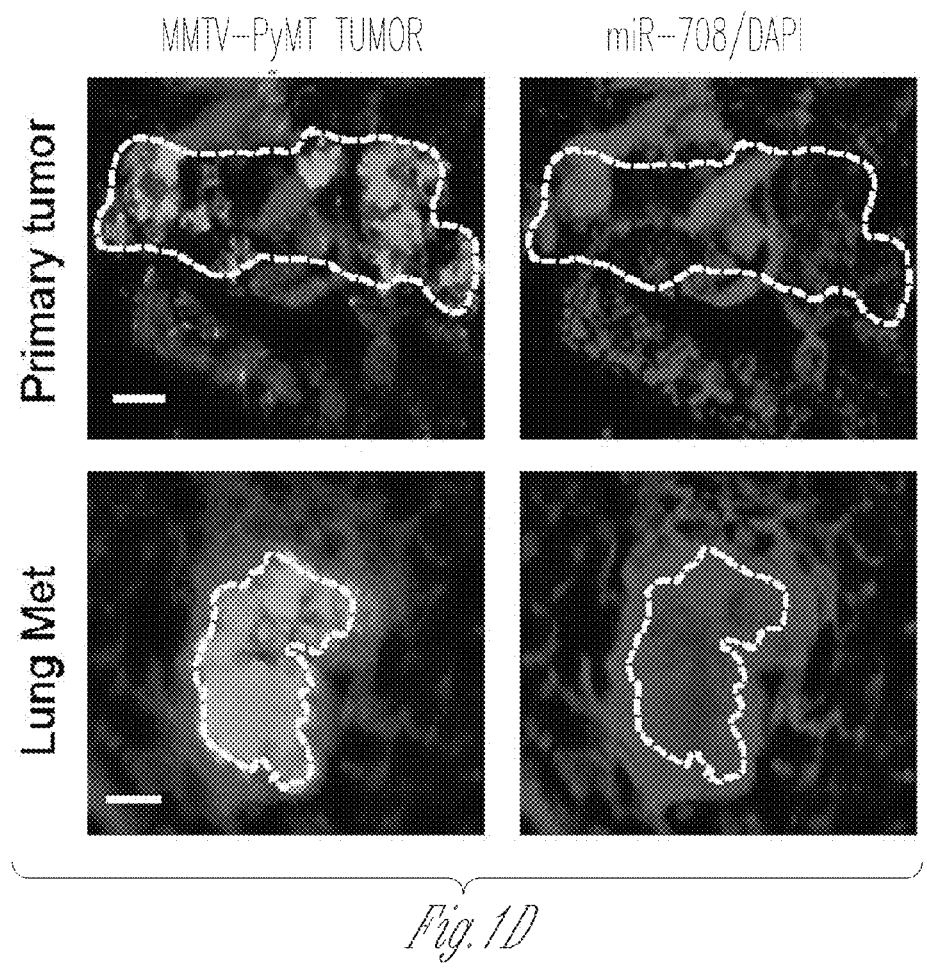
FIG. 1D illustrates miR-708 expression in GFP+ primary breast tumors and lung metastases as detected by in situ hybridization of miR-708 (red) in GFP+ primary breast tumors and lung metastases obtained from MMTV-PyMT/WAP-Cre/CAG-CAT-EGFP transgenic mice. Dotted line indicates primary tumor (green) in mammary gland and metastatic tumor (green) in the lung. DAPI was used to label the nuclei of all cells. Scale bar, 50 µm.
Figure 1E:
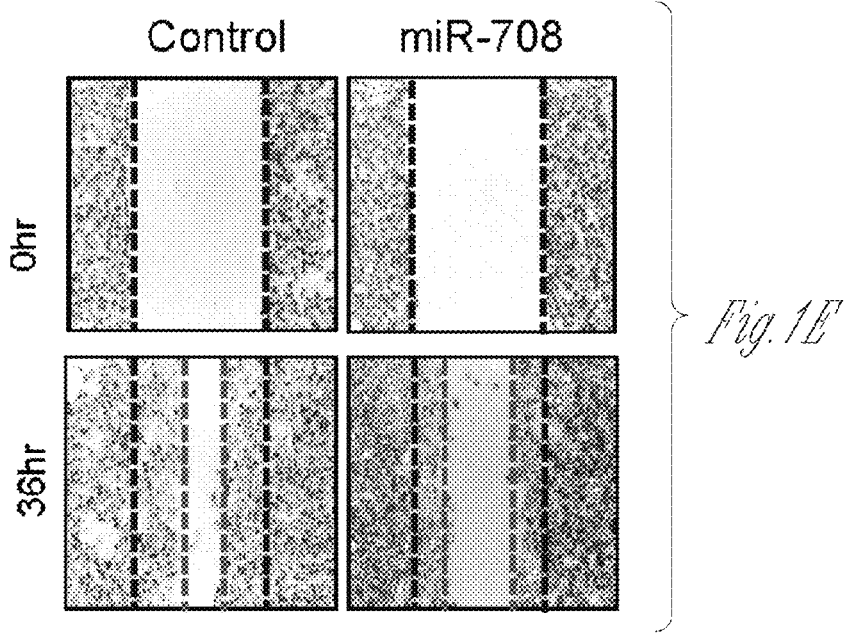
FIG. 1E shows representative images of cell migration assays performed with $1\times10^6$ MDA control (MDA) and MDA expressing miR-708 (MDA-miR-708) cells. Cells were plated into 6 well dishes and allowed to grow for 12 hours, after which a scratch was created and cells imaged immediately (0 hr) and at 36 hr.
Figure 1F:
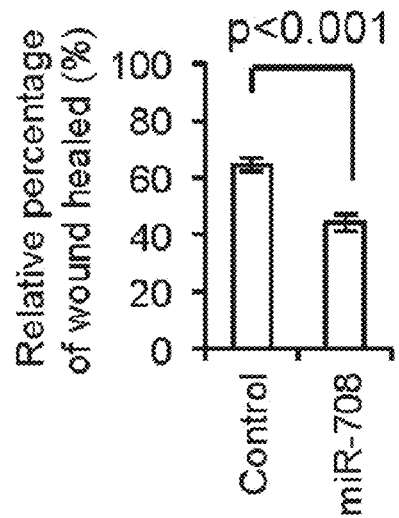
FIG. 1F graphically illustrates cell migration as quantified by the percentage of wound healed area. Data represent mean±s.d. of nine randomly selected areas from three independent experiments. p<0.001.
Figure 1G:
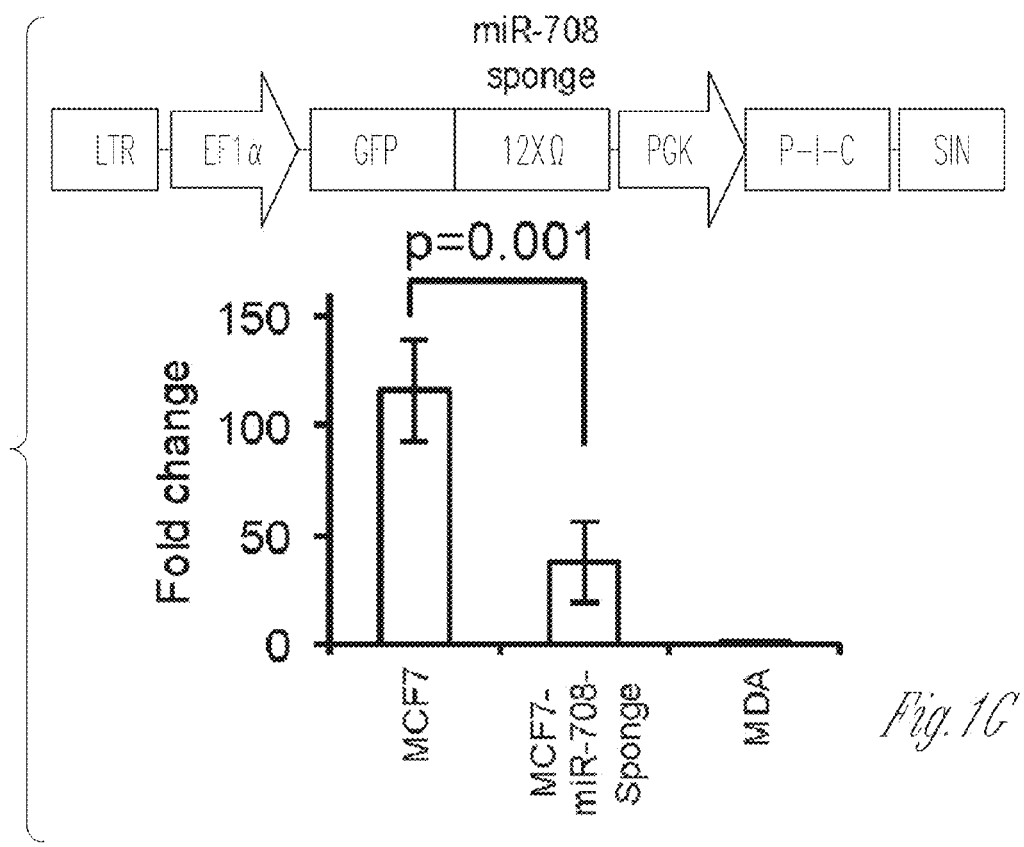
FIG. 1G (upper diagram) shows a schematic of a lentiviral vector used to express miRNA 'sponge.' The sponge includes an EF1α, elongation factor 1 alpha promoter; PGK, Phosphoglycerate kinase gene promoter; P-I-C, Puromycin-IRES-CFP; LTR, long terminal repeat and sponge (12×Ω); with twelve miR-708 binding sites.
Figure 1H:
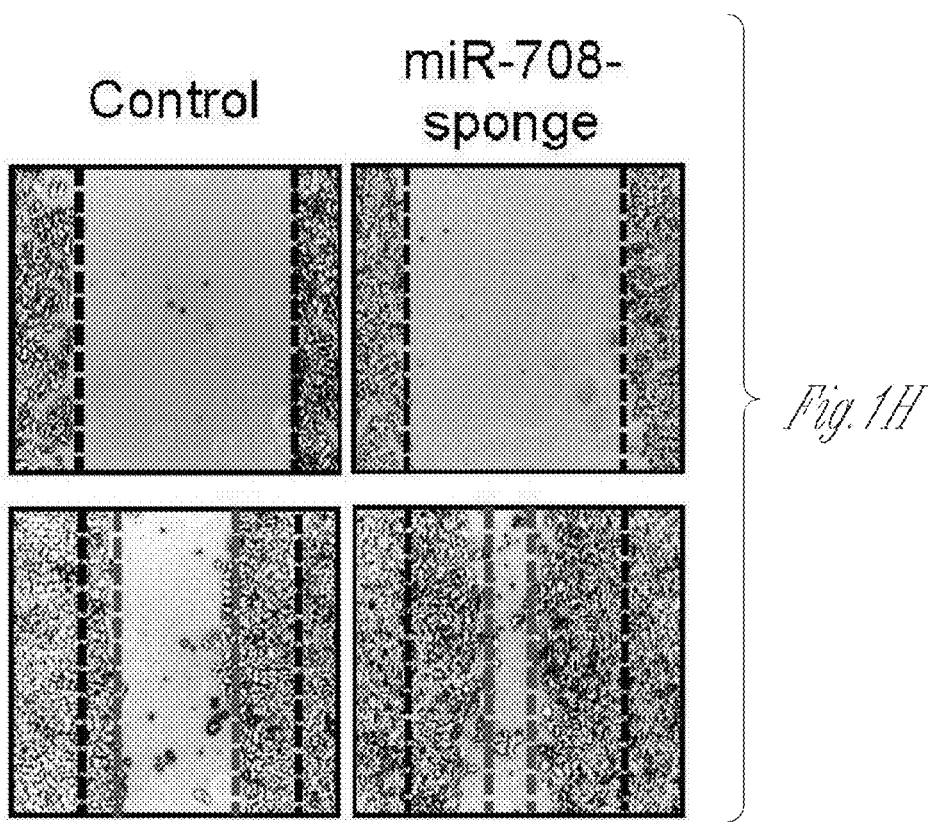
FIG. 1H shows representative images of cell migration during an assay performed with $1\times10^6$ MCF7 control (Control) and MCF7 'sponge' (miR-708-sponge) cells. Cells were plated into 6 well dishes and allowed to grow for 12 hours, after which a scratch was created and cells imaged immediately (0 hr) and 60 hr.
Figure 1I:
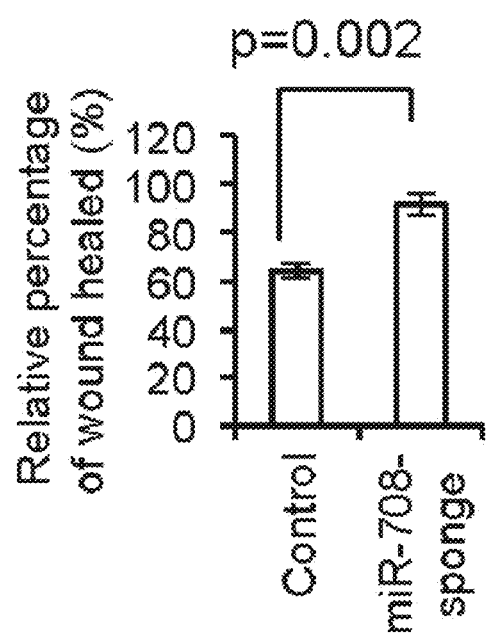
FIG. 1I graphically illustrates cell migration quantified as a percentage of wound healed area from MCF7 control cells (Control) and MCF7 'sponge' cells (miR-708-sponge). Data represent mean±s.d. of nine randomly selected areas from three independent experiments. p=0.002.
Figure 1J:
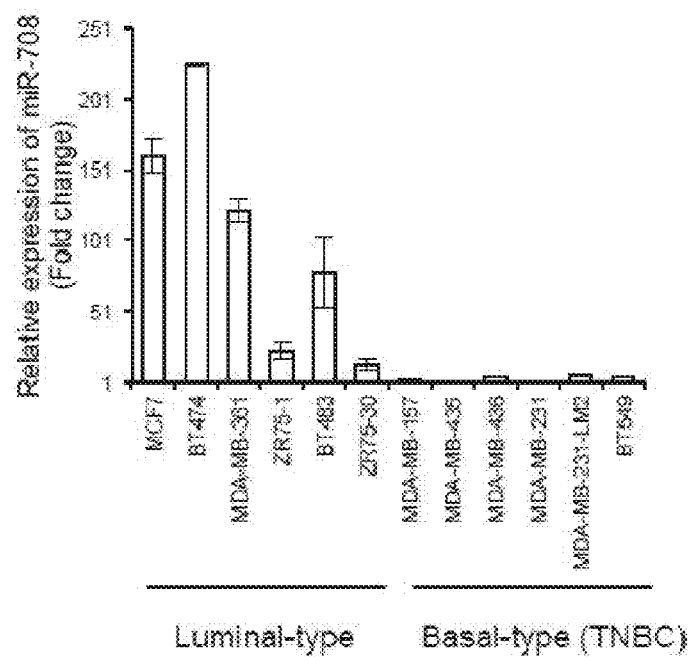
FIG. 1J graphically illustrates miR-708 expression in various cell types.
Figure 1K:
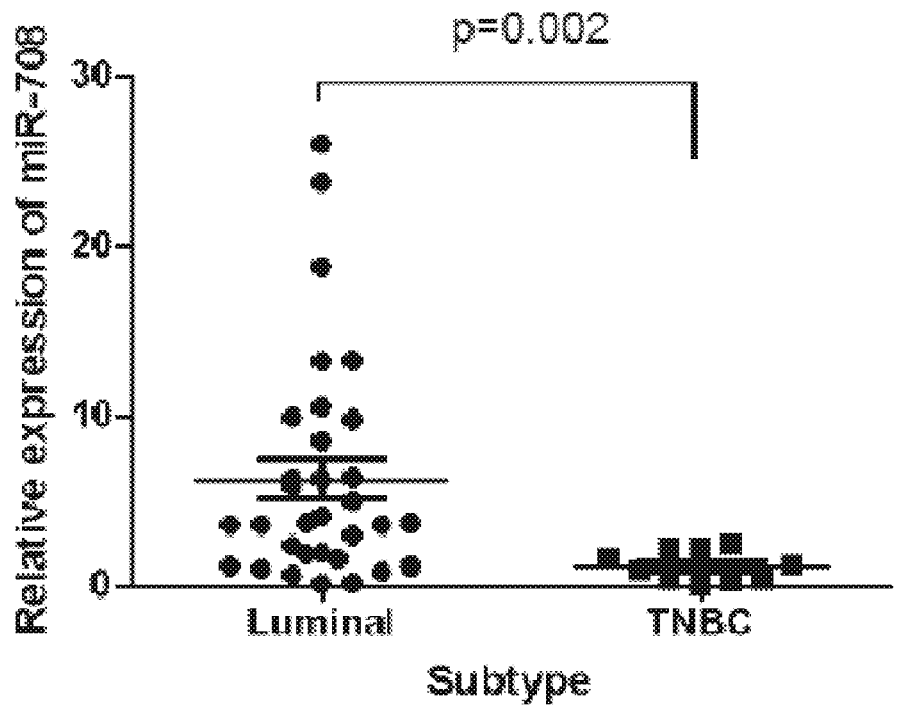
FIG. 1K graphically illustrates miR-708 expression in triple negative breast cancer cells compared to luminal cancer cells.
Figure 1L:
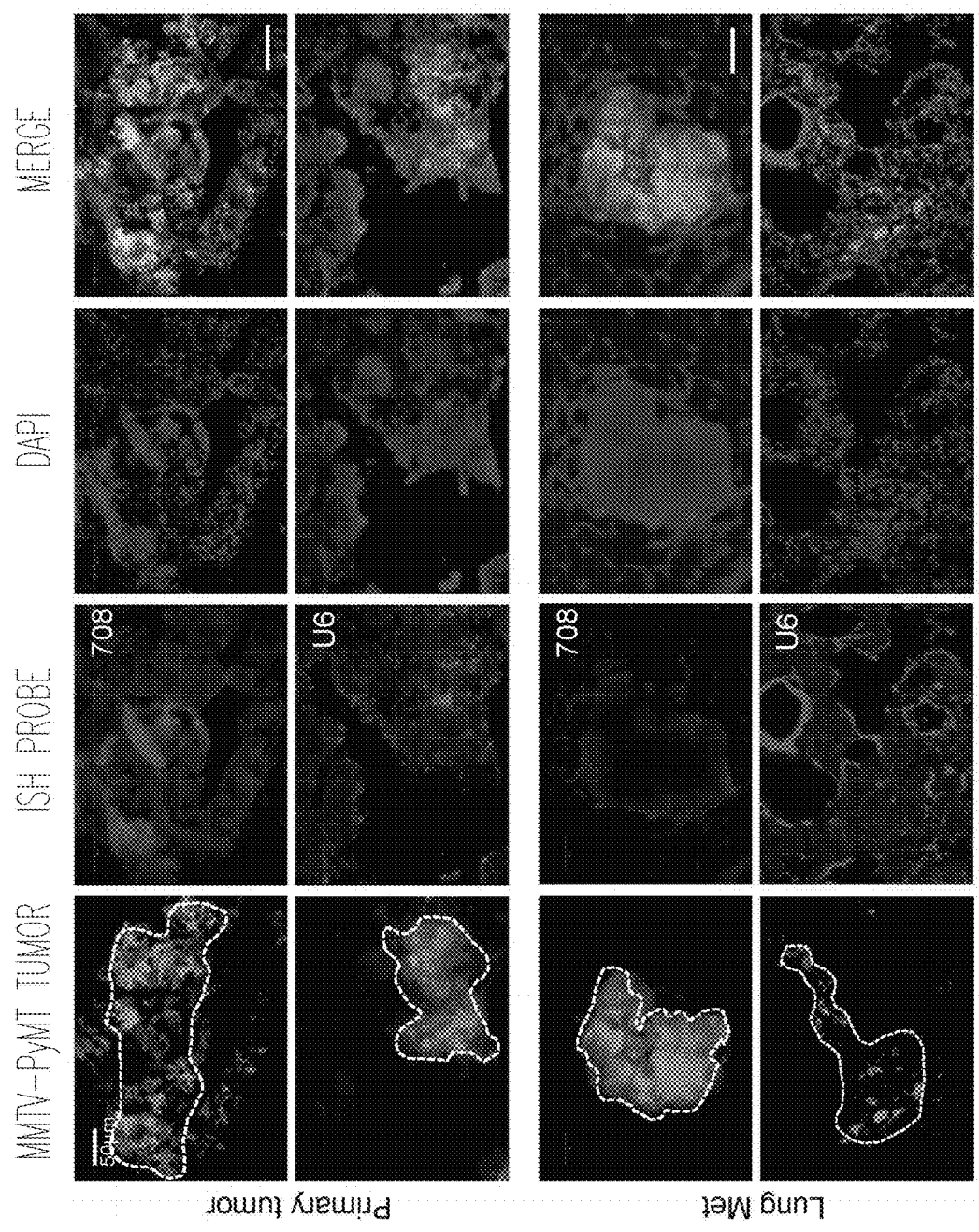
FIG. 1L shows expression of miR-708 and U6 (control) in primary tumor cells and lung metastatic cells.

Example 3 miR-708 is Down-Regulated in Metastatic Tumor Cells Both In Vitro and In Vivo The inventors focused on miR-708 from the list of differentially regulated miRNAs, because as it was one of the most down-regulated miRNAs in metastatic tumor cells. miR-708 is highly conserved across species, as shown by the following sequence alignments of precursor miR-708 from various species. The numbers at the end indicate the length of each precursor. Red letters indicate sequences corresponding to mature miR-708.

transgenes (MMTV-PyMT/WAP-Cre/CAG-CAT-EGFP) (Ahmed et al., 2002). In this mouse system, the Cre transgene results in the expression of GFP in spontaneous mammary tumors, and enables analysis of GFP-tagged primary tumors and matched pulmonary metastases in immunocompetent mice. In situ hybridization with the miR-708 LNA probe revealed distinct miR-708 expression in GFP+ primary breast tumors. However, the GFP+ pulmonary metastases generated from these tumors were devoid of miR-708 expression (FIG. 1D), an observation further confirmed by RT-PCR analysis of several excised primary tumors and matched metastases (FIGS. 1L-1M). As a control, expression of ubiquitously expressing U6 snRNA was observed in both primary tumors and lung metastases (FIG. 1N). Hence, miR-708 expression is suppressed in cancer cells.

```
                        10        20        30        40        50        60        70        80
                ---------+---------+---------+---------+---------+---------+---------+---------+
chimpanzee                     ---------------AACUGCCCUCAAGGAGCUUACAAUCUAGCUGGGGGUAAAUGACUUGCACAUGAACACAACUAGA
(SEQ ID NO: 100)

cow             CUGUGUGUGAAGUGGUAACUGCCCUCAAGGAGCUUACAAUCUAGCUGGGGGUAAACGACUUGCACAUGAACGCAUCUAGA
(SEQ ID NO: 101)

dog                            ------------------------AAGGAGCUUACAAUCUAGCUGGGGGUGAACGGCUUGCACAUGAACGCAACUAGA
(SEQ ID NO: 102)

horse                          -------------GGUAACUGCCCUCAAGGAGCUUACAAUCUAGCUGGGGGUAAAUGACUUGCACAUGAACGCAACUAGA
(SEQ ID NO: 103)

human                          ----------------AACUGCCCUCAAGGAGCUUACAAUCUAGCUGGGGGUAAAUGACUUGCACAUGAACACAACUAGA
(SEQ ID NO: 104)

mouse           CUGUGUUUGAAAUGGGGACUGCCCUCAAGGAGCUUACAAUCUAGCUGGGGGUAGAUGACUUGCACUUGAACACAACUAGA
(SEQ ID NO: 105)

orangutan                      ----------------AACUGCCCUCAAGGAGCUUACAAUCUAGCUGGGGGUAAAUGACUUGCACAUGAACACAACUAGA
(SEQ ID NO: 106)

pig                            --------------------CCCUCAAGGAGCUUACAAUCUAGCUGGGGGUGAAUGACUUGCACAUGAACGCAACUAGA
(SEQ ID NO: 107)

rat                            ----------------GACUGCCCUCAAGGAGCUUACAAUCUAGCUGGGGGUAGAUGACUUGCACUUGAACACAACUAGA
(SEQ ID NO: 108)

Rhesus monkey                  ----------------AACUGCCCUCAAGGAGCUUACAAUCUAGCUGGGGGUAAAUGACUUGCACAUGAACACAACUAGA
(SEQ ID NO: 109)
```

However, the role of miR-708 in tumor metastasis has remained elusive. Analysis of miR-708 expression levels in an expanded panel of human mammary tumor cells showed that miR-708 was markedly suppressed in metastatic cells compared with either non-metastatic (tumorigenic), or primary mammary epithelial cells (FIG. 1B). In agreement with RT-PCR analysis, in situ hybridization with a miR-708 locked nucleic acid (LNA) probe showed abundant miR-708 expression in non-metastatic MCF7 cells, compared with metastatic MDA cells (FIG. 1C). Further analysis showed lower levels of miR-708 in basal subtype breast cancer cells compared to a luminal cancer subtype (FIG. 1J). Consistent with the results observed in cell lines, basal/TNBC specimens from patients showed lower levels of miR-708 compared to the luminal subtype (FIG. 1K). To evaluate miR-708 expression in spontaneous metastatic breast tumors, the MMTV-PyMT transgenic mouse model was used. MMTV-PyMT cells develop primary breast tumors (6-7 weeks of age), which progress to metastases in the lungs (12-16 weeks of age) (Guy et al., 1992) (Gao et al., 2008; Nolan et al., 2007). To reliably detect tumor cells at both the primary sites and in the metastatic organs, mice were used that contain MMTV-PyMT tumor cells and also express two additional Having demonstrated suppression of miR-708 expression in metastatic cancer cells, the anti-metastatic role of miR-708 was evaluated. A lentiviral delivery system (Ryu et al., 2011) was used to stably express miR-708 in the human metastatic breast tumor cell line MDA-MB-231 (MDA) and MDA-MB-LM2 (LM2). FIG. 1O illustrates such expression. MDA cells stably expressing miR-708 exhibited suppressed migration rates compared with controls (FIGS. 1Q-1R). No significant change in cell proliferation was observed (FIG. 1P). Consistent with observations in breast cancer, ectopic expression of miR-708 also suppressed migration of metastatic prostate cancer cells PC3 (FIGS. 1Q-1R). Thus overexpression of miR-708 in metastatic breast cancer cells inhibited migration.

To evaluate whether inhibiting miR-708 in non-metastatic breast cancer cells might stimulate migration, a lentiviral vector was constructed that expressed a miRNA-708 'sponge' (FIG. 1G) to suppress miR-708 expression. The sponge contains multiple miRNA recognition motifs that can to 'soak up' endogenous miR-708, a strategy that has previously been used for other miRNA blockades (Ebert et al., 2007; Valastyan et al., 2009). As shown in FIG. 1G, the 'miR-708 sponge' inhibited miR-708 expression by more than 2-fold. Moreover, this miR-708 loss-of-function enhanced migration rates of MCF-7 cells (FIGS. 1H-1I). These results demonstrate that metastatic breast cancer cells exhibit reduced levels of miR-708, and ectopic expression of miR-708 attenuates cell migration. In contrast, non-metastatic breast cancer cells exhibit increased levels of miR-708, and suppression of miR-708 enhances cell migration.

Example 4 miR-708 Expression Impairs Formation of Metastases

Figure 2A:
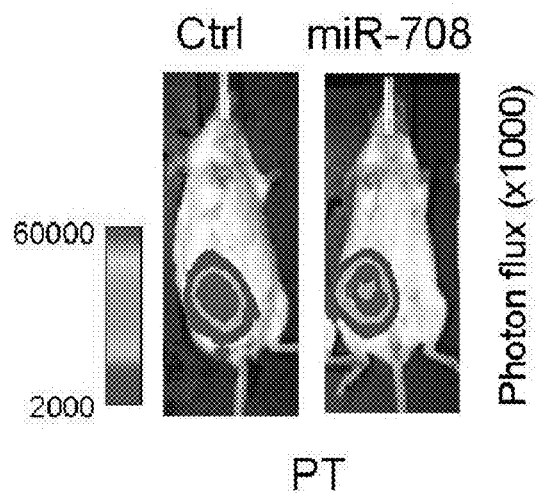
FIG. 2A-2N illustrate that miR-708 expression attenuates metastasis in vivo.
Figure 2B:
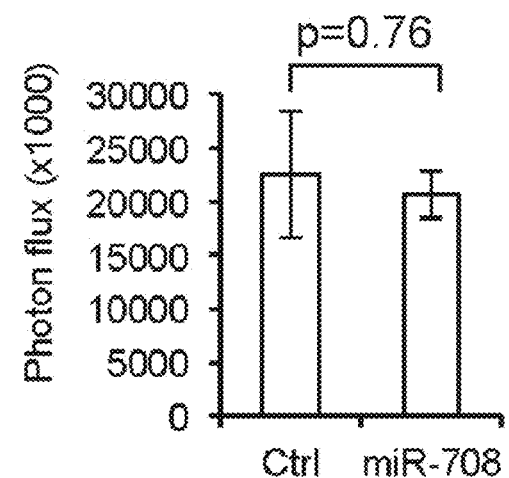
FIG. 2B graphically illustrates photon flux from primary tumors as assessed by bioluminescence measurements at day 60.
Figure 2C:
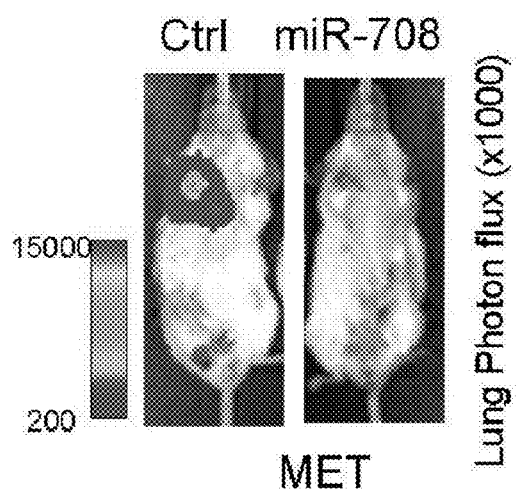
FIG. 2C shows representative bioluminescence images of animals generated as described in FIG. 2A and exhibiting lung metastases (MET) (n=8, per group, p<0.01) at day 74. In this case primary tumors were resected at day 60. The color scale bar depicts the photon flux (photons per second) emitted from these mice.
Figure 2D:
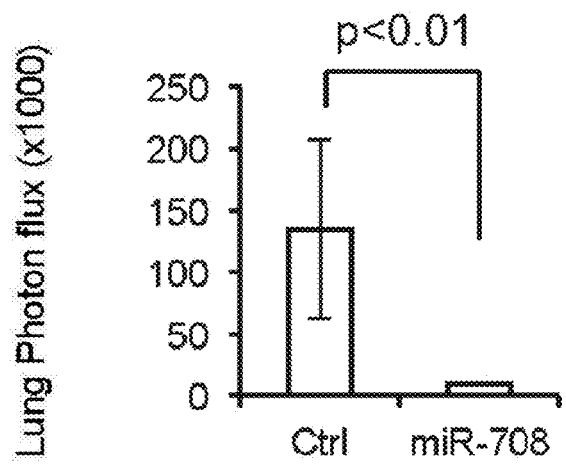
FIG. 2D graphically illustrates photon flux from pulmonary metastases as assessed by bioluminescence measurements on day 74 after tumor cell introduction.
Figure 2I:
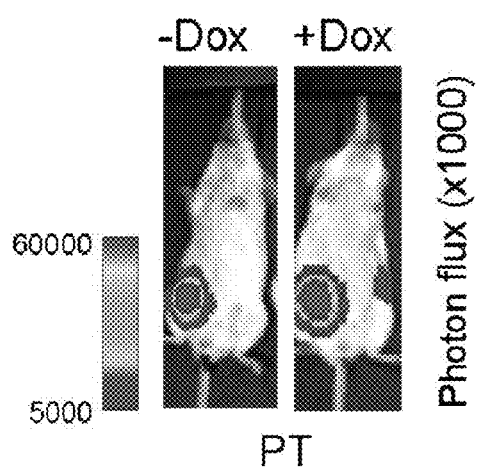
FIG. 2I shows representative bioluminescence images of animals with primary tumors generated following orthotopic injections of MDA-miR-708 in the mammary glands of SCID mice in the presence of Dox (+Dox) or in the absence of Dox (−Dox) (n=10, per group, day 60).
Figure 2J:
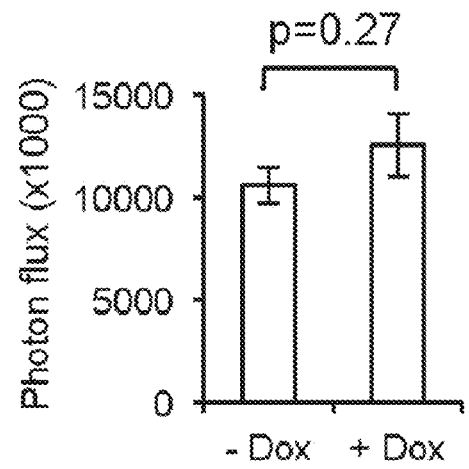
FIG. 2J graphically illustrates photon flux from primary tumors as assessed by bioluminescence measurements (day 60, p=0.27 between groups).
Figure 2K:
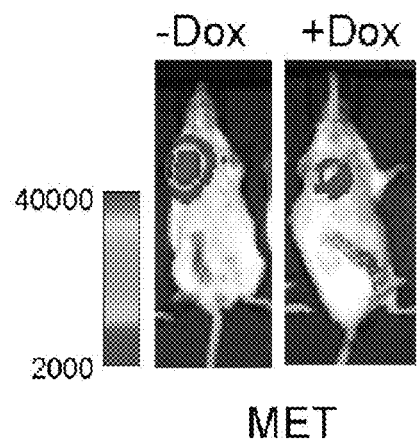
FIG. 2K shows representative bioluminescence images of animals exhibiting lung metastases from the primary tumors shown in FIG. 2I on day 74 after tumor cell implantation, where the animals were treated with Dox (+Dox) or not treated with Dox (−Dox). The primary tumors were resected at day 60.
Figure 2L:
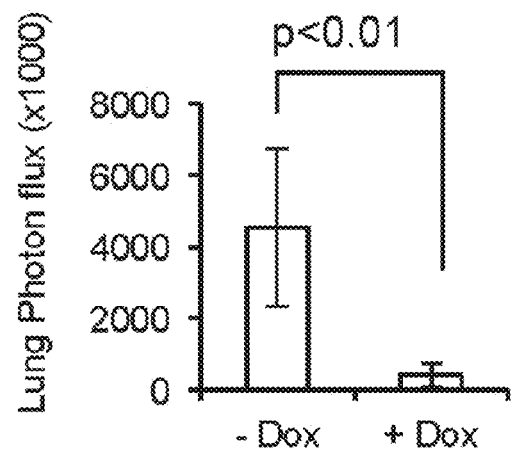
FIG. 2L graphically illustrates photon flux from pulmonary metastases assessed by bioluminescence measurements. p<0.01 between groups.
Figures 2M, 2N:
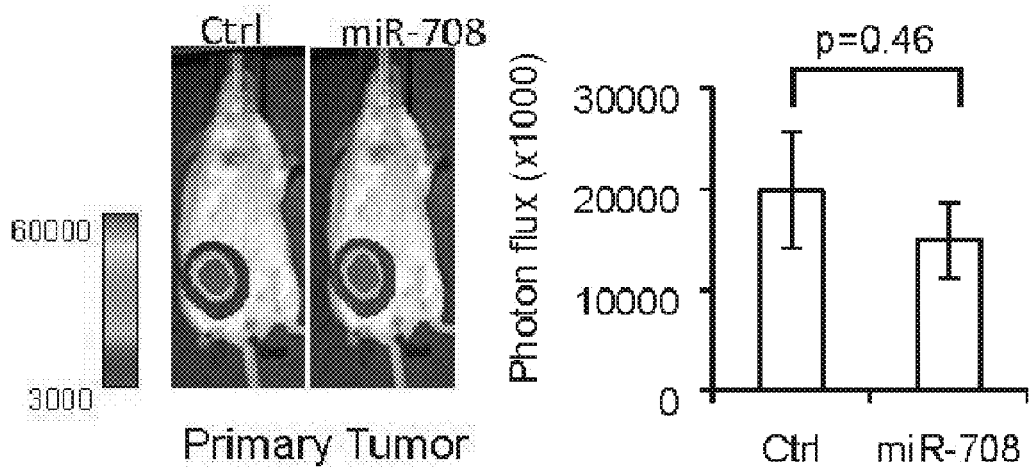
FIG. 2M shows representative bioluminescence (BLI) images of animals with primary tumors derived from orthotopic injections of MDA-LM2-miR-708 cells and control MDA-LM2 cells into the mammary fat pad (n=10 per group). The color scale bar depicts the photon flux (photons per second) emitted from these mice.

To explore whether miR-708-enhanced cell migration directly related to metastasis of breast cancer cells in vivo, MDA cells were injected with stably expressing miR-708 and a luciferase reporter transgene orthotopically into the mammary fat pad of mice. Bioluminescence imaging (BLI) showed no significant difference in the primary tumor growth in these animals as a result of miR-708 expression (FIGS. 2A-2B). Notably however, miR-708 expression suppressed lung metastases in these animals, compared with controls (FIGS. 2C-2D). The anti-metastatic role of miR-708 was confirmed in another highly metastatic breast cancer variant MDA-LM2 (LM2). Consistent with the MDA observations, primary tumor growth in animals with LM2 cells that over-expressed miR-708 remained unperturbed. However there was a pronounced reduction in lung metastases (FIGS. 2E-2F, 2M-2N) in these animals. To exclude the remote possibility that constitutive expression of miR-708 during the establishment of stable breast cancer cells could have inadvertently conferred an anti-metastatic phenotype, doxycycline-based conditional expression of miR-708 was used. Thus, acute miR-708 expression could then be generated only after the cells were administered in vivo. miR-708 was cloned into a doxycycline inducible vector and the specific and tight regulation of miR-708 expression by the inducible system was assessed in vitro (FIGS. 2G-2H). Administration of these cells into the mammary fat pad of SCID mice followed by doxycycline-mediated induction of miR-708 resulted in attenuated metastases (FIGS. 2K-2L), while primary tumor growth was not affected (FIGS. 2I-2J), consistent with results using the constitutive system. Although miR-708 loss-of-function enhanced migration rates in the MCF7 model, it was not sufficient to promote metastases in vivo (data not shown), suggesting that the MCF7 cells may need additional pro-metastatic properties to accomplish successful metastasis.

Taken together, these results demonstrate that metastatic breast cancer cells exhibit reduced levels of miR-708, and that expression of miR-708 attenuates cell migration in vitro and metastatic tumor formation in vivo. miR-708 did not impact primary tumor growth, which provided a unique opportunity to determine its precise role in metastatic progression.

Figure 3A:
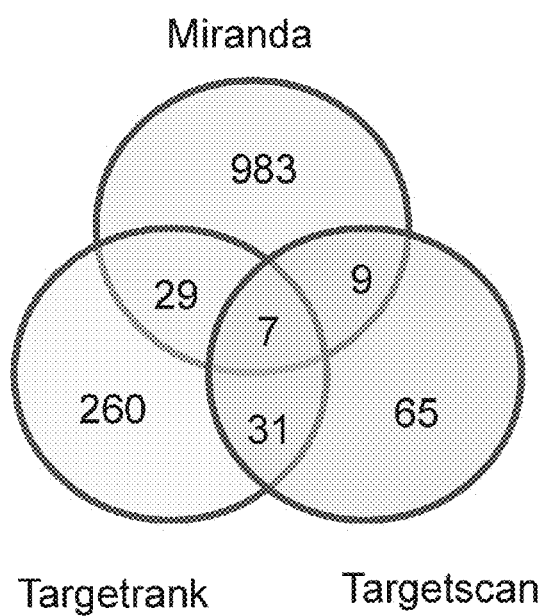
FIG. 3A-3J illustrate that miR-708 regulates expression of Neuronatin.

Example 5 miR-708 Regulates Expression of Neuronatin, a Regulator of Intracellular Calcium To identify downstream effectors of miR-708, mRNA target predicting algorithms (TargetScan, Miranda, and Target Rank) were used that were based on the presence of binding sites in the 3'-untranslated region (3'-UTR). Of the seven genes that overlapped amongst these algorithms (FIG. 3A), four genes (Gon4l, Hoxb3, Nnat, Cntfr) were selected that were associated with metastasis-related functions such as cell proliferation, apoptosis, cell cycle, migration, adhesion, invasion, and cell differentiation (FIG. 3H). Six more genes (Ssh2, Epdr1, Ssrp1, Hnrnpk, Ywahz, Usp9x) were selected that were predicted by more than one algorithm with prometastatic function (FIG. 3H), and three additional genes (CD44, Enah, Ntrk2) were also selected that had multiple binding sites as determined by an independent algorithm developed in-house. The following table shows some of the genes associated with metastasis, cell migration, development and differentiation.

TABLE 6 miR-708 downstream genes associated with metastasis, cell migration, development and differentiation.

| Function | Genes |
| --- | --- |
| Metastasis | HNRNPK |
| Migration | EPDR1* |
| Development & Differentiation | HoxB3*, GON4L, NNAT*†, SSH2, SSRP1, CD44**, ENAH**, NTRK2**, USP9X, YWAH |

Figure 3B:
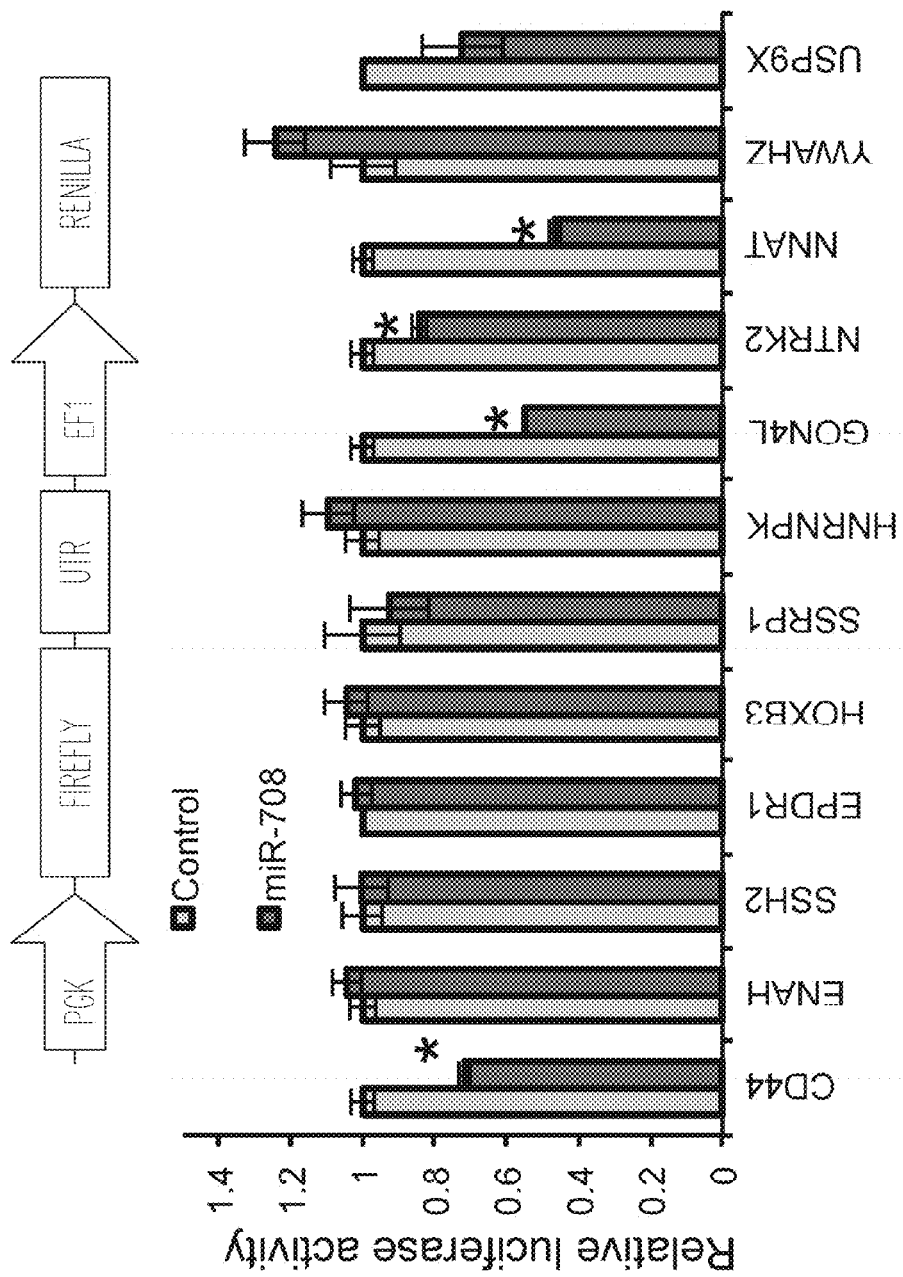

*Significantly up-regulated gene expression (ratio ≥ 2)
†binding site with perfect homology
**has multiple binding sites To establish a direct relationship between miR-708 and predicted target genes, the 3'-UTR of key target genes were cloned into a Dual luciferase UTR vector (FIG. 3B). Notably, 3'-UTR of Nnat (Neuronatin), Gon4l, Ntrk2 (neurotrophic tyrosine receptor kinase receptor 2), and CD44 showed significant repression by miR-708 (FIG. 3B). This suppression was confirmed at the protein level by Western blot analysis for proteins for which reliable antibodies were available.

Figure 3C:
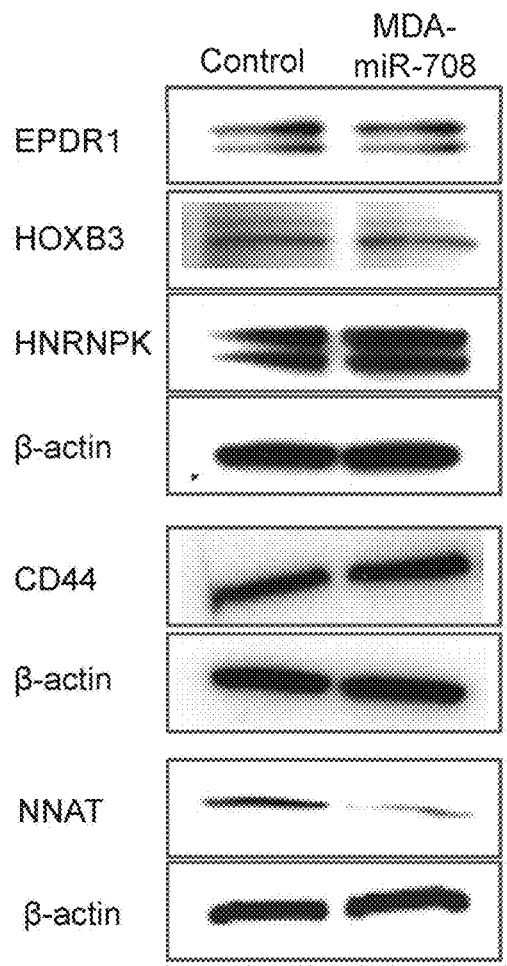

Of the genes tested, only expression of NNAT protein was significantly decreased by miR-708 (FIG. 3C). These results are in agreement with RT-PCR analysis (FIG. 3I). Akt2 which was recently shown to be a target of miR-708 in primary prostate cancer (Saini et al., 2012) was also evaluated. However, Akt2 was not suppressed by miR-708 in breast cancer (data not shown).

Consistent with the constitutive expression system, doxycycline-mediated acute and conditional expression of miR-708 resulted in significant reduction in NNAT levels (FIG. 3J), obviating the possibility that selection effects during culture of constitutively expressing miR-708 stable cell lines may be responsible for Nnat suppression. An inverse correlation between miR-708 and Nnat levels was observed in MCF7 and MDA cells (FIGS. 3I-3J; FIG. 1B). To further validate Nnat as a direct target of miR-708 regulation, the 3'-UTR sequence of Nnatwas evaluated and is shown below as SEQ ID NO:110, which has a miR-708 binding site (underlined segment; see also FIG. 3D).

```
  1 TGAGGCCCCA GCTCCCAGCC CTGGGCGGCC GTATCATCAG

41 GTGCTCCTGT GCATCTCGGC CAGCACGGGA GCCAGTGCCG

81 CGCAGGAATG TGGGGTCCCC TGTGTTCCCT CGCCAGAGGA

121 GCACTTGGCA AGGTCAGTGA GGGGCCAGTA GACCCCCGGA

161 GAAGCAGTAC CGACAATGAC GAAGATACCA GATCCCTTCC

201 CAACCCCTTT GCACCGGTCC CACTAAGGGG CAGGGTCGAG

241 AGAGGAGGGG GGATAGGGGG AGCAGACCCC TGAGATCTGG
```

-continued

```
281 GCATAGGCAC CGCATTCTGA TCTGGACAAA GTCGGGACAG

321 CACCATCCCA GCCCCGAAGC CAGGGCCATG CCAGCAGGCC

361 CCACCATGGA AATCAAAACA CCGCACCAGC CAGCAGAATG

401 GACATTCTGA CATCGCCAGC CGACGCCCTG AATCTTGGTG

441 CAGCACCAAC CGCGTGCCTG TGTGGCGGGA CTGGAGGGCA

481 CAGTTGAGGA AGGAGGGTGG TTAAGAAATA CAGTGGGGCC

521 CTCTCGCTGT CCCTTGCCCA GGGCACTTGC ATTCCAGCCT

561 CGCTGCATTT GCTCTCTCGA TTCCCCTTTC CTCCTCACTG

601 CCTCCCAAGC CCACCCTACT CCAAAATAAT GTGTCACTTG

641 ATTTGGAACT ATTCAAGCAG TAAAAGTAAA TGAATCCCAC

681 CTTTACTAAA ACACTTTCTC TGAACCCCCC TTGCCCCTCA

721 CTGATCTTGC TTTTCCCTGG TCTCATGCAG TTGTGGTCAA

761 TATTGTGGTA ATCGCTAATT GTACTGATTG TTTAAGTGTG

801 CATTAGTTGT GTCTCCCCAG CTAGATTGTA AGCTCCTGGA

841 GGACAGGGAC CACCTCTACA AAAAATAAAA AAAGTACCTC

881 CCCTGTCTCG CACAGTGTCC CAGGACCCTG CGGTGCAGTA

921 GAGGCGCACC AAAA
```

The 3'-UTR sequence of Nnat has perfect matches both in the seed and flanking sequences for miR-708 (FIG. 3D), and both miR-708 and the binding site in the Nnat are highly conserved across species, as shown below.

| SEQ | | |
|---|---|---|
| ID NO: 123 | hsa-miR-708 | 3'-GGGUCGAUCUAACAUUCGAGGA-5' |
| ID NO: 124 | Human-NNAT-3'UTR | 5'-CCCAGCUAGAUUGUAAGCUCCU-3' |
| ID NO: 125 | Chimpanzee-NNAT-3'UTR | 5'-CCCAGCUAGAUUGUAAGCUCCU-3'- |
| ID NO: 126 | Gibbon-NNAT-3'UTR | 5'-CCCAGCUAGAUUGUAAGCUCCU-3'- |
| ID NO: 127 | Rhesus_monkey-NNAT-3'UTR | 5'-CCCAGCUAGAUUGUAAGCUCCU-3'- |
| ID NO: 128 | Marmoset-NNAT-3'UTR | 5'-CCCAGCUAGAUUGUAAGCUCCU-3'- |
| ID NO: 129 | Rat-NNAT-3'UTR | 5'-CCCAGCUAGAUUGUAAGCUCCU-3'- |
| ID NO: 130 | Horse-NNAT-3'UTR | 5'-CCCAGCUAGAUUGUAAGCUCCU-3'- |
| ID NO: 131 | Cow-NNAT-3'UTR | 5'-CCCAGCUAGAUUGUAAGCUCCU-3'- |

Figure 3D:
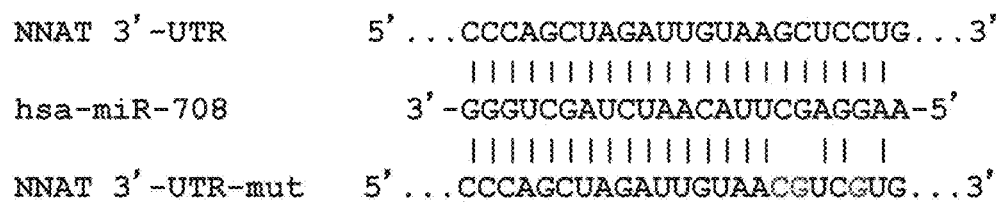
Figure 3E:
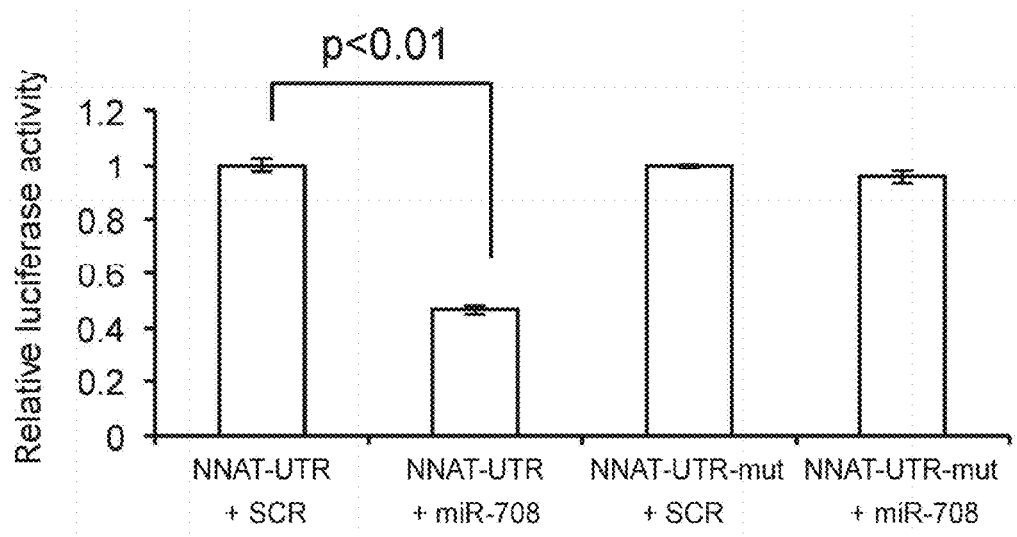
Figure 3F:
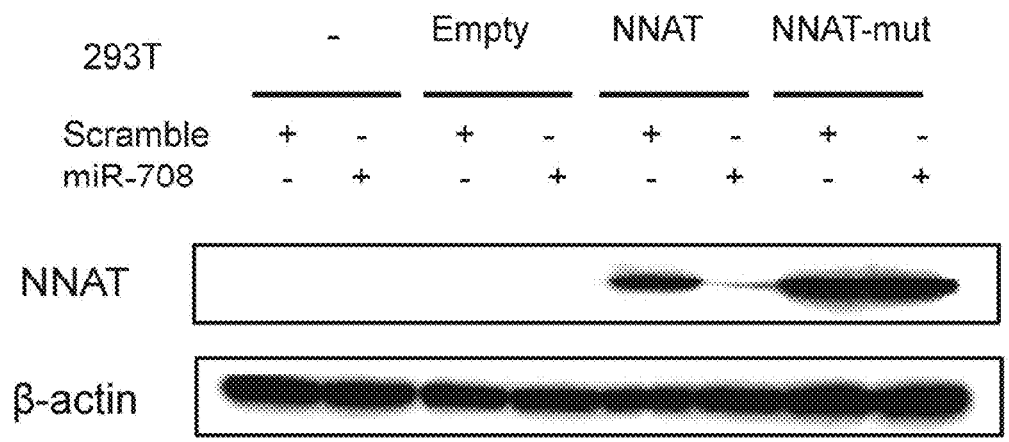
Figures 3G, 3H:
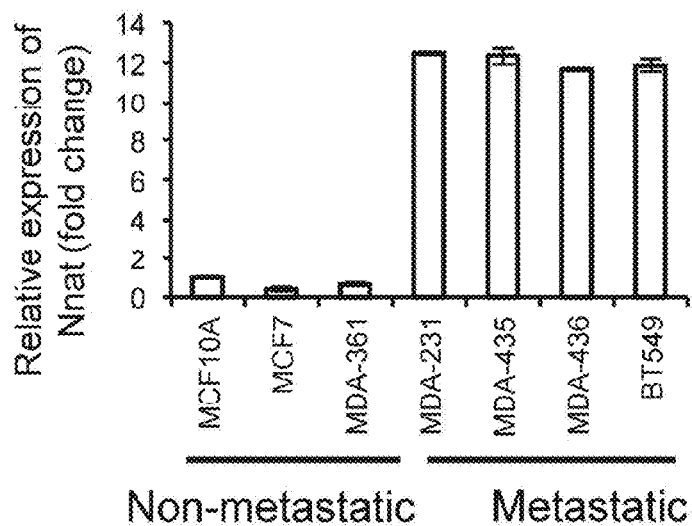
Figure 3I:
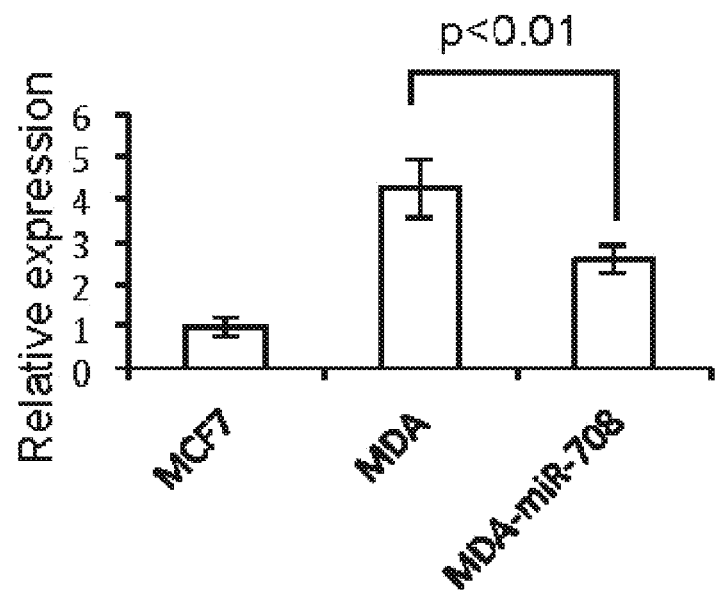
Figure 3J:
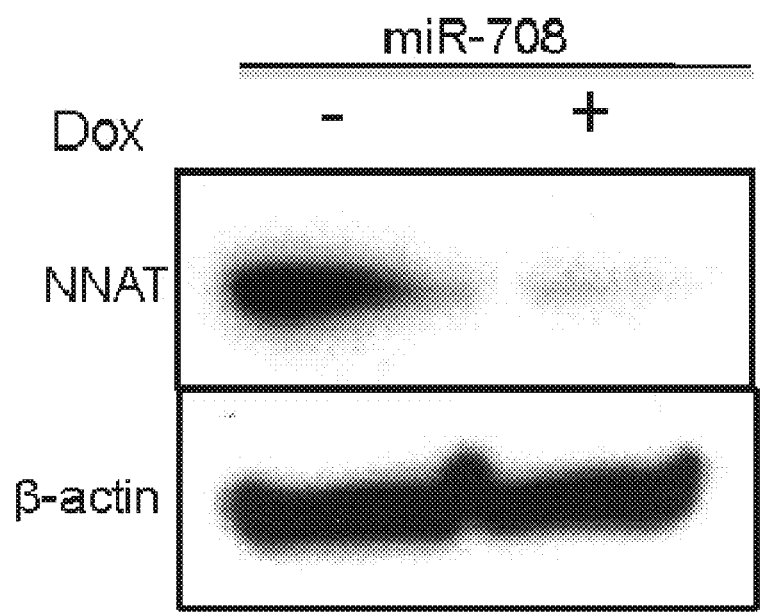

Based on this sequence information, mutations were generated in the miR-708 binding site to abrogate the miR-708-Nnat 3'-UTR interaction (FIG. 3D). As expected, while Nnat with an intact UTR was effectively suppressed by miR-708, Nnat 3'-UTR carrying a mutated binding site was refractory to suppression by miR-708 (FIG. 3E), showing that Nnat may be regulated by miR-708. To determine if the NNAT produced by the Nnat with a 3'-mut UTR was also refractory to miR-708-mediated suppression, a cDNA was expressed that harbored a mutation in the 3'-UTR containing the miR-708 binding sites. This mutant UTR abolished miR-708-mediated suppression of the NNAT, further confirming that Nnat expression is negatively regulated by miR-708 (FIG. 3F).

Figure 5A:
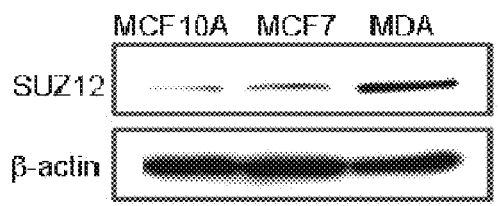
FIG. 5A-5S illustrates that the Polycomb complex, PRC2, suppresses miR-708 expression in metastatic tumor cells.
Figure 5B:
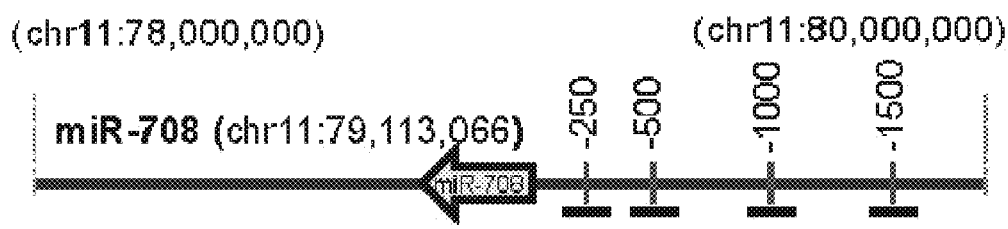
FIG. 5B shows a schematic diagram illustrating the genomic location of miR-708. The upstream regions used for ChIP-PCR are indicated.
Figure 5C:
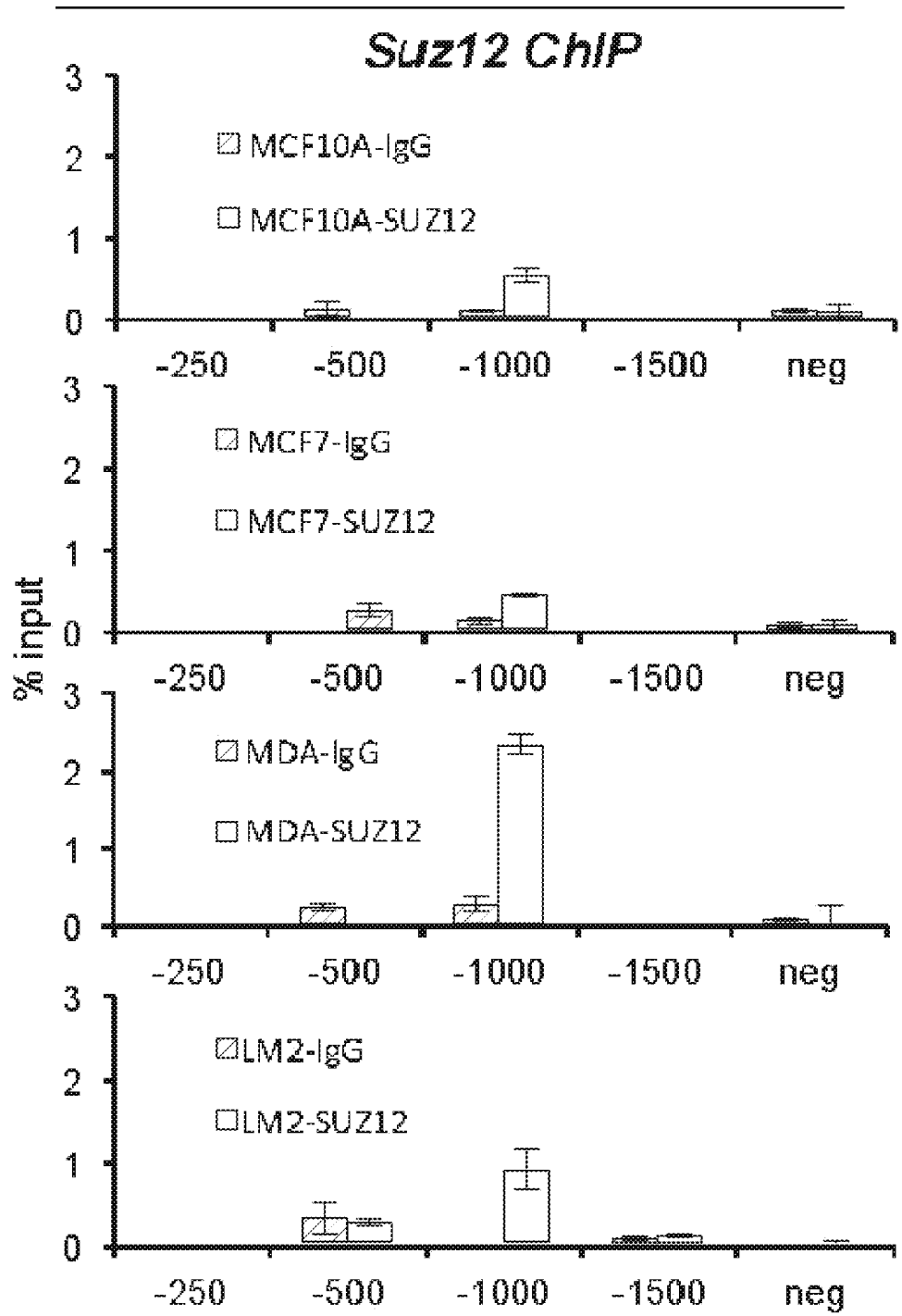
FIG. 5C graphically illustrates PCR results of immunoprecipitated chromatin showing % input of Suz12 at the indicated locations upstream of miR-708 in non-tumorigenic breast cells (MCF1 OA), tumorigenic and non-metastatic breast cancer cells (MCF7) and metastatic breast cancer cells (MDA, LM2). As shown, a 5-fold change was observed in MDA compared to MCF7. IgG was used as control. Data are representative of three independent experiments (mean±SD.).
Figure 5D:
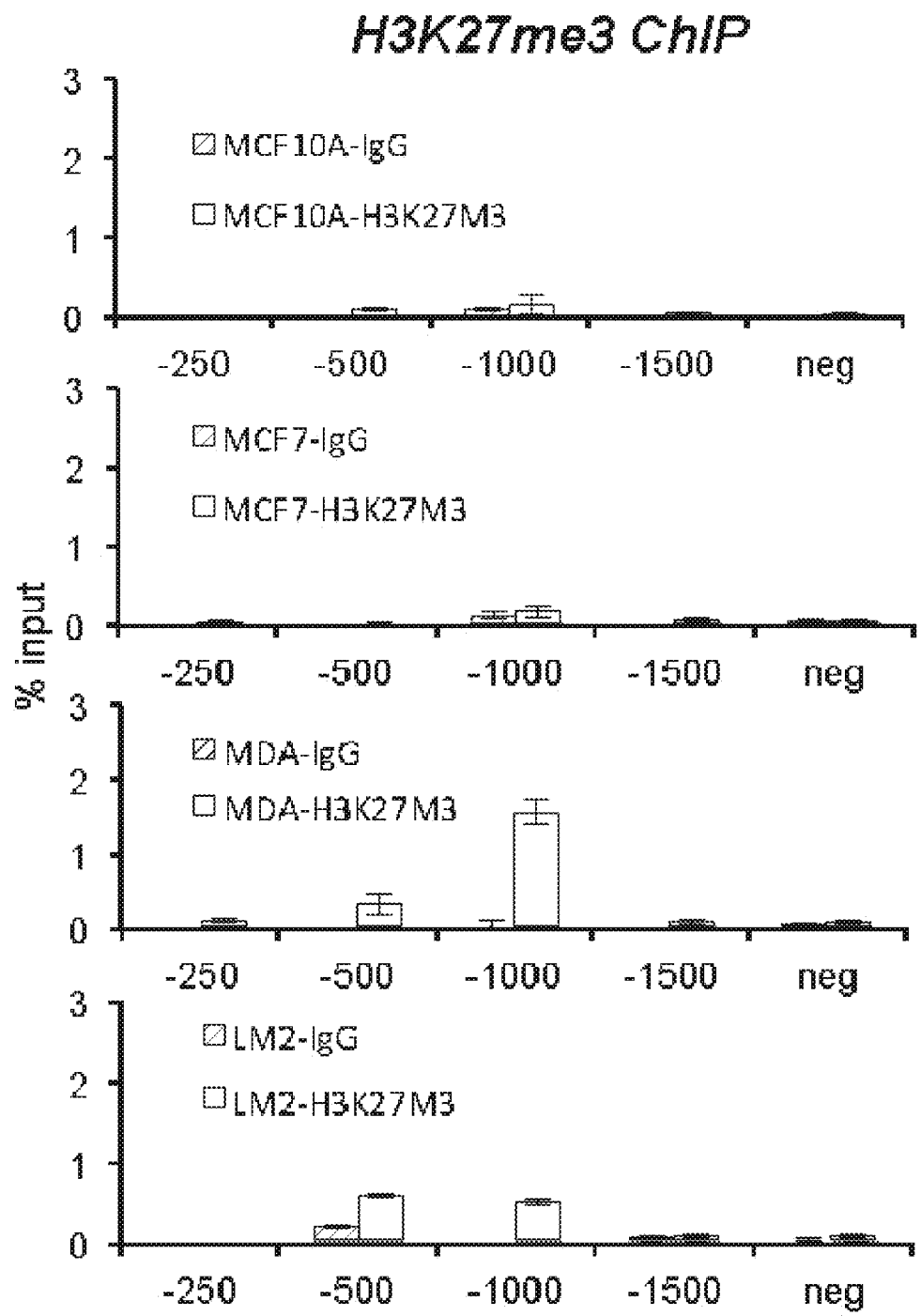
FIG. 5D graphically illustrates PCR results of immunoprecipitated chromatin showing % input of H3K27 trimethylation at indicated locations upstream of miR-708. As shown, a 9-fold change was observed in MDA compared to MCF7. Data are representative of three independent experiments (mean±SD.).
Figures 3, 5E:
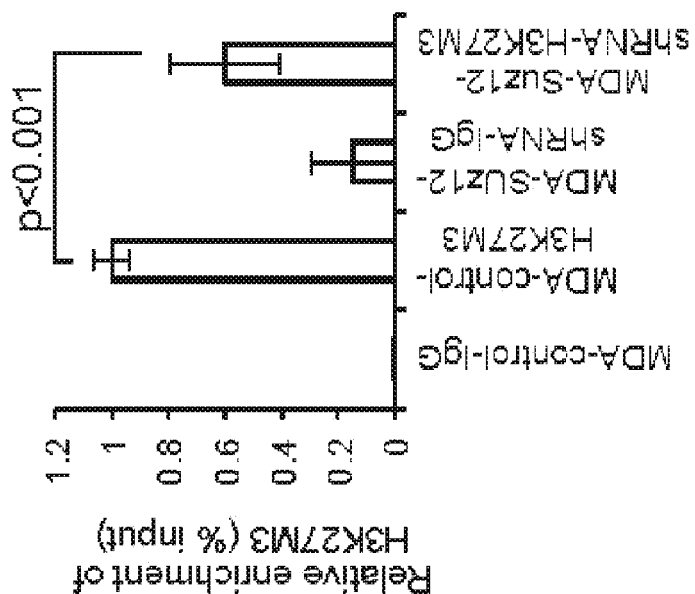
FIG. 5E-1 to 5E-3 graphically illustrate that siRNA knock down of Suz12 (FIG. 5E-1, left panel) relieves repression of miR-708 expression (FIG. 5E-2, middle panel) and increases H3-K27 trimethylation (FIG. 5E-3, right panel) in metastatic MDA cells.
Figures 2, 5E:
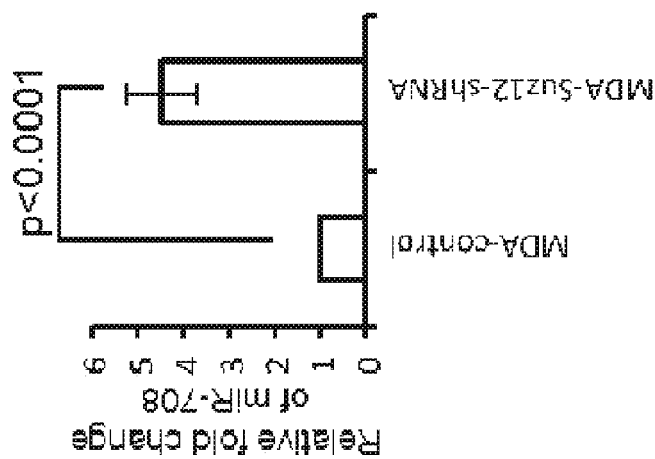
Figures 1, 5E:
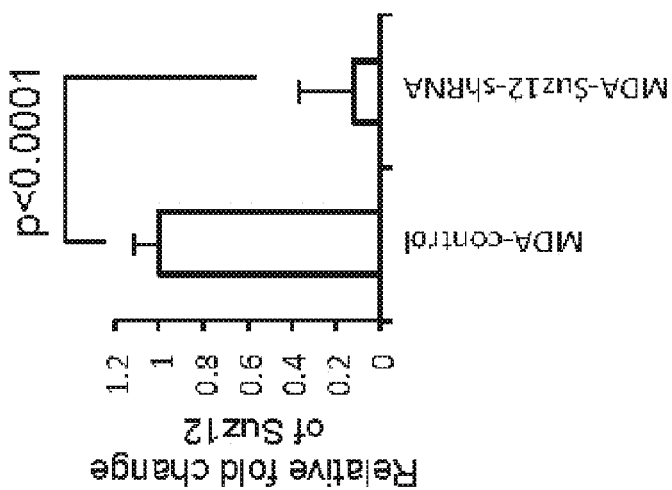

Experiments were then performed to determine if there was an inverse correlation between miR-708 and Nnat levels in the breast cancer cell lines examined as described for FIG. 1. Notably, Nnat levels inversely correlated with miR-708 expression (FIG. 3G). Taken together, these results firmly establish an inverse correlation between miR-708 and Nnat levels, and suggest that miR-708 regulates Nnat expression through the binding site in the 3'-UTR.

Example 6 miR-708 Mediated Suppression of Neuronatin Impacts the Release of Store Operated Ca2+

This Example addresses whether suppression of Nnat by miR-708 has functional consequences in metastasis.

NNAT is a membrane protein in the endoplasmic reticulum (Joseph et al., 1994) that resembles phospholamban, an inhibitor of sarcoplasmic reticulum $Ca^{2+}$-ATPase (SERCA). NNAT-mediated regulation of intracellular $Ca^{2+}$ has been implicated in neural induction in embryonic stem cells (Lin et al., 2010) and in adipogenesis (Suh et al., 2005). Notably, the second messenger $Ca^{2+}$ is one of the critical regulators of cell migration (Pettit and Fay, 1998; Yang et al., 2009).

The inventors hypothesized that miR-708-mediated targeting of Nnat may lead to impaired regulation of intracellular $Ca^{2+}$. This would explain the inhibitory effect on the migratory phenotype of metastatic tumor cells observed earlier (see, e.g., FIG. 1E). To test this hypothesis, MDA and MDA-miR-708 cells were loaded with the intracellular calcium indicator, Fura-2, and the 340/380 ratios were monitored in the absence and presence of exogenous ATP. ATP binds ATP receptors on the cell surface, resulting in the cleavage of PIP2 into IP3 and DAG. IP3 binds IP3 receptors on the endoplasmic reticulum membrane, and releases ionized calcium from the endoplasmic reticulum (Vandewalle et al., 1994), (Berridge et al., 2003; Swanson et al., 1998). Thus, ATP-stimulated calcium release from endoplasmic reticulum was used to evaluate the consequence of Nnat suppression by miR-708.

Figure 4A:
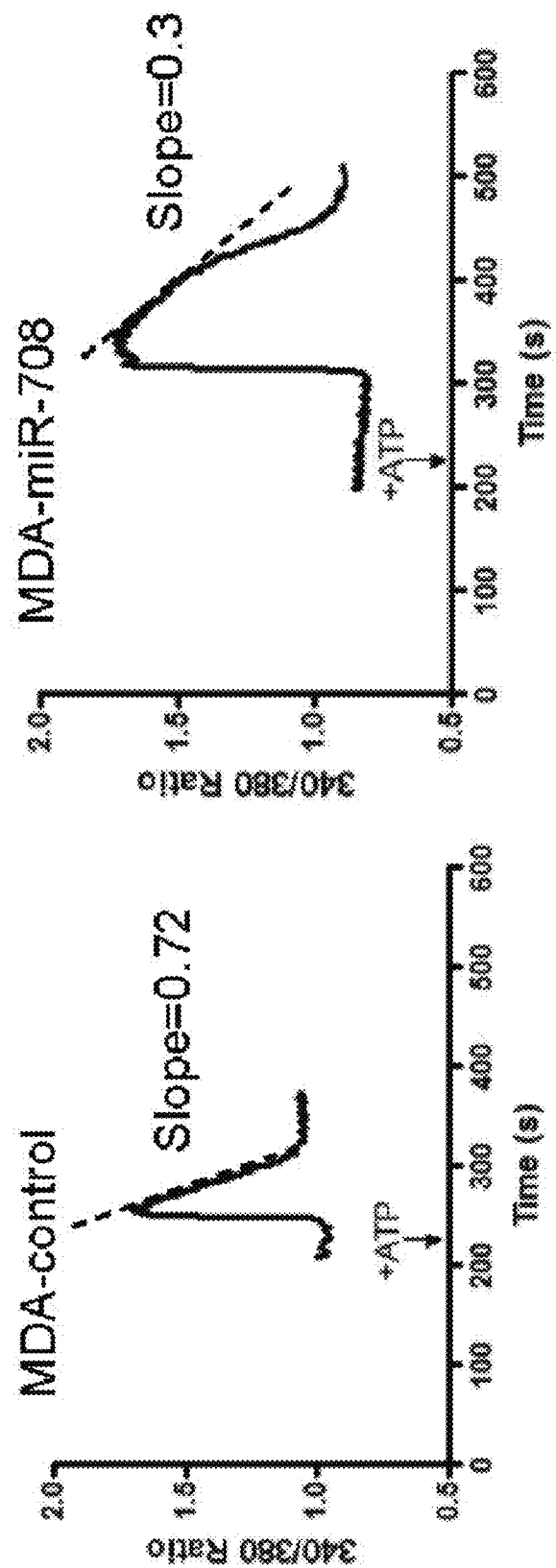
FIG. 4A-4U illustrate that miR-708 mediated suppression of Neuronatin results in aberrant $Ca^{2+}$ regulation and inactivation of Erk and FAK.
Figure 4B:
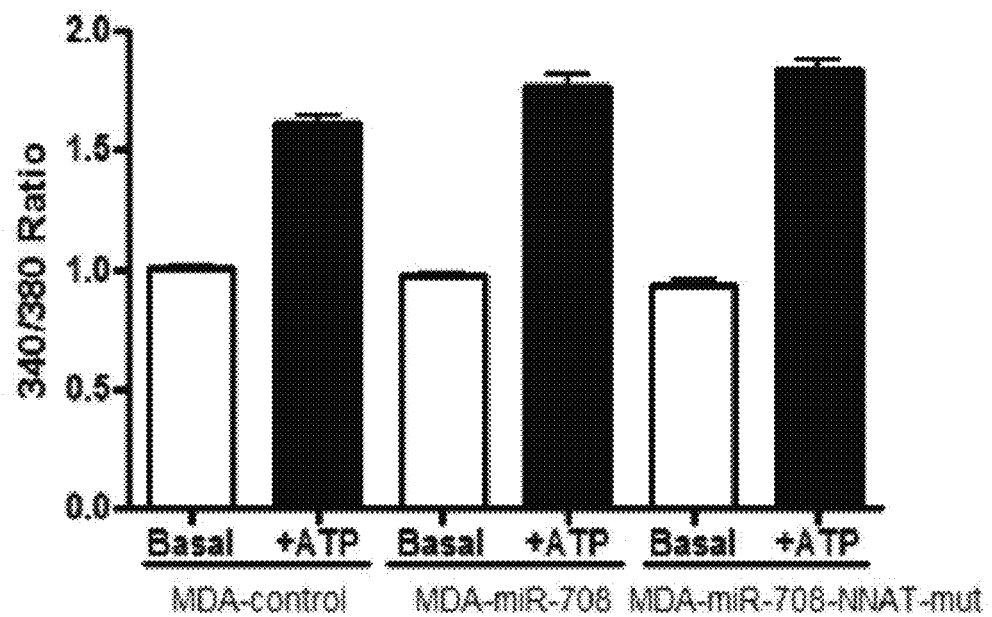
FIG. 4B graphically illustrates peak calcium responses due to ATP stimulation (MDA-control (1.61±0.04), MDA-miR-708 (1.77±0.06), and MDA-miR-708-Nnat-mut (1.84±0.05), respectively. For the ratios, pre-ATP stimulation (basal) values were 1.00±0.01, 0.97±0.01, 0.93±0.02, respectively. n=115, 107 and 72 cells respectively). Transfection efficiency in MDA-miR-708-Nnat-mut cells was 30%. Data are shown as means±SEM.
Figure 4C:
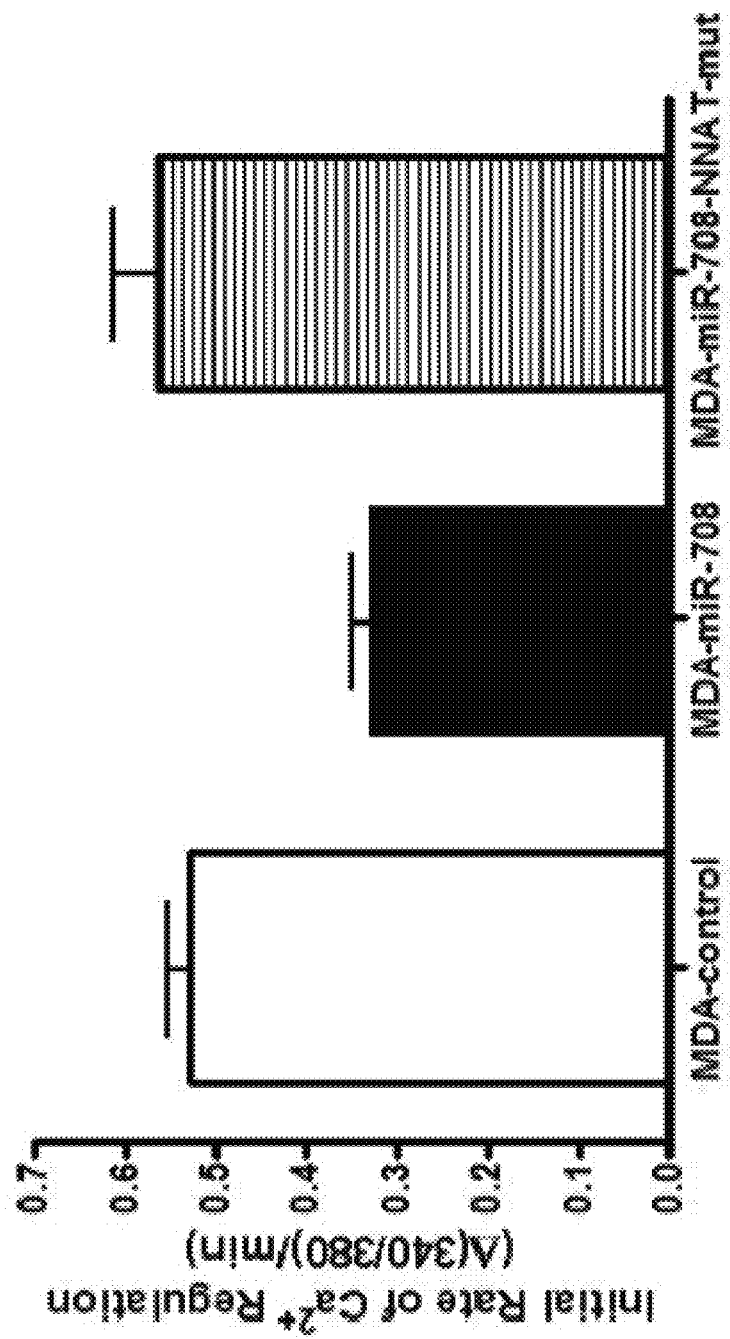
FIG. 4C graphically illustrates the initial rate of calcium regulation back to baseline. (Values for MDA-control, MDA-miR-708, MDA-miR-708-Nnat-mut respectively, 0.52±0.03, 0.33±0.02, 0.56±0.05 with n=115, 105 and 72 cells.)
Figure 4D:
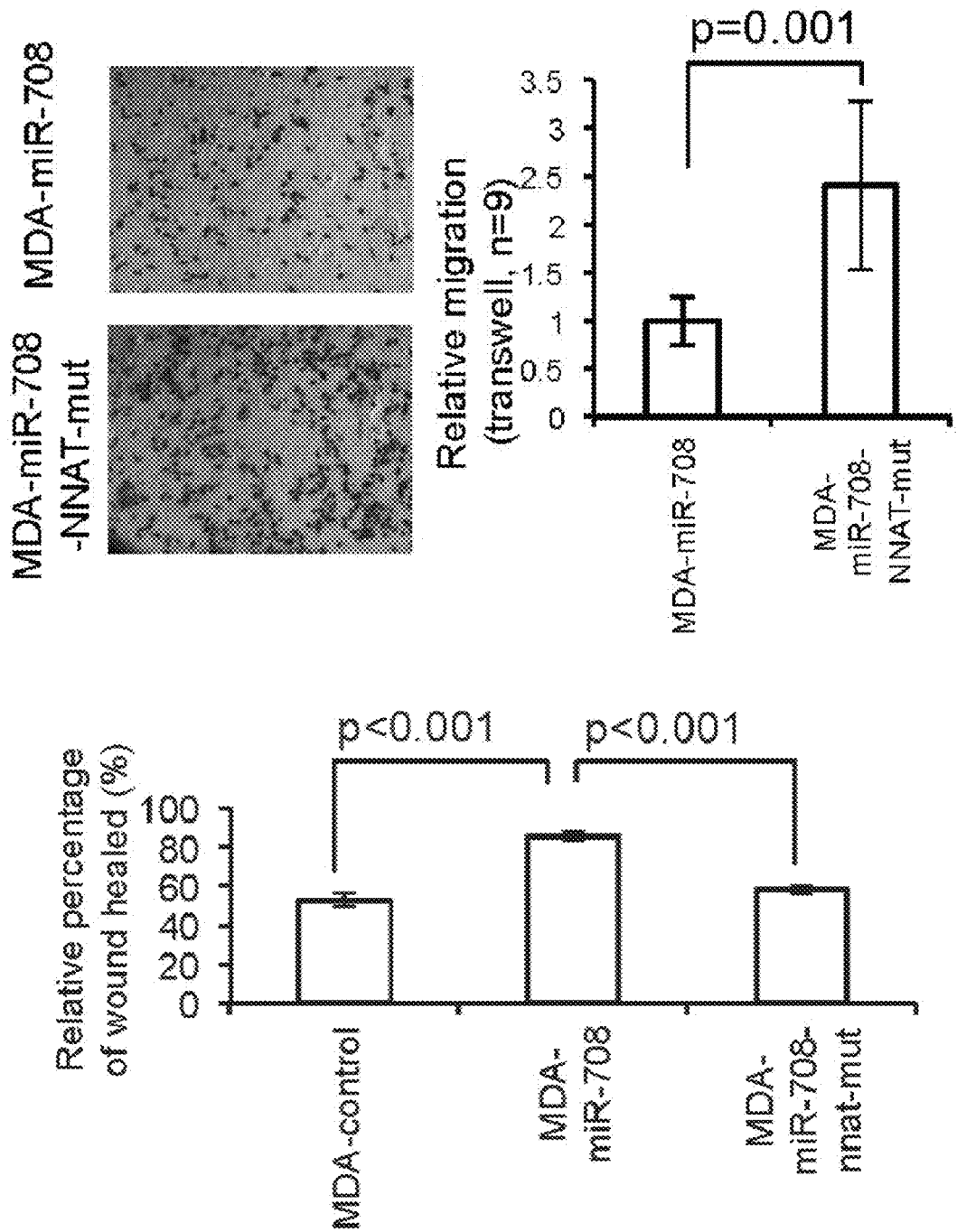
FIG. 4D shows transwell cell migration (FIG. 4D upper left panel) demonstrating that expression of the Nnat 3'-mutant UTR can rescue migration defects in miR-708 expressing MDA cells. Data in FIG. 4D (upper right panel) graphically illustrate the mean±SD of six randomly selected areas from two independent experiments.
Figure 4E:
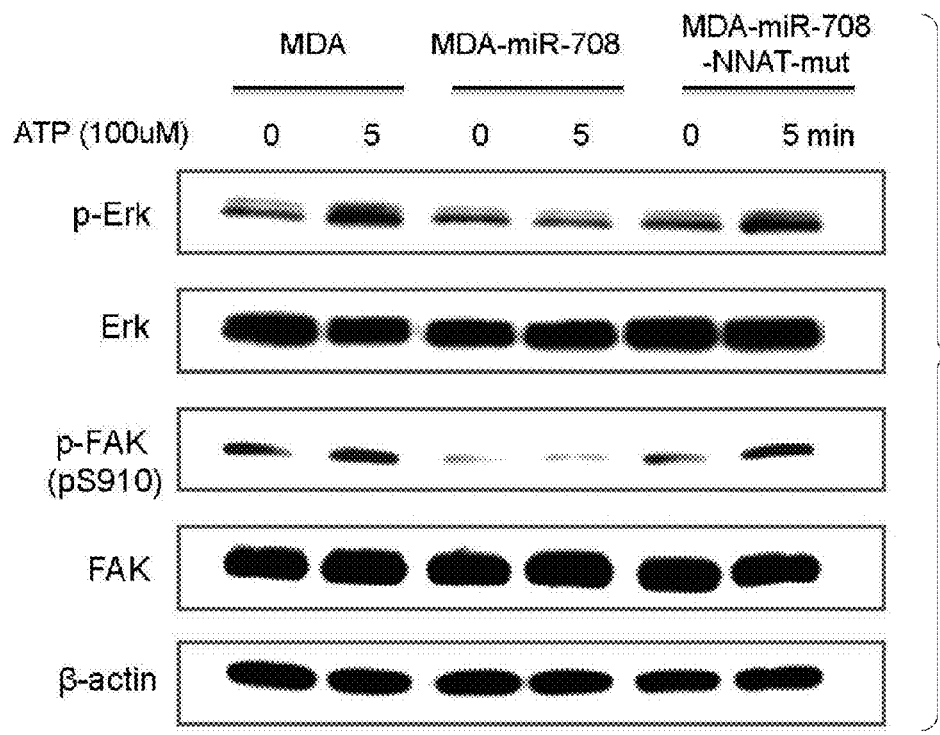
FIG. 4E shows levels of p-ERK (T202), Erk, FAK, and p-FAK (S910) following stimulation with ATP (0 and 5 min) in MDA, MDA-control, MDA-708, and MDA-miR-708-Nnat-mut cells as detected by Western blot analysis. β-actin serves as an internal control. Quantifications are shown in FIG. 4P-4Q.
Figure 4F:
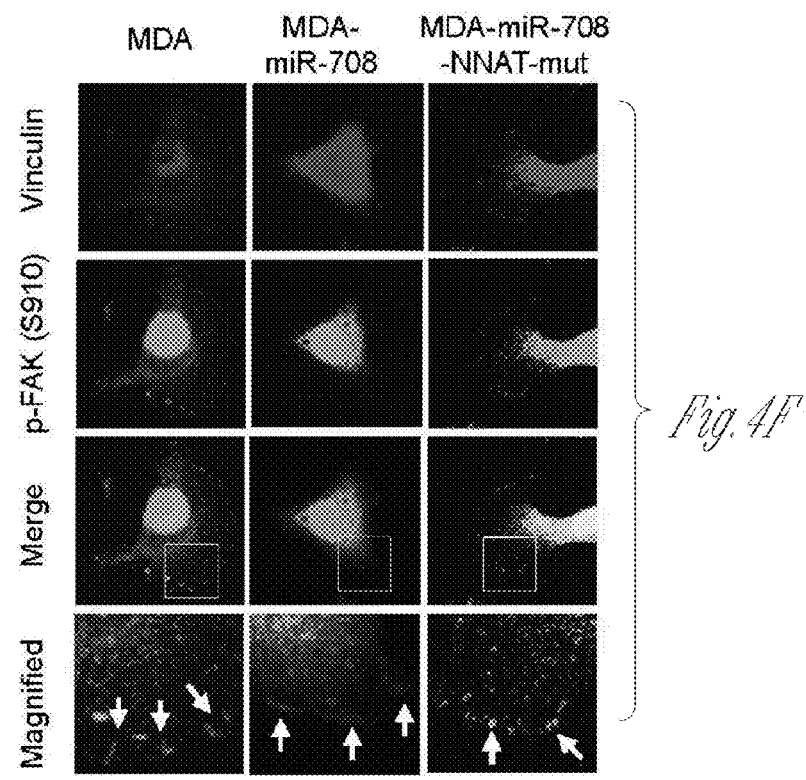
FIG. 4F shows MDA-control, MDA-miR-708, and MDA-miR-708-Nnat-mut cells immunostained for Vlinculin and p-FAK. As shown, p-FAK co-localized well with vinculin+ focal adhesions in MDA and MDA-miR-708 Nnat 3'-mutant UTR cells, while the focal adhesions in MDA-miR-708 cells remained devoid of p-FAK. Arrows indicate focal adhesions.
Figure 4J:
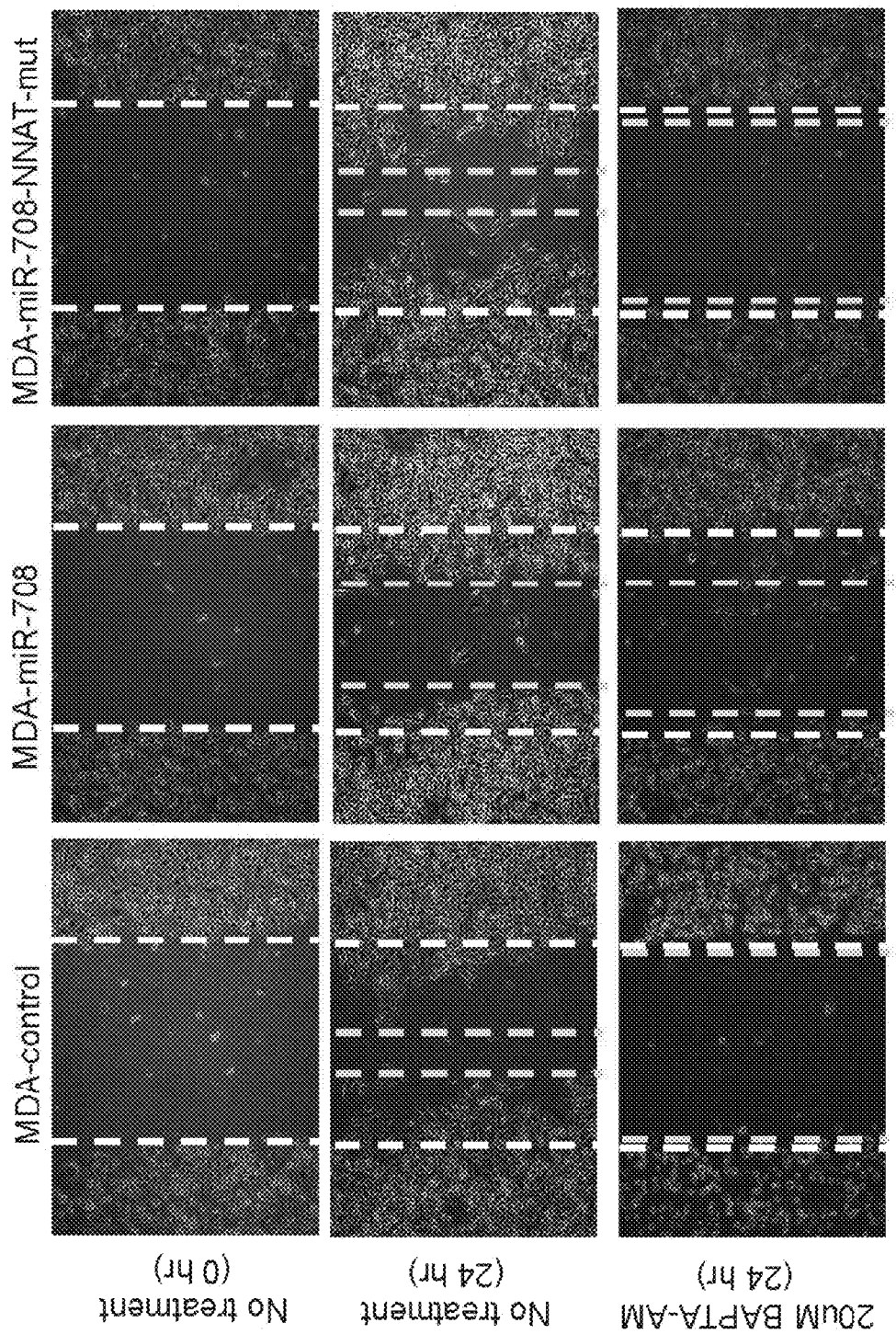
FIG. 4J shows representative images of cell migration assays performed with 1×10⁶ MDA control cells (MDA), MDA-miR-708 cells and MDA-miR-708-NNAT-mut cells. Cells were plated into 6 well dishes and allowed to grow for 12 hours, after which a scratch was created and cells imaged immediately (0 hr). Cells were incubated for 24 hours with or without the inhibitor, 20 μM BAPTA-AM.
Figure 4K:
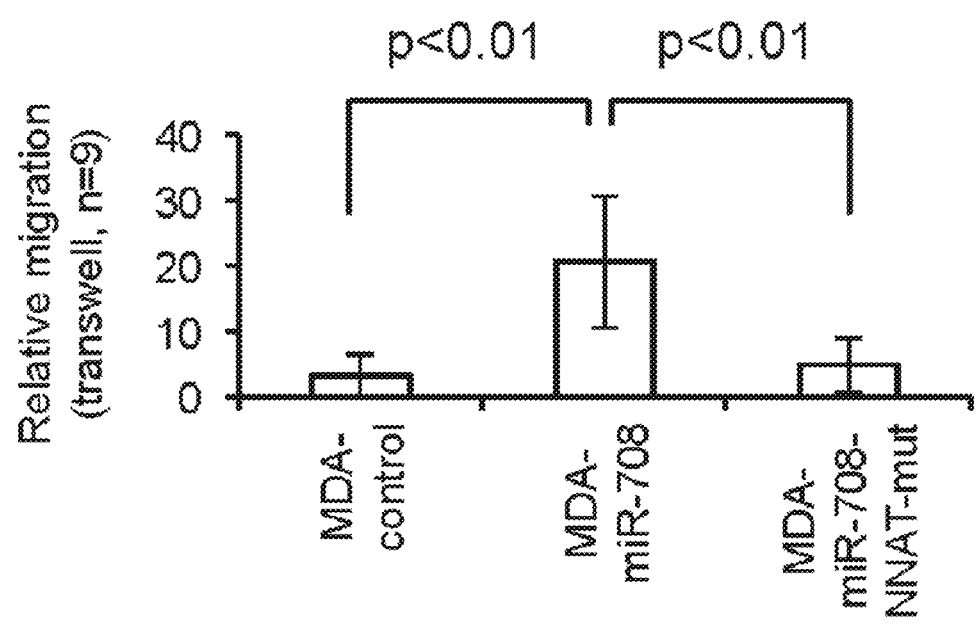
FIG. 4K graphically illustrates transwell cell migration assay performed with 50,000 MDA control cells (MDA), MDA-miR-708 cells and MDA-miR-708-NNAT-mut cells. Cells were incubated for 48 hours with 20 μM BAPTA-AM. Cell migration in the presence of BAPTA-AM was quantified in triplicates. Data represent mean±s.d.
Figure 4L:
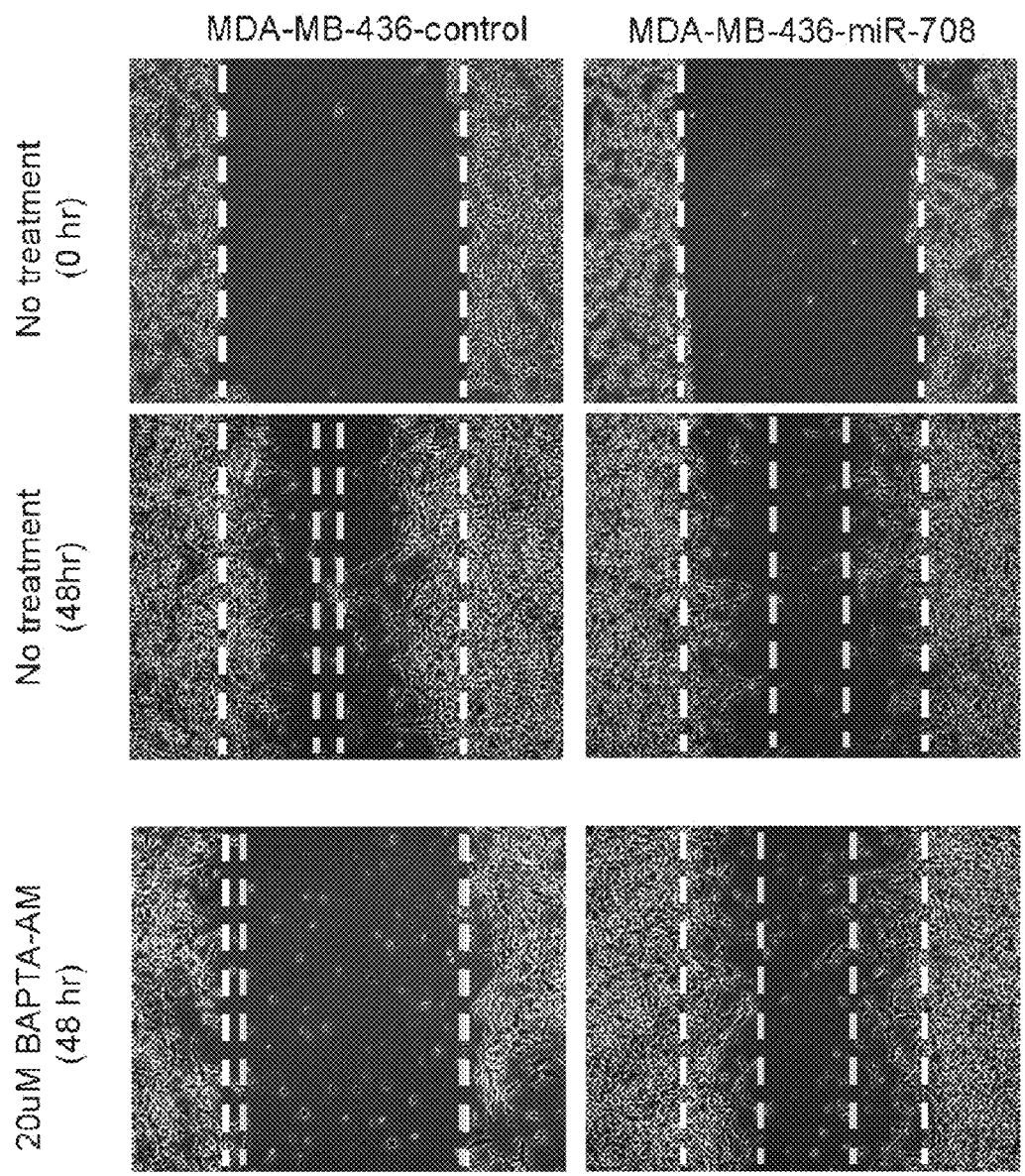
FIG. 4L shows representative images of cell migration assays performed with 1×10⁶ MDA-MB-436 control cells and MDA MB-436 cells expressing miR-708. Cells were plated into 6 well dishes and allowed to grow for 12 hours, after which a scratch was created and cells imaged immediately (0 hr) or at 48 hours. Treatment with BAPTA-AM (20 μM) rescued the migration defects in MDA-MB-436 cells expressing miR-708 cells, consistent with previous observations in MDA-MB-231 cells.
Figure 4M:
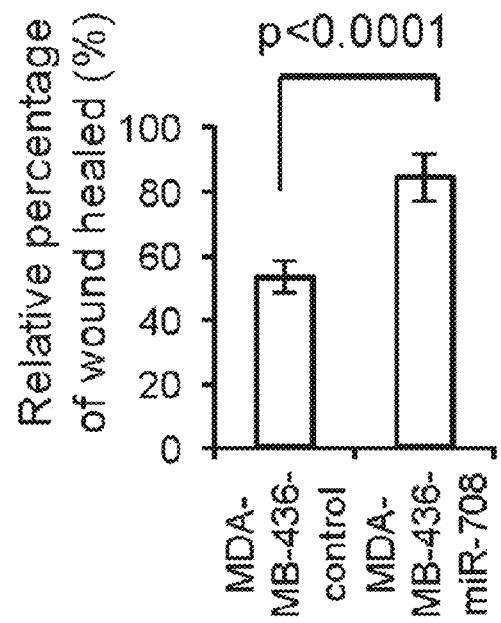
FIG. 4M graphically illustrates the relative cell migration of cells in the presence of BAPTAAM as a percentage of wound healed. Data represent mean±s.d. of nine randomly selected areas from three independent experiments like those shown in FIG. 4L.
Figure 4N:
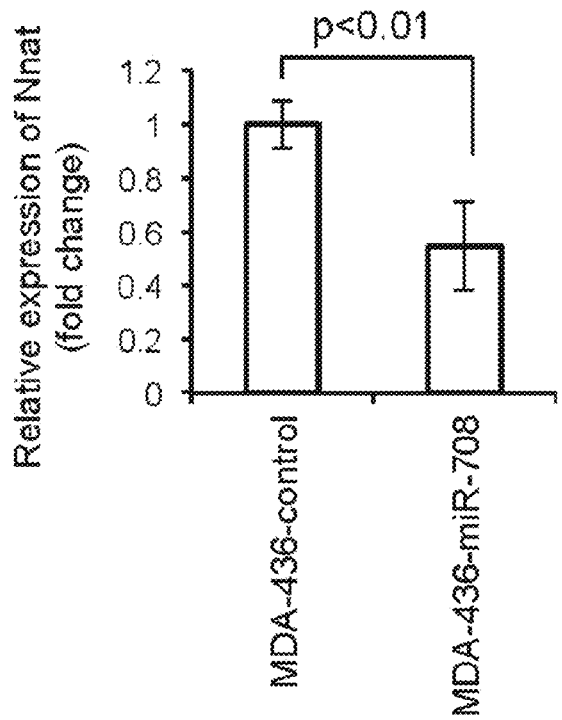
FIG. 4N graphically illustrates the relative expression of Nnat in control metastatic MDA-MD-436 cells and in metastatic MDA-MD-436 cells that overexpress miR-708. As shown miR-708 expression suppresses Nnat expression.

MDA cells responded to ATP by exhibiting a rapid increase of $Ca^{2+}$, followed by a regulatory phase back to basal levels (FIG. 4A. left panel). In contrast, MDA cells expressing miR-708 exhibited a similar $Ca^{2+}$ transient but attenuated regulation of intracellular $Ca^{2+}$, indicating that Nnat knockdown by miR-708 may be responsible for the aberrant $Ca^{2+}$ re-uptake mechanism to the endoplasmic reticulum (FIG. 4A, right panel). To directly demonstrate that suppression of Nnat by miR-708 was responsible for the decreased $Ca^{2+}$ influx, a rescue experiment was performed where the Nnat cDNA was expressed with a 3'-mutant UTR into MDA-miR-708 (MDA-miR-708-Nnat-mut) cells. There were no differences in the basal intracellular $Ca^{2+}$ levels or peak response to ATP between the MDA-control, MDA-miR-708, and MDA-miR-708-Nnat-mut cells (FIG. 4B). Strikingly, expression of the Nnat 3'-mutant UTR rescued the defects in intracellular $Ca^{2+}$ regulation in miR-708 expressing MDA cells (FIG. 4C), as well as the migration phenotype (FIG. 4D, left panel). Notably, expression of Nnat-mut alone in control MDA cells did not impact migration rates (FIGS. 4G-4I), suggesting that the miR-708-Nnat axis is an important determinant of cell migration. To directly demonstrate that the regulation of $Ca^{2+}$ is the main reason for the miR-708-Nnat-mediated migration phenotype, we used BAPTA-AM, an intracellular calcium chelator (Hoth and Penner, 1992). As expected, BAPTA-AM showed a dramatic impairment in MDA cell migration (FIGS. 4D, 4J-4K), while migration in MDA-miR708 cells remained less affected. More importantly, expression of Nnat in MDA-miR-708 cells rescued the BAPTA-AM-induced cell migration defects, directly implicating the miR-708-Nnat-$Ca^{2+}$ axis in the migration of metastatic breast cancer cells. To exclude the possibility that the migration effects were not confined to the metastatic MDA-MB-231 cells alone, another metastatic cell line, MDA-MB-436 was used. Consistent with previous data, MDA-MB-436 cells expressing miR-708 also showed decreased levels of Nnat (FIG. 4N), and increased migration that remained less affected by BAPTA-AM (FIGS. 4L-4M). These results suggest that suppression of miR-708 in metastatic tumor cells is necessary for Nnat to maintain adequate levels of intracellular $Ca^{2+}$ stores required for the migratory phenotype. Furthermore, given that intracellular $Ca^{2+}$ is mediator of key biological processes, it has previously remained unclear how genes mediating intracellular $Ca^{2+}$ levels are regulated. Thus, in this study, the demonstration that miR-708 regulates Nnat expression provides a novel insight into $Ca^{2+}$ regulation in metastatic tumor cells.

Example 7 miR-708 Induced Aberrant Ca2+Regulation Impacts Focal Adhesion Kinase

This Example describes evaluation of downstream signaling pathways to further elucidate the mechanisms by which the miR-708-Nnat-$Ca^{2+}$ axis regulates cell migration.

Figure 4O:
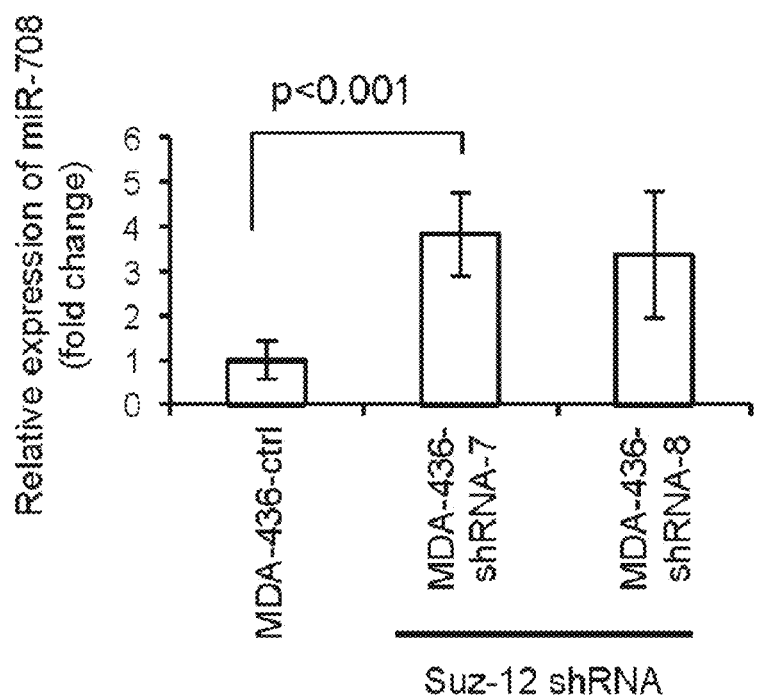
FIG. 4O graphically illustrates miR-708 expression in metastatic MDAMD-436 cells after knock down of Suz12 expression by Suz12-specific shRNAs #7 and #8. As shown, Suz12 knock-down increased miR-708 expression.
Figure 4P:
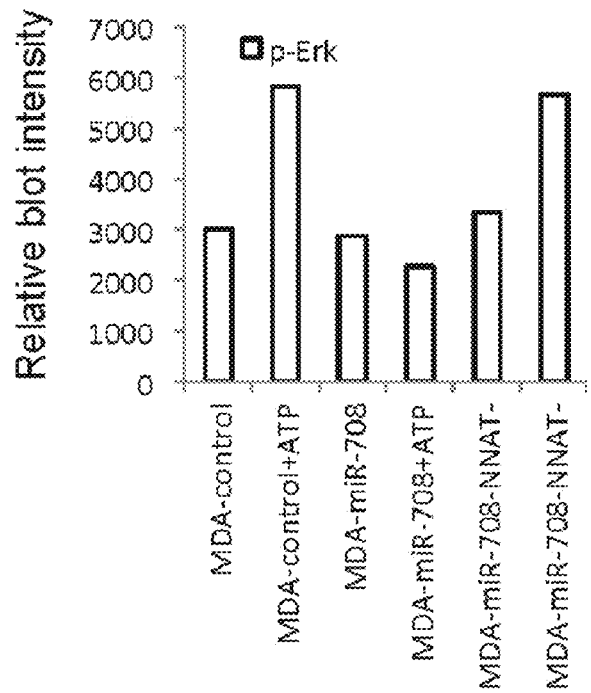
FIG. 4P graphically illustrates p-Erk protein levels from the Western blots in FIG. 4E.
Figure 4Q:
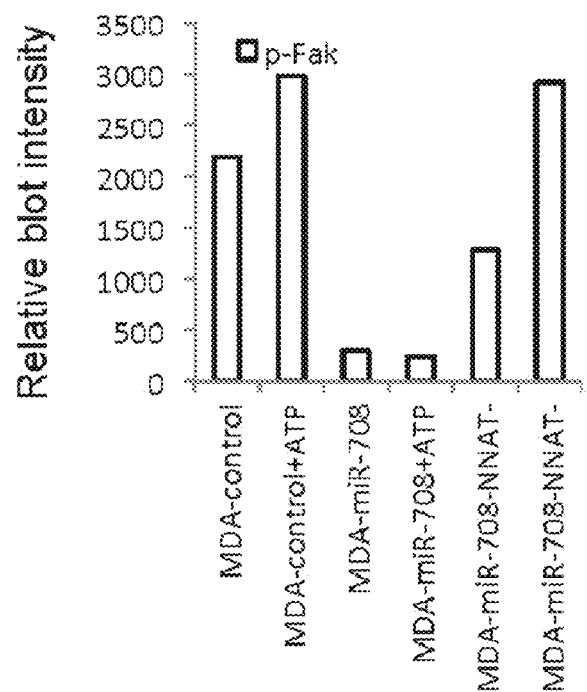
FIG. 4Q graphically illustrates p-FAK protein levels from Western blots in FIG. 4E.
Figure 4R:
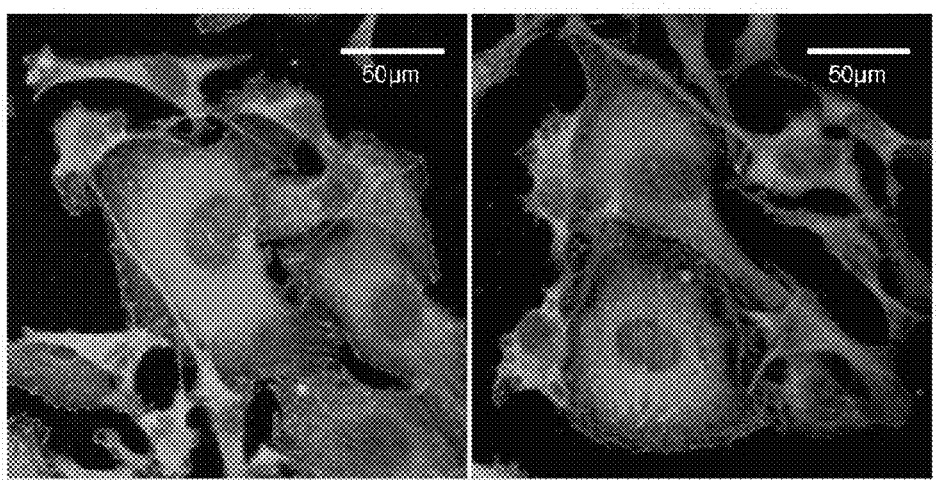
FIG. 4R shows MDA-control and MDA-miR-708 cells immunostained for vinculin and F-actin (phalloidin). Cells were scored for shape and presence of thick cortactin fibers (more than 2 cortical fiber layers surrounding each cell). At least 25 cells per 10 random fields were counted for each experimental condition.
Figure 4S:
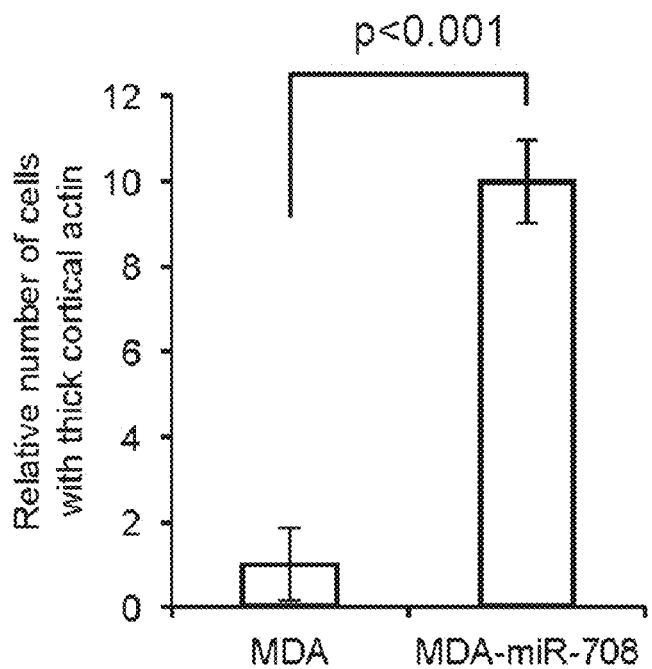
FIG. 4S graphically illustrates the relative number of cells with thick cortical actin assessed as described above. These experiments were performed on at least three different occasions with similar results. Data were analyzed by Student's t-test, and p values and number of measured cells (n) in this experiment are indicated.

ATP-induced transient elevation of intracellular $Ca^{2+}$ has been shown to trigger key components of numerous signaling pathways, including protein kinases such as the calmodulin-dependent kinases (CaMKs) and the extracellular signal-regulated kinases (Erk) (Swanson et al., 1998). Following $Ca^{2+}$ release by ATP, MDA cells showed a rapid and transient increase in phospho (p)-p44/Erk1 and p42/Erk2 over basal levels as compared with MDA-miR-708 cells (FIGS. 4E, 4P-4Q), suggesting that aberrant intracellular $Ca^{2+}$ regulation in MDA-miR-708 cells may be responsible for reduced levels of activated Erk. Importantly, expression of mutant Nnat rescued p-Erk levels in MDA-miR-708 cells (FIG. 4E, 4P). Erk has been implicated in the migration of numerous cell types by virtue of its ability to phosphorylate several protein kinases, including focal adhesion kinase (FAK) (Huang et al., 2004). Indeed, fibroblasts derived from Fak knockout mice show diminished migration ability (Ilić et al., 1995; Zhao and Guan, 2009). In fact, an elevated level of basal p-FAK (S910) was observed in MDA compared to MDA-miR-708 cells (FIG. 4E, 4P). Notably, following ATP-mediated $Ca^{2+}$ release, p-FAK levels increased in MDA and not in MDA-miR-708 cells (FIG. 4E, 4Q). Again, as expected, expression of Nnat 3'-mutant UTR restored both the basal and ATP-induced p-FAK in MDA-miR-708 cells (FIG. 4E, 4Q). These data are consistent with studies showing that FAK phosphorylation at S910 (Hunger-Glaser et al., 2004) is associated with increased cell migration and metastasis (Zheng et al., 2009) and suggests that alleviated FAK activation may explain the attenuated migration attributes of miR-708 expressing cells. Focal adhesions were then evaluated at the cellular level by immunostaining for vinculin, a well-known focal adhesion molecule, and p-FAK (S910). Strikingly, p-FAK colocalized well with vinculin+ focal adhesions in MDA and MDA-miR-708 Nnat 3'-mutant UTR cells, while the focal adhesions in MDA-miR-708 cells remained devoid of p-FAK (FIG. 4F). Furthermore, MDAmiR-708 cells exhibited thick bands of cortical actin rings around the cells' periphery (FIGS. 4R-4S), a phenotype previously associated with migration defects in FAK null cells (Sieg et al., 1999).

Figure 4T:
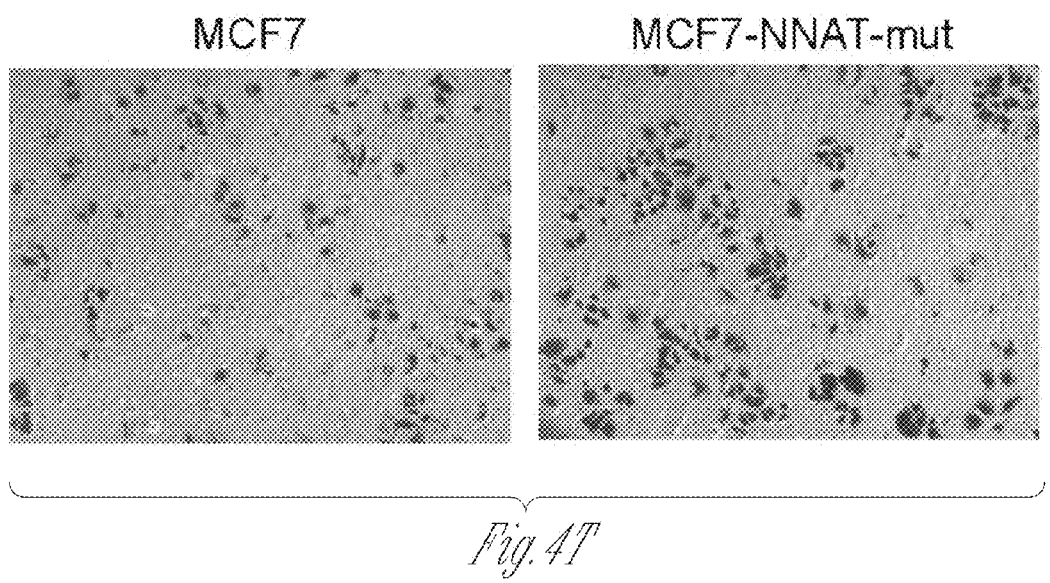
FIG. 4T shows images of transwell cell migration assays showing that expression of Nnat 3'-mutant UTR rescues migration defects in MCF cells.
Figure 4U:
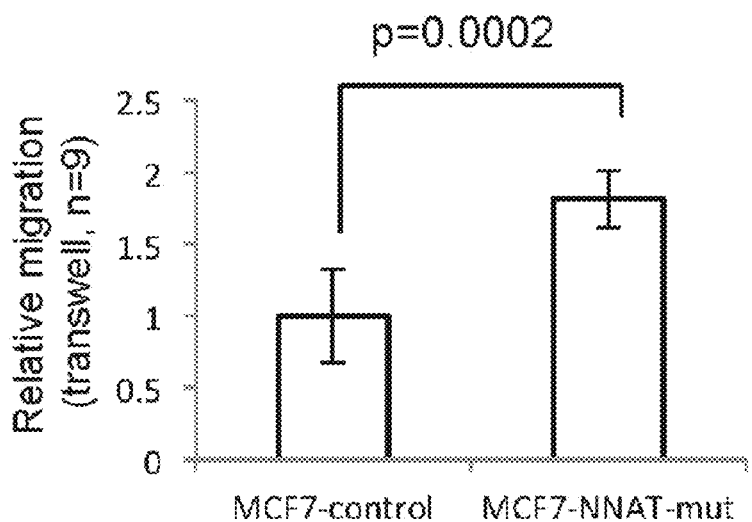

Taken together, these results indicate that miR-708-induced aberrant $Ca^{2+}$ levels are responsible for impacting Erk and FAK activation. Importantly, expressing Nnat with a mutant 3'-UTR which is refractory to miR-708 suppression rescued aberrant $Ca^{2+}$ levels, restored activated Erk/FAK, and promoted cell migration (FIGS. 4T-4U). This data is in agreement with a previous study showing that enhanced efflux of store-operated $Ca^{2+}$ into the cytoplasm is critical for serum-induced breast cancer cell migration via induction of FAK (Yang et al., 2009).

Example 8

The Polycomb Group Complex PRC2 is Involved in the Suppression of miR-708 in Metastatic Cells This Example explores the mechanisms underlying miR-708 repression including the PcG group of transcriptional repressors that may suppress miR-708 during metastasis.

Figure 5F:
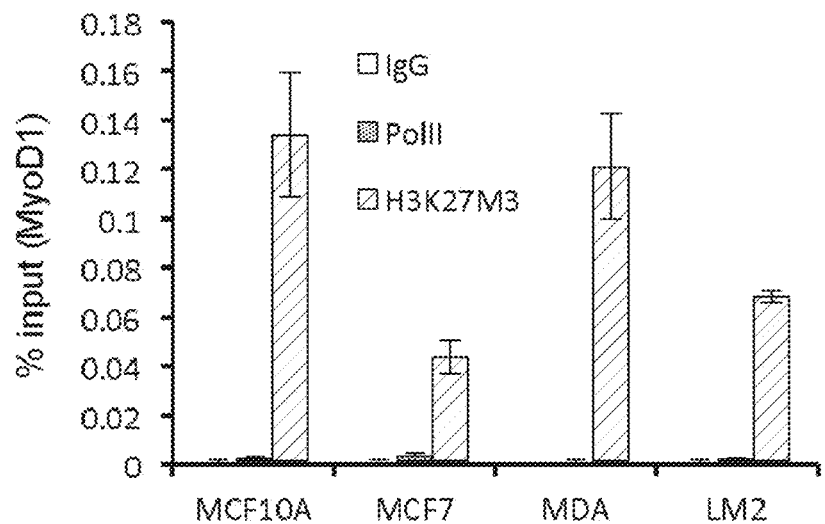
FIG. 5F shows graphically illustrates % input of MyoD1 as detected by ChIP-PCR following pull down with indicated antibodies in breast cancer cell lines MCF10A, MCF7, MDA and MDA-LM2. IgG, control antibody; PolII, RNA polymerase II; an anti-histone H3K27M3 antibody.
Figure 5G:
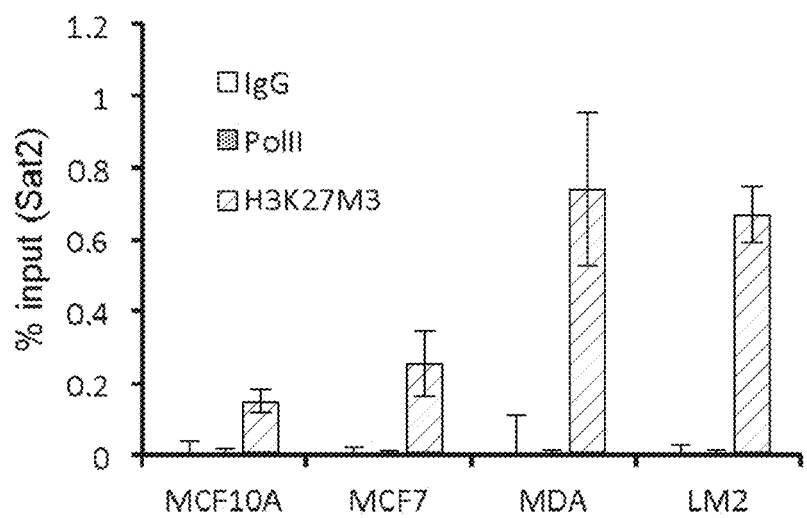
FIG. 5G graphically illustrates Sat2 (satellite repeat 2) as detected by ChIP-PCR following pull down with indicated antibodies in breast cancer cell lines MCF10A, MCF7, MDA and MDA-LM2. IgG, control antibody; PolII, RNA polymerase II; an anti-histone H3K27M3 antibody.
Figure 5H:
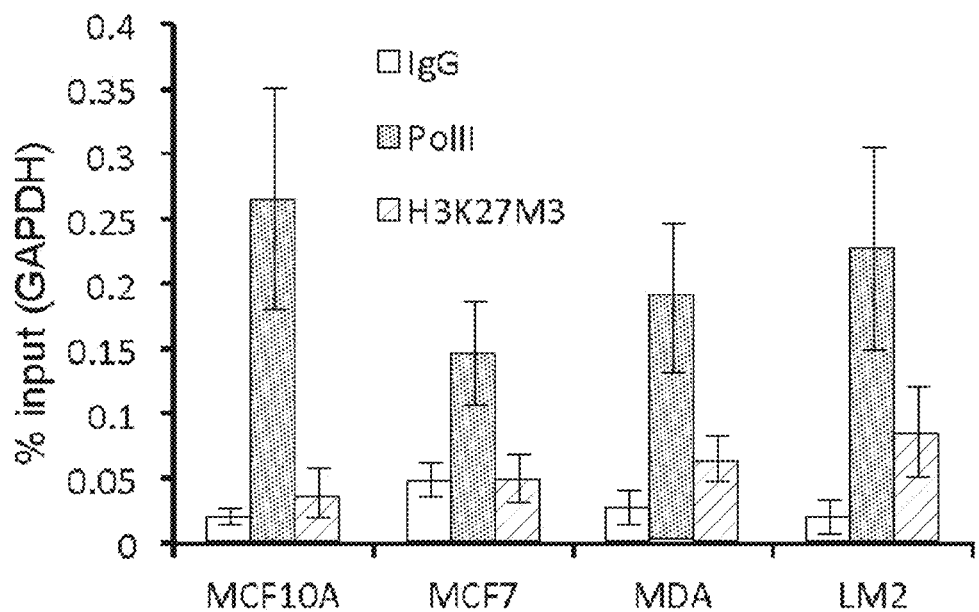
FIG. 5H shows graphically illustrates % input of GAPDH as detected by ChIP-PCR following pull down with indicated antibodies in breast cancer cell lines MCF10A, MCF7, MDA and MDA-LM2ChIP-PCR.
Figure 5I:
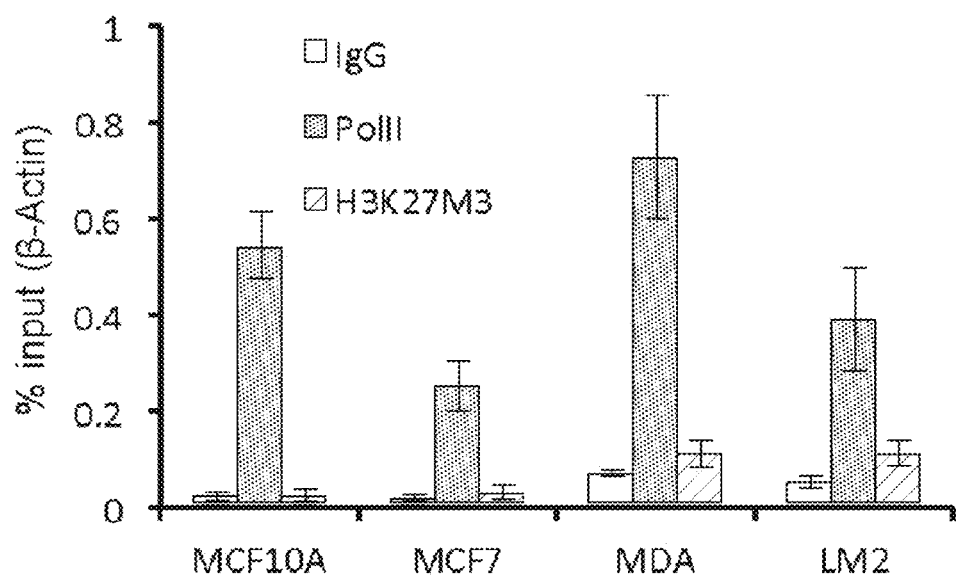
FIG. 5J graphically illustrates Suz12 expression in metastatic MDA cells after knock down by Suz12-specific shRNAs #6 and #7.
FIG. 5K graphically illustrates miR-708 expression and that shRNA-mediated suppression of Suz12 relieves repression of miR-708 expression in metastatic MDA cells.
FIG. 5L graphically illustrates Nnat expression and that shRNA-mediated suppression of Suz12 suppresses Nnat expression in metastatic MDA cells.
FIG. 5M graphically illustrates EZH2 expression and that shRNA-mediated suppression of Suz12 reduces EZH2 expression in metastatic MDA cells.
FIG. 5N graphically illustrates miR-708 expression and that shRNA-mediated suppression of Ezh2 relieves repression of miR-708 expression in metastatic MDA cells.
FIG. 5O graphically illustrates Suz12 expression in primary tumors and in metastatic lung cells excised from a 14 week old MMTV-PyMT-EGFP mice. GAPDH serves as an internal control.
FIG. 5P graphically illustrates miR-708 expression in two MMTV-PyMT cell lines, MMTV-DB7 (nonmetastatic) and MMTV-Met1 (metastatic) cells.
FIG. 5Q graphically illustrates Nnat expression in two MMTV-PyMT cell lines, MMTV-DB7 (nonmetastatic) and MMTV-Met1 (metastatic) cells.
FIG. 5R graphically illustrates miR-708 expression in control and Suz12 knockdown MMTV-Met1 cells, showing that Suz12 knockdown relieves repression of miR-708 expression in metastatic MMTV-Met1 cells.

Western blot analysis of breast cancer cells indicated that SUZ12 was upregulated by approximately 7.5-fold in metastatic MDA cells compared with controls (FIG. 5A), consistent with observations in metastatic prostate and breast cancer (Bracken et al., 2009; Kleer et al., 2003; Sellers and Loda, 2002). To determine whether the miR-708 promoter associates with the PcG complex, ChIP experiments were performed for SUZ12 using cross-linked chromatin from non-metastatic and metastatic breast cancer cells. The enriched DNA from the immunoprecipitates was quantified by RT-PCR using primers spanning the miR-708 upstream regions (FIG. 5B). Enrichment of SUZ12 was found to be associated with the miR-708 upstream region in metastatic MDA and LM2 cells compared with non-metastatic cells MCF10A and MCF7 (FIG. 5C). No enrichment was detected with an isotype matched IgG antibody. As expected from this regulated SUZ12 binding, H3-K27 trimethylation in the miR-708 region was strongly enhanced in the metastatic cells but not in the non-metastatic cells (FIG. 5D). As a control, SUZ12 target promoters MyoD1 and SAT2 (a known target of heterochromatin-associated H3-K27Me3) were efficiently pulled down with H3K27Me3 antibody compared to GAPDH and #-Actin (FIGS. 5F-5G). These data suggest that SUZ12 interaction with the miR-708 promoter may result in the suppression of miR-708.

Figure 5J:
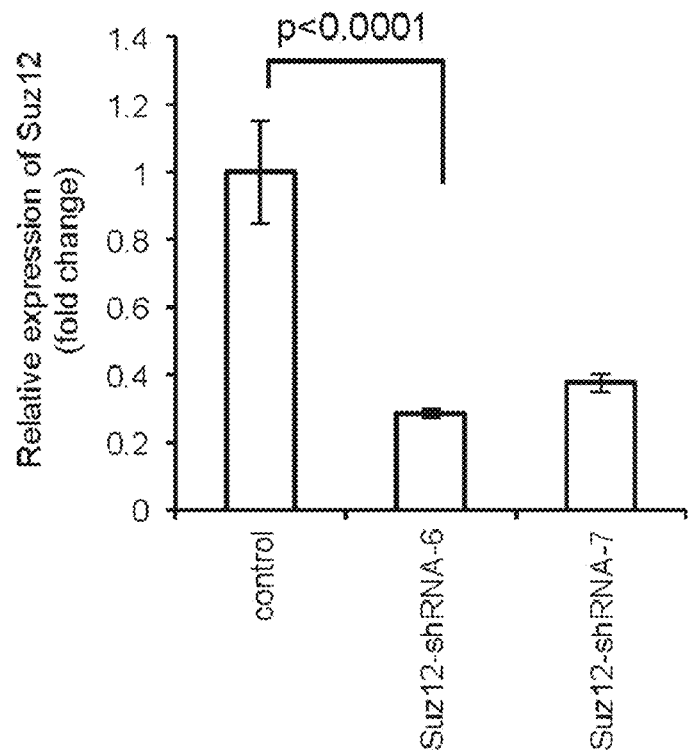
Figure 5K:
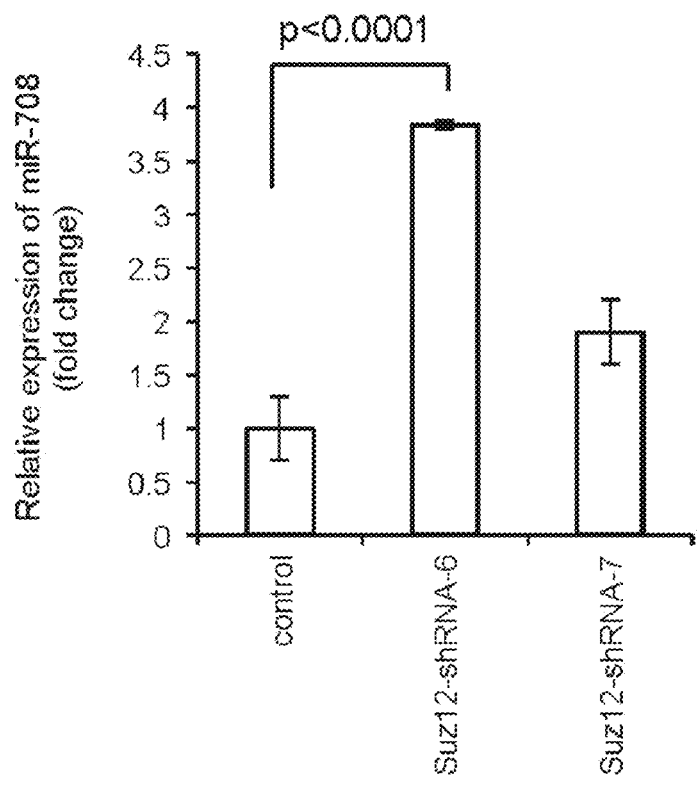
Figure 5L:
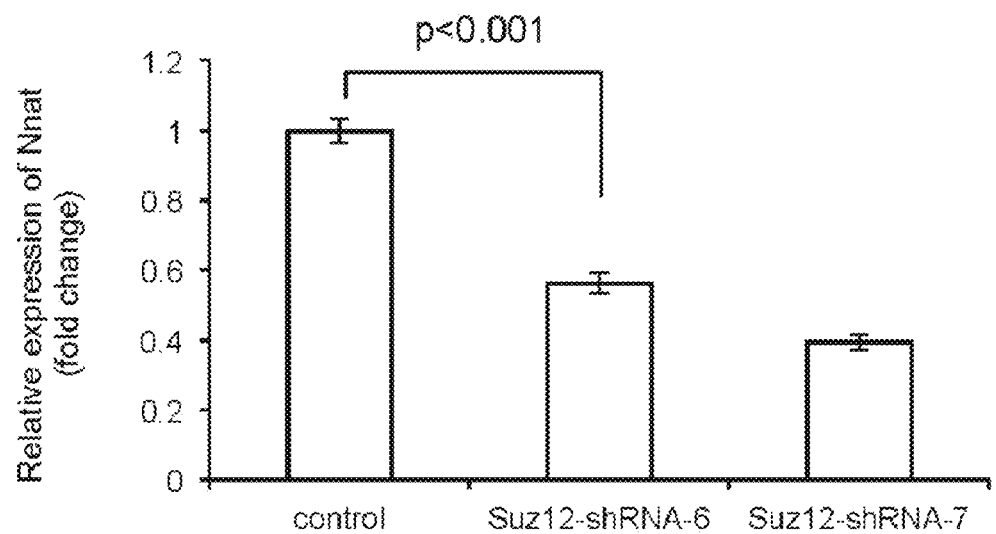
Figure 5M:
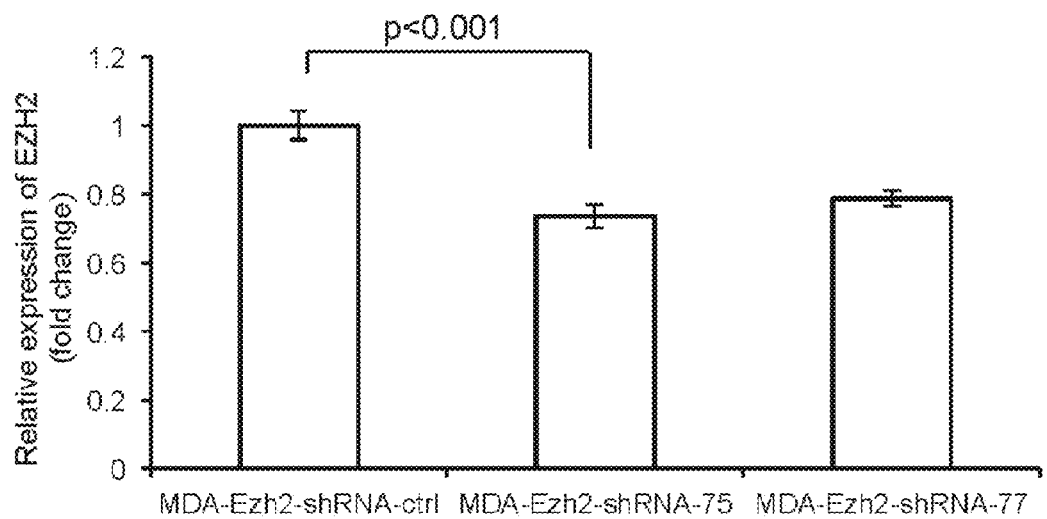

To further demonstrate that the PRC2 activity is directly responsible for miR-708 silencing, siRNA-mediated knockdown of PRC2 subunit SUZ12 was performed. Strikingly, Suz12 knockdown restored expression of miR708 in metastatic MDA breast cancer cells (FIG. 5E left and middle panel, FIGS. 5J-5K). Similar results were obtained with another metastatic breast cancer cell line MDA-MB-436 (FIG. 4O). As expected, upregulation of miR-708 expression following Suz12 knockdown resulted in decreased Nnat expression (FIG. 5L). Similarly, suppression of Ezh2, another key subunit of the PRC2 complex also restored expression of miR708 in metastatic MDA breast cancer cells (FIGS. 5M-5N).

Experiments were then designed to determine if the PRC2-induced H3-K27 trimethylation was the cause of miR-708 suppression. As shown in FIG. 5E (right panel), Suz12 knockdown resulted in decreased levels of H3-K27 trimethylation on the mir-708 promoter. These data establish that the PRC2 complex mediates suppression of miR-708 in metastatic breast cancer cells.

Figure 5Q:
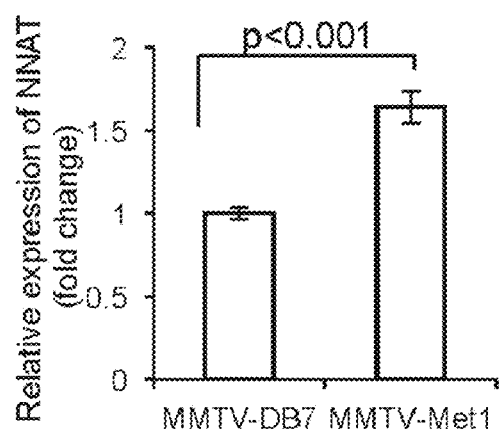
Figure 5R:
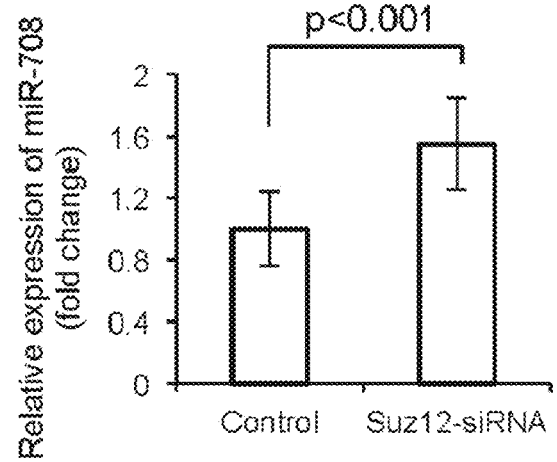
Figure 5S:
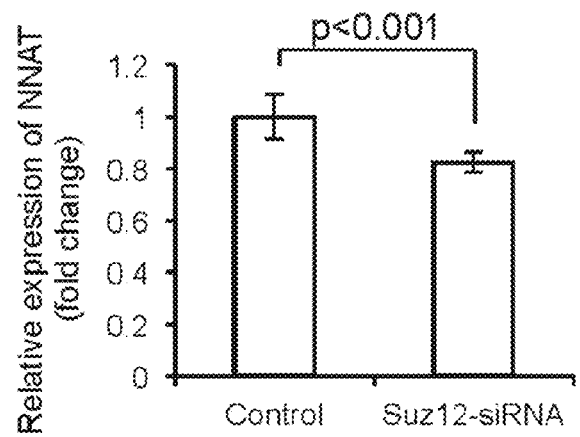

To determine if the PRC2-miR-708 axis was also involved in metastasis in vivo, the MMTV-PyMT breast cancer model was examined. Evaluation of primary breast tumors and matched lung metastases from these mice showed an inverse correlation between Suz12 and miR-708 expression (FIG. 5O; FIGS. 1D, 1L-1N). To evaluate whether there is a direct connection between SUZ12 and mir-708 in the MMTV-PyMT model, metastatic and non-metastatic variants of MMTV-PyMT cell lines were evaluated (Borowsky et al., 2005). Increased miR-708 expression associated with Nnat suppression was observed in nonmetastatic MMTV-DB7 cells compared to the metastatic variant MMTV-Met1 (FIG. 5P-5Q), consistent with observations in human breast cancer cells. As expected, siRNA-mediated knockdown of Suz12 relieved repression of miR-708 and decreased Nnat levels in metastatic MMTV-Met1 cells (FIG. 5R-5S). While there is a possibility that a repressor or a loss of a transactivator may be involved, our human and the murine studies indicate that PRC2-induced H3-K27 trimethylation contributes to the regulation of miR-708 expression in metastatic cancer cells.

Example 9 miR-708 Expression is Suppressed in Both Lymph Node and Distal Metastases in Breast Cancer Patients This Example addresses whether metastatic lesions in breast cancer patients exhibit attenuated levels of miR-708, as observed in human breast cancer cell models and in mouse model of breast cancer that metastasizes to the lung. A panel of frozen human primary breast tumors and matched lymph node metastases were analyzed by in situ hybridization for miR-708 expression.

Figure 6A:
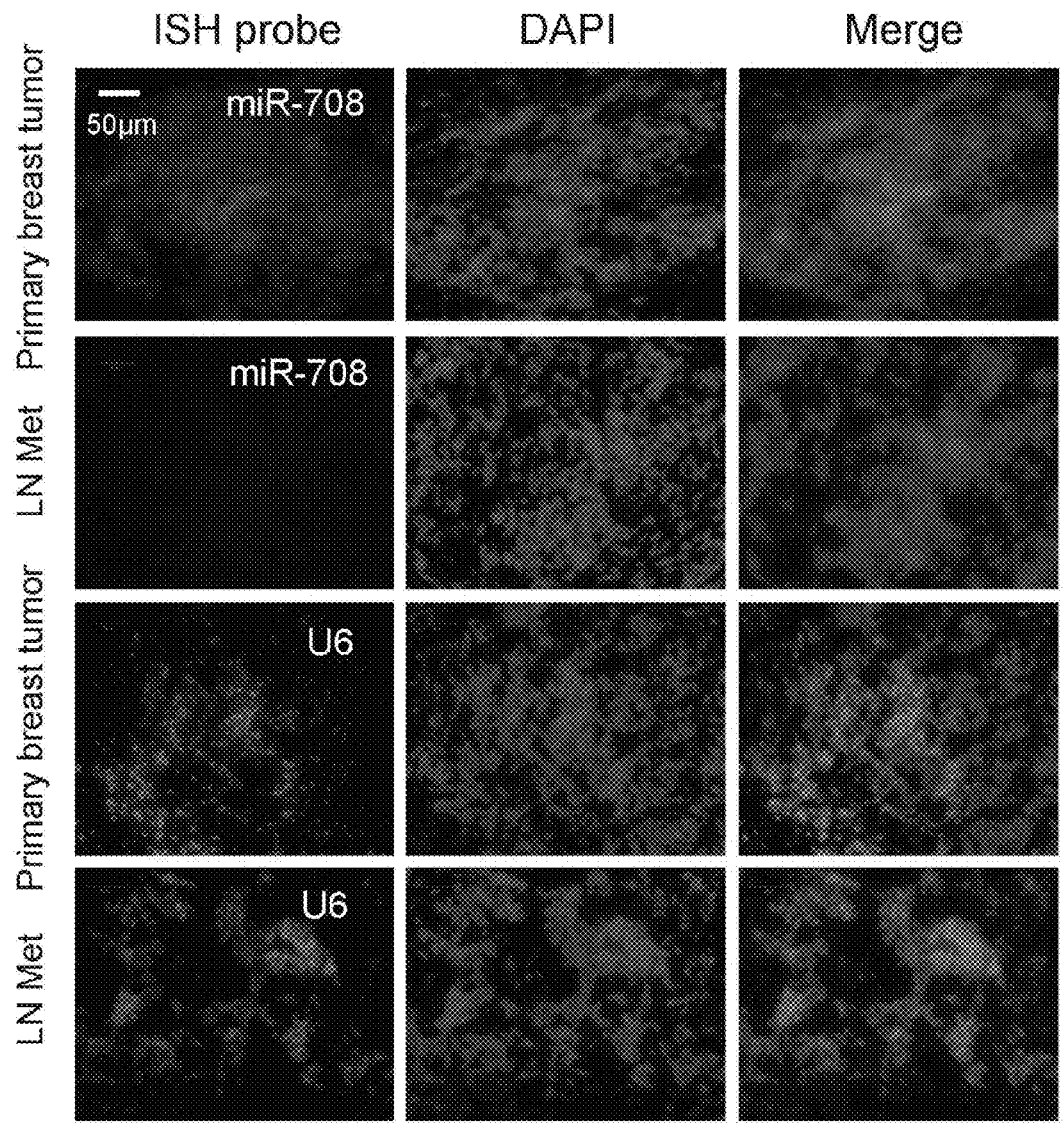
FIG. 6A-6K illustrates reduced miR-708 levels in metastases of breast cancer patients as detected by in situ hybridization analysis.
Figure 6B:
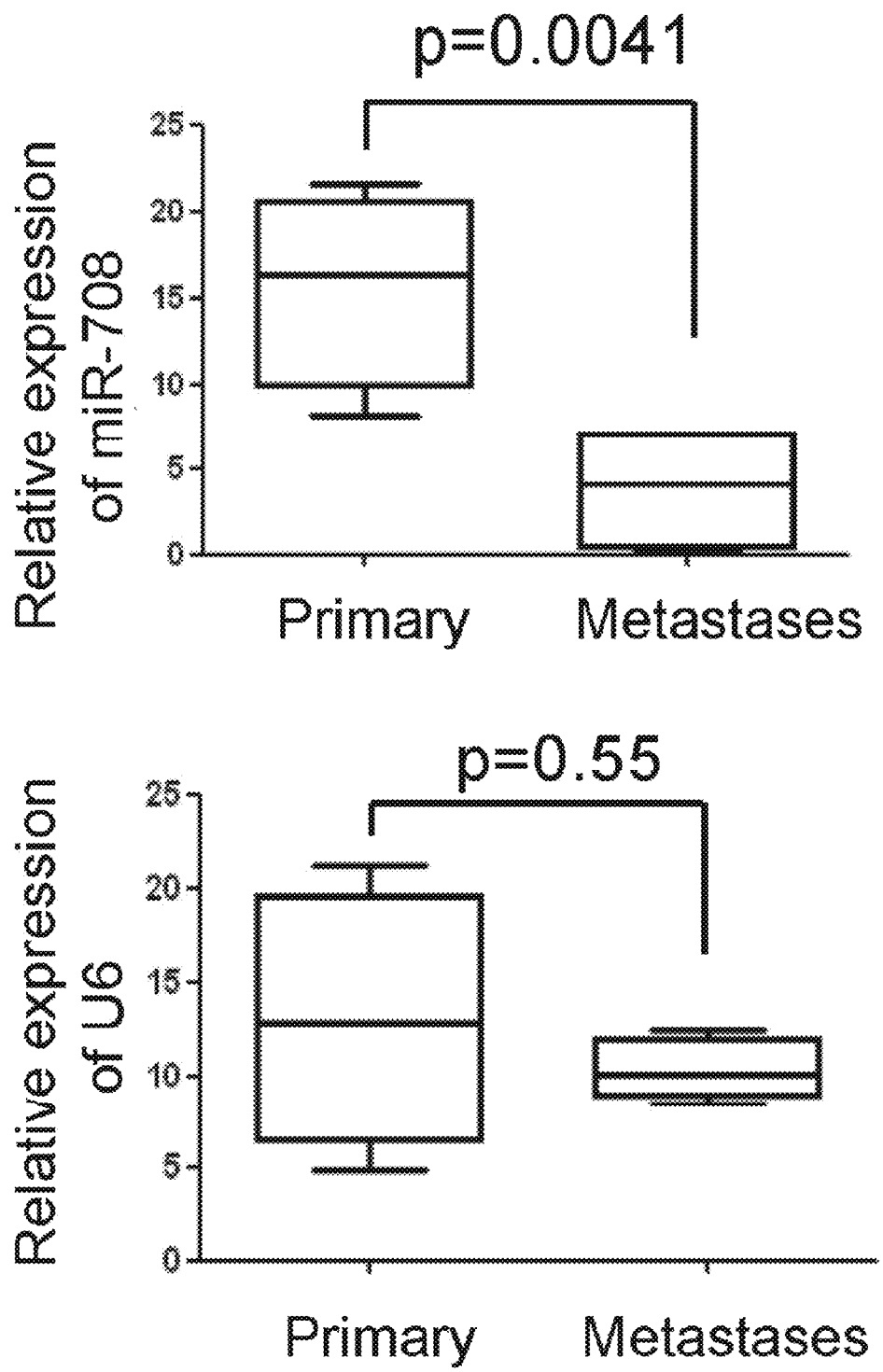
Figure 6C:
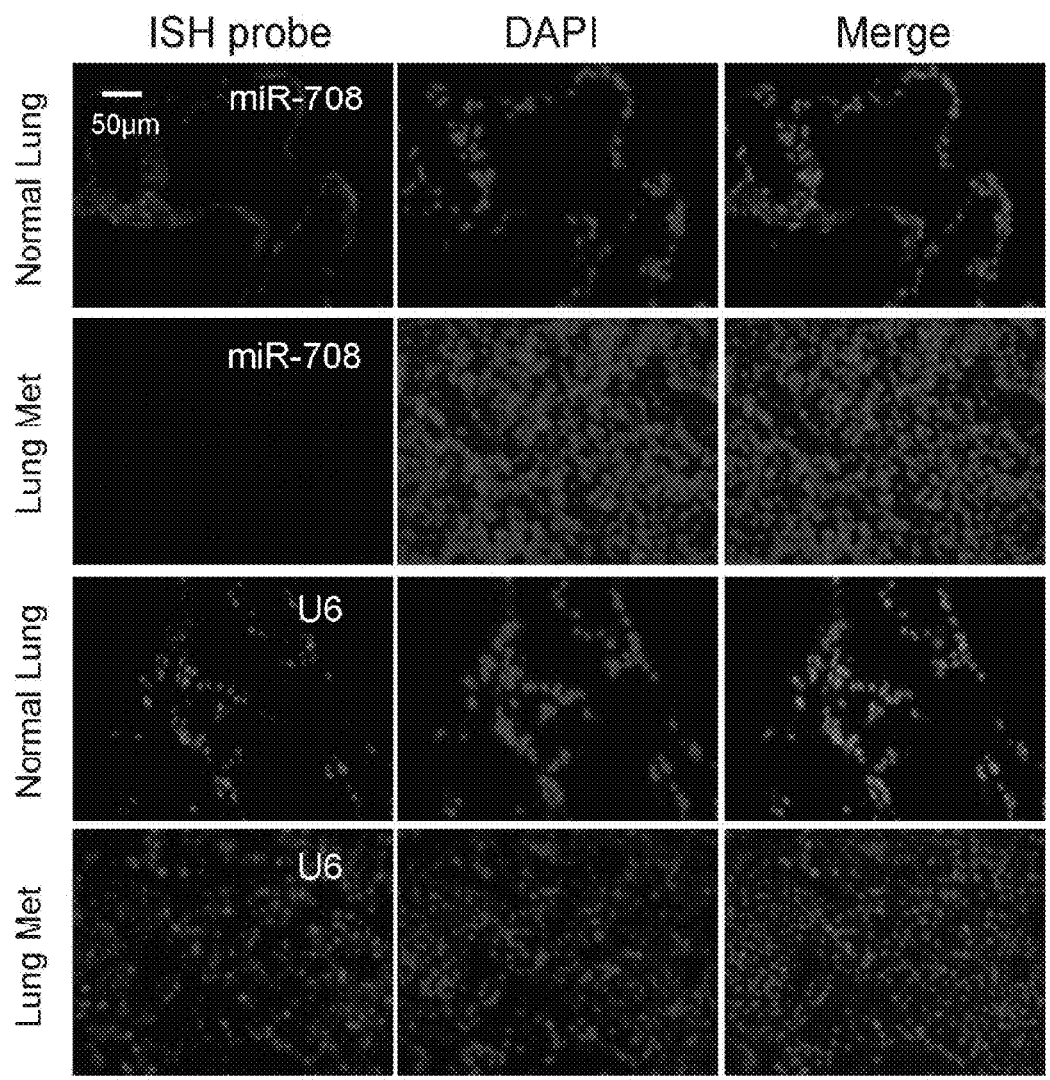
Figure 6D:
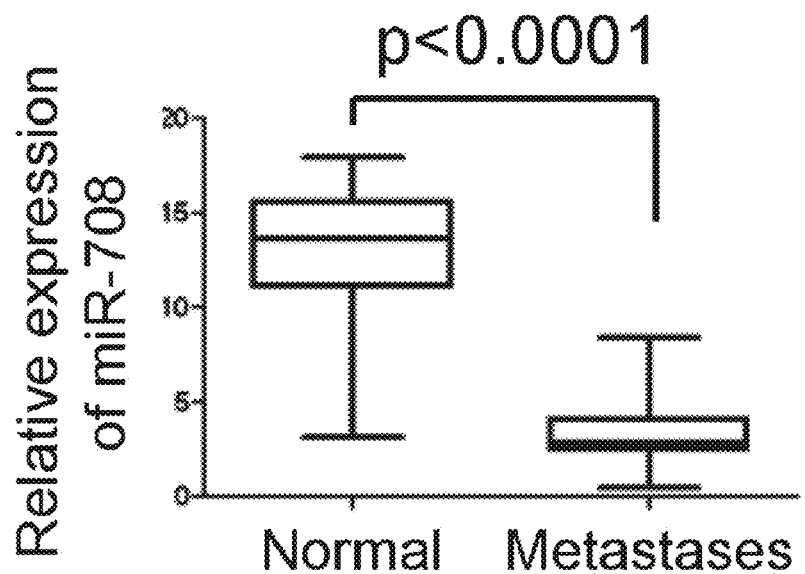
Figure 6E:
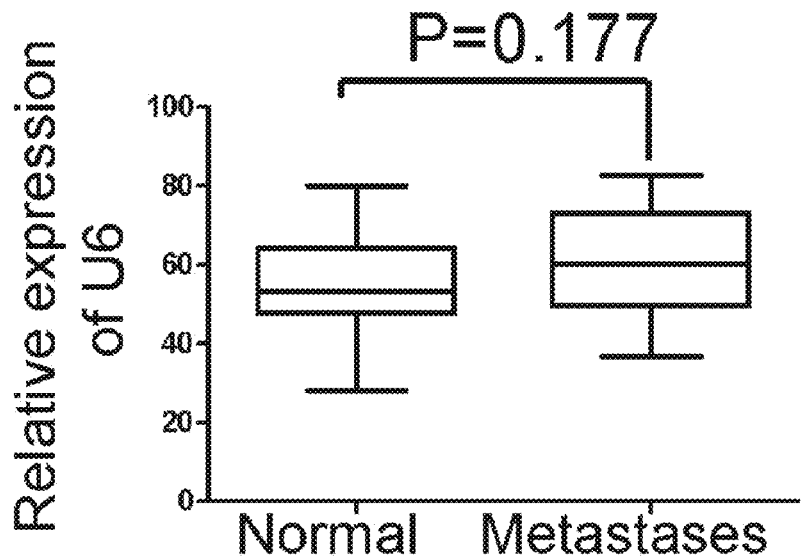
Figure 6F:
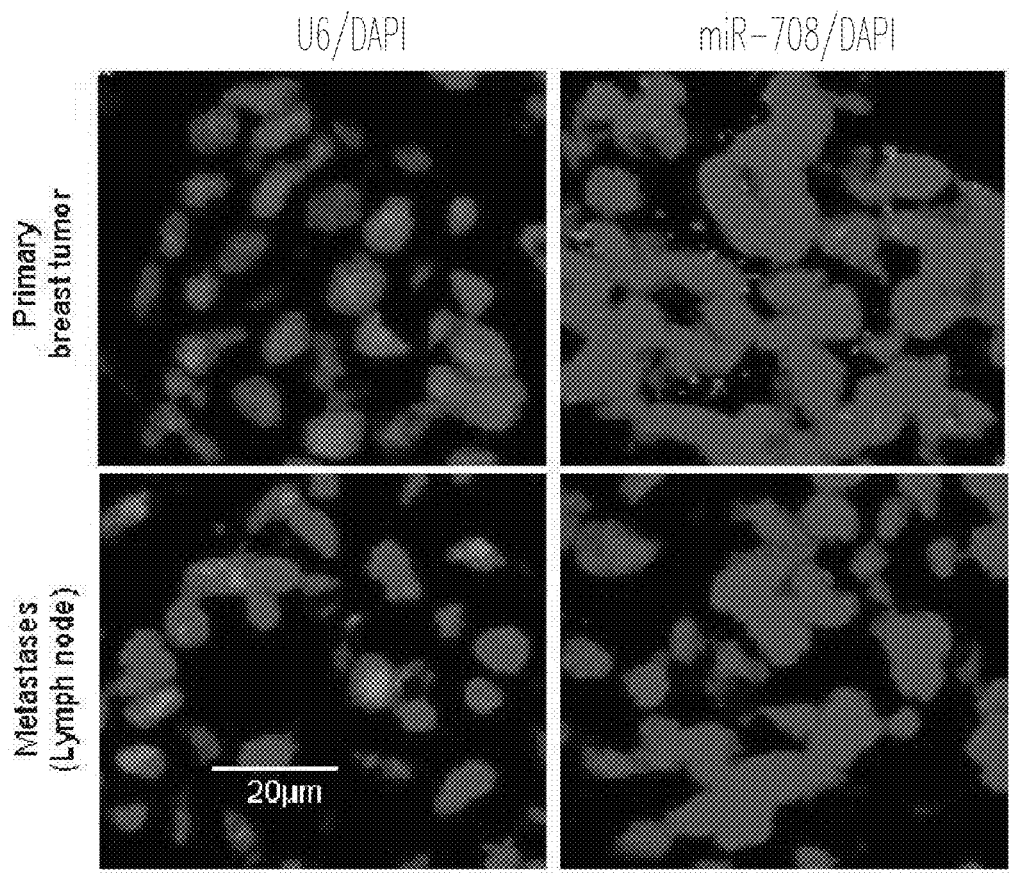
Figure 6G:
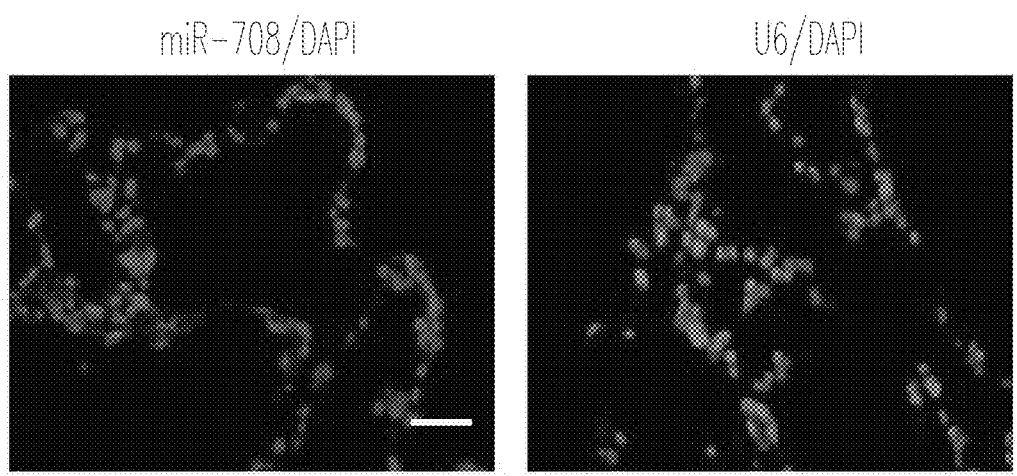
Figure 6H:
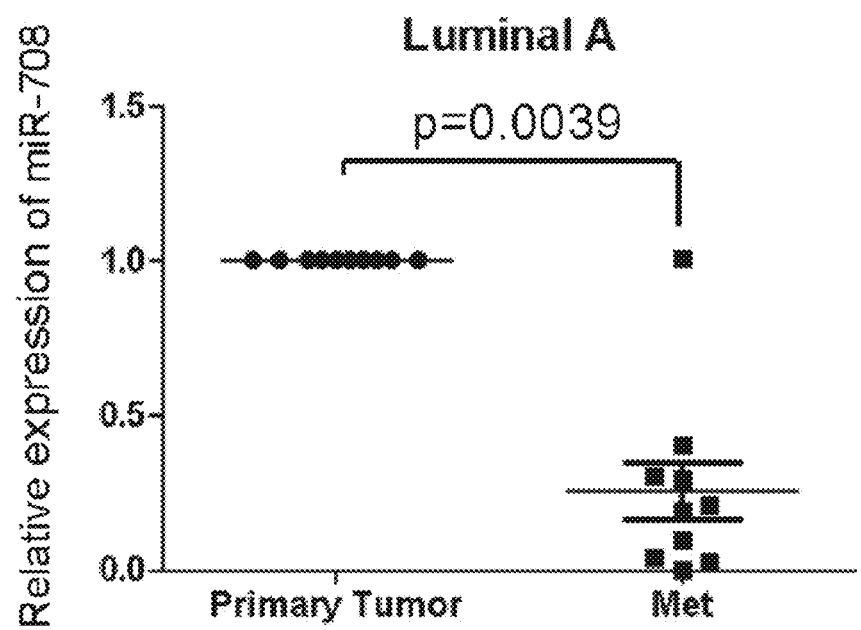
Figure 6I:
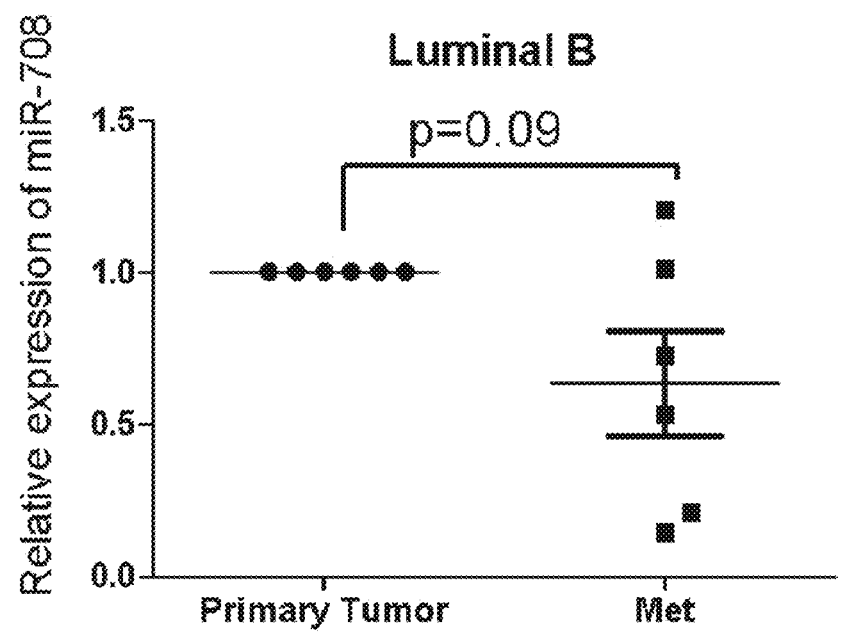
Figure 6J:
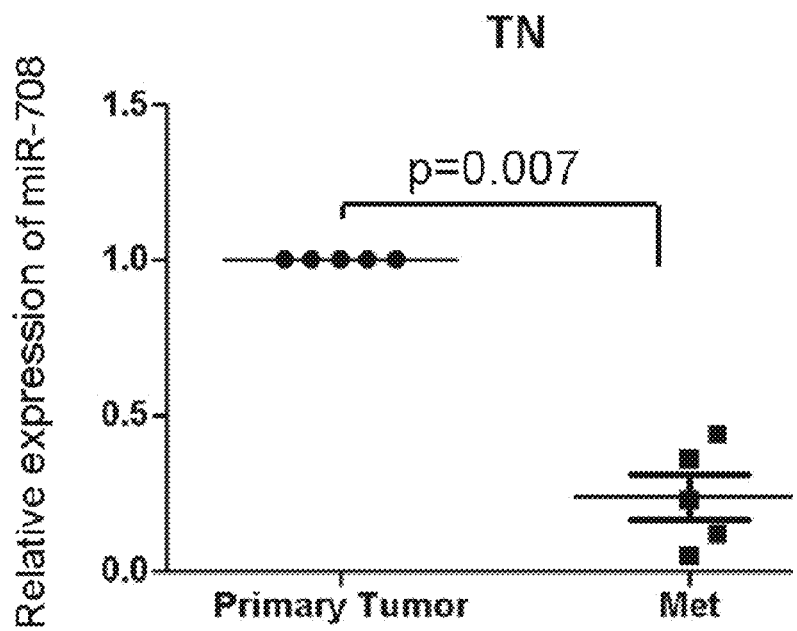

As shown in FIG. 6A-6B, compared to primary breast tumors from human patients, miR-708 expression level was significantly reduced in the patients' matched lymph node metastases while control U6 snRNA expression levels remained unchanged (p=0.004 and 0.55 respectively, see also FIG. 6F). This panel was expanded further and miR-708 levels were quantitated in FFPE samples by Taqman Q-PCR. Consistent with the in situ hybridization data, suppression of miR-708 was observed in metastases compared to primary tumors (FIGS. 6H-6J). Similarly, distal lung metastases in breast cancer patients exhibited a dramatic reduction in miR-708 expression (FIGS. 6C-6D, 6G).

Figure 6K:
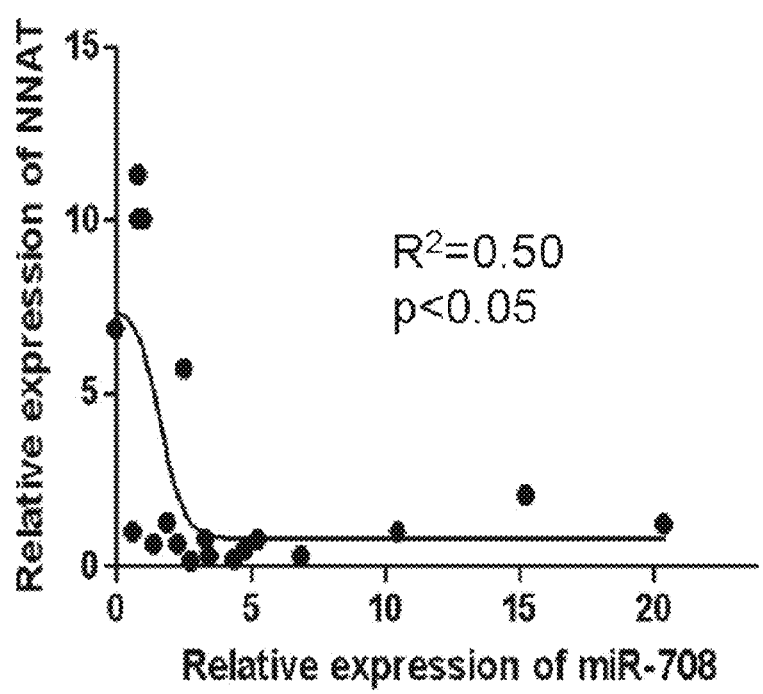

Nnat expression was also evaluated in breast cancer patient samples because Nnat is a target of miR-708. As shown in FIG. 6K, Nnat expression was inversely correlated with miR-708 expression in primary tumor and matched metastatic tissue, indicating that miR-708 regulate Nnat expression in tumors.

As shown above, suppression of miR-708 by the polycomb group of transcriptional repressors increases expression of the endoplasmic reticulum protein Neuronatin, and thus elevates intracellular levels of store operated $Ca^{2+}$ to promote cell migration and metastases. Having demonstrated that ectopic expression of Nnat can rescue miR-708 phenotypes pertaining to cell migration in vitro, and regulation of intracellular $Ca^{2+}$ and p-ERK/p-FAK levels, tests were performed to determine whether Nnat would also increase metastases in vivo. MDA-pZeo (control), MDA-miR-708, MDA-miR-708-Nnat-mut cells were injected orthotopically into the mammary glands of SCID mice and the injected cells were allowed to develop lung metastases. As described above, the Nnat-mut vector has a mutated miR-708 binding site so that miR-708 does not modulate Nnat expression from the 3'-UTR of the pMSCV retroviral vector.

Figure 7A:
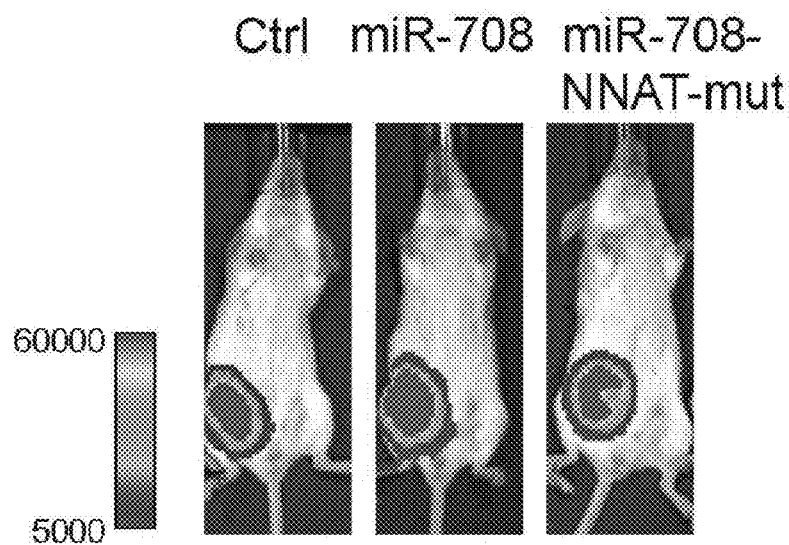
FIG. 7A-7H illustrate that the NNAT protein can partially obviate miR-708-inhibited metastases in vivo.
Figure 7B:
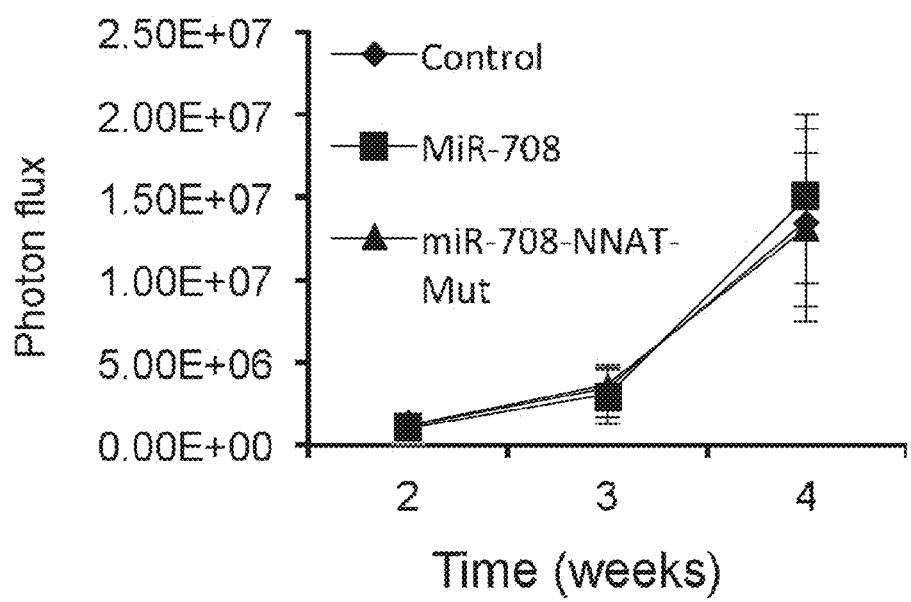
Figure 7C:
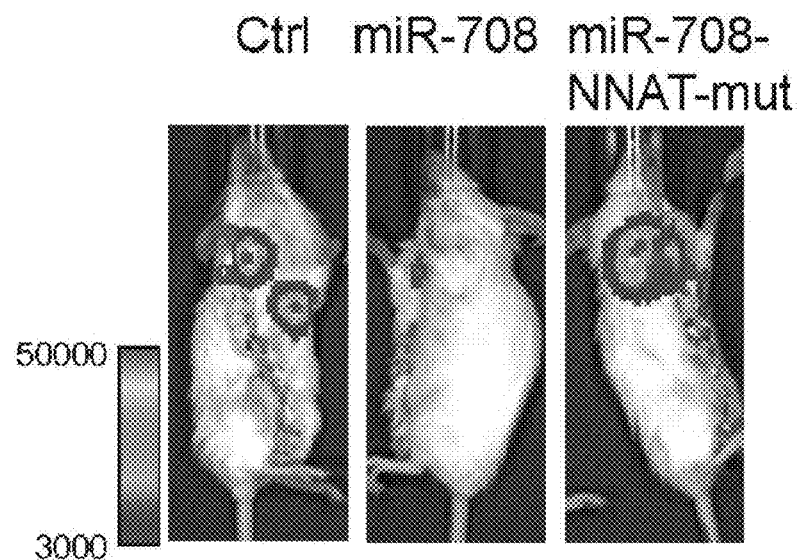
Figure 7D:
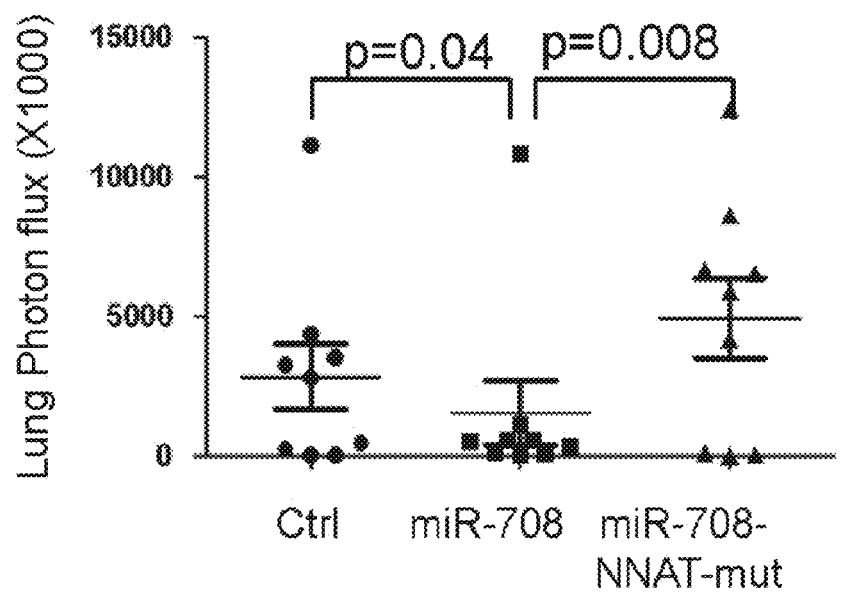
Figure 7E:
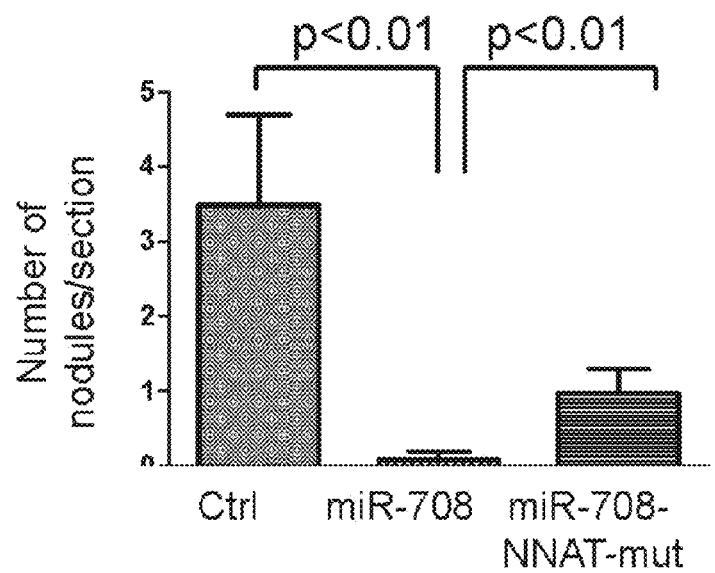
Figure 7F:
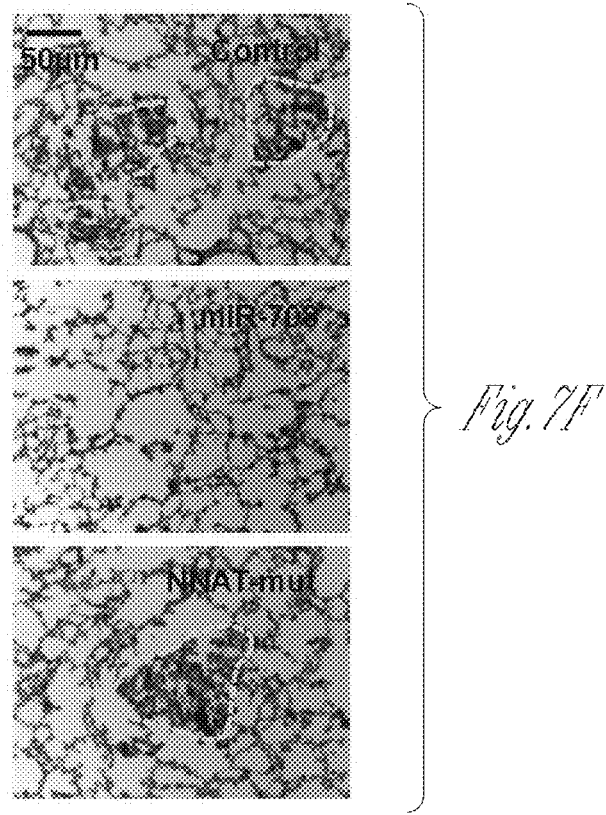
Figure 7G:
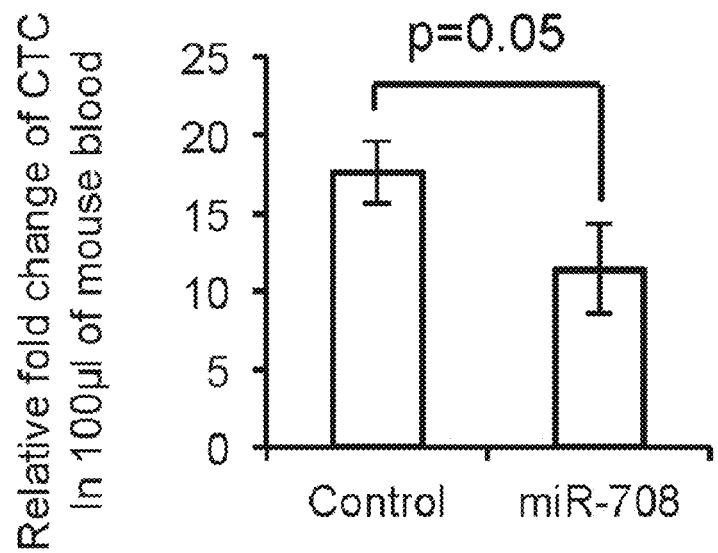
Figure 7H:
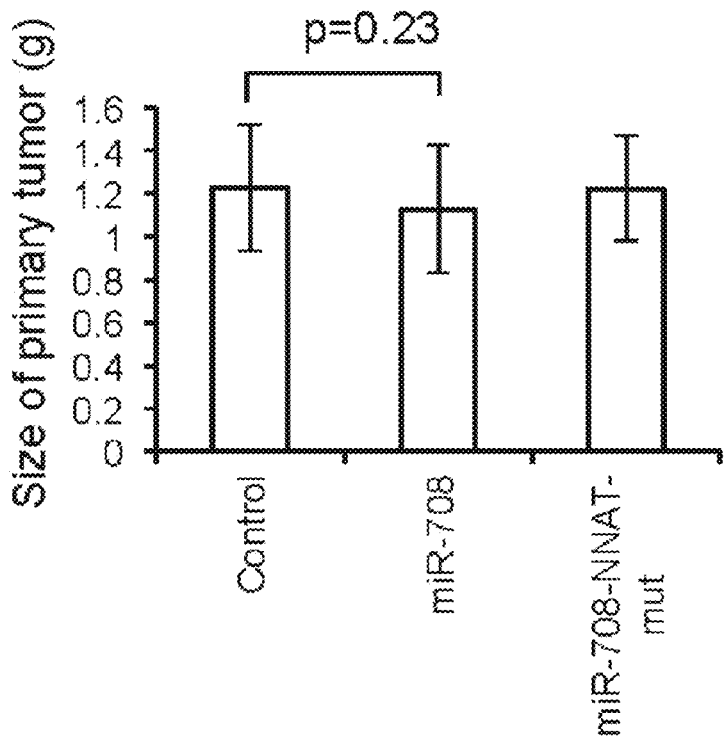

As shown in FIG. 7A-7B, there was no change in primary tumor growth as determined by bioluminescence imaging. Primary tumor size measurements were also unaffected (FIG. 7H). However, metastases were significantly suppressed in animals receiving miR-708 with the MDA cells (FIGS. 7C-7D). Expression of Nnat-mut lead to metastases even when miR-708 was expressed (FIGS. 7C-7D). Immunohistochemical analysis showed that there were reduced numbers of lung metastatic nodules in MDA-LM2-miR-708 compared to controls (FIGS. 7E-7F). Consistent with these observations, MDA-LM2-miR-708 tumor bearing mice had reduced number of circulating tumor cells (CTCs) compared to controls (FIG. 7G). Hence, miR-708-mediated inhibition of cell migration reduces dissemination of circulating tumor cells.

Analysis of clinical samples from breast cancer patients also showed that compared to primary tumors there was a marked suppression of miR-708 in both matched lymph node metastases and distal metastases. Hence, miR-708 can be a good therapeutic agent against breast cancer metastases in breast cancer patients.

Example 10

Liposomal miR-708 Reduces Triple Negative Breast Cancer Metastasis

Figure 8A:
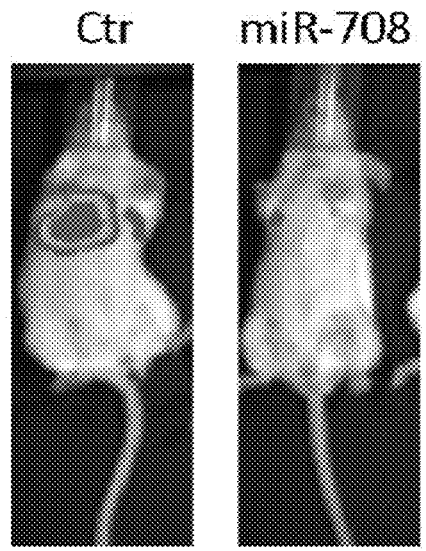
FIG. 8A-8B illustrates that liposome delivered miR-708 reduces triple negative breast cancer (TNBC) cell metastasis in vivo.
Figure 8B:
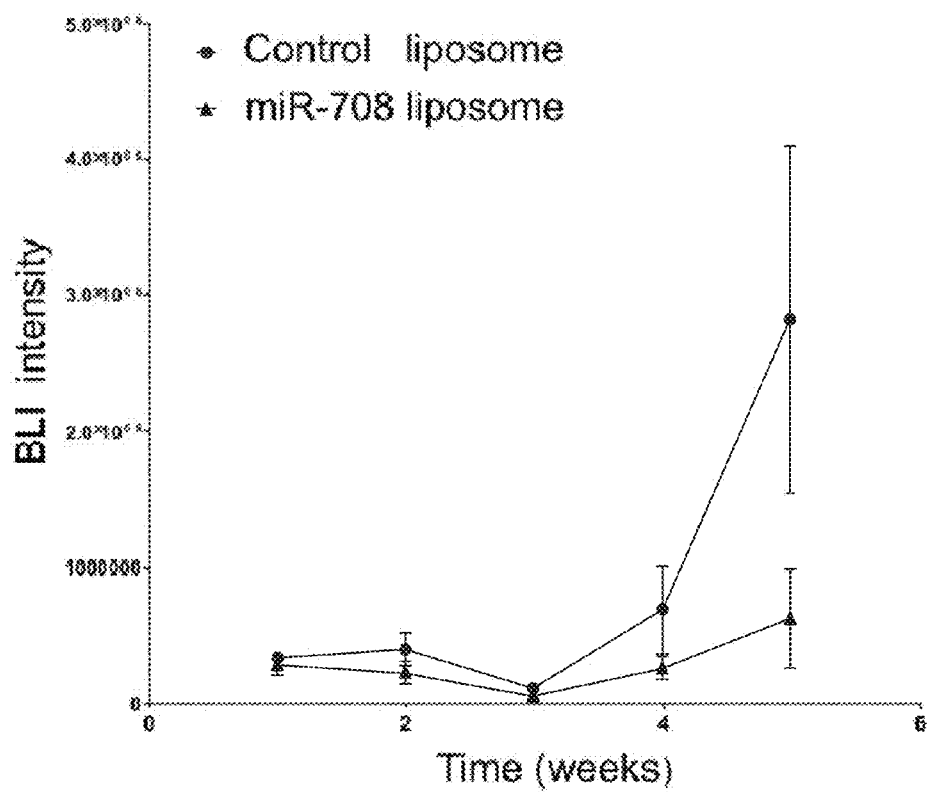

Experimental metastasis generated from human TNBC MDA-MB-231 cells in SCID mice (n=12). Three days post-injection, treatment was initiated with cationic DOTAP/DOPE liposomes (50:50 mol/mol, mean particle size 67.2±0.3 nm, 37.0 Zeta potential) loaded with custom-synthesized 23-mer miR-708 oligo duplex plus 2 [dT] (5'-AAGGAGCTTACAATCTAGCTGGGTT-3' (SEQ ID NO: 116)) overhangs to deliver 15 micrograms of mature miR-708 per injection (i.v.) twice weekly for 5 weeks. As shown in FIGS. 8A and 8B, liposomal delivery of miR-708 significantly reduced metastatic burden in the lungs of these animals.

Example 11

Sequences of Neuronatin and Suz-12

Sequences for neuronatin and Suz-12 are available, for example, from the NCBI database.

One example of an amino acid sequence for human neuronatin is the sequence shown below, which has NCBI accession number AAH01768.1 (GI:12804685), provided herein as SEQ ID NO: 111.

```
  1 MAAVAAASAE LLIIGWYIFR VLLQVFLECC IYWVGFAFRN
 41 PPGTQPIARS EVFRYSLQKL AYTVSRTGRQ VLGERRQRAP
 81 N
```

A cDNA encoding this human neuronatin protein can have the following sequence, which is available from the NCBI database as accession number BC001768.1 (GI:12804684), and provided herein as SEQ ID NO:112.

```
   1 AGCGGACTCC GAGACCAGCG GATCTCGGCA AACCCTCTTT
  41 CTCGACCACC CACCTACCAT TCTTGGAACC ATGGCGGCAG
  81 TGGCGGCGGC CTCGGCTGAA CTGCTCATCA TCGGCTGGTA
 121 CATCTTCCGC GTGCTGCTGC AGGTGTTCCT GGAATGCTGC
 161 ATTTACTGGG TAGGATTCGC TTTTCGAAAT CCTCCAGGGA
 201 CACAGCCCAT TGCGAGAAGT GAGGTGTTCA GGTACTCCCT
 241 GCAGAAGCTG CATACACGG TGTCGCGGAC CGGGCGGCAG
 281 GTGTTGGGGG AGCGCAGGCA GCGAGCCCCC AACTGAGGCC
 321 CCAGCTCCCA GCCCTGGGCG GCCGTATCAT CAGGTGCTCC
 361 TGTGCATCTC GGCCAGCACG GGAGCCAGTG CCGCGCAGGA
 401 ATGTGGGGTC CCCTGTGTTC CCTCGCCAGA GGAGCACTTG
 441 GCAAGGTCAG TGAGGGGCCA GTAGACCCCC GGAGAAGCAG
 481 TACCGACAAT GACGAAGATA CCAGATCCCT TCCCAACCCC
 521 TTTGCACCGG TCCCACTAAG GGGCAGGGTC GAGAGAGGAG
 561 GGGGGATAGG GGGAGCAGAC CCCTGAGATC TGGGCATAGG
 601 CACCGCATTC TGATCTGGAC AAAGTCGGGA CAGCACCATC
 641 CCAGCCCCGA AGCCAGGGCC ATGCCAGCAG GCCCCACCAT
 681 GGAAATCAAA ACACCGCACC AGCCAGCAGA ATGGACATTC
 721 TGACATCGCC AGCCGACGCC CTGAATCTTG GTGCAGCACC
 761 AACCGCGTGC CTGTGTGGCG GGACTGGAGG GCACAGTTGA
 801 GGAAGGAGGG TGGTTAAGAA ATACAGTGGG GCCCTCTCGC
 841 TGTCCCTTGC CCAGGGCACT TGCATTCCAG CCTCGCTGCA
 881 TTTGCTCTCT CGATTCCCCT TTCCTCCTCA CTGCCTCCCA
 921 AGCCCACCCT ACTCCAAAAT AATGTGTCAC TTGATTTGGA
 961 ACTATTCAAG CAGTAAAAGT AAATGAATCC CACCTTTACT
1001 AAAACACTTT CTCTGAACCC CCCTTGCCCC TCACTGATCT
1041 TGCTTTTCCC TGGTCTCATG CAGTTGTGGT CAATATTGTG
1081 GTAATCGCTA ATTGTACTGA TTGTTTAAGT GTGCATTAGT
1121 TGTGTCTCCC CAGCTAGATT GTAAGCTCCT GGAGGACAGG
1161 GACCACCTCT ACAAAAAATA AAAAAGTAC CTCCCCTGTC
1201 TCGCACAGTG TCCCAGGACC CTGCGGTGCA GTAGAGGCGC
1241 ACCAAAAAAA AAAAAAAAA AAAAAAAAA AAAAAAAAA
1281 A
```

Sequences are also available from the NCBI database for human Suz-12. One example of a human Suz-12 sequence is available from the NCBI database as accession number NP_056170.2 (GI:197333809), provided below as SEQ ID NO:113.

```
  1 MAPQKHGGGG GGGSGPSAGS GGGGFGGSAA VAAATASGGK
 41 SGGGSCGGGG SYSASSSSSA AAAGAAVLP VKKPKMEHVQ
 81 ADHELFLQAF EKPTQIYRFL RTRNLIAPIF LHRTLTYMSH
121 RNSRTNIKRK TFKVDDMLSK VEKMKGEQES HSLSAHLQLT
161 FTGFFHKNDK PSPNSENEQN SVTLEVLLVK VCHKKRKDVS
201 CPIRQVPTGK KQVPLNPDLN QTKPGNFPSL AVSSNEFEPS
241 NSHMVKSYSL LFRVTRPGRR EFNGMINGET NENIDVNEEL
281 PARRKRNRED GEKTFVAQMT VFDKNRRLQL LDGEYEVAMQ
321 EMEECPISKK RATWETILDG KRLPPFETFS QGPTLQFTLR
361 WTGETNDKST APIAKPLATR NSESLHQENK PGSVKPTQTI
401 AVKESLTTDL QTRKEKDTPN ENRQKLRIFY QFLYNNNTRQ
441 QTEARDDLHC PWCTLNCRKL YSLLKHLKLC HSRFIFNYVY
481 HPKGARIDVS INECYDGSYA GNPQDIHRQP GFAFSRNGPV
521 KRTPITHILV CRPKRTKASM SEFLESEDGE VEQQRTYSSG
561 HNRLYFHSDT CLPLRPQEME VDSEDEKDPE WLREKTITQI
601 EEFSDVNEGE KEVMKLWNLH VMKHGFIADN QMNHACMLFV
641 ENYGQKIIKK NLCRNFMLHL VSMHDFNLIS IMSIDKAVTK
681 LREMQQKLEK GESASPANEE ITEEQNGTAN GFSEINSKEK
721 ALETDSVSGV SKQSKKQKL
```

A cDNA sequence for this human Suz-12 protein is available from the NCBI database as accession number NM_015355.2 (GI:197333808), which is provided below as SEQ ID NO:114.

```
  1 GGTGAGCGGC CTCCGAAGCG GAGCGGGGCT CTGAGGAGAC
 41 ACTTTTTTTT TCCTCCCTCC TTCCCTCCTC TCCTCCTCCC
 81 TTCCCTTCCC CTCTCCTCCC CTCTCTCCTC CTTCCCCCCT
121 CGGTCCGCCG GAGCCTGCTG GGGCGAGCGG TTGGTATTGC
161 AGGCGCTTGC TCTCCGGGGC CGCCCGGCGG GTAGCTGGCG
201 GGGGGAGGAG GCAGGAACCG CGATGGCGCC TCAGAAGCAC
241 GGCGGTGGGG GAGGGGGCGG CTCGGGGCCC AGCGCGGGGT
281 CCGGGGGAGG CGGCTTCGGG GGTTCGGCGG CGGTGGCGGC
321 GGCGACGGCT TCGGGCGGCA AATCCGGCGG CGGGAGCTGT
361 GGAGGGGGTG GCAGTTACTC GGCCTCCTCC TCCTCCTCCG
401 CGGCGGCAGC GGCGGGGGCT GCGGTGTTAC CGGTGAAGAA
441 GCCGAAAATG GAGCACGTCC AGGCTGACCA CGAGCTTTTC
```

```
 481 CTCCAGGCCT TGAGAAGCC AACACAGATC TATAGATTTC
 521 TTCGAACTCG AATCTCATA GCACCAATAT TTTTGCACAG
 561 AACTCTTACT TACATGTCTC ATCGAAACTC CAGAACAAAC
 601 ATCAAAAGGA AAACATTTAA AGTTGATGAT ATGTTATCAA
 641 AAGTAGAGAA AATGAAAGGA GAGCAAGAAT CTCATAGCTT
 681 GTCAGCTCAT TTGCAGCTTA CGTTTACTGG TTTCTTCCAC
 721 AAAAATGATA AGCCATCACC AAACTCAGAA AATGAACAAA
 761 ATTCTGTTAC CCTGGAAGTC CTGCTTGTGA AAGTTTGCCA
 801 CAAAAAAGA AAGGATGTAA GTTGTCCAAT AAGGCAAGTT
 841 CCCACAGGTA AAAGCAGGT GCCTTTGAAT CCTGACCTCA
 881 ATCAAACAAA ACCCGGAAAT TCCCGTCCC TTGCAGTTTC
 921 CAGTAATGAA TTTGAACCTA GTAACAGCCA TATGGTGAAG
 961 TCTTACTCGT TGCTATTTAG AGTGACTCGT CCAGGAAGAA
1001 GAGAGTTTAA TGGAATGATT AATGGAGAAA CCAATGAAAA
1041 TATTGATGTC AATGAAGAGC TTCCAGCCAG AAGAAAACGA
1081 AATCGTGAGG ATGGGGAAAA GACATTTGTT GCACAAATGA
1121 CAGTATTTGA TAAAAACAGG CGCTTACAGC TTTTAGATGG
1161 GGAATATGAA GTAGCCATGC AGGAAATGGA AGAATGTCCA
1201 ATAAGCAAGA AAAGAGCAAC ATGGGAGACT ATTCTTGATG
1241 GGAAGAGGCT GCCTCCATTC GAAACATTTT CTCAGGGACC
1281 TACGTTGCAG TTCACTCTTC GTTGGACAGG AGAGACCAAT
1321 GATAAATCTA CGGCTCCTAT TGCCAAACCT CTTGCCACTA
1361 GAAATTCAGA GAGTCTCCAT CAGGAAAACA AGCCTGGTTC
1401 AGTTAAACCT ACTCAAACTA TTGCTGTTAA AGAATCATTG
1441 ACTACAGATC TACAAACAAG AAAAGAAAAG GATACTCCAA
1481 ATGAAAACCG ACAAAAATTA AGAATATTTT ATCAGTTTCT
1521 CTATAACAAC AATACAAGGC AACAAACTGA AGCAAGAGAT
1561 GACCTGCATT GCCCTTGGTG TACTCTGAAC TGCCGCAAAC
1601 TTTTATAGTTT ACTCAAGCAT CTTAAACTCT GCCATAGCAG
1641 ATTTATCTTC AACTATGTTT ATCATCCAAA AGGTGCTAGG
1681 ATAGATGTTT CTATCAATGA GTGTTATGAT GGCTCCTATG
1721 CAGGAAATCC TCAGGATATT CATCGCCAAC CTGGATTTGC
1761 TTTTAGTCGC AACGGACCAG TTAAGAGAAC ACCTATCACA
1801 CATATTCTTG TGTGCAGGCC AAAACGAACA AAAGCAAGCA
1841 TGTCTGAATT TCTTGAATCT GAAGATGGGG AAGTAGAACA
1881 GCAAGAACA TATAGTAGTG GCCACAATCG TCTGTATTTC
1921 CATAGTGATA CCTGCTTACC TCTCCGTCCA CAAGAAATGG
1961 AAGTAGATAG TGAAGATGAA AAGGATCCTG AATGGCTAAG
2001 AGAAAAACC ATTACACAAA TTGAAGAGTT TTCTGATGTT
2041 AATGAAGGAG AGAAAGAAGT GATGAAACTC TGGAATCTCC
2081 ATGTCATGAA GCATGGGTTT ATTGCTGACA ATCAAATGAA
2121 TCATGCCTGT ATGCTGTTTG TAGAAAATTA TGGACAGAAA
2161 ATAATTAAGA AGAATTTATG TCGAAACTTC ATGCTTCATC
2201 TAGTCAGCAT GCATGACTTT AATCTTATTA GCATAATGTC
2241 AATAGATAAA GCTGTTACCA AGCTCCGTGA AATGCAGCAA
2281 AAATTAGAAA AGGGGGAATC TGCTTCCCCT GCAAACGAAG
2321 AAATAACTGA AGAACAAAAT GGGACAGCAA ATGGATTTAG
2361 TGAAATTAAC TCAAAAGAGA AAGCTTTGGA ACAGATAGT
2401 GTCTCAGGGG TTTCAAAACA GAGCAAAAAA CAAAAACTCT
2441 GAAAAGCTCT AACCCCATGT TATGGACAAA CACTGAAATT
2481 ACATTTTAGG GAATTCATCC TCTAAGAATT ATGTTTTTGT
2521 TTTTAATCAT ATGTTCCAAA CAGGCACTGT TAGATGAAGT
2561 AAATGATTTC AACAAGGATA TTTGTATCAG GGTTCTACTT
2601 CACTTCATTA TGCAGCATTA CATGTATATC ACTTTTATTG
2641 ATGTCATTAA ACATTCTGT ACTTTAAGCA TGAAAAGCAA
2681 TATTTCAAAG TATTTTTAAA CTCAACAAAT GTCATCAAAT
2721 ATGTTGAATT GATCTAGAAA TTATTTCATA TATAAATCAG
2761 AATTTTTTTG CATTTATGAA CGGCTGTTTT TCTACTTTGT
2801 AATTGTGAGA CATTTTCTTG GGGAGGGAAA ATTGGAATGG
2841 TTCCCTTTTT TAGAAATTGA AGTGGTCTTC ATATGTCAAC
2881 TACAGAAAAG GAAAAAAATA GAAATTGAAG GATTTTTATG
2921 AAATTATATT GCATTACTAT TTGCAGTCAA ACTTTGATCC
2961 TTGTTTTTGA AATCATTTGT CAATTCGGAA TGAAAAATTA
3001 TAATGTAATT TTACATTACA TAAGTTCCTT TTACAATTAA
3041 AAAATAGCAC TTCTTCATCT TATGCCTGTT TGAGAAGATA
3081 TTAAATTTTC ACATTGTTGA CAGTGAAATG CTATGTTGGT
3121 TTATAAGATT ACAGACCATT TGTTTTCATG TGGATAATTT
3161 TAGTGCATTG CTCACCCGGT ATGTTTTTTT TTTTTAACTT
3201 GAACATTTTG CTTGTTTTGT TTTTCTTTTT TAATTAGATA
3241 ATCACACGGA AAATTAAGCT GTTCATATCT TTAAATTAGG
3281 ATTGCAAACC AAGGAAAGAA CGCATTTGAG ATTTTAAGAT
3321 GTCACTTATA AGGGGAGAAG TGTTCTTAAA AAGTCAACCA
3361 GAAAACTGTT ATGCCTTTTA TTTGTTTGCA AGGATGTCTT
3401 TGTAATGTGT TTCATGAATA GAATATCCAA TAGAGATAAG
3441 CTGACTTGAA TCATTTTGAG CAATTTTGCC CTGTGTTATA
3481 TGTGTTTCAC GCACATATTT GCAGTTGGAT TTTCTCCAAC
3521 AGAAAGTGGA TTCACTACTG GCACATTAAC AAGCACCAAT
3561 AGGTTTTTAT TCCAACTCCG AGCACTGTGG TTGAGTAACA
3601 TCACCTCAAT TTTTTATTAT CCTTAAAGAT ATTGCATTTT
3641 CATATTCTTT ATTTATAAAG GATCAATGCT GCTGTAAATA
3681 CAGGTATTTT TAATTTTAAA ATTTCATTCC ACCACCATCA
```

```
3721 GATGCAGTTC CCTATTTTGT TTAATGAAGG GATATATAAG

3761 CTTTCTAATG GTGTCTTCAG AAATTTATAA AATGTAAATA

3801 CTGATTTGAC TGGTCTTTAA GATGTGTTTA ACTGTGAGGC

3841 TATTTAACGA ATAGTGTGGA TGTGATTTGT CATCCAGTAT

3981 TAAGTTCTTA GTCATTGATT TTTGTGTTTA AAAAAAAATA

3921 GGAAAGAGGG AAACTGCAGC TTTCATTACA GATTCCTTGA

3961 TTGGTAAGCT CTCCAAATGA TGAGTTCTAG TAAACTCTGA

4001 TTTTTGCCTC TGGATAGTAG ATCTCGAGCG TTTATCTCGG

4041 GCTTTAATTT GCTAAAGCTG TGCACATATG TAAAAAAAAA

4081 AAAAAAAAGA TTATTTTAGG GGAGATGTAG GTGTAGAATT

4121 ATTGCTTATG TCATTTCTTA AGCAGTTATG CTCTTAATGC

4161 TTAAAAGAAG GCTAGCATTG TTTGCACAAA AAGTTGGTGA

4201 TTCCCACCCC AAATAGTAAT AAAATTACTT CTGTTGAGTA

4241 AACTTTTTAT GTCATCGTAA AAGCTGAAAA AATCCCTTTG

4281 TTTCTATTTA TAAAAAAGT GCTTTTCTAT ATGTACCCTT

4321 GATAACAGAT TTTGAAGAAA TCCTGTAAGA TGATAAAGCA

4361 TTTGAATGGT ACAGTAGATG TAAAAAAAAT TCAGTTTAAA

4401 AGAACATTTG TTTTTACATT AAATGTTTAT TTGAAATCAA

4441 ATGATTTTGT ACATAAAGTT CAATAATATA AAAGCTG
```

BIBLIOGRAPHY

Ahmed, F., Wyckoff, J., Lin, E. Y., Wang, W., Wang, Y., Hennighausen, L., Miyazaki, J., Jones, J., Pollard, J. W., Condeelis, J. S., and Segall, J. E. (2002). GFP expression in the mammary gland for imaging of mammary tumor cells in transgenic mice. Cancer Res 62, 7166-7169.

Alvarez-Garcia, I., and Miska, E. A. (2005). MicroRNA functions in animal development and human disease. Development 132, 4653-4662.

Asangani, I. A., Rasheed, S. A., Nikolova, D. A., Leupold, J. H., Colburn, N. H., Post, S., and Allgayer, H. (2008). MicroRNA-21 (miR-21) post-transcriptionally down-regulates tumor suppressor Pdcd4 and stimulates invasion, intravasation and metastasis in colorectal cancer. Oncogene 27, 2128-2136.

Bartel, D. P. (2004). MicroRNAs: genomics, biogenesis, mechanism, and function. Cell 116, 281-297.

Berridge, M. J., Bootman, M. D., and Roderick, H. L. (2003). Calcium signalling: dynamics, homeostasis and remodelling. Nat Rev Mol Cell Biol 4, 517-529.

Borowsky, A. D., Namba, R., Young, L. J., Hunter, K. W., Hodgson, J. G., Tepper, C. G., McGoldrick, E. T., Muller, W. J., Cardiff, R. D., and Gregg, J. P. (2005). Syngeneic mouse mammary carcinoma cell lines: two closely related cell lines with divergent metastatic behavior. Clin Exp Metastasis 22, 47-59.

Boyer, L. A., Plath, K., Zeitlinger, J., Brambrink, T., Medeiros, L. A., Lee, T. I., Levine, S. S., Wernig, M., Tajonar, A., Ray, M. K., et al. (2006). Polycomb complexes repress developmental regulators in murine embryonic stem cells. Nature 441, 349-353.

Bracken, C. P., Gregory, P. A., Khew-Goodall, Y., and Goodall, G. J. (2009). The role of microRNAs in metastasis and epithelial-mesenchymal transition. Cell Mol Life Sci 66, 1682-1699.

Calin, G. A., and Croce, C. M. (2006). MicroRNA signatures in human cancers. Nat Rev Cancer 6, 857-866.

Calin, G. A., Sevignani, C., Dumitru, C. D., Hyslop, T., Noch, E., Yendamuri, S., Shimizu, M., Rattan, S., Bullrich, F., Negrini, M., and Croce, C. M. (2004). Human microRNA genes are frequently located at fragile sites and genomic regions involved in cancers. Proc Natl Acad Sci USA 101, 2999-3004.

Cao, R., Wang, L., Wang, H., Xia, L., Erdjument-Bromage, H., Tempst, P., Jones, R. S., and Zhang, Y. (2002). Role of histone H3 lysine 27 methylation in Polycomb-group silencing. Science 298, 1039-1043.

Cao, R., and Zhang, Y. (2004). SUZ12 is required for both the histone methyltransferase activity and the silencing function of the EED-EZH2 complex. Mol Cell 15, 57-67.

Ebert, M. S., Neilson, J. R., and Sharp, P. A. (2007). MicroRNA sponges: competitive inhibitors of small RNAs in mammalian cells. Nat Methods 4, 721-726.

Fidler, I. J. (2003). The pathogenesis of cancer metastasis: the 'seed and soil' hypothesis revisited. Nat Rev Cancer 3, 453-458.

Gao, D., Nolan, D. J., Mellick, A. S., Bambino, K., McDonnell, K., and Mittal, V. (2008). Endothelial progenitor cells control the angiogenic switch in mouse lung metastasis. Science 319, 195-198.

Gregory, P. A., Bert, A. G., Paterson, E. L., Barry, S. C., Tsykin, A., Farshid, G., Vadas, M. A., Khew-Goodall, Y., and Goodall, G. J. (2008). The miR-200 family and miR-205 regulate epithelial to mesenchymal transition by targeting ZEB1 and SIP1. Nat Cell Biol 10, 593-601.

Gupta, G. P., and Massague, J. (2006). Cancer metastasis: building a framework. Cell 127, 679-695.

Guy, C. T., Cardiff, R. D., and Muller, W. J. (1992). Induction of mammary tumors by expression of polyomavirus middle T oncogene: a transgenic mouse model for metastatic disease. Mol Cell Biol 12, 954-961.

Hoth, M., and Penner, R. (1992). Depletion of intracellular calcium stores activates a calcium current in mast cells. Nature 355, 353-356.

Huang, C., Jacobson, K., and Schaller, M. D. (2004). MAP kinases and cell migration. J Cell Sci 117, 4619-4628.

Huang, Q., Gumireddy, K., Schrier, M., le Sage, C., Nagel, R., Nair, S., Egan, D. A., Li, A., Huang, G., Klein-Szanto, A. J., et al. (2008). The microRNAs miR-373 and miR-520c promote tumour invasion and metastasis. Nat Cell Biol 10, 202-210.

Hunger-Glaser, I., Fan, R. S., Perez-Salazar, E., and Rozengurt, E. (2004). PDGF and FGF induce focal adhesion kinase (FAK) phosphorylation at Ser-910: dissociation from Tyr-397 phosphorylation and requirement for ERK activation. J Cell Physiol 200, 213-222.

Ilić, D., Furuta, Y., Kanazawa, S., Takeda, N., Sobue, K., Nakatsuji, N., Nomura, S., Fujimoto, J., Okada, M., and Yamamoto, T. (1995). Reduced cell motility and enhanced focal adhesion contact formation in cells from FAK-deficient mice. Nature 377, 539-544.

Inui, M., Martello, G., and Piccolo, S. (2010). MicroRNA control of signal transduction. Nat Rev Mol Cell Biol 11, 252-263.

Iorio, M. V., Ferracin, M., Liu, C. G., Veronese, A., Spizzo, R., Sabbioni, S., Magri, E., Pedriali, M., Fabbri, M., Campiglio, M., et al. (2005). MicroRNA gene expression deregulation in human breast cancer. Cancer Res 65, 7065-7070.

Joseph, R., Dou, D., and Tsang, W. (1994). Molecular cloning of a novel mRNA (neuronatin) that is highly expressed in neonatal mammalian brain. Biochem Biophys Res Commun 201, 1227-1234.

Joyce, J. A., and Pollard, J. W. (2009). Microenvironmental regulation of metastasis. Nat Rev Cancer 9, 239-252.

Kang, S. Y., Halvorsen, 0. J., Gravdal, K., Bhattacharya, N., Lee, J. M., Liu, N. W., Johnston, B. T., Johnston, A. B., Haukaas, S. A., Aamodt, K., et al. (2009). Prosaposin inhibits tumor metastasis via paracrine and endocrine stimulation of stromal p53 and Tsp-1. Proc Natl Acad Sci USA 106, 12115-12120.

Kleer, C. G., Cao, Q., Varambally, S., Shen, R., Ota, I., Tomlins, S. A., Ghosh, D., Sewalt, R. G., Otte, A. P., Hayes, D. F., et al. (2003). EZH2 is a marker of aggressive breast cancer and promotes neoplastic transformation of breast epithelial cells. Proc Natl Acad Sci USA 100, 11606-11611.

Koyanagi, M., Baguet, A., Martens, J., Margueron, R., Jenuwein, T., and Bix, M. (2005). EZH2 and histone 3 trimethyl lysine 27 associated with 114 and 1113 gene silencing in Th1 cells. J Biol Chem 280, 31470-31477.

Lin, H. H., Bell, E., Uwanogho, D., Perfect, L. W., Noristani, H., Bates, T. J., Snetkov, V., Price, J., and Sun, Y. M. (2010). Neuronatin promotes neural lineage in ESCs via Ca(2+) signaling. Stem Cells 28, 1950-1960.

Lu, J., Getz, G., Miska, E. A., Alvarez-Saavedra, E., Lamb, J., Peck, D., Sweet-Cordero, A., Ebert, B. L., Mak, R. H., Ferrando, A. A., et al. (2005). MicroRNA expression profiles classify human cancers. Nature 435, 834-838.

Lujambio, A., Calin, G. A., Villanueva, A., Ropero, S., S. nchez-C. spedes, M., Blanco, D., Montuenga, L. M., Rossi, S., Nicoloso, M. S., Faller, W. J., et al. (2008). A microRNA DNA methylation signature for human cancer metastasis. Proc Natl Acad Sci USA 105, 13556-13561.

Ma, L., Teruya-Feldstein, J., and Weinberg, R. A. (2007). Tumour invasion and metastasis initiated by microRNA-10b in breast cancer. Nature 449, 682-688.

Magalhaes, G. S., Muotri, A. R., Marchetto, M. C., Menck, C. F., and Ventura, A. M. (2002). An adenovirus vector containing the suicide gene thymidine kinase for a broad application in cancer gene therapy. Mem Inst Oswaldo Cruz 97, 547-552.

Margueron, R., Justin, N., Ohno, K., Sharpe, M. L., Son, J., Drury, W. J., Voigt, P., Martin, S. R., Taylor, W. R., De Marco, V., et al. (2009). Role of the polycomb protein EED in the propagation of repressive histone marks. Nature 461, 762-767.

Marson, A., Levine, S. S., Cole, M. F., Frampton, G. M., Brambrink, T., Johnstone, S., Guenther, M. G., Johnston, W. K., Wernig, M., Newman, J., et al. (2008). Connecting microRNA genes to the core transcriptional regulatory circuitry of embryonic stem cells. Cell 134, 521-533.

Minn, A. J., Gupta, G. P., Siegel, P. M., Bos, P. D., Shu, W., Giri, D. D., Viale, A., Olshen, A. B., Gerald, W. L., and Massague, J. (2005). Genes that mediate breast cancer metastasis to lung. Nature 436, 518-524.

Nolan, D. J., Ciarrocchi, A., Mellick, A. S., Jaggi, J. S., Bambino, K., Gupta, S., Heikamp, E., McDevitt, M. R., Scheinberg, D. A., Benezra, R., and Mittal, V. (2007). Bone marrow-derived endothelial progenitor cells are a major determinant of nascent tumor neovascularization. Genes Dev 21, 1546-1558.

O'Connor, N., and Silver, R. B. (2007). Ratio imaging: practical considerations for measuring intracellular Ca2+ and pH in living cells. Methods Cell Biol 81, 415-433.

Ozen, M., Creighton, C. J., Ozdemir, M., and Ittmann, M. (2008). Widespread deregulation of microRNA expression in human prostate cancer. Oncogene 27, 1788-1793.

Pettit, E. J., and Fay, F. S. (1998). Cytosolic free calcium and the cytoskeleton in the control of leukocyte chemotaxis. Physiol Rev 78, 949-967.

Ryu, S., Joshi, N., McDonnell, K., Woo, J., Choi, H., Gao, D., McCombie, W. R., and Mittal, V. (2011). Discovery of Novel Human Breast Cancer MicroRNAs from Deep Sequencing Data by Analysis of Pri-MicroRNA Secondary Structures. PLoS One 6, e16403.

Saini, S., Majid, S., Shahryari, V., Arora, S., Yamamura, S., Chang, I., Zaman, M. S., Deng, G., Tanaka, Y., and Dahiya, R. (2012). miRNA-708 Control of CD44+Prostate Cancer-Initiating Cells. Cancer Res 72, 3618-3630.

Schwartz, Y. B., and Pirrotta, V. (2007). Polycomb silencing mechanisms and the management of genomic programmes. Nat Rev Genet 8, 9-22.

Sellers, W. R., and Loda, M. (2002). The EZH2 polycomb transcriptional repressor—a marker or mover of metastatic prostate cancer? Cancer Cell 2, 349-350.

Shimono, Y., Zabala, M., Cho, R. W., Lobo, N., Dalerba, P., Qian, D., Diehn, M., Liu, H., Panula, S. P., Chiao, E., et al. (2009). Downregulation of miRNA-200c links breast cancer stem cells with normal stem cells. Cell 138, 592-603.

Sieg, D. J., Hauck, C. R., and Schlaepfer, D. D. (1999). Required role of focal adhesion kinase (FAK) for integrin-stimulated cell migration. J Cell Sci 112 (Pt 16), 2677-2691.

Simon, J. A., and Kingston, R. E. (2009). Mechanisms of polycomb gene silencing: knowns and unknowns. Nat Rev Mol Cell Biol 10, 697-708.

Steeg, P. S. (2006). Tumor metastasis: mechanistic insights and clinical challenges. Nat Med 12, 895-904.

Stegmeier, F., Hu, G., Rickles, R. J., Hannon, G. J., and Elledge, S. J. (2005). A lentiviral microRNA-based system for single-copy polymerase II-regulated RNA interference in mammalian cells. Proc Natl Acad Sci USA 102, 13212-13217.

Suh, Y. H., Kim, W. H., Moon, C., Hong, Y. H., Eun, S. Y., Lim, J. H., Choi, J. S., Song, J., and Jung, M. H. (2005). Ectopic expression of Neuronatin potentiates adipogenesis through enhanced phosphorylation of cAMP-response element-binding protein in 3T3-L1 cells. Biochem Biophys Res Commun 337, 481-489.

Suzuki, H., Takatsuka, S., Akashi, H., Yamamoto, E., Nojima, M., Maruyama, R., Kai, M., Yamano, H. O., Sasaki, Y., Tokino, T., et al. (2011). Genome-wide Profiling of Chromatin Signatures Reveals Epigenetic Regulation of Micro RNA Genes in Colorectal Cancer. Cancer Res 71, 5646-5658.

Swanson, K. D., Reigh, C., and Landreth, G. E. (1998). ATP-stimulated activation of the mitogen-activated protein kinases through ionotrophic P2X2 purinoreceptors in PC12 cells. Difference in purinoreceptor sensitivity in two PC12 cell lines. J Biol Chem 273, 19965-19971.

Tavazoie, S. F., Alarcon, C., Oskarsson, T., Padua, D., Wang, Q., Bos, P. D., Gerald, W. L., and Massague, J. (2008). Endogenous human microRNAs that suppress breast cancer metastasis. Nature 451, 147-152.

Valastyan, S., Reinhardt, F., Benaich, N., Calogrias, D., Szasz, A. M., Wang, Z. C., Brock, J. E., Richardson, A. L., and Weinberg, R. A. (2009). A pleiotropically acting microRNA, miR-31, inhibits breast cancer metastasis. Cell 137, 1032-1046.

Valastyan, S., and Weinberg, R. A. (2009). MicroRNAs: Crucial multi-tasking components in the complex circuitry of tumor metastasis. Cell Cycle 8, 3506-3512.

Vandewalle, B., Hornez, L., Revillion, F., and Lefebvre, J. (1994). Effect of extracellular ATP on breast tumor cell growth, implication of intracellular calcium. Cancer Lett 85, 47-54.

Ventura, A., Young, A. G., Winslow, M. M., Lintault, L., Meissner, A., Erkeland, S. J., Newman, J., Bronson, R. T., Crowley, D., Stone, J. R., et al. (2008). Targeted deletion reveals essential and overlapping functions of the miR-17 through 92 family of miRNA clusters. Cell 132, 875-886.

Volinia, S., Calin, G. A., Liu, C. G., Ambs, S., Cimmino, A., Petrocca, F., Visone, R., Iorio, M., Roldo, C., Ferracin, M., et al. (2006). A microRNA expression signature of human solid tumors defines cancer gene targets. Proc Natl Acad Sci USA 103, 2257-2261.

Yang, S., Zhang, J. J., and Huang, X. Y. (2009). Orai1 and STIM1 are critical for breast tumor cell migration and metastasis. Cancer Cell 15, 124-134.

Zhao, J., and Guan, J. L. (2009). Signal transduction by focal adhesion kinase in cancer. Cancer Metastasis Rev 28, 35-49.

Zheng, Y., Xia, Y., Hawke, D., Halle, M., Tremblay, M. L., Gao, X., Zhou, X. Z., Aldape, K., Cobb, M. H., Xie, K., et al. (2009). FAK phosphorylation by ERK primes ras-induced tyrosine dephosphorylation of FAK mediated by PIN1 and PTP-PEST. Mol Cell 35, 11-25.

Zhu, S., Wu, H., Wu, F., Nie, D., Sheng, S., and Mo, Y. Y. (2008). MicroRNA-21 targets tumor suppressor genes in invasion and metastasis. Cell Res 18, 350-359.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention.

The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a nucleic acid" or "an expression cassette" or "a cell" includes a plurality of such nucleic acids, expression vectors or cells (for example, a solution or dried preparation of nucleic acids or expression cassettes, or a population of cells), and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The following statements describe some of the elements or features of the invention.

Statements:

1. A method of inhibiting migration of cancer cells comprising contacting the cancer cells with micro RNA-708.
2. The method of statement 1, wherein the microRNA-708 comprises a nucleic acid molecule.
3. The method of statement 1 or 2, wherein the microRNA-708 comprises a RNA molecule.
4. The method of any of statements 1-3, wherein the microRNA-708 comprises a nucleic acid with non-natural nucleotides.
5. The method of any of statements 1-4, wherein the microRNA-708 comprises a nucleic acid with non-natural bonds between nucleotides.
6. The method of any of statements 1-4, wherein the micro RNA-708 is a segment in an expression cassette or expression vector, or is encoded by a segment in an expression cassette or expression vector.
7. The method of any of statements 1-6, wherein the micro RNA-708 is a segment in an expression cassette or expression vector, or is encoded by a segment in an expression cassette or expression vector, and wherein the expression cassette or the expression vector that also comprises a promoter operably linked to the micro RNA-708 segment.

8. The method of any of statements 1-7, wherein the microRNA-708 is formulated into a composition.

9. The method of any of statements 1-8, wherein the microRNA-708 is within a vehicle or carrier.

10. The method of any of statements 1-9, wherein the microRNA-708 is within an exosome, liposome, or microvesicle.

11. The method of any of statements 1-10, wherein contacting comprises addition of the microRNA-708 to cells in vitro or in vivo.

12. The method of any of statements 1-11, wherein contacting the cancer cells with microRNA-708 comprises production of the microRNA-708 from a transgenic cell that comprises an expression vector or expression cassette encoding the microRNA-708.

13. The method of any of statements 1-12, wherein contacting the cancer cells with microRNA-708 comprises production of the microRNA-708 from a transgenic cell that comprises an expression vector or expression cassette that encodes the microRNA-708, and wherein the expression cassette or the expression vector also comprises a promoter operably linked to a nucleic acid segment that encodes the microRNA-708.

14. The method of any of statements 1-13, wherein contacting the cancer cells with microRNA-708 comprises production of the microRNA-708 from a transgenic cell that produces exosomes or microvesicles containing microRNA-708.

15. The method of any of statements 1-13, wherein the microRNA-708 comprises a sequence with at least 95% sequence identity to any of SEQ ID NO:1, 65, 100, 101, 102, 103, 104, 105, 106, 107, 108, 109, or 116, wherein the microRNA-708 sequence has natural nucleotides, non-natural nucleotides, phosphodiester bonds, non-phosphodiester bonds, or a combination thereof.

16. A method of inhibiting migration of cancer cells comprising administering microRNA-708 to the cancer cells.

17. The method of statement 16, wherein the microRNA-708 comprises a nucleic acid molecule.

18. The method of statement 16 or 17, wherein the microRNA-708 comprises a RNA molecule.

19. The method of any of statements 16-18, wherein the microRNA-708 comprises a nucleic acid with non-natural nucleotides.

20. The method of any of statements 16-19, wherein the microRNA-708 comprises a nucleic acid with non-natural bonds between nucleotides.

21. The method of any of statements 16-20, wherein the microRNA-708 is a segment in an expression cassette or expression vector, or is encoded by a segment in an expression cassette or expression vector.

22. The method of any of statements 16-21, wherein the microRNA-708 is a segment in an expression cassette or expression vector, or is encoded by a segment in an expression cassette or expression vector, and wherein the expression cassette or the expression vector that also comprises a promoter operably linked to the micro RNA-708 segment.

23. The method of any of statements 16-22, wherein the microRNA-708 is formulated into a composition.

24. The method of any of statements 16-23, wherein the microRNA-708 is within a vehicle or carrier.

25. The method of any of statements 16-24, wherein the microRNA-708 is within an exosome, liposome, or microvesicle.

26. The method of any of statements 16-25, wherein the microRNA-708 is expressed from a transgenic cell that comprises an expression vector or expression cassette encoding the micro RNA-708.

27. The method of any of statements 16-26, wherein the microRNA-708 is produced from a transgenic cell that comprises an expression vector or expression cassette that encodes the microRNA-708, and wherein the expression cassette or the expression vector also comprises a promoter operably linked to a nucleic acid segment that encodes the micro RNA-708.

28. The method of any of statements 16-27, wherein the micro RNA-708 is produced from a transgenic cell that produces exosomes or microvesicles containing microRNA-708.

29. The method of any of statements 16-28, wherein the microRNA-708 comprises a sequence with at least 95% sequence identity to any of SEQ ID NO:1, 65, 100, 101, 102, 103, 104, 105, 106, 107, 108, 109, or 116, wherein the microRNA-708 sequence has natural nucleotides, non-natural nucleotides, phosphodiester bonds, non-phosphodiester bonds, or a combination thereof.

30. The method of any of statements 16-29, wherein administering comprises systemic or local administration to an animal.

31. The method of any of statements 16-30, wherein administering comprises systemic or local administration to an animal, and wherein the animal is a laboratory animal, a domesticated animal, a zoo animal, or a human.

32. The method of any of statements 1-31, wherein the microRNA-708 is contacted or administered in an amount sufficient to inhibit migration of cancer cells.

33. The method of any of statements 1-32, wherein the micro RNA-708 is contacted or administered in an amount sufficient to inhibit metastasis of cancer cells.

34. The method of any of statements 1-33, wherein the cancer cells are prostate or breast cancer cells.

35. The method of any of statements 1-34, wherein the microRNA-708 is expressed in the cancer cells from a heterologous expression cassette or expression vector.

36. The method of any of statements 1-35, wherein one or more cancer cells are transformed with an expression cassette or expression vector that can express microRNA-708.

37. The method of any of statements 1-36, where the method further comprises inhibiting expression or function of neuronatin or Suz-12.

38. A composition comprising a microRNA-708 nucleic acid comprising a sequence with at least 90%, at least 91%, at least 92%, at least 93%, at least 94%, at least 95%, at least 96%, at least 97%, at least 98%, at least 99% sequence identity to any of SEQ ID NO:1, 65, 100, 101, 102, 103, 104, 105, 106, 107, 108, 109, or 116.

39. The composition of statement 38, wherein the micro RNA-708 consists essentially of a sequence with at least 90%, at least 91%, at least 92%, at least 93%, at least 94%, at least 95%, at least 96%, at least 97%, at least 98%, at least 99% sequence identity to any of SEQ ID NO:1, 65, 100, 101, 102, 103, 104, 105, 106, 107, 108, 109, or 116.

40. The composition of statement 38 or 39, wherein the microRNA-708 consists of a sequence with at least 90%, at least 91%, at least 92%, at least 93%, at least 94%, at least 95%, at least 96%, at least 97%, at least 98%, at least 99% sequence identity to any of SEQ ID NO:1, 65, 100, 101, 102, 103, 104, 105, 106, 107, 108, 109, or 116.

41. The composition of any of statements 38-40, wherein the microRNA-708 sequence is any of SEQ ID NO:1, 65, 100, 101, 102, 103, 104, 105, 106, 107, 108, 109, or 116.

42. The composition of any of statements 38-41, wherein the composition further comprises a carrier or vehicle.

43. The composition of any of statements 38-42, wherein the composition further comprises a carrier or vehicle selected from the group consisting of a liposome, a exosome, a microvesicle, or a combination thereof.

44. The composition of any of statements 38-43, wherein the microRNA-708 is present in an amount sufficient to inhibit cell migration or metastasis of cancer cells in an animal.

45. Use of micro RNA-708 for treatment of cancer.

46. The use of statement 45, wherein the cancer is breast cancer or prostrate cancer.

47. The use of statement 45 or 46, wherein the microRNA is in the composition of any of statements 38-44.

The following claims also describe aspects of the invention.

---

What is claimed:

1. A method of inhibiting migration of breast cancer cells in an animal comprising systemic or local administration of microRNA-708 to the animal.

2. The method of claim 1, wherein the microRNA-708 comprises an RNA molecule with natural nucleotides and natural bonds between the nucleotides.

3. The method of claim 1, wherein the microRNA-708 comprises a nucleic acid with non-natural nucleotides.

4. The method of claim 1, wherein the microRNA-708 comprises a nucleic acid with non-natural bonds between nucleotides.

5. The method of claim 1, wherein the microRNA-708 is a segment in an expression cassette or expression vector, or is encoded by a segment in an expression cassette or expression vector.

6. The method of claim 1, wherein the microRNA-708 is a segment in an expression cassette or expression vector, or is encoded by a segment in an expression cassette or expression vector, and wherein the expression cassette or the expression vector comprises a promoter operably linked to the microRNA-708 segment.

7. The method of claim 1, wherein the microRNA-708 is formulated into a pharmaceutical composition.

8. The method of claim 1, wherein the microRNA-708 is within a composition comprising a vehicle or carrier.

9. The method of claim 1, wherein the microRNA-708 is within an exosome, liposome, microvesicle, or a combination thereof.

10. The method of claim 1, wherein the microRNA-708 is administered in an amount sufficient to inhibit metastasis of breast cancer cells.

11. The method of claim 1, wherein the breast cancer cells are transformed with an expression cassette or expression vector that can express microRNA-708.

12. The method of claim 1, where the method further comprises inhibiting expression or function of neuronatin or Suz-12.

13. The method of claim 1, wherein the method comprises administration of a microRNA-708 nucleic acid comprising or consisting essentially of a sequence with at least 90% sequence identity to any of SEQ ID NO:1, 65, 100, 101, 102, 103, 104, 105, 106, 107, 108, 109, or 116.

* * * * *

SEQUENCE LISTING

<160> NUMBER OF SEQ ID NOS: 131

<210> SEQ ID NO 1
<211> LENGTH: 88
<212> TYPE: DNA
<213> ORGANISM: Homo sapiens

<400> SEQUENCE: 1
aactgccctc aaggagctta caatctagct gggggtaaat gacttgcaca tgaacacaac     60
tagactgtga gcttctagag ggcaggga                                        88

<210> SEQ ID NO 2
<211> LENGTH: 23
<212> TYPE: RNA
<213> ORGANISM: Artificial Sequence
<220> FEATURE:
<223> OTHER INFORMATION: A synthetic ribonucleotiide sequence

<400> SEQUENCE: 2
aaggagcuua caaucuagcu ggg                                             23

<210> SEQ ID NO 3
<211> LENGTH: 22
<212> TYPE: DNA
<213> ORGANISM: Artificial Sequence
<220> FEATURE:
<223> OTHER INFORMATION: A synthetic oligonucleotiide

<400> SEQUENCE: 3
cccagctaga tcatagctcc tt                                              22

<210> SEQ ID NO 4
<211> LENGTH: 20
<212> TYPE: DNA
<213> ORGANISM: Artificial Sequence
<220> FEATURE:
<223> OTHER INFORMATION: A synthetic primer

<400> SEQUENCE: 4
caggaaacca ggaataggtg                                                 20

<210> SEQ ID NO 5
<211> LENGTH: 20
<212> TYPE: DNA
<213> ORGANISM: Artificial Sequence
<220> FEATURE:
<223> OTHER INFORMATION: A synthetic primer

<400> SEQUENCE: 5
gaattgatcg cagaggagga                                                 20

```
<210> SEQ ID NO 6
<211> LENGTH: 20
<212> TYPE: DNA
<213> ORGANISM: Artificial Sequence
<220> FEATURE:
<223> OTHER INFORMATION: A synthetic primer

<400> SEQUENCE: 6
cccaggacac caagtcagtt                                               20

<210> SEQ ID NO 7
<211> LENGTH: 20
<212> TYPE: DNA
<213> ORGANISM: Artificial Sequence
<220> FEATURE:
<223> OTHER INFORMATION: A synthetic primer

<400> SEQUENCE: 7
atcgcgggca attacataag                                               20

<210> SEQ ID NO 8
<211> LENGTH: 20
<212> TYPE: DNA
<213> ORGANISM: Artificial Sequence
<220> FEATURE:
<223> OTHER INFORMATION: A synthetic primer

<400> SEQUENCE: 8
ggtactgttg agggctctgc                                               20

<210> SEQ ID NO 9
<211> LENGTH: 20
<212> TYPE: DNA
<213> ORGANISM: Artificial Sequence
<220> FEATURE:
<223> OTHER INFORMATION: A synthetic primer

<400> SEQUENCE: 9
ccatttttaa atgcggtcgt                                               20

<210> SEQ ID NO 10
<211> LENGTH: 20
<212> TYPE: DNA
<213> ORGANISM: Artificial Sequence
<220> FEATURE:
<223> OTHER INFORMATION: A synthetic primer

<400> SEQUENCE: 10
cctcagttgg ctcctagacg                                               20

<210> SEQ ID NO 11
<211> LENGTH: 20
<212> TYPE: DNA
<213> ORGANISM: Artificial Sequence
<220> FEATURE:
<223> OTHER INFORMATION: A synthetic primer

<400> SEQUENCE: 11
gaagaggcaa gctgttctgg                                               20

<210> SEQ ID NO 12
<211> LENGTH: 22
<212> TYPE: DNA
<213> ORGANISM: Homo sapiens

<400> SEQUENCE: 12
```

```
tgagaactga attccatggg tt                                              22

<210> SEQ ID NO 13
<211> LENGTH: 22
<212> TYPE: DNA
<213> ORGANISM: Homo sapiens

<400> SEQUENCE: 13
aagctgccag ttgaagaact gt                                              22

<210> SEQ ID NO 14
<211> LENGTH: 23
<212> TYPE: DNA
<213> ORGANISM: Homo sapiens

<400> SEQUENCE: 14
caaagtgctt acagtgcagg tag                                             23

<210> SEQ ID NO 15
<211> LENGTH: 22
<212> TYPE: DNA
<213> ORGANISM: Homo sapiens

<400> SEQUENCE: 15
tggctcagtt cagcaggaac ag                                              22

<210> SEQ ID NO 16
<211> LENGTH: 21
<212> TYPE: DNA
<213> ORGANISM: Homo sapiens

<400> SEQUENCE: 16
ttcacagtgg ctaagttccg c                                               21

<210> SEQ ID NO 17
<211> LENGTH: 22
<212> TYPE: DNA
<213> ORGANISM: Homo sapiens

<400> SEQUENCE: 17
aacccgtaga tccgaacttg tg                                              22

<210> SEQ ID NO 18
<211> LENGTH: 21
<212> TYPE: DNA
<213> ORGANISM: Homo sapiens

<400> SEQUENCE: 18
tcgaggagct cacagtctag t                                               21

<210> SEQ ID NO 19
<211> LENGTH: 21
<212> TYPE: DNA
<213> ORGANISM: Homo sapiens

<400> SEQUENCE: 19
agctacatct ggctactggg t                                               21

<210> SEQ ID NO 20
<211> LENGTH: 21
<212> TYPE: DNA
<213> ORGANISM: Homo sapiens
```

```
<400> SEQUENCE: 20
atcacattgc cagggatttc c                                        21

<210> SEQ ID NO 21
<211> LENGTH: 23
<212> TYPE: DNA
<213> ORGANISM: Homo sapiens

<400> SEQUENCE: 21
taaggtgcat ctagtgcaga tag                                      23

<210> SEQ ID NO 22
<211> LENGTH: 23
<212> TYPE: DNA
<213> ORGANISM: Homo sapiens

<400> SEQUENCE: 22
tagcaccatt tgaaatcagt gtt                                      23

<210> SEQ ID NO 23
<211> LENGTH: 23
<212> TYPE: DNA
<213> ORGANISM: Homo sapiens

<400> SEQUENCE: 23
taaagtgctt atagtgcagg tag                                      23

<210> SEQ ID NO 24
<211> LENGTH: 23
<212> TYPE: DNA
<213> ORGANISM: Homo sapiens

<400> SEQUENCE: 24
agctacattg tctgctgggt ttc                                      23

<210> SEQ ID NO 25
<211> LENGTH: 21
<212> TYPE: DNA
<213> ORGANISM: Homo sapiens

<400> SEQUENCE: 25
ttcacagtgg ctaagttctg c                                        21

<210> SEQ ID NO 26
<211> LENGTH: 22
<212> TYPE: DNA
<213> ORGANISM: Homo sapiens

<400> SEQUENCE: 26
cagtgcaatg ttaaaagggc at                                       22

<210> SEQ ID NO 27
<211> LENGTH: 23
<212> TYPE: DNA
<213> ORGANISM: Homo sapiens

<400> SEQUENCE: 27
tgtgcaaatc catgcaaaac tga                                      23

<210> SEQ ID NO 28
<211> LENGTH: 22
<212> TYPE: DNA
<213> ORGANISM: Homo sapiens
```

<400> SEQUENCE: 28
tattgcactt gtcccggcct gt                                          22

<210> SEQ ID NO 29
<211> LENGTH: 22
<212> TYPE: DNA
<213> ORGANISM: Homo sapiens

<400> SEQUENCE: 29
aaggagctca cagtctattg ag                                          22

<210> SEQ ID NO 30
<211> LENGTH: 22
<212> TYPE: DNA
<213> ORGANISM: Homo sapiens

<400> SEQUENCE: 30
tccctgagac cctaacttgt ga                                          22

<210> SEQ ID NO 31
<211> LENGTH: 22
<212> TYPE: DNA
<213> ORGANISM: Homo sapiens

<400> SEQUENCE: 31
tagcaccatc tgaaatcggt ta                                          22

<210> SEQ ID NO 32
<211> LENGTH: 23
<212> TYPE: DNA
<213> ORGANISM: Homo sapiens

<400> SEQUENCE: 32
tgtaaacatc ctacactctc agc                                         23

<210> SEQ ID NO 33
<211> LENGTH: 22
<212> TYPE: DNA
<213> ORGANISM: Homo sapiens

<400> SEQUENCE: 33
cagtgcaatg atgaaagggc at                                          22

<210> SEQ ID NO 34
<211> LENGTH: 23
<212> TYPE: DNA
<213> ORGANISM: Homo sapiens

<400> SEQUENCE: 34
aacattcatt gctgtcggtg ggt                                         23

<210> SEQ ID NO 35
<211> LENGTH: 22
<212> TYPE: DNA
<213> ORGANISM: Homo sapiens

<400> SEQUENCE: 35
aaaagctggg ttgagagggc ga                                          22

<210> SEQ ID NO 36
<211> LENGTH: 22
<212> TYPE: DNA

<213> ORGANISM: Homo sapiens

<400> SEQUENCE: 36
tgtaaacatc ctcgactgga ag                                    22

<210> SEQ ID NO 37
<211> LENGTH: 23
<212> TYPE: DNA
<213> ORGANISM: Homo sapiens

<400> SEQUENCE: 37
aacattcaac gctgtcggtg agt                                   23

<210> SEQ ID NO 38
<211> LENGTH: 23
<212> TYPE: DNA
<213> ORGANISM: Homo sapiens

<400> SEQUENCE: 38 tgagggcag agagcgagac ttt                                    23

<210> SEQ ID NO 39
<211> LENGTH: 22
<212> TYPE: DNA
<213> ORGANISM: Homo sapiens

<400> SEQUENCE: 39
cagcagcaat tcatgttttg aa                                    22

<210> SEQ ID NO 40
<211> LENGTH: 23
<212> TYPE: DNA
<213> ORGANISM: Homo sapiens

<400> SEQUENCE: 40
agctggtgtt gtgaatcagg ccg                                   23

<210> SEQ ID NO 41
<211> LENGTH: 22
<212> TYPE: DNA
<213> ORGANISM: Homo sapiens

<400> SEQUENCE: 41
tctacagtgc acgtgtctcc ag                                    22

<210> SEQ ID NO 42
<211> LENGTH: 22
<212> TYPE: DNA
<213> ORGANISM: Homo sapiens

<400> SEQUENCE: 42
tgaggtagta ggttgtatgg tt                                    22

<210> SEQ ID NO 43
<211> LENGTH: 22
<212> TYPE: DNA
<213> ORGANISM: Homo sapiens

<400> SEQUENCE: 43
agagcttagc tgattggtga ac                                    22

<210> SEQ ID NO 44
<211> LENGTH: 22

```
<212> TYPE: DNA
<213> ORGANISM: Homo sapiens

<400> SEQUENCE: 44
agggcttagc tgcttgtgag ca                                          22

<210> SEQ ID NO 45
<211> LENGTH: 23
<212> TYPE: DNA
<213> ORGANISM: Homo sapiens

<400> SEQUENCE: 45
cacccggctg tgtgcacatg tgc                                         23

<210> SEQ ID NO 46
<211> LENGTH: 23
<212> TYPE: DNA
<213> ORGANISM: Homo sapiens

<400> SEQUENCE: 46
taccctgtag atccgaattt gtg                                         23

<210> SEQ ID NO 47
<211> LENGTH: 22
<212> TYPE: DNA
<213> ORGANISM: Homo sapiens

<400> SEQUENCE: 47
ctttcagtcg gatgtttgca gc                                          22

<210> SEQ ID NO 48
<211> LENGTH: 22
<212> TYPE: DNA
<213> ORGANISM: Homo sapiens

<400> SEQUENCE: 48
aaaagctggg ttgagagggc aa                                          22

<210> SEQ ID NO 49
<211> LENGTH: 22
<212> TYPE: DNA
<213> ORGANISM: Homo sapiens

<400> SEQUENCE: 49
ttatggtttg cctgggactg ag                                          22

<210> SEQ ID NO 50
<211> LENGTH: 22
<212> TYPE: DNA
<213> ORGANISM: Homo sapiens

<400> SEQUENCE: 50
caagcttgta tctataggta tg                                          22

<210> SEQ ID NO 51
<211> LENGTH: 23
<212> TYPE: DNA
<213> ORGANISM: Homo sapiens

<400> SEQUENCE: 51
tagcagcggg aacagttctg cag                                         23

<210> SEQ ID NO 52
```

-continued

```
<211> LENGTH: 22
<212> TYPE: DNA
<213> ORGANISM: Homo sapiens

<400> SEQUENCE: 52
actgatttct tttggtgttc ag                                              22

<210> SEQ ID NO 53
<211> LENGTH: 23
<212> TYPE: DNA
<213> ORGANISM: Homo sapiens

<400> SEQUENCE: 53
tgagtgtgtg tgtgtgagtg tgt                                             23

<210> SEQ ID NO 54
<211> LENGTH: 17
<212> TYPE: DNA
<213> ORGANISM: Homo sapiens

<400> SEQUENCE: 54
tccctgttcg ggcgcca                                                    17

<210> SEQ ID NO 55
<211> LENGTH: 23
<212> TYPE: DNA
<213> ORGANISM: Homo sapiens

<400> SEQUENCE: 55
agcagcattg tacagggcta tca                                             23

<210> SEQ ID NO 56
<211> LENGTH: 23
<212> TYPE: DNA
<213> ORGANISM: Homo sapiens

<400> SEQUENCE: 56
tgtgcaaatc tatgcaaaac tga                                             23

<210> SEQ ID NO 57
<211> LENGTH: 22
<212> TYPE: DNA
<213> ORGANISM: Homo sapiens

<400> SEQUENCE: 57
tattgcactc gtcccggcct cc                                              22

<210> SEQ ID NO 58
<211> LENGTH: 21
<212> TYPE: DNA
<213> ORGANISM: Homo sapiens

<400> SEQUENCE: 58
ttgtgcttga tctaaccatg t                                               21

<210> SEQ ID NO 59
<211> LENGTH: 21
<212> TYPE: DNA
<213> ORGANISM: Homo sapiens

<400> SEQUENCE: 59
gcagtccatg ggcatataca c                                               21
```

```
<210> SEQ ID NO 60
<211> LENGTH: 22
<212> TYPE: DNA
<213> ORGANISM: Homo sapiens

<400> SEQUENCE: 60
actgcagtga aggcacttgt ag                                              22

<210> SEQ ID NO 61
<211> LENGTH: 20
<212> TYPE: DNA
<213> ORGANISM: Homo sapiens

<400> SEQUENCE: 61
aaaagctggg ttgagagggt                                                 20

<210> SEQ ID NO 62
<211> LENGTH: 17
<212> TYPE: DNA
<213> ORGANISM: Homo sapiens

<400> SEQUENCE: 62
tctcgctggg gcctcca                                                    17

<210> SEQ ID NO 63
<211> LENGTH: 22
<212> TYPE: DNA
<213> ORGANISM: Homo sapiens

<400> SEQUENCE: 63
gtgacatcac atatacggca gc                                              22

<210> SEQ ID NO 64
<211> LENGTH: 22
<212> TYPE: DNA
<213> ORGANISM: Homo sapiens

<400> SEQUENCE: 64
gtgaaatgtt taggaccact ag                                              22

<210> SEQ ID NO 65
<211> LENGTH: 23
<212> TYPE: DNA
<213> ORGANISM: Homo sapiens

<400> SEQUENCE: 65
aaggagctta caatctagct ggg                                             23

<210> SEQ ID NO 66
<211> LENGTH: 22
<212> TYPE: DNA
<213> ORGANISM: Homo sapiens

<400> SEQUENCE: 66
taacactgtc tggtaaagat gg                                              22

<210> SEQ ID NO 67
<211> LENGTH: 23
<212> TYPE: DNA
<213> ORGANISM: Homo sapiens

<400> SEQUENCE: 67
taatactgcc gggtaatgat gga                                             23
```

<210> SEQ ID NO 68
<211> LENGTH: 22
<212> TYPE: DNA
<213> ORGANISM: Homo sapiens

<400> SEQUENCE: 68
taggtagttt catgttgttg gg                                              22

<210> SEQ ID NO 69
<211> LENGTH: 22
<212> TYPE: DNA
<213> ORGANISM: Homo sapiens

<400> SEQUENCE: 69
taatactgcc tggtaatgat ga                                              22

<210> SEQ ID NO 70
<211> LENGTH: 21
<212> TYPE: DNA
<213> ORGANISM: Homo sapiens

<400> SEQUENCE: 70
agggGtgcta tctgtgattg a                                               21

<210> SEQ ID NO 71
<211> LENGTH: 23
<212> TYPE: DNA
<213> ORGANISM: Homo sapiens

<400> SEQUENCE: 71
tctcacacag aaatcgcacc cgt                                             23

<210> SEQ ID NO 72
<211> LENGTH: 22
<212> TYPE: DNA
<213> ORGANISM: Homo sapiens

<400> SEQUENCE: 72
taatactgtc tggtaaaacc gt                                              22

<210> SEQ ID NO 73
<211> LENGTH: 22
<212> TYPE: DNA
<213> ORGANISM: Homo sapiens

<400> SEQUENCE: 73
taacactgtc tggtaacgat gt                                              22

<210> SEQ ID NO 74
<211> LENGTH: 22
<212> TYPE: DNA
<213> ORGANISM: Homo sapiens

<400> SEQUENCE: 74
taatgcccct aaaaatcctt at                                              22

<210> SEQ ID NO 75
<211> LENGTH: 22
<212> TYPE: DNA
<213> ORGANISM: Homo sapiens

<400> SEQUENCE: 75
tatggcactg gtagaattca ct                                              22

<210> SEQ ID NO 76
<211> LENGTH: 22
<212> TYPE: DNA
<213> ORGANISM: Homo sapiens

<400> SEQUENCE: 76
tccttcattc caccggagtc tg                                              22

<210> SEQ ID NO 77
<211> LENGTH: 22
<212> TYPE: DNA
<213> ORGANISM: Homo sapiens

<400> SEQUENCE: 77
taggtagttt cctgttgttg gg                                              22

<210> SEQ ID NO 78
<211> LENGTH: 24
<212> TYPE: DNA
<213> ORGANISM: Homo sapiens

<400> SEQUENCE: 78
tttggcaatg gtagaactca cact                                            24

<210> SEQ ID NO 79
<211> LENGTH: 23
<212> TYPE: DNA
<213> ORGANISM: Homo sapiens

<400> SEQUENCE: 79
tttggcacta gcacattttt gct                                             23

<210> SEQ ID NO 80
<211> LENGTH: 22
<212> TYPE: DNA
<213> ORGANISM: Homo sapiens

<400> SEQUENCE: 80
aactggccct caaagtcccg ct                                              22

<210> SEQ ID NO 81
<211> LENGTH: 21
<212> TYPE: DNA
<213> ORGANISM: Homo sapiens

<400> SEQUENCE: 81
tagcagcaca gaaatattgg c                                               21

<210> SEQ ID NO 82
<211> LENGTH: 21
<212> TYPE: DNA
<213> ORGANISM: Homo sapiens

<400> SEQUENCE: 82
cagcagcaca ctgtggtttg t                                               21

<210> SEQ ID NO 83
<211> LENGTH: 23
<212> TYPE: DNA
<213> ORGANISM: Homo sapiens

<400> SEQUENCE: 83
cagtgcaata gtattgtcaa agc                                           23

<210> SEQ ID NO 84
<211> LENGTH: 22
<212> TYPE: DNA
<213> ORGANISM: Homo sapiens

<400> SEQUENCE: 84
tggcagtgtc ttagctggtt gt                                            22

<210> SEQ ID NO 85
<211> LENGTH: 23
<212> TYPE: DNA
<213> ORGANISM: Homo sapiens

<400> SEQUENCE: 85
tcaagagcaa taacgaaaaa tgt                                           23

<210> SEQ ID NO 86
<211> LENGTH: 23
<212> TYPE: DNA
<213> ORGANISM: Homo sapiens

<400> SEQUENCE: 86
tagtgcaata ttgcttatag ggt                                           23

<210> SEQ ID NO 87
<211> LENGTH: 23
<212> TYPE: DNA
<213> ORGANISM: Homo sapiens

<400> SEQUENCE: 87
tggaagacta gtgattttgt tgt                                           23

<210> SEQ ID NO 88
<211> LENGTH: 23
<212> TYPE: DNA
<213> ORGANISM: Homo sapiens

<400> SEQUENCE: 88
tctggctccg tgtcttcact ccc                                           23

<210> SEQ ID NO 89
<211> LENGTH: 22
<212> TYPE: DNA
<213> ORGANISM: Homo sapiens

<400> SEQUENCE: 89
tggagagaaa ggcagttcct ga                                            22

<210> SEQ ID NO 90
<211> LENGTH: 22
<212> TYPE: DNA
<213> ORGANISM: Homo sapiens

<400> SEQUENCE: 90
gctgactcct agtccagggc tc                                            22

<210> SEQ ID NO 91
<211> LENGTH: 22
<212> TYPE: DNA
<213> ORGANISM: Homo sapiens

<400> SEQUENCE: 91
tgaggtagga ggttgtatag tt          22

<210> SEQ ID NO 92
<211> LENGTH: 23
<212> TYPE: DNA
<213> ORGANISM: Homo sapiens

<400> SEQUENCE: 92
atcaacagac attaattggg cgc          23

<210> SEQ ID NO 93
<211> LENGTH: 21
<212> TYPE: DNA
<213> ORGANISM: Homo sapiens

<400> SEQUENCE: 93
aatggcgcca ctagggttgt g          21

<210> SEQ ID NO 94
<211> LENGTH: 21
<212> TYPE: DNA
<213> ORGANISM: Homo sapiens

<400> SEQUENCE: 94
tacagtactg tgataactga a          21

<210> SEQ ID NO 95
<211> LENGTH: 22
<212> TYPE: DNA
<213> ORGANISM: Homo sapiens

<400> SEQUENCE: 95
tagcttatca gactgatgtt ga          22

<210> SEQ ID NO 96
<211> LENGTH: 22
<212> TYPE: DNA
<213> ORGANISM: Homo sapiens

<400> SEQUENCE: 96
tgaggtagta agttgtattg tt          22

<210> SEQ ID NO 97
<211> LENGTH: 24
<212> TYPE: DNA
<213> ORGANISM: Homo sapiens

<400> SEQUENCE: 97
tccctgagac cctttaacct gtga          24

<210> SEQ ID NO 98
<211> LENGTH: 21
<212> TYPE: DNA
<213> ORGANISM: Homo sapiens

<400> SEQUENCE: 98
tcagtgcatg acagaacttg g          21

<210> SEQ ID NO 99
<211> LENGTH: 23
<212> TYPE: DNA
<213> ORGANISM: Homo sapiens

```
<400> SEQUENCE: 99
tgagcgcctc gacgacagag ccg                                              23

<210> SEQ ID NO 100
<211> LENGTH: 64
<212> TYPE: DNA
<213> ORGANISM: Pan troglodytes

<400> SEQUENCE: 100
aacugcccuc aaggagcuua caaucuagcu gggggnaaau gacuugcaca ugaacacaac      60
uaga                                                                   64

<210> SEQ ID NO 101
<211> LENGTH: 80
<212> TYPE: DNA
<213> ORGANISM: Bos primigenius

<400> SEQUENCE: 101
cuguguguga agugguaacu gcccucaagg agcuuacaau cuagcugggg guaaacgacu      60
ugcacaugaa cgcaucuaga                                                  80

<210> SEQ ID NO 102
<211> LENGTH: 54
<212> TYPE: DNA
<213> ORGANISM: Canis lupus

<400> SEQUENCE: 102
aaggagcuua caaucuagcu gggggugaac ggcuugcaca ugaacgcaac uaga            54

<210> SEQ ID NO 103
<211> LENGTH: 67
<212> TYPE: DNA
<213> ORGANISM: Equus ferus

<400> SEQUENCE: 103
gguaacugcc cucaaggagc uuacaaucua gcuggggua aaugacuugc acaugaacgc       60
aacuaga                                                                67

<210> SEQ ID NO 104
<211> LENGTH: 64
<212> TYPE: DNA
<213> ORGANISM: Homo sapiens

<400> SEQUENCE: 104
aacugcccuc aaggagcuua caaucuagcu gggggnaaau gacuugcaca ugaacacaac      60
uaga                                                                   64

<210> SEQ ID NO 105
<211> LENGTH: 80
<212> TYPE: DNA
<213> ORGANISM: Mus musculus

<400> SEQUENCE: 105
cuguguuuga auggggacu gcccucaagg agcuuacaau cuagcugggg guagaugacu       60 ugcacauugaa cacaacuaga                                                 80

<210> SEQ ID NO 106
<211> LENGTH: 64
<212> TYPE: DNA
<213> ORGANISM: Pongo pygmaeus
```

<400> SEQUENCE: 106

```
aacugcccuc aaggagcuua caaucuagcu gggggguaaau gacuugcaca ugaacacaac    60
uaga                                                                  64
```

<210> SEQ ID NO 107
<211> LENGTH: 59
<212> TYPE: DNA
<213> ORGANISM: Sus scrofa

<400> SEQUENCE: 107

```
cccucaagga gcuuacaauc uagcuggggg ugaaugacuu gcacaugaac gcaacuaga      59
```

<210> SEQ ID NO 108
<211> LENGTH: 64
<212> TYPE: DNA
<213> ORGANISM: Rattus norvegicus

<400> SEQUENCE: 108

```
gacugcccuc aaggagcuua caaucuagcu gggggguagau gacuugcacu ugaacacaac    60
uaga                                                                  64
```

<210> SEQ ID NO 109
<211> LENGTH: 64
<212> TYPE: DNA
<213> ORGANISM: Macaca mulatta

<400> SEQUENCE: 109

```
aacugcccuc aaggagcuua caaucuagcu gggggguaaau gacuugcaca ugaacacaac    60
uaga                                                                  64
```

<210> SEQ ID NO 110
<211> LENGTH: 934
<212> TYPE: DNA
<213> ORGANISM: Homo sapiens

<400> SEQUENCE: 110

```
tgaggcccca gctcccagcc ctgggcggcc gtatcatcag gtgctcctgt gcatctcggc    60
cagcacggga gccagtgccg cgcaggaatg tggggtcccc tgtgttccct cgccagagga   120
gcacttggca aggtcagtga gggggccagta accccccgga gaagcagtac cgacaatgac   180
gaagatacca gatcccttcc caacccctt gcaccggtcc cactaagggg cagggtcgag   240
agaggagggg ggatagggggg agcagacccc tgagatctgg gcataggcac cgcattctga   300
tctggacaaa gtcgggacag caccatccca gccccgaagc cagggccatg ccagcaggcc   360
ccaccatgga aatcaaaaca ccgcaccagc cagcagaatg gacattctga catcgccagc   420
cgacgccctg aatcttggtg cagcaccaac cgcgtgcctg tgtggcggga ctggagggca   480
cagttgagga aggagggtgg ttaagaaata cagtggggcc ctctcgctgt cccttgccca   540
gggcacttgc attccagcct cgctgcattt gctctctcga ttcccctttc ctcctcactg   600
cctcccaagc ccaccctact ccaaaataat gtgtcacttg atttggaact attcaagcag   660
taaaagtaaa tgaatcccac ctttactaaa acactttctc tgaacccccc ttgccctca    720
ctgatcttgc ttttcctgg tctcatgcag ttgtggtcaa tattgtggta atcgctaatt   780
gtactgattg tttaagtgtg cattagttgt gtctccccag ctagattgta agctcctgga   840
ggacagggac cacctctaca aaaataaaa aaagtacctc ccctgtctcg cacagtgtcc   900
```

```
caggaccctg cggtgcagta gaggcgcacc aaaa                                    934
```

<210> SEQ ID NO 111
<211> LENGTH: 81
<212> TYPE: PRT
<213> ORGANISM: Homo sapiens

<400> SEQUENCE: 111

```
Met Ala Val Ala Ala Ser Ala Glu Leu Leu Ile Ile Gly Trp
 1               5                  10                  15

Tyr Ile Phe Arg Val Leu Leu Gln Val Phe Leu Glu Cys Cys Ile Tyr
                20                  25                  30

Trp Val Gly Phe Ala Phe Arg Asn Pro Pro Gly Thr Gln Pro Ile Ala
            35                  40                  45

Arg Ser Glu Val Phe Arg Tyr Ser Leu Gln Lys Leu Ala Tyr Thr Val
50                  55                  60

Ser Arg Thr Gly Arg Gln Val Leu Gly Glu Arg Arg Gln Arg Ala Pro
65                  70                  75                  80

Asn
```

<210> SEQ ID NO 112
<211> LENGTH: 1281
<212> TYPE: DNA
<213> ORGANISM: Homo sapiens

<400> SEQUENCE: 112

```
agcggactcc gagaccagcg gatctcggca aaccctcttt ctcgaccacc cacctaccat      60
tcttggaacc atggcggcag tggcggcggc ctcggctgaa ctgctcatca tcggctggta     120
catcttccgc gtgctgctgc aggtgttcct ggaatgctgc atttactggg taggattcgc     180
ttttcgaaat cctccaggga cacagcccat tgcgagaagt gaggtgttca ggtactccct     240
gcagaagctg gcatacacgg tgtcgcggac cgggcggcag gtgttggggg agcgcaggca     300
gcgagccccc aactgaggcc ccagctccca gccctgggcg gccgtatcat caggtgctcc     360
tgtgcatctc ggccagcacg ggagccagtc ccgcgcagga atgtgggggtc ccctgtgttc     420
cctcgccaga ggagcacttg gcaaggtcag tgaggggcca gtagaccccc ggagaagcag     480
taccgacaat gacgaagata ccagatccct tcccaacccc tttgcaccgg tcccactaag     540
gggcagggtc gagagaggag gggggatagg gggagcagac ccctgagatc tgggcatagg     600
caccgcattc tgatctggac aaagtcggga cagcaccatc ccagccccga agccagggcc     660
atgccagcag gccccaccat ggaaatcaaa acaccgcacc agccagcaga atggacattc     720
tgacatcgcc agccgacgcc ctgaatcttg gtgcagcacc aaccgcgtgc ctgtgtggcg     780
ggactggagg gcacagttga ggaaggaggg tggttaagaa atacagtggg gccctctcgc     840
tgtcccttgc ccagggcact tgcattccag cctcgctgca tttgctctct cgattcccct     900
ttcctcctca ctgcctccca agcccaccct actccaaaat aatgtgtcac ttgatttgga     960
actattcaag cagtaaaagt aaatgaatcc cacctttact aaaacacttt ctctgaaccc    1020
cccttgcccc tcactgatct tgcttttccc tggtctcatg cagttgtggt caatattgtg    1080
gtaatcgcta attgtactga ttgtttaagt gtgcattagt tgtgtctccc cagctagatt    1140
gtaagctcct ggaggacagg gaccacctct acaaaaaata aaaaagtac ctcccctgtc     1200
tcgcacagtg tcccaggacc ctgcggtgca gtagaggcgc accaaaaaaa aaaaaaaaaa    1260
aaaaaaaaaa aaaaaaaaa a                                               1281
```

<210> SEQ ID NO 113
<211> LENGTH: 739
<212> TYPE: PRT
<213> ORGANISM: Homo sapiens

<400> SEQUENCE: 113

| | | | | | | | | | | | | | | | |
|---|---|---|---|---|---|---|---|---|---|---|---|---|---|---|---|
| Met | Ala | Pro | Gln | Lys | His | Gly | Gly | Gly | Gly | Gly | Ser | Gly | Pro | | |
| 1 | | | | 5 | | | | | 10 | | | | | 15 | |
| Ser | Ala | Gly | Ser | Gly | Gly | Gly | Phe | Gly | Gly | Ser | Ala | Ala | Val | Ala | |
| | | 20 | | | | | 25 | | | | | 30 | | | |
| Ala | Ala | Thr | Ala | Ser | Gly | Gly | Lys | Ser | Gly | Gly | Ser | Cys | Gly | Gly | |
| | | | 35 | | | | | 40 | | | | | 45 | | |
| Gly | Gly | Ser | Tyr | Ser | Ala | Ser | Ser | Ser | Ser | Ala | Ala | Ala | Ala | | |
| 50 | | | | | 55 | | | | | 60 | | | | | |
| Gly | Ala | Ala | Val | Leu | Pro | Val | Lys | Lys | Pro | Lys | Met | Glu | His | Val | Gln |
| 65 | | | | | 70 | | | | | 75 | | | | | 80 |
| Ala | Asp | His | Glu | Leu | Phe | Leu | Gln | Ala | Phe | Glu | Lys | Pro | Thr | Gln | Ile |
| | | | | 85 | | | | | 90 | | | | | 95 | |
| Tyr | Arg | Phe | Leu | Arg | Thr | Arg | Asn | Leu | Ile | Ala | Pro | Ile | Phe | Leu | His |
| | | | 100 | | | | | 105 | | | | | 110 | | |
| Arg | Thr | Leu | Thr | Tyr | Met | Ser | His | Arg | Asn | Ser | Arg | Thr | Asn | Ile | Lys |
| | | | 115 | | | | | 120 | | | | | 125 | | |
| Arg | Lys | Thr | Phe | Lys | Val | Asp | Asp | Met | Leu | Ser | Lys | Val | Glu | Lys | Met |
| | 130 | | | | | 135 | | | | | 140 | | | | |
| Lys | Gly | Glu | Gln | Glu | Ser | His | Ser | Leu | Ser | Ala | His | Leu | Gln | Leu | Thr |
| 145 | | | | | 150 | | | | | 155 | | | | | 160 |
| Phe | Thr | Gly | Phe | Phe | His | Lys | Asn | Asp | Lys | Pro | Ser | Pro | Asn | Ser | Glu |
| | | | | 165 | | | | | 170 | | | | | 175 | |
| Asn | Glu | Gln | Asn | Ser | Val | Thr | Leu | Glu | Val | Leu | Leu | Val | Lys | Val | Cys |
| | | | 180 | | | | | 185 | | | | | 190 | | |
| His | Lys | Lys | Arg | Lys | Asp | Val | Ser | Cys | Pro | Ile | Arg | Gln | Val | Pro | Thr |
| | | | 195 | | | | | 200 | | | | | 205 | | |
| Gly | Lys | Lys | Gln | Val | Pro | Leu | Asn | Pro | Asp | Leu | Asn | Gln | Thr | Lys | Pro |
| | 210 | | | | | 215 | | | | | 220 | | | | |
| Gly | Asn | Phe | Pro | Ser | Leu | Ala | Val | Ser | Ser | Asn | Glu | Phe | Glu | Pro | Ser |
| 225 | | | | | 230 | | | | | 235 | | | | | 240 |
| Asn | Ser | His | Met | Val | Lys | Ser | Tyr | Ser | Leu | Leu | Phe | Arg | Val | Thr | Arg |
| | | | | 245 | | | | | 250 | | | | | 255 | |
| Pro | Gly | Arg | Arg | Glu | Phe | Asn | Gly | Met | Ile | Asn | Gly | Glu | Thr | Asn | Glu |
| | | | 260 | | | | | 265 | | | | | 270 | | |
| Asn | Ile | Asp | Val | Asn | Glu | Glu | Leu | Pro | Ala | Arg | Arg | Lys | Arg | Asn | Arg |
| | | | 275 | | | | | 280 | | | | | 285 | | |
| Glu | Asp | Gly | Glu | Lys | Thr | Phe | Val | Ala | Gln | Met | Thr | Val | Phe | Asp | Lys |
| | 290 | | | | | 295 | | | | | 300 | | | | |
| Asn | Arg | Arg | Leu | Gln | Leu | Leu | Asp | Gly | Glu | Tyr | Glu | Val | Ala | Met | Gln |
| 305 | | | | | 310 | | | | | 315 | | | | | 320 |
| Glu | Met | Glu | Glu | Cys | Pro | Ile | Ser | Lys | Lys | Arg | Ala | Thr | Trp | Glu | Thr |
| | | | | 325 | | | | | 330 | | | | | 335 | |
| Ile | Leu | Asp | Gly | Lys | Arg | Leu | Pro | Pro | Phe | Glu | Thr | Phe | Ser | Gln | Gly |
| | | | 340 | | | | | 345 | | | | | 350 | | |
| Pro | Thr | Leu | Gln | Phe | Thr | Leu | Arg | Trp | Thr | Gly | Glu | Thr | Asn | Asp | Lys |
| | | | 355 | | | | | 360 | | | | | 365 | | |
| Ser | Thr | Ala | Pro | Ile | Ala | Lys | Pro | Leu | Ala | Thr | Arg | Asn | Ser | Glu | Ser |
| | 370 | | | | | 375 | | | | | 380 | | | | |

| | | | | | | | | | | | |
|---|---|---|---|---|---|---|---|---|---|---|---|
| Leu 385 | His | Gln | Glu | Asn 390 | Lys | Pro | Gly | Ser 395 | Val | Lys | Pro | Thr | Gln | Thr | Ile 400 |

Leu His Gln Glu Asn Lys Pro Gly Ser Val Lys Pro Thr Gln Thr Ile
385                              390                            395                            400

Ala Val Lys Glu Ser Leu Thr Thr Asp Leu Gln Thr Arg Lys Glu Lys
                      405                            410                            415

Asp Thr Pro Asn Glu Asn Arg Gln Lys Leu Arg Ile Phe Tyr Gln Phe
        420                            425                            430

Leu Tyr Asn Asn Asn Thr Arg Gln Gln Thr Glu Ala Arg Asp Asp Leu
                435                        440                      445

His Cys Pro Trp Cys Thr Leu Asn Cys Arg Lys Leu Tyr Ser Leu Leu
        450                            455                            460

Lys His Leu Lys Leu Cys His Ser Arg Phe Ile Phe Asn Tyr Val Tyr
465                              470                            475                            480

His Pro Lys Gly Ala Arg Ile Asp Val Ser Ile Asn Glu Cys Tyr Asp
                      485                            490                            495

Gly Ser Tyr Ala Gly Asn Pro Gln Asp Ile His Arg Gln Pro Gly Phe
                500                        505                          510

Ala Phe Ser Arg Asn Gly Pro Val Lys Arg Thr Pro Ile Thr His Ile
                515                        520                          525

Leu Val Cys Arg Pro Lys Arg Thr Lys Ala Ser Met Ser Glu Phe Leu
530                              535                            540

Glu Ser Glu Asp Gly Glu Val Glu Gln Gln Arg Thr Tyr Ser Ser Gly
545                              550                            555                            560

His Asn Arg Leu Tyr Phe His Ser Asp Thr Cys Leu Pro Leu Arg Pro
                      565                            570                          575

Gln Glu Met Glu Val Asp Ser Asp Glu Lys Asp Pro Glu Trp Leu
                580                        585                          590

Arg Glu Lys Thr Ile Thr Gln Ile Glu Glu Phe Ser Asp Val Asn Glu
            595                        600                            605

Gly Glu Lys Glu Val Met Lys Leu Trp Asn Leu His Val Met Lys His
610                              615                            620

Gly Phe Ile Ala Asp Asn Gln Met Asn His Ala Cys Met Leu Phe Val
625                              630                            635                            640

Glu Asn Tyr Gly Gln Lys Ile Ile Lys Lys Asn Leu Cys Arg Asn Phe
                      645                            650                          655

Met Leu His Leu Val Ser Met His Asp Phe Asn Leu Ile Ser Ile Met
                660                        665                          670

Ser Ile Asp Lys Ala Val Thr Lys Leu Arg Glu Met Gln Gln Lys Leu
        675                            680                            685

Glu Lys Gly Glu Ser Ala Ser Pro Ala Asn Glu Glu Ile Thr Glu Glu
                690                        695                          700

Gln Asn Gly Thr Ala Asn Gly Phe Ser Glu Ile Asn Ser Lys Glu Lys
705                              710                            715                            720

Ala Leu Glu Thr Asp Ser Val Ser Gly Val Ser Lys Gln Ser Lys Lys
                725                        730                          735

Gln Lys Leu

```
<210> SEQ ID NO 114
<211> LENGTH: 4477
<212> TYPE: DNA
<213> ORGANISM: Homo sapiens

<400> SEQUENCE: 114
ggtgagcggc ctccgaagcg gagcggggct ctgaggagac acttttttttt tcctccctcc      60
```

-continued

| | |
|---|---|
| ttccctcctc tcctcctccc ttcccttccc ctctcctccc ctctctcctc cttccccct | 120 |
| cggtccgccg gagcctgctg gggcgagcgg ttggtattgc aggcgcttgc tctccggggc | 180 |
| cgcccggcgg gtagctggcg gggggaggag gcaggaaccg cgatggcgcc tcagaagcac | 240 |
| ggcggtgggg gaggggcgg ctcggggccc agcgcgggt ccggggagg cggcttcggg | 300 |
| ggttcggcgg cggtggcggc ggcgacggct tcggcggca aatccggcgg cgggagctgt | 360 |
| ggagggggtg gcagttactc ggcctcctcc tcctcctccg cggcggcagc ggcgggggct | 420 |
| gcggtgttac cggtgaagaa gccgaaaatg gagcacgtcc aggctgacca cgagcttttc | 480 |
| ctccaggcct ttgagaagcc aacacagatc tatagatttc ttcgaactcg gaatctcata | 540 |
| gcaccaatat ttttgcacag aactcttact tacatgtctc atcgaaactc cagaacaaac | 600 |
| atcaaaagga aaacatttaa agttgatgat atgttatcaa agtagagaa atgaaagga | 660 |
| gagcaagaat ctcatagctt gtcagctcat ttgcagctta cgtttactgg tttcttccac | 720 |
| aaaaatgata agccatcacc aaactcagaa aatgaacaaa attctgttac cctggaagtc | 780 |
| ctgcttgtga agtttgcca caaaaaaga aaggatgtaa gttgtccaat aaggcaagtt | 840 |
| cccacaggta aaaagcaggt gcctttgaat cctgacctca atcaaacaaa acccggaaat | 900 |
| ttcccgtccc ttgcagtttc cagtaatgaa tttgaaccta gtaacagcca tatggtgaag | 960 |
| tcttactcgt tgctatttag agtgactcgt ccaggaagaa gagagtttaa tggaatgatt | 1020 |
| aatggagaaa ccaatgaaaa tattgatgtc aatgaagagc ttccagccag aagaaaacga | 1080 |
| aatcgtgagg atggggaaaa gacatttgtt gcacaaatga cagtatttga taaaaacagg | 1140 |
| cgcttacagc ttttagatgg ggaatatgaa gtagccatgc aggaaatgga agaatgtcca | 1200 |
| ataagcaaga aaagagcaac atgggagact attcttgatg ggaagaggct gcctccattc | 1260 |
| gaaacatttt ctcagggacc tacgttgcag ttcactcttc gttggacagg agagaccaat | 1320 |
| gataaatcta cggctcctat tgccaaacct cttgccacta gaaattcaga gagtctccat | 1380 |
| caggaaaaca agcctggttc agttaaacct actcaaacta ttgctgttaa agaatcattg | 1440 |
| actacagatc tacaaacaag aaaagaaaag gatactccaa atgaaaaccg acaaaaatta | 1500 |
| agaatatttt atcagtttct ctataacaac aatacaaggc aacaaactga agcaagagat | 1560 |
| gacctgcatt gcccttggtg tactctgaac tgccgcaaac tttatagttt actcaagcat | 1620 |
| cttaaactct gccatagcag atttatcttc aactatgttt atcatccaaa aggtgctagg | 1680 |
| atagatgttt ctatcaatga gtgttatgat ggctcctatg caggaaatcc tcaggatatt | 1740 |
| catcgccaac ctggatttgc ttttagtcgc aacggaccag ttaagagaac acctatcaca | 1800 |
| catattcttg tgtgcaggcc aaaacgaaca aaagcaagca tgtctgaatt tcttgaatct | 1860 |
| gaagatgggg aagtagaaca gcaaagaaca tatagtagtg gccacaatcg tctgtatttc | 1920 |
| catagtgata cctgcttacc tctccgtcca caagaaatgg aagtagatag tgaagatgaa | 1980 |
| aaggatcctg aatggctaag agaaaaaacc attacacaaa ttgaagagtt ttctgatgtt | 2040 |
| aatgaaggag agaaagaagt gatgaaactc tggaatctcc atgtcatgaa gcatgggttt | 2100 |
| attgctgaca atcaaatgaa tcatgcctgt atgctgtttg tagaaaatta tggacagaaa | 2160 |
| ataattaaga gaatttatg tcgaaacttc atgcttcatc tagtcagcat gcatgacttt | 2220 |
| aatcttatta gcataatgtc aatagataaa gctgttacca agctccgtga atgcagcaa | 2280 |
| aaattagaaa aggggaatc tgcttcccct gcaaacgaag aaataactga gaacaaaat | 2340 |
| gggacagcaa atggatttag tgaaattaac tcaaagagaa aagctttgga acagatagt | 2400 |
| gtctcagggg tttcaaaaca gagcaaaaaa caaaaactct gaaaagctct aaccccatgt | 2460 |

-continued

```
tatggacaaa cactgaaatt acattttagg gaattcatcc tctaagaatt atgttttgt    2520 ttttaatcat atgttccaaa caggcactgt tagatgaagt aaatgatttc aacaaggata    2580
tttgtatcag ggttctactt cacttcatta tgcagcatta catgtatatc acttttattg    2640
atgtcattaa aacattctgt actttaagca tgaaaagcaa tatttcaaag tattttaaa     2700 ctcaacaaat gtcatcaaat atgttgaatt gatctagaaa ttatttcata tataaatcag    2760 aattttttg catttatgaa cggctgtttt tctactttgt aattgtgaga cattttcttg     2820
gggagggaaa attggaatgg ttccctttt tagaaattga agtggtcttc atatgtcaac    2880
tacagaaaag gaaaaaaata gaaattgaag gattttatg aaattatatt gcattactat    2940
ttgcagtcaa actttgatcc ttgttttga aatcatttgt caattcggaa tgaaaaatta    3000
taatgtaatt ttacattaca taagttcctt ttacaattaa aaaatagcac ttcttcatct    3060
tatgcctgtt tgagaagata ttaaattttc acattgttga cagtgaaatg ctatgttggt    3120
ttataagatt acagaccatt tgttttcatg tggataattt tagtgcattg ctcacccggt    3180
atgttttttt tttttaactt gaacattttg cttgttttgt ttttcttttt taattagata    3240
atcacacgga aaattaagct gttcatatct ttaaattagg attgcaaacc aaggaaagaa    3300
cgcatttgag attttaagat gtcacttata aggggagaag tgttcttaaa aagtcaacca    3360
gaaaactgtt atgccttta tttgtttgca aggatgtctt tgtaatgtgt tcatgaata     3420 gaatatccaa tagagataag ctgacttgaa tcatttgag caattttgcc ctgtgttata    3480
tgtgtttcac gcacatattt gcagttggat tttctccaac agaaagtgga ttcactactg    3540
gcacattaac aagcaccaat aggtttttat tccaactccg agcactgtgg ttgagtaaca    3600
tcacctcaat tttttattat ccttaaagat attgcatttt catattcttt atttataaag    3660
gatcaatgct gctgtaaata caggtatttt taattttaaa atttcattcc accaccatca    3720
gatgcagttc cctattttgt ttaatgaagg gatatataag cttcctaatg gtgtcttcag    3780
aaatttataa aatgtaaata ctgatttgac tggtctttaa gatgtgttta actgtgaggc    3840
tatttaacga atagtgtgga tgtgattgt catccagtat taagttctta gtcattgatt    3900
tttgtgttta aaaaaaata ggaaagaggg aaactgcagc tttcattaca gattccttga    3960
ttggtaagct ctccaaatga tgagttctag taaactctga ttttgcctc tggatagtag    4020 atctcgagcg tttatctcgg gctttaattt gctaaagctg tgcacatatg taaaaaaaaa    4080 aaaaaaaga ttattttagg ggagatgtag gtgtagaatt attgcttatg tcatttctta    4140
agcagttatg ctcttaatgc ttaaaagaag gctagcattg tttgcacaaa aagttggtga    4200
ttcccacccc aaatagtaat aaaattactt ctgttgagta aacttttat gtcatcgtaa     4260 aagctgaaaa aatcccttg tttctattta taaaaaagt gcttttctat atgtacccttt    4320 gataacagat tttgaagaaa tcctgtaaga tgataaagca tttgaatggt acagtagatg    4380 taaaaaaat tcagtttaaa agaacatttg ttttacatt aaatgtttat ttgaaatcaa      4440
atgattttgt acataaagtt caataatata aaagctg                             4477
```

<210> SEQ ID NO 115
<211> LENGTH: 9
<212> TYPE: RNA
<213> ORGANISM: Artificial Sequence
<220> FEATURE:
<223> OTHER INFORMATION: A synthetic ribonucleotide sequence

<400> SEQUENCE: 115 uucaagaga                                                           9

<210> SEQ ID NO 116
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 116
aaggagctta caatctagct gggtt                                        25

<210> SEQ ID NO 117
<211> LENGTH: 23
<212> TYPE: RNA
<213> ORGANISM: Homo sapiens

<400> SEQUENCE: 117
cccagcuaga uuguaagcuc cug                                          23

<210> SEQ ID NO 118
<211> LENGTH: 23
<212> TYPE: RNA
<213> ORGANISM: Homo sapiens

<400> SEQUENCE: 118
aaggagcuua caaucuagcu ggg                                          23

<210> SEQ ID NO 119
<211> LENGTH: 23
<212> TYPE: RNA
<213> ORGANISM: Homo sapiens

<400> SEQUENCE: 119
cccagcuaga uuguaacguc gug                                          23

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

<210> SEQ ID NO 123
<211> LENGTH: 22
<212> TYPE: RNA
<213> ORGANISM: Homo sapiens

<400> SEQUENCE: 123
aggagcuuac aaucuagcug gg                                           22

<210> SEQ ID NO 124
<211> LENGTH: 22
<212> TYPE: RNA

```
<213> ORGANISM: Homo sapiens

<400> SEQUENCE: 124
cccagcuaga uuguaagcuc cu                                               22

<210> SEQ ID NO 125
<211> LENGTH: 22
<212> TYPE: RNA
<213> ORGANISM: Pan troglodytes

<400> SEQUENCE: 125
cccagcuaga uuguaagcuc cu                                               22

<210> SEQ ID NO 126
<211> LENGTH: 22
<212> TYPE: RNA
<213> ORGANISM: Hylobates lar

<400> SEQUENCE: 126
cccagcuaga uuguaagcuc cu                                               22

<210> SEQ ID NO 127
<211> LENGTH: 22
<212> TYPE: RNA
<213> ORGANISM: Macaca mulatta

<400> SEQUENCE: 127
cccagcuaga uuguaagcuc cu                                               22

<210> SEQ ID NO 128
<211> LENGTH: 22
<212> TYPE: RNA
<213> ORGANISM: Callithrix jacchus

<400> SEQUENCE: 128
cccagcuaga uuguaagcuc cu                                               22

<210> SEQ ID NO 129
<211> LENGTH: 22
<212> TYPE: RNA
<213> ORGANISM: Rattus norvegicus

<400> SEQUENCE: 129
cccagcuaga uuguaagcuc cu                                               22

<210> SEQ ID NO 130
<211> LENGTH: 22
<212> TYPE: RNA
<213> ORGANISM: Equus ferus

<400> SEQUENCE: 130
cccagcuaga uuguaagcuc cu                                               22

<210> SEQ ID NO 131
<211> LENGTH: 22
<212> TYPE: RNA
<213> ORGANISM: Bos taurus

<400> SEQUENCE: 131
cccagcuaga uuguaagcuc cu                                               22
```